US009462793B2

(12) United States Patent
Schilling et al.

(10) Patent No.: US 9,462,793 B2
(45) Date of Patent: Oct. 11, 2016

(54) MOUSE CARRYING A KNOCK-OUT MUTATION OF THE QPCT-GENE

(75) Inventors: Stephan Schilling, Halle/Saale (DE); Torsten Hoffmann, Halle/Saale (DE); Hans-Ulrich Demuth, Halle/Saale (DE)

(73) Assignee: PROBIODRUG AG, Halle-Saale (DE)

( * ) Notice: Subject to any disclaimer, the term of this patent is extended or adjusted under 35 U.S.C. 154(b) by 535 days.

(21) Appl. No.: 12/353,463

(22) Filed: Jan. 14, 2009

(65) Prior Publication Data

US 2009/0183267 A1 Jul. 16, 2009

Related U.S. Application Data

(60) Provisional application No. 61/020,784, filed on Jan. 14, 2008.

(51) Int. Cl.

| | |
|---|---|
| ***C12N 15/01*** | (2006.01) |
| ***A01K 67/027*** | (2006.01) |
| ***C12N 9/10*** | (2006.01) |
| ***C12N 15/85*** | (2006.01) |

(52) U.S. Cl.

CPC ........... *A01K 67/0276* (2013.01); *C12N 9/104* (2013.01); *C12N 15/8509* (2013.01); *A01K 2217/075* (2013.01); *A01K 2227/105* (2013.01); *A01K 2267/03* (2013.01); *C12N 2800/30* (2013.01); *G01N 2500/00* (2013.01); *G01N 2800/2814* (2013.01)

(58) Field of Classification Search

USPC ....................... 800/3, 8, 18, 20, 21; 435/325

See application file for complete search history.

(56) References Cited

U.S. PATENT DOCUMENTS

| | | | |
|---|---|---|---|
| 4,873,191 | A | 10/1989 | Wagner et al. |
| 4,873,316 | A | 10/1989 | Meade et al. |
| 5,175,384 | A | 12/1992 | Krimpenfort et al. |
| 5,602,299 | A | 2/1997 | Lazzarini |
| 5,981,830 | A | 11/1999 | Wu et al. |
| 6,037,521 | A | 3/2000 | Sato et al. |
| 6,066,778 | A | 5/2000 | Ginsburg et al. |
| 7,304,086 | B2 | 12/2007 | Schilling |
| 7,371,871 | B2 | 5/2008 | Schilling |
| 7,381,537 | B2 | 6/2008 | Demuth |
| 7,462,599 | B2 | 12/2008 | Schilling |
| 2005/0137142 | A1 | 6/2005 | Schultz |
| 2005/0171112 | A1 | 8/2005 | Schultz |
| 2006/0100253 | A1 | 5/2006 | Niestroj |
| 2007/0191366 | A1 | 8/2007 | Hoffmann |
| 2008/0153892 | A1 | 6/2008 | Schilling |
| 2008/0200567 | A1 | 8/2008 | Schilling |
| 2008/0207715 | A1 | 8/2008 | Thormann |
| 2008/0214620 | A1 | 9/2008 | Heiser |
| 2008/0221086 | A1 | 9/2008 | Thormann |
| 2008/0234313 | A1 | 9/2008 | Ramsbeck |
| 2008/0249083 | A1 | 10/2008 | Schilling |
| 2008/0260688 | A1 | 10/2008 | Buchholz |
| 2008/0262063 | A1 | 10/2008 | Buchholz |
| 2008/0262065 | A1 | 10/2008 | Buchholz |
| 2008/0267911 | A1 | 10/2008 | Buchholz |
| 2008/0267912 | A1 | 10/2008 | Buchholz |
| 2008/0286231 | A1 | 11/2008 | Buchholz |
| 2008/0286810 | A1 | 11/2008 | Demuth |
| 2008/0292582 | A1 | 11/2008 | Buchholz |
| 2009/0018087 | A1 | 1/2009 | Schilling |
| 2009/0068699 | A1 | 3/2009 | Schilling |
| 2009/0098052 | A1 | 4/2009 | Schilling |
| 2009/0149394 | A1 | 6/2009 | Schilling |

FOREIGN PATENT DOCUMENTS

| | | |
|---|---|---|
| EP | 0264166 | 4/1986 |
| EP | 1262552 | 4/2002 |
| WO | WO 90/08832 | 9/1990 |
| WO | WO 2004/098625 | 11/2004 |
| WO | WO 2005/039548 | 5/2005 |
| WO | WO 2008/034891 | 3/2008 |
| WO | WO 2008/087197 | 7/2008 |

OTHER PUBLICATIONS

Zambrowicz (PNAS, Nov. 25, 2003, vol. 100, No. 24, p. 14109-14114).*
MGI website for Qpct "References", 2010.*
MGI website for Qpct, 2010.*
Schilling (Biochem., 2005, vol. 44, p. 13415-13424).*
Leu, Plos One, 2009, vol. 4, No. 11, e7734.*
Lieberman, PNAS, Jul. 1996, vol. 93, p. 7923-7926.*
Shi, Mol. and Cell. Biol., Aug. 2001, vol. 21, No. 16, p. 5389-5395.*
Liu (Genome Res., 2003, vol. 13, p. 476-484).*
Wang (Cancer Cell, Sep. 2003, vol. 4, p. 209-221).*
Lesche (Genesis, 2002, vol. 32, p. 148-149).*
Huang (Cancer Res., Aug. 2002, vol. 62, p. 4812-4819).*
Abdulkadir (Mol. and Cell. Biol., Mar. 2002, vol. 22, No. 5, p. 1495-1503).*
Wong (Neuron, Sep. 2000, vol. 27, p. 487-497).*
Schulz (J. Clin. Invest., 1997, vol. 100, p. 1590-1595).*
Domino (Mol. Cell. Biology, Dec. 2001, vol. 21, No. 24, p. 8336-8345).*
Engle (Toxicology & Applied Pahrmacol., 2004, vol. 194, p. 296-308).*
Ellies (Immunity, Dec. 1998, vol. 9, p. 881-890).*
McGowan (Trends in Genetics, 2006, vol. 22, p. 281-289).*
Schilling (J. Biol. Chem., 2011, vol. 286, p. 14199-14208).*
Amyloid plaque chart for Alzheimer's disease, Cell Signaling Technology (Jun. 2012).*

(Continued)

*Primary Examiner* — Michael Wilson

(74) *Attorney, Agent, or Firm* — Dentons US LLP

(57) ABSTRACT

The present invention provides a knock-out non-human animal, in particular a mouse carrying a Qpct knock-out mutation. The present invention additionally provides the respective cells and cell lines and methods and compositions for evaluating agents that affect Qpct, for use in compositions for the treatment of Qpct-related diseases.

37 Claims, 32 Drawing Sheets

(56) References Cited

OTHER PUBLICATIONS

Banerji, Julian, et al., "A Lymphocyte-Specific Cellular Enhancer is Located Downstream of the Joining Region in Immunoglobulin Heavy Chain Genes", Cell, 1983, 33:729-740.
Bateman, Jr., Robert C., et al., "Evidence for Essential Histidines in Human Pituitary Glutaminyl Cyclase", Biochemistry, 2001, 40:11246-11250.
Bhatia, Madhav, et al., "Treatment with Bindarit, a Blocker of MCP-1 Synthesis, Protects Mice Against Acute Pancreatitis", Am J Physiol Gastrointest. Liver Physiol, 2005, 288:G1259-1265.
Binder, Elisabeth, et al., "The Role of Neurotensin in the Pathophysiology of Schizophrenia and the Mechanism of Action of Antipsychotic Drugs", Society of the Biological Psychiatry, 2001, 50:856-872.
Bockers, Tobias M., et al., "Glutaminyl-Cyclase Expression in the Bovine/Porcine Hypothalamus and Pituitary", Journal of Neuroendocrinology, 1995, 7:445-453.
Booth, Rachell E., et al., "Human Glutaminyl Cyclase and Bacterial Zinc Aminopeptidase Share a Common Fold and Active Site", BMC Biology, 2004, 2:2.
Borchelt, David R., et al., "Familial Alzheimer's Disease-Linked Presenilin 1 Variants Elevate Aβ1-42/1-40 Ratio in Vitro and in Vivo", Neuron, 1996, 17:1005-1013.
Buchholz, Mirko, et al., "The First Potential Inhibitors for Human Glutaminyl Cyclase: Synthesis and Structure—Activity Relationship", J Med Chemical, 2006, 49:664-667.
Busby, Walker H., et al., "An Enzyme(s) that Converts Glutaminyl-Peptides into Pyroglutamyl-Peptides", The Journal of Biological Chemistry, 1987, 262:8532-8536.
Byrne, G.W. and Ruddle, F. H., "Multiplex Gene Regulation: A Two-Tiered Approach to Transgene Regulation in Transgenic Mice", Proc. Natl. Acad. Sci., 1989, 86:5473-5477.
Calame, Kathryn and Eaton, Suzanne, "Transcriptional Controlling Elements in the Immunoglobulin and T Cell Receptor Loci", Advances in Immunology, 1988, 43:235-275.
Casas, Caty, et al., "Massive CA1/2 Neuronal Loss with Intraneuronal and N-Terminal Truncated $Aβ_{42}$ Accumulation in a Novel Alzheimer Transgenic Model", American Journal of Pathology, 2004, 165:1289-1300.
Ceballos-Picot, I., et al., "Neuronal-Specific Expression of Human Copper—Zinc Superoxide Dismutase Gene in Transgenic Mice: Animal Model of Gene Dosage Effects in Down's Syndrome" Brain Research, 1991, 552:198-214.
Citron, Martin, et al., "Mutant Presenilins of Alzheimer's Disease Increase Production of 42-Residue Amyloid β-Protein in Both Transfected Cells and Transgenic Mice", Nature Medicine, 1997, 3:67-72.
Coll, Blai, et al., "HIV-Infected Patients with Lipodystrophy have Higher Rates of Carotid Atherosclerosis: The Role of Monocyte Chemoattractant Protein-1", Cytokine, 2006, 34:51-55.
Comery, Thomas A., et al., "Acute γ-Secretase Inhibition Improves Contextual Fear Conditioning in the Tg2576 Mouse Model of Alzheimer's Disease", The Journal of Neuroscience, 2005, 25:8898-8902.
Consalvo, Angelo P., et al., "A Rapid Fluorometric Assay for N-Terminal Glutaminyl Cyclase Activity Using High-Performance Liquid Chromatography", Analytical Biochemistry, 1988, 175:131-138.
Cynis, Holger, et al., "Inhibition of Glutaminyl Cyclase Alters Pyroglutamate Formation in Mammalian Cells", Biochimica et Biopysica Acta, 2006, 64:1618-1625.
Dahl, Seren, et al., "*Caria papaya* Glutamine Cyclotransferase Belongs to a Novel Plant Enzyme Subfamily: Cloning and Characterization of the Recombinant Enzyme", Protein Expression and Purification, 2000, 20:27-36.
Darnell, J. et al., Molecular Cell Biology $2^{nd}$ Edition, Scientific American Books, 1990, 63.
Edlund, Thomas et al., "Cell-Specific Expression of the Rat Insulin Gene: Evidence for Role of Two Distinct 5' Flanking Elements", Science, 1985, 230:912-916.
El Moussaoui, A., et al., "Revisiting the Enzymes Stored in the Laticifers of *Carica papaya* in the context of their Possible-Participation in the Plant Defense Mechanism", Cell Mol Life Sci, 2001, 58:556-570.
Faessler, Reinhard, et al., "Knockout Mice: How to Make Them and Why. The Immunological Approach", International Archives of Allergy and Immunology, 1995, 106:4:323-334.
Fischer, Wolfgang H. and Spiess, Joachim, "Identification of a Mammalian Glutaminyl Cyclase Converting Glutaminyl into Pyroglutamyl Peptides", Proc. Natl. Acad. Sci., 1987, 84:3628-3632.
Forss-Petter, Sonja, et al., "Transgenic Mice Expressing β-Galactosidase in Mature Neurons Under Neuron-Specific Enolase Promoter Control", Neuron, 1990, 5:187-197.
Fraser, Lynn R. and Adeoya-Osiguwa, Susan A., "Fertilization Promoting Peptide—A Possible Regulator of Sperm Function in Vivo", Vitamins and Hormones, 2001, 63:1-28.
Funato, Hiromasa et al., "Quantitation of Amyloid β-Protein (Aβ) in the Cortex during Aging and in Alzheimer's Disease", American Journal of Pathology, 1998, 152(6):1633-1640.
Funato, Hiromasa et al., "Astrocytes Containing Amyloid β-Protein (Aβ)-Positive Granules Are Associated with Aβ40-Positive Diffuse Plaques in the Aged Human Brain," American Journal of Pathology, 1998, 152(4): 983-992.
Garden, Rebecca W., et al., "Formation of N-Pyroglutamyl Peptides from N-Glu and N-Gln Precursors in Aplysia Neurons", Journal of Neurochemistry, 1999, 72:676-681.
Geddes, James W., et al., "N-Terminus Truncated β-Amyloid Peptides and C-Terminus Truncated Secreted Forms of Amyloid Precursor Protein: Distinct Roles in the Pathogenesis of Alzheimer's Disease", Neurology of Aging, 1999, 20:75-79.
Ghiso, Jorge, et al., "Chromosome 13 Dementia Syndromes as Models of Neurodegeneration", Amyloid J. Protein Folding Disord, 2001, 8:277-284.
Glenner, George C., et al., "Alzheimer's Disease: Initial Report of the Purification and Characterization of a Novel Cerebrovascular Amyloid Protein", Biochemical and Biophysical Research Communications, 1984, 120:885-890.
Golobov, Mikhail Yu., et al., "Substrate and Inhibitor Specificity of Glutamine Cyclotransferase (QC)", Biol Chem. Hoppe Seyler, 1996, 377:395-398.
Gong, Jiang-Hong., et al., "An Antagonist of Monocyte Chemoattractant Protein 1 (MCP-1) Inhibits Arthritis in the MRL-lpr Mouse Model", J. Exp. Med, 1997, 186:131-137.
Gosling, Jennifa, et al., "MCP-1 Deficiency Reduces Susceptibility to Atherosclerosis in Mice that Overexpress Human Apolipoprotein B", The Journal of Clinical Investigation, 1999, 103:773-778.
Gossen, Manfred and Bojard, Hermann, "Tight Control of Gene Expression in Mammalian Cells by Tetracycline-Responsive Promoters", Proc. Natl. Acad. Sci., 1992, 89:5547-5551.
Gossen, Manfred, et al., "Transcriptional Activation by Tetracyclines in Mammalian Cells", Science, 1995, 268:1766-1769.
Gu, Long., et al., "Absence of Monocyte Chemoattractant Protein-1 Reduces Atherosclerosis in Low Density Lipoprotein Receptor-Deficient Mice", Molecular Cell, 1998, 2:275-281.
Guntert, A., et al., "High Sensitivity Analysis of Amyloid-Beta Peptide Composition in Amyloid Deposits from Human and Ps2App Mouse Brain", Neuroscience, 2006, 143:461-475.
Haase, Christian and Selkoe, Dennis, "Cellular Processing of β-Amyloid Precursor Protein and the Genesis of Amyloid β-Peptides", Cell, 1993, 75:1039-1042.
Harigaya, Yasuo, et al., "Amyloid β Protein Starting Pyroglutamate at Position 3 is a Major Component of the Amyloid Deposits in the Alzheimer's Disease Brain", Biochemical and Biophysical Research Communication, 2000, 276: 422-427.
Haskell, R.E., and Bowen, R.A., "Efficient Production of Transgenic Cattle by Retroviral Infection of Early Embryos", Molecular Reproduction and Development, 1995, 40:386-390.

(56) References Cited

OTHER PUBLICATIONS

He, Weilan and Barrow, Celio J., "The Aβ 3-Pyroglutamyl and 11-Pyroglutamyl Peptides Found in Senile Plaque Have Greater β-Sheet Forming and Aggregation Propensities in Vitro than Full-Length Aβ", Biochemistry, 1999, 38:10871-10877.
He, Xi, et al., "Expression of a Large Family of POU-Domain Regulatory Genes in Mammalian Brain Development", Nature, 1989, 340:35-42.
Hemmerich, S., et al., "Identification of Residues in the Monocyte Chemotactic Protein-1 that Contact the MCP-1 Receptor, CCR2", Biochemistry, 1999, 38:13013-13025.
Hosoda, Ritsuko, et al., "Quantification of Modified Amyloid β Peptides in Alzheimer Disease and Down Syndrome Brains", Journal of Neuropathology and Experimental Neurology, 1998, 57:1089-1095.
Huse, Jason T., et al., "β-Secretase Processing in the Trans-Golgi Network Preferentially Generates Truncated Amyloid Species That Accumulate in Alzheimer's Disease Brain", The Journal of Biological Chemistry, 2002, 277(18):16278-16284.
Inoshima, I., et al., "Anti-Monocyte Chemoattractant Protein-1 Gene Therapy Attenuates Pulmonary Fibrosis in Mice", American Journal of Physiology/Lung Cellular and Molecular Physiology, 2004, 286:L1038-L1044.
Itagaki, S., et al., "Relationship of Microglia and Astrocytes to Amyloid Deposits of Alzheimer Disease", Journal of Neuroimmunology, 1989, 24:173-182.
Iwatsubo, Takeshi, et al., "Full-Length Amyloid-β(1-42(43)) and Amino-Terminally Modified and Truncated Amyloid-β42(43) Deposit in Diffuse Plaques", American Journal of Pathology, 1996, 149:1823-1830.
Jacobsen, J. Steven, et al., "Early-Onset Behavioral and Synaptic Deficits in a Mouse Model of Alzheimer's Disease", Proc. Natl. Acad. Sci USA, 2006, 103:5161-5166.
Jaenisch, Rudolf, "Germ Line Integration and Mendelian Transmission of the Exogenous Moloney Leukemia Virus", Proc. Nat. Acad. Sci. USA, 1976, 73:1260-1264.
Janeisch, Rudolf, "Transgenic Animals", Science, 1988, 240:1468-1474.
Jahner, Detlev, et al., "De Novo Methylation and Expression of Retroviral Genomes During Mouse Embryogenesis", Nature, 1982, 298:623-628.
Jahner, et al., "Insertion of the Bacterial gpt Gene into the Germ Line of Mice by Retroviral Infection", Proc. Natl. Acad. Sci. USA, 1985, 82:6927-6931.
Johnson, Jason, et al., "Plaque Rupture after Short Period of Fat Feedings in the Apolipoprotein E-Knockout Mouse: Model Characterization and Effects of Pravastatin Treatment", Circulation, 2005, 111:1422-1430.
Kang, Jie, et al., "The Precursor of Alzheimer's Disease Amyloid A4 Protein Resembles a Cell-Surface Receptor", Nature, 1987, 325:733-736.
Katabuchi, Hidetaka, et al., "Characterization of Macrophages in the Decidual Atherotic Spiral Artery with Special Reference to the Cytology of Foam Cells", Med Electron Microsc, 2003, 36:253-262.
Lalowski, Maciej, et al., "The "Nonamyloidogenic" p3 Fragment(Amyloid β17-42) Is a Major Constituent of Down's Syndrome Cerebellar Preamyloid", The Journal of Biological Chemistry, 1996, 271:33623-33631.
Lavitrano, Marialulsa, et al., "Sperm Cells as Vectors for Introducing Foreign DNA into Eggs: Genetic Transformation of Mice", Cell, 1989, 57:717-723.
Lee, Frank et al., "Glucocorticoids Regulate Expression of Dihydrofolate Reductase cDNA in Mouse Mammary Tumour Virus Chimaeric Plasmids", Nature, 1981, 294:228-232.
Lemere, Cynthia A., et al., "The E280A Presenilin 1 Alzheimer Mutation Produces Increased Aβ42 Deposition and Severe Cerebellar Pathology", Nature Medicine, 1996, 2:1146-1150.
Li, Shaowei, et al., "MCP-1 Overexpressed in Tuberous Sclerosis Lesions Acts as a Paracrine Factor for Tumor Developments", J Exp Med., 2005, 202:617-624.
Lo, Cecilia W., "Transformation by Iontophoretic Microinjection of DNA: Multiple Integrations Without Tandem Insertions", Molecular and Cellular Biology, 1983, 3:1803-1814.
Mann, D.M.A. and Iwatsubo, T., "Diffuse Plaques in the Cerebellum and Corpus Striatum in Down's Syndrome Contain Amyloid β Protein (Aβ) only in the Form of $Aβ_{42(43)}$", Neurodegeneration, 1996, 5:115-120.
Masure, Stefan, et al., "Expression of a Human Mutant Monocyte Chemotactic Protein 3 in *Pichia pastoris* and Characterization as an MCP-3 Receptor Antagonist", Journal of Interferon and Cytokine Research, 1995, 15:955-963.
Maue, et al., "Neuron-Specific Expression of the Rat Brain Type II Sodium Channel Gene is Directed by Upstream Regulatory Elements", Neuron, 1990, 4:223-231.
Meir, Karen s. and Leitersdorf, Eran, "Atherosclerosis in the Apolipoprotein E-Deficient Mouse: A Decade of Progress", Arteriosclerosis, Thrombosis, and Vascular Biology, 2004, 24:1006-1014.
Messer, Michael, "Enzymatic Cyclization of L-Glutamine and L-Glutaminyl Peptides", 1963, Nature , 4874:1299.
Mori, Hiroshi, et al., "Mass Spectrometry of Purified Amyloid β Protein in Alzheimer's Disease", The Journal of Biological Chemistry, 1992, 267:17082-17086.
Morris, Richard G.M., "Spatial Localization Does Not Require the Presence of Local Cues", Learning and Motivation, 1981, 12:239-260.
No, et al., "Ecdysone-inducible Gene Expression in Mammalian Cells and Transgenic Mice", Proc. Natl. Acad. Sci. USA, 1996, 93:3346-3351.
Ogata, Hirgomi, et al., "The Role of Monocyte Chemoattractant Protein-1 (MCP-1) in the Pathogenesis of Collagen-Induced Arthritis in Rats", Journal of Pathology, 1997, 182:106-114.
Ohta, Masahiro, et al., "Monocyte Chemoattractant Protein-1 Expression Correlates with Macrophage Infiltration and Tumor Vascularity in Human Gastric Carcinomas", International Journal of Oncology, 2003, 22:773-778.
Park, In-Woo, et alk, "HIV-1 Tat Promotes Monocyte Chemoatrractant Protein-1 Secretion Followed by Transmigration of Monocytes", Blood, 2001, 97:352-358.
Pike, Christian J., et al., "Amino-Terminal Deletions Enhance Aggregation of β-Amyloid Peptides in Vitro", The Journal of Biological Chemistry, 1995, 270:23895-23898.
Pinkert, Carl A., et al., "An Albumin Enhancer Located 10 kb Upstream Functions Along with its Promoter to Direct Efficient, Liver-Specific Expression in Transgenic Mice", Genes & Development, 1987, 1:268-277.
Pohl, Thomas, et al., "Primary Structure and Functional Expression of a Glutaminyl Cyclase", Proc. Natl. Acad. Sci USA., 1991, 88:10059-10063.
Prokal, Laszlo, et al., "Metabolism-Based Brain-Targeting System for a Thyrotropin-Releasing Hormone Analogue", J. Med. Chem., 1999, 42:4563-4571.
Proost, Paul., et al., "Posttranslational Modifications Affect the Activity of the Human Monocyte Chemotactic Proteins MCP-1 and MCP-2: Identification of MCP-2(6-76) as a Natural Chemokins Inhibitor", Journal of Immunology, 1998, 160:4034-4041.
Queen, Cary, et al., "Immunoglobulin Gene Transcription is Activated by Downstream Sequence Elements", Cell, 1983, 33:741-748.
Ray, Prabir, et al., "Ectopic Expression of a C-Kit$^{W42}$ Minigene in Transgenic Mice: Recapitulation of W Phenotypes and Evidence for C-Kit Function in Melanoblast Progenitors", Genes & Development, 1991, 5:2265-2273.
Russo, C., et al., "Presenilin-1 Mutations in Alzheimer's Disease", Nature, 2000, 405:531-532.

(56) References Cited

OTHER PUBLICATIONS

Russo, Claudio, et al., "Identification of Amino-Terminally and Phosphotyrosine-Modified Carboxy-Terminal Fragments of the Amyloid Precursor Protein in Alzheimer's Disease and Down's Syndrome Brain", Neurobiology of Disease, 2001, 8:173-180.
Russo, Claudio, et al., "Heterogeneity of Water-Soluble Amyloid β-Peptide in Alzheimer's Disease and Down's Syndrome Brains", FEBS Letters, 1997, 409:411-416.
Russo, Claudio, et al., "Pyroglutamate-Modified Amyloid β-Peptides—AβN3(pE)—Strongly Affect Cultured Neuron and Astrocyte Survival", Journal of Neurochemistry, 2002, 82:1480-1489.
Saido, Takaomi C., "Involvement of Polyglutamine Endolysis Followed by Pyroglutamate Formation in the Pathogenesis of Triplet Repeat/Polyglutamine-Expansion Diseases", Medical Hypothesis, 2000, 54(3):427-429.
Saido, Takaomi C., et al., "Dominant and Differential Deposition of Distinct β-Amyloid Peptide Species, $A\beta_{N3(pE)}$, in Senile Plaques", Neuron, 1995, 14:457-466.
Saiura, Akio, et al., "Antimonocyte Chemoattractant Protein-1 Gene Therapy Attenuates Graft Vasculopathy", Arterioscler. Thromb. Vasc. Biol., 2004, 24:1886-1890.
Sasahara, Masakiyo, et al., "PDFG B-Chain in Neurons of the Central Nervous System, Posterior Pituitary, and in a Transgenic Model", Cell, 1991, 64:217-227.
Schilling, Stephan, et al., "Isolation, Catalytic Properties, and Competitive Inhibitors of the Zinc-Dependent Murine Glutaminyl Cyclase", Biochemistry, 2005, 44(40):13415-13424.
Schilling, Stephan, et al., "Inhibition of Glutaminyl Cyclase Prevents pGlu-Aβ Formation after Intracortical/Hippocampal Microinjection in Vivo/in Situ", Journal of Neurochemistry, 2008, 106(3):1225-36.
Selkoe, Dennis J., "The Cell Biology of β-Amyloid Precursor Protein and Presenilin in Alzheimer's Disease", Trends in Cell Biology, 1998, 8:447-453.
Selkoe, Dennis J., "Alzheimer's Disease: Genes, Proteins, and Therapy", Physiological Review, 2001, 81:741-765.
Shirotani, Keiro, et al., "Generation of Amyloid β Peptide with Pyroglutamate at Position 3 in Primary Cortical Neurons", Neuroscience Letters, 2002, 327:25-28.
Simons, Mikael, et al., "Amyloidogenic Processing of the Human Amyloid Precursor Protein in Primary Cultures of Rat Hippocampal Neurons", The Journal of Neuroscience, 1996, 16:899-908.
Stewart, Colin L., "Expression of Retroviral Vectors in Transgenic Mice Obtained by Embryo Infection", The EMBO Journal, 1987, 6:383-388.
Sturchler-Pierrat, Christine, et al., "Two Amyloid Precursor Protein Transgenic Mouse Models with Alzheimer Disease-Like Pathology", Proc. Natl. Acad. Sci., 1997, 94:13287-13292.
Subramaniam, Arun, et al., "Tissue-Specific Regulation of the a-Myosin Heavy Chain Gene Promoter in Transgenic Mice", The Journal of Biological Chemistry, 1991, 266:24613-24620.
Tekirian, Tina L., "N-Terminal Heterogeneity of Parenchymal and Cerebrovascular Aβ Deposits", Journal of Neuropathology and Experimental Neurology, 1999, 57:76-94.
Tekirian, Tina L., et al., "Toxicity of Pyroglutaminated Amyloid β-Peptides 3(pE)-40 and -42 is Similar to That of Aβ1-40 and -42", Journal of Neurochemistry, 1999, 73:1584-1589.
Terry, Robert D. and Katzman, Robert, "Senile Dementia of the Alzheimer Type", Ann Neurol, 1983, 14:497-506.
Thompson, Simon, et al., "Germ Line Transmission and Expression of a Corrected HPRT Gene Produced by Gene Targeting in Embryonic Stem Cells", Cell, 1989, 56:313-321.
Van Damme, Jo Van, et al., "The Role of CD26/DPP IV in Chemokine Processing", Chem Immunol, 1999, 72:42-56.
Van Der Putten, Herman, et al., "Efficient Insertion of Genes into the Mouse Germ Line Via Retroviral Vectors", Proc. Natl. Acad. Sci USA, 1985, 82:6148-6152.
Wada, Takashi, et al., "Gene Therapy via Blockage of Monocyte Chemoattractant Protein-1 for Renal Fibrosis", J. Am. Soc. Nephrol, 2004, 15:940-948.
White, Fletcher A., et al., "Excitatory Monocyte Chemoattractant Protein-1 Signaling is Up-Regulated in Sensory Neurons after Chronic Compression of the Dorsal Root Ganglion", PNAS, 2005, 102:14092-14097.
Winoto, Astar and Baltimore, David, "A Novel, Inducible and T Cell-Specific Enhancer Located at the 3' End of the T Cell Receptor α Locus", The EMBO Journal, 1989, 8:729-733.
Yamamoto, Masaru, et al., "Overexpression of Monocyte Chemotactic Protein-1/CCL2 in β-Amyloid Precursor Protein Transgenic Mice Show Accelerated Diffuse β-Amyloid Deposition", American Journal of Pathology, 2005, 166:475-1485.
Yao, Tso-Pang, et al., "Functional Ecdysone receptor is the Product of EcR and Ultraspiracle Genes", Letters to Nature, 1993, 366:476-479.
Zhang, Yo Jun, et al., "Structure/Activity Analysis of Human Monocyte Chemoattractant Protein-1 (MCP-1) by Mutagenesis", The Journal of Biological Chemistry, 1994, 269:15918-15924.
Huang et al., Structures and mechanism of human glutaminyl cyclase, an enzyme possible involved in Alzheimer's disease and osteoperosis, Biophysical Society of Japan, 2006, pp. S444, vol. 46, Supplement 2, Abstract 2P593.
Database NCBI Nucleotide (GenBank) Accession No. AK045974, 2006, downloaded from the internet at www.ncbi.nlm.nih.gov/nuccore/2633740?sat=43&satkey=1571303, 4 pages.
Japanese Office Action dated Sep. 17, 2013 in related Japanese Application No. 2010-541803, English translation of Japanese Office Action, 2 pages.

* cited by examiner

MOUSE CARRYING A KNOCK-OUT MUTATION OF THE QPCT-GENE

CROSS-REFERENCE TO RELATED APPLICATIONS

This application claims priority from U.S. Provisional Application Ser. No. 61/020,784 filed on Jan. 14, 2008, which is incorporated herein by reference in its entirety.

INCORPORATION-BY-REFERENCE OF SEQUENCE LISTING

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The present invention relates generally to knock-out animals, in particular mouse models having a knock-out mutation of the Qpct gene.

BACKGROUND OF THE INVENTION

Qpct (i.e. glutaminyl peptide cyclotransferase), also termed glutaminyl cyclase (QC, EC 2.3.2.5) catalyzes the intramolecular cyclization of N-terminal glutamine residues into pyroglutamic acid (5-oxo-proline, pGlu*) under liberation of ammonia and the intramolecular cyclization of N-terminal glutamate residues into pyroglutamic acid under liberation of water.

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the Latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

EP 02 011 349.4 discloses polynucleotides encoding insect glutaminyl cyclase, as well as polypeptides encoded thereby. This application further provides host cells comprising expression vectors comprising polynucleotides of the invention. Isolated polypeptides and host cells comprising insect QC are useful in methods of screening for agents that reduce glutaminyl cyclase activity. Such agents are described as useful as pesticides.

The subject matter of the present invention is particularly useful in the field of Qpct-related diseases, one example of those being Alzheimer's Disease. Alzheimer's disease (AD) is characterized by abnormal accumulation of extracellular amyloidotic plaques closely associated with dystrophic neurones, reactive astrocytes and microglia (Terry, R. D. and Katzman, R. 1983 Ann Neurol 14, 497-506; Glenner, G. G. and Wong, C. W. 1984 Biochem Biophys Res Comm 120, 885-890; Intagaki, S. et al. 1989 J Neuroimmunol 24, 173-182; Funato, H. et al. 1998 Am J Pathol 152, 983-992; Selkoe, D. J. 2001 Physiol Rev 81, 741-766). Amyloid-beta (abbreviated as Aβ) peptides are the primary components of senile plaques and are considered to be directly involved in the pathogenesis and progression of Aβ, a hypothesis supported by genetic studies (Glenner, G. G. and Wong, C. W. 1984 Biochem Biophys Res Comm 120, 885-890; Borchelt, D. R. et al. 1996 Neuron 17, 1005-1013; Lemere, C. A. et al. 1996 Nat Med 2, 1146-1150; Mann, D. M. and Iwatsubo, T. 1996 Neurodegeneration 5, 115-120; Citron, M. et al. 1997 Nat Med 3, 67-72; Selkoe, D. J. 2001 Physiol Rev 81, 741-766). Aβ is generated by proteolytic processing of the β-amyloid precursor protein (APP) (Kang, J. et al. 1987 Nature 325, 733-736; Selkoe, D. J. 1998 Trends Cell Biol 8, 447-453), which is sequentially cleaved by β-secretase at the N-terminus and by 7-secretase at the C-terminus of Aβ (Haass, C. and Selkoe, D. J. 1993 Cell 75, 1039-1042; Simons, M. et al. 1996 J Neurosci 16 899-908). In addition to the dominant Aβ peptides starting with L-Asp at the N-terminus (Aβ1-42/40), a great heterogeneity of N-terminally truncated forms occurs in senile plaques. Such shortened peptides are reported to be more neurotoxic in vitro and to aggregate more rapidly than the full-length isoforms (Pike, C. J. et al. 1995 J Biol Chem 270, 23895-23898). N-truncated peptides are known to be overproduced in early onset familial Aβ (FAD) subjects (Saido, T. C. et al. 1995 Neuron 14, 457-466; Russo, C, et al. 2000 Nature 405, 531-532), to appear early and to increase with age in Down's syndrome (DS) brains (Russo, C. et al. 1997 FEBS Lett 409, 411-416, Russo, C. et al. 2001 Neurobiol Dis 8, 173-180; Tekirian, T. L. et al. 1998 J Neuropathol Exp Neurol 57, 76-94). Finally, their amount reflects the progressive severity of the disease (Russo, C. et al. 1997 FEBS Lett 409, 411-416; Guntert, A. et al. 2006 Neuroscience 143, 461-475). Additional posttranslational processes may further modify the N-terminus by isomerization or racemization of the aspartate at position 1 and 7 and by cyclization of glutamate at residues 3 and 11. Pyroglutamate-containing isoforms at position 3 [$pGlu^3A\beta3$-40/42] represent the prominent forms—approximately 50% of the total Aβ amount—of the N-truncated species in senile plaques (Mori, H. et al. 1992 J Biol Chem 267, 17082-17086, Saido, T. C. et al. 1995 Neuron 14, 457-466; Russo, C. et al. 1997 FEBS Lett 409, 411-416; Tekirian, T. L. et al. 1998 J Neuropathol Exp Neurol 57, 76-94; Geddes, J. W. et al. 1999 Neurobiol Aging 20, 75-79; Harigaya, Y. et al. 2000 Biochem Biophys Res Commun 276, 422-427) and they are also present in pre-amyloid lesions (Lalowski, M. et al. 1996 J Biol Chem 271, 33623-33631). The accumulation of AβN3(pE) peptides is likely due to the structural modification that enhances aggregation and confers resistance to most aminopeptidases (Saido, T. C. et al. 1995 Neuron 14, 457-466; Tekirian, T. L. et al. 1999 J Neurochem 73, 1584-1589). This evidence provides clues for a pivotal rote of AβN3(pE) peptides in Aβ pathogenesis. However, relatively little is known about their neurotoxicity and aggregation properties (He, W. and Barrow, C. J. 1999 Biochemistry 38, 10871-10877; Tekirian, T. L. et al. 1999 J Neurochem 73, 1584-1589). Moreover, the action of these isoforms on glial cells and the glial response to these peptides are completely unknown, although activated glia is strictly associated to senile plaques and might actively contribute to the accumulation of amyloid deposits. In recent studies the toxicity, aggregation properties and catabolism of Aβ1-42, Aβ1-40, [$pGlu^3$]Aβ3-42, [$pGlu^3$]Aβ3-40, [$pGlu^{11}$]Aβ11-42 and [$pGlu^{11}$]Aβ11-40 peptides were investigated in neuronal and glial cell cultures, and it was shown that pyroglutamate modification exacerbates the toxic properties of Aβ-peptides and also inhibits their degradation by cultured astrocytes. Shirotani et al. investigated the generation of [$pGlu^3$]Aβ peptides in primary cortical neurons infected by Sindbis virus in vitro. They constructed amyloid precursor protein complementary DNAs, which encoded a potential precursor for [$pGlu^3$]Aβ by amino acid substitution and deletion. For one artificial precursor starting with a N-terminal glutamine residue instead of glutamate in the natural precursor, a spontaneous conversion or an enzymatic conversion by glutaminyl cyclase to pyroglutamate was suggested. The cyclization mechanism of N-terminal glutamate at position 3 in the natural precursor of [$pGlu^3$]Aβ was neither determined in vitro, in situ nor in vivo (Shirotani, K. et al. 2002 NeuroSci Lett 327, 25-28).

Thus, there is a clear need in the art for the provision of knock-out animals, in particular knock-out mice which carry a knock-out mutation in the Qpct gene, preferably wherein this mutation should be provided in both a constitutive and a conditional manner so as to enable exact investigations as to the relevance and potential of the Qpct gene.

The aim of this invention was to develop knock-out animals, i.e. mouse models carrying a constitutive or a conditional knock-out mutation of the Qpct gene, respectively.

SUMMARY OF THE INVENTION

The present invention comprises methods and compositions for non-human knock-out, in particular mammalian, models for Qpct-related diseases. Specifically, the present invention comprises non-human animal models that have a knock-out mutation in the Qpct gene, resulting in the knock-out of Qpct.

Another aspect of the present invention comprises methods and compositions for screening for Qpct inhibitors/effectors.

Additionally, the present invention comprises methods and compositions for the treatment and/or prevention of Qpct-related diseases, particularly methods and compositions that inhibit or promote Qpct.

Accordingly, it is an object of the invention to provide an animal, which carries a Qpct knock-out mutation.

It is another object of the invention to provide DNA constructs carrying a Qpct knock-out mutation.

It is an additional object of the invention to provide DNA constructs carrying the Qpct knock-out mutation linked to a promoter.

It is a further object of the invention to provide a non-human animal model system, which carries a Qpct knock-out mutation.

It is an additional object of the invention to provide a non-human animal model system to study the in vivo and in vitro regulation and effects of Qpct in specific tissue types.

It is a further object of the invention to provide a non-human animal model system to study the function and concentrations of pyroglutamate-modified hormones, most preferably cytokine and chemokine function.

The present invention provides pharmaceutical compositions for parenteral, enteral or oral administration, comprising at least one effector of QC optionally in combination with customary carriers and/or excipients, wherein said effector of QC was identified by employing the screening methods and Qpct knock-out animals of the present invention.

Other objects and features will be in part apparent and in part pointed out hereinafter.

BRIEF DESCRIPTION OF THE DRAWINGS

Further understanding of these and other aspects of the present invention will be gained by reference to the figures described below. Those of skill in the art will understand that the drawings, described below, are for illustrative purposes only. The drawings are not intended to limit the scope of the present teachings in any way.

Figure 1A:
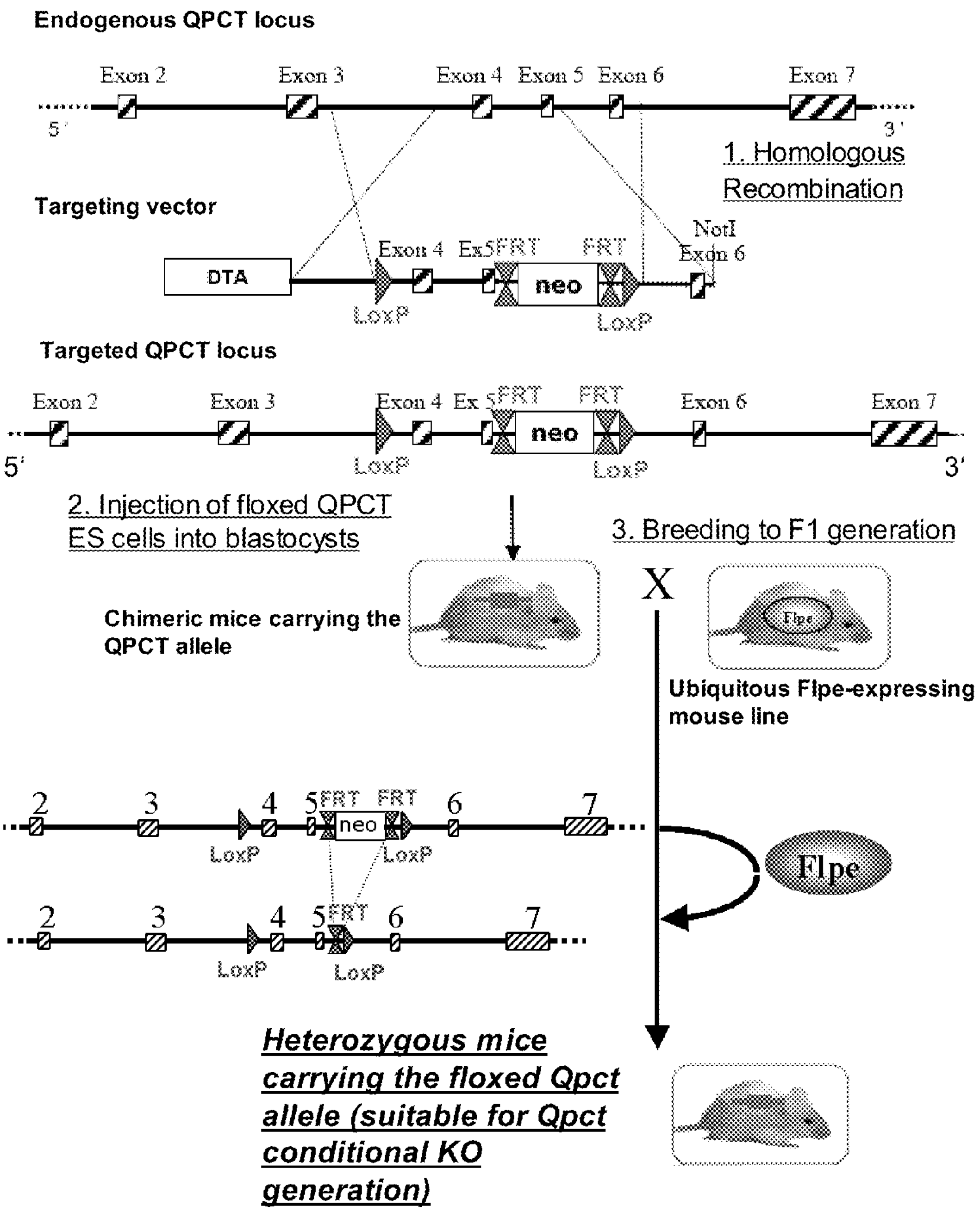
FIG. 1 is a series of diagrams demonstrating the principle for the generation of constitutive and conditional knock-out Qcpt mouse lines. Dashed boxes represent exons. Solid line represents intronic sequence. LoxP and FRT elements are shown as triangles and are indicated. Neo and DTA boxes represent the neomycin positive selection cassette and the DTA negative selection cassette, respectively.

Other objects, advantages and features of the invention will become apparent upon consideration of the following detailed description.

DETAILED DESCRIPTION OF THE PRESENTLY PREFERRED EMBODIMENTS

The present invention pertains to

1. A non-human animal comprising cells containing a DNA Qpct gene carrying a knock-out mutation.
2. The non-human animal of item 1, wherein the animal is a rat.
3. The non-human animal of item 1, wherein the animal is a mouse.
4. The non-human animal of any of items 1 to 3, wherein the Qpct gene is of murine origin.
5. The non-human animal of item 4, wherein the murine Qpct gene has the sequence of SEQ ID No. 22.
6. The non-human animal of any of items 1 to 3, wherein the Qpct gene is of human origin.
7. The non-human animal of any of items 1 to 6, wherein the animal is heterozygous for the Qpct gene.
8. The non-human animal of any of items 1 to 6, wherein the animal is homozygous for the Qpct gene.
9. The non-human animal of any of items 1 to 8, wherein the Qpct gene is a recombinant gene.
10. The non-human animal of any of items 1 to 9, wherein the Qpct gene carries a constitutive knock-out mutation.
11. The non-human animal of any of items 1 to 9, wherein the Qpct gene carries a conditional knock-out mutation.
12. The non-human animal of any of items 1 to 11, for use in determining effects of target compounds on Qpct-related disorders and/or diseases.
13. The non-human animal of any of items 1 to 11, wherein the animal carries at least one Qpct allele where exons 4 and 5 are deleted.
14. The non-human animal of any of items 1 to 11 and 13, wherein said Qpct allele has the sequence of SEQ ID No. 23.
15. The non-human animal of item 13 or 14, wherein the animal is a mouse of the mouse line Pbd2.
16. The non-human animal according to any of items 13 to 15, wherein the Qpct gene is operably linked to a tissue-specific promoter.
17. The mouse according to any of items 3 to 16, wherein the mouse demonstrates a phenotype that can be reversed or ameliorated with a Qpct inhibitor.

18. A screening method for biologically active agents that inhibit or promote Qpct production in vivo, comprising: administering a test agent to the non-human animal of any of items 1 to 17, and determining the effect of the agent.
19. The method of item 18, wherein the non-human animal is heterozygous for the Qpct gene.
20. The method of item 18, wherein the non-human animal is homozygous for the Qpct gene.
21. The method according to any of items 18 to 20, wherein the animal is a mouse.
22. The method according to any of items 18 to 21, wherein the Qpct gene is of murine origin.
23. The method according to any of items 18 to 21, wherein the Qpct gene is of human origin.
24. The method according to any of items 18 to 23, wherein the Qpct gene is a recombinant gene.
25. The method of any of items 18 to 24, wherein the recombinant Qpct gene carries a constitutive knock-out mutation.
26. The method of any of items 18 to 24, wherein the Qpct gene carries a conditional knock-out mutation.
27. The method of item 18 for use in target drug discovery.
28. The method of any of items 18 to 27, wherein the animal carries at least one Qpct allele where exons 4 and 5 are deleted.
29. The method of any of items 18 to 28, wherein the animal is a mouse of the mouse line Pbd2.
30. The method of any of items 18 to 29, wherein the Qpct gene is operably linked to a tissue-specific promoter.
31. The method of any of items 18 to 30, wherein the mouse demonstrates a phenotype that can be reversed or ameliorated with a Qpct inhibitor.
32. A cell or cell line derived from the non-human animal according to any of items 1 to 17.
33. A method for screening for therapeutic agents that inhibit or promote Qpct activity comprising
(a) administering test agents to the mouse of any of items 3 to 17
(b) evaluating the effects of the test agent on the phenotype of the mouse, and
(c) selecting a test agent which inhibits or promotes Qpct activity.
34. A method of treatment or prevention of a Qpct-related disease comprising
(a) administering the selected test agent of item 33; and
(b) monitoring the patient for a decreased clinical index for Qpct-related diseases.
35. The method of item 34 wherein the Qpct-related disease is Alzheimer's disease.
36. The method of item 34 wherein the Qpct-related disease is atherosclerosis or restenosis.
37. A method for analysing the disease-related physiological function of Qpct catalysis with regard to pyroglutamate-peptide formation comprising
(a) administering of test agents to the mouse of any of items 3 to 17
(b) evaluating the pyroglutamate-peptide concentration and effects of the test agent on the phenotype of the mouse, and
(c) selecting a test agent which inhibits or promotes pyroglutamate-peptide activity.
38. A pharmaceutical composition comprising the selected test agent of item 34.
39. Use of a test agent as selected according to item 33 for the preparation of a medicament for the treatment and/or prevention of a Qpct-related disease.
40. Modified cell comprising a Qpct-knockout gene for use in the production of compounds, which would be negatively affected by Qpct.
41. Use of the non-human animal, according to any of items 1 to 17 or the cell according to item 32 or 40, for the provision of models with Qpct expression in specific tissue and/or particular points in time only.
42. A screening method for biologically active compounds that inhibit or promote Qpct activity in vivo comprising steps of:
i) administering a test compound to a non-human animal model, which is specific for the treatment of at least one disease selected from Mild Cognitive Impairment, Alzheimer's disease, neurodegeneration in Down Syndrome, Familial Danish Dementia, Familial British Dementia, rheumatoid arthritis, atherosclerosis, restenosis, and pancreatitis,
ii) determining the effect of the test compound in said non-human animal model;
iii) compare the effect of the test compound in said non-human animal model with the effect of the Qpct gene disruption in the Qpct knockout animals according to any one of items 1 to 17, and
iv) select test compounds that in said non-human animal model alleviate the specific disease similar to the effect of the Qpct gene disruption in the Qpct knockout animals according to any one of items 1 to 17.
43. The screening method of item 42, wherein said non-human animal model is specific for a diseases selected from the group consisting of Mild Cognitive Impairment, Alzheimer's disease, neurodegeneration in Down Syndrome, Familial Danish Dementia and Familial British Dementia.
44. The screening method of item 43, wherein said non-human animal model is specific for Alzheimer's disease.
45. The screening method of any of items 42 to 44, wherein said animal model is selected from the group consisting of PDAPP, Tg2576, APP23, TgCRND8, $PSEN_{1M146V}$ or $PSEN_{1M146L}$, PSAPP, $APPD_{Dutch}$, BRI-A□40 and BRI-A□42, JNPL3, $Tau_{P301S}$, $Tau_{V337M}$, $Tau_{R406W}$, rTg4510, $H_{tau}$, TAPP and 3×TgAD.
46. The screening method of any of items 42 to 45, wherein the effect of the test compounds is the lowering of the $[pGlu^3]$A□3-40/42/43 or $[pGlu^{11}]$A□11-40/42/43 peptides.
47. The screening method of any of items 42 to 46, wherein the effect of the test compounds is the lowering of the $[pGlu^3]$A□3-40 peptides.
48. The screening method of any of items 42 to 47, wherein the effect of the test compounds is the lowering of the $[pGlu^3]$A□3-42 peptides.
49. The screening method of item 42, wherein said non-human animal model is specific for a diseases selected from the group consisting of rheumatoid arthritis, atherosclerosis, restenosis, and pancreatitis.
50. The screening method of item 49, wherein said non-human animal model is specific for rheumatoid arthritis.
51. The screening method of item 49, wherein said non-human animal model is specific for atherosclerosis.
52. The screening method of any of items 42 and 49 to 50, wherein said animal model is selected from the group consisting of the apolipoprotein E knockout mouse model, the thioglycollate-induced inflammation model in mice, the collagen-induced arthritis model in rat and rat models of restenosis.

53. The screening method of any of items 42 and 49 to 51, wherein the effect of the test compounds is the inhibition of the chemotaxis of THP-1 cells.
54. The screening method of any of items 42 and 49 to 51, wherein the effect of the test compounds is the inhibition of the formation of pGlu-MCP-1.
55. A pharmaceutical composition comprising the selected test agent according to any of items 42 to 54.
56. Use of a test agent as selected according to any of items 42 to 54 for the preparation of a medicament for the treatment and/or prevention of a Qpct-related disease.
57. A method of treatment or prevention of a Qpct-related disease comprising
    (a) administering the selected test agent according to any of items 42 to 54; and
    (b) monitoring the patient for a decreased clinical index for Qpct-related diseases.
58. The use or method of items 56 or 57, wherein the Qpct-related disease is selected from the group consisting of Mild Cognitive Impairment, Alzheimer's disease, neurodegeneration in Down Syndrome, Familial Danish Dementia and Familial British Dementia.
59. The use or method of any items 56 to 57, wherein the Qpct-related disease is Alzheimer's disease.
60. The use or method of items 56 or 57, wherein the Qpct-related disease is selected from the group consisting of rheumatoid arthritis, atherosclerosis, restenosis, and pancreatitis.
61. The use or method of any of items 56, 57 or 60, wherein the Qpct-related disease is rheumatoid arthritis.
62. The use or method of any of items 56, 57 or 60, wherein the Qpct-related disease is atherosclerosis.

The non-human knock-out animal, in particular the knock-out mouse as described above, is useful inter alia in the following aspects:

- screening assays for Qpct-effectors/inhibitors
- drug development, in particular screening for targets, target specificity and/or off target effects of drug candidates,
- provision of a disease model,
- recovery of modified cells, e.g. for use in the production of compounds which would be negatively affected by Qpct. "Negatively affected" in this context encompasses e.g. a decreased or slowed-down yield/production rate and/or a decreased affectivity and/or an increased antigenicity. Such compounds could be e.g. antibodies, peptides, proteins etc.
- target discovery, e.g. by determining the differences detected in the above knock-out animal like up- or down-regulation of a specific substance which could become a suitable drug target,
- provision of an assay to determine the importance of certain polypeptides, e.g. Aβ peptide or TRH etc.,
- providing the basis for "clean" transgenic models, e.g. with a controlled expression of Qpct only in specific cells/tissues and/or organs or only at specific points in time;
- optimization of peptide formulation and protective groups without being limited thereto.

The following definitions and methods are provided to better define the present invention and to guide those of ordinary skill in the art in the practice of the present invention. Unless otherwise noted, terms are to be understood according to conventional usage by those of ordinary skill in the relevant art.

The term "knock-out animal" means a non-human animal, usually a mammal, which carries one or more genetic manipulations leading to deactivation of one or more genes.

The term "construct" means a recombinant nucleic acid, generally recombinant DNA, that has been generated for the purpose of the expression of a specific nucleotide sequence(s), or is to be used in the construction of other recombinant nucleotide sequences. The recombinant nucleic acid can encode e.g. a chimeric or humanized polypeptide.

Polypeptide here pertains to all possible amino acid sequences comprising more than 10 amino acids.

The term "operably linked" means that a DNA sequence and a regulatory sequence(s) are connected in such a way as to permit gene expression when the appropriate molecules (e.g., transcriptional activator proteins) are bound to the regulatory sequence(s).

The term "operatively inserted" means that a nucleotide sequence of interest is positioned adjacent a nucleotide sequence that directs transcription and translation of the introduced nucleotide sequence of interest.

Knock-Out Genes

The Qpct polynucleotides comprising the gene of the present invention include Qpct cDNA and shall also include modified Qpct cDNA. As used herein, a "modification" of a nucleic acid can include one or several nucleotide additions, deletions, or substitutions with respect to a reference sequence. A modification of a nucleic acid can include substitutions that do not change the encoded amino acid sequence due to the degeneracy of the genetic code, or which result in a conservative substitution. Such modifications can correspond to variations that are made deliberately, such as the addition of a Poly A tail, or variations which occur as mutations during nucleic acid replication.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence, can have an identity ranging from at least 60% to at least 95% with respect to the reference nucleotide sequence.

The phrase "moderately stringent hybridization" refers to conditions that permit a target-nucleic acid to bind a complementary nucleic acid. The hybridized nucleic acids will generally have an identity within a range of at least about 60% to at least about 95%. Moderately stringent conditions are conditions equivalent to hybridization in 50% formamide, 5× Denhart's solution, 5× saline sodium phosphate EDTA buffer (SSPE), 0.2% SDS (Aldrich) at about 42° C., followed by washing in 0.2×SSPE, 0.2% SDS (Aldrich), at about 42° C.

High stringency hybridization refers to conditions that permit hybridization of only those nucleic acid sequences that form stable hybrids in 0.018M NaCl at about 65° C., for example, if a hybrid is not stable in 0.018M NaCl at about 65° C., it will not be stable under high stringency conditions, as contemplated herein. High stringency conditions can be provided, for example, by hybridization in 50% formamide, 5× Denhart's solution, 5×SSPE, 0.2% SDS at about 42° C., followed by washing in 0.1×SSPE, and 0.1% SDS at about 65° C.

Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al. (Current Protocols in Molecular Biology (Supplement 47), John Wiley & Sons, New York (1999)).

Nucleotide and/or amino acid sequence identity percent (%) is understood as the percentage of nucleotide or amino acid residues that are identical with nucleotide or amino acid residues in a candidate sequence in comparison to a reference sequence when the two sequences are aligned. To determine percent identity, sequences are aligned and if necessary, gaps are introduced to achieve the maximum percent sequence identity. Sequence alignment procedures to determine percent identity are well known to those of skill in the art. Often publicly available computer software such as BLAST, BLAST2, ALIGN2 or Megalign (DNASTAR) software is used to align sequences. Those skilled in the art can determine appropriate parameters for measuring alignment, including any algorithms needed to achieve maximal alignment over the full-length of the sequences being compared. When sequences are aligned, the percent sequence identity of a given sequence A to, with, or against a given sequence B (which can alternatively be phrased as a given sequence A that has or comprises a certain percent sequence identity to, with, or against a given sequence B) can be calculated as: percent sequence identity =X/Y100, where X is the number of residues scored as identical matches by the sequence alignment program's or algorithm's alignment of A and B and Y is the total number of residues in B. If the length of sequence A is not equal to the length of sequence B, the percent sequence identity of A to B will not equal the percent sequence identity of B to A.

The amino acid sequence encoded by the knock-out gene of the present invention can be a Qpct sequence from a human or the Qpct homologue from any species, preferably from a murine species. The amino acid sequence encoded by the knock-out gene of the present invention can also be a fragment of the Qpct amino acid sequence so long as the fragment retains some or all of the function of the full-length Qpct sequence. The sequence may also be a modified Qpct sequence. Individual substitutions, deletions or additions, which alter, add or delete a single amino acid or a small percentage of amino acids (typically less than 10%, more typically less than 5%, and still more typically less than 1%.) A "modification" of the amino acid sequence encompasses conservative substitutions of the amino acid sequence. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (1), Leucine (L), Methionine (M), Valine (V); and
6) Phenylalanine (F), Tyrosine (Y), Tryptophan (W).

Other minor modifications are included within the sequence so long as the polypeptide retains some or all of the structural and/or functional characteristics of a Qpct polypeptide. Exemplary structural or functional characteristics include sequence identity or substantial similarity, antibody reactivity, the presence of conserved structural domains such as RNA binding domains or acidic domains.

DNA Constructs and Vectors

The invention further provides a DNA construct comprising the Qpct knock-out gene as described above. As used herein, the term "DNA construct" refers to a specific arrangement of genetic elements in a DNA molecule. In addition to human Qpct, or mutant forms thereof, the invention also provides a DNA construct using polypeptides from other species as well as Qpct mutant non-human mammals expressing BACE1 from non-human species.

If desired, the DNA constructs can be engineered to be operatively linked to appropriate expression elements such as promoters or enhancers to allow expression of a genetic element in the DNA construct in an appropriate cell or tissue. The use of the expression control mechanisms allows for the targeted delivery and expression of the gene of interest. For example, the constructs of the present invention may be constructed using an expression cassette which includes in the 5'-3' direction of transcription, a transcriptional and translational initiation region associated with gene expression in brain tissue, DNA encoding a mutant or wild-type Qpct protein, and a transcriptional and translational termination region functional in the host animal. One or more introns also can be present. The transcriptional initiation region can be endogenous to the host animal or foreign or exogenous to the host animal.

The DNA constructs described herein may be incorporated into vectors for propagation or transfection into appropriate cells to generate Qpct overexpressing mutant non-human mammals and are also comprised by the present invention. One skilled in the art can select a vector based on desired properties, for example, for production of a vector in a particular cell such as a mammalian cell or a bacterial cell.

Vectors can contain a regulatory element that provides tissue specific or inducible expression of an operatively linked nucleic acid. One skilled in the art can readily determine an appropriate tissue-specific promoter or enhancer that allows expression of Qpct polypeptides in a desired tissue. It should be noted that tissue-specific expression as described herein does not require a complete absence of expression in tissues other than the preferred tissue. Instead, "cell-specific" or "tissue-specific" expression refers to a majority of the expression of a particular gene of interest in the preferred cell type or tissue.

Any of a variety of inducible promoters or enhancers can also be included in the vector for expression of a Qpct polypeptide or nucleic acid that can be regulated. Such inducible systems, include, for example, tetracycline inducible System (Gossen & Bizard, Proc. Natl. Acad. Sci. USA, 89:5547-5551 (1992); Gossen et al., Science, 268:17664769 (1995); Clontech, Palo Alto, Calif.); metallothionein promoter induced by heavy metals; insect steroid hormone responsive to ecdysone or related steroids such as muristerone (No et al., Proc. Natl. Acad. Sci. USA, 93:3346-3351 (1996); Yao et al., Nature, 366:476-479 (1993); Invitrogen, Carlsbad, Calif.); mouse mammary tumor virus (MMTV) induced by steroids such as glucocorticoid and estrogen (Lee et al., Nature, 294:228-232 (1981); and heat shock promoters inducible by temperature changes; the rat neuron specific enolase gene promoter (Forss-Petter, et al., Neuron 5; 197-197 (1990)); the human β-actin gene promoter (Ray, et al., Genes and Development (1991) 5:2265-2273); the human platelet derived growth factor B (PDGF-B) chain gene promoter (Sasahara, et al., Cell (1991) 64:217-227); the rat sodium channel gene promoter (Maue, et al., Neuron (1990) 4:223-231); the human copper-zinc superoxide dismutase gene promoter (Ceballos-Picot, et al., Brain Res. (1991) 552:198-214); and promoters for members of the mammalian POU-domain regulatory gene family (Xi et al., (1989) Nature 340:35-42).

Regulatory elements, including promoters or enhancers, can be constitutive or regulated, depending upon the nature of the regulation, and can be regulated in a variety of tissues, or one or a few specific tissues. The regulatory sequences or regulatory elements are operatively linked to one of the polynucleotide sequences of the invention such that the physical and functional relationship between the polynucleotide sequence and the regulatory sequence allows transcription of the polynucleotide sequence. Vectors useful for expression in eukaryotic cells can include, for example, regulatory elements including the CAG promoter, the SV40 early promoter, the cytomegalovirus (CMV) promoter, the mouse mammary tumor virus (MMTV) steroid-inducible promoter, Pgtf Moloney marine leukemia virus (MMLV) promoter, thy-1 promoter and the like.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (Current Protocols in Molecular Biology (Supplement 47), John Wiley & Sons, New York (1999)) and U.S. Pat. No. 5,981,830. Drugs useful for selecting for the presence of a selectable marker include, for example, G418 for Neo, hygromycin for Hyg, histidinol for hisD, xanthine for Gpt, and bleomycin for Ble (see Ausubel et al, supra, (1999); U.S. Pat. No. 5,981,830). DNA constructs of the invention can incorporate a positive selectable marker, a negative selectable marker, or both (see, for example, U.S. Pat. No. 5,981,830).

Non-Human Knock-out Animals

The invention primarily provides a non-human knock-out animal whose genome comprises a knock-out Qpct gene. The DNA fragment can be integrated into the genome of an animal by any method known to those skilled in the art. The DNA molecule containing the desired gene sequence can be introduced into pluripotent cells, such as ES cells, by any method that will permit the introduced molecule to undergo recombination at its regions of homology. Techniques that can be used include, but are not limited to, calcium phosphate/DNA co-precipitates, microinjection of DNA into the nucleus, electroporation, bacterial protoplast fusion with intact cells, transfection, and polycations, (e.g., polybrene, polyornithine, etc.) The DNA can be single or double stranded DNA, linear or circular. (See for example, Hogan et al., Manipulating the Mouse Embryo: A Laboratory Manual Cold Spring Harbor Laboratory (1986); Hogan et al., Manipulating the Mouse Embryo: A Laboratory Manual, second ed., Cold Spring Harbor Laboratory (1994), U.S. Pat. Nos. 5,602,299; 5,175,384; 6,066,778; 4,873,191 and 6,037,521; retrovirus mediated gene transfer into germ lines (Van der Putten et al., Proc. Natl. Acad. Sci. USA 82:6148-6152 (1985)); gene targeting in embryonic stem cells (Thompson et al., Cell 56:313-321 (1989)); electroporation of embryos (Lo, Mol. Cell. Biol. 3:1803-1814 (1983)); and sperm-mediated gene transfer (Lavitrano et al., Cell 57:717-723 (1989))).

For example, the zygote is a good target for microinjection, and methods of microinjecting zygotes are well known (see U.S. Pat. No. 4,873,191).

Embryonal cells at various developmental stages can also be used to introduce genes for the production of knock-out animals. Different methods are used depending on the stage of development of the embryonal cell. Such transfected embryonic stem (ES) cells can thereafter colonize an embryo following their introduction into the blastocoele of a blastocyst-stage embryo and contribute to the germ line of the resulting chimeric animal (reviewed in Jaenisch, Science 240:1468-1474 (1988)). Prior to the introduction of transfected ES cells into the blastocoele, the transfected ES cells can be subjected to various selection protocols to enrich the proportion of ES cells that have integrated the knock-out gene if the knock-out gene provides a means for such selection. Alternatively, PCR can be used to screen for ES cells that have integrated the knock-out.

In addition, retroviral infection can also be used to introduce knock-out genes into a non-human animal. The developing non-human embryo can be cultured in vitro to the blastocyst stage. During this time, the blastomeres can be targets for retroviral infection (Jaenisch, Proc. Natl. Acad. Sci. USA 73:1260-1264 (1976)). Efficient infection of the blastomeres is obtained by enzymatic treatment to remove the zona pellucida (Hogan et al., supra, 1986). The viral vector system used to introduce the knock-out is typically a replication-defective retrovirus carrying the knock-out (Jahner et al., Proc. Natl. Acad. Sci. USA 82:6927-6931 (1985); Van der Putten et al., Proc. Natl. Acad. Sci. USA 82:6148-6152 (1985)). Transfection is easily and efficiently obtained by culturing the blastomeres on a monolayer of virus-producing cells (Van der Putten, supra, 1985; Stewart et al., EMBO J. 6:383-388 (1987)). Alternatively, infection can be performed at a later stage. Virus or virus-producing cells can be injected into the blastocoele (Jahner D. et al., Nature 298:623-628 (1982)). Most of the founders will be mosaic for the knock-out gene since incorporation occurs only in a subset of cells, which form the knock-out animal. Further, the founder can contain various retroviral insertions of the knock-out gene at different positions in the genome, which generally will segregate in the offspring. In addition, knock-out genes may be introduced into the germline by intrauterine retroviral infection of the mid-gestation embryo (Jahner et al., supra, 1982). Additional means of using retroviruses or retroviral vectors to create knock-out animals known to those of skill in the art involves the micro-injection of retroviral particles or mitomycin C-treated cells producing retrovirus into the perivitelline space of fertilized eggs or early embryos (WO 90/08832 (1990); Haskell and Bowen, Mal. Reprod. Dev. 40:386 (1995)).

Any other technology to introduce knock-out genes into a non-human animal, e.g. the knock-in or the rescue technologies can also be used to solve the problem of the present invention. The knock-in technology is well known in the art as described e.g. in Casas et al. (2004) Am J Pathol 165, 1289-1300.

Once the founder animals are produced, they can be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the effects of expression.

The knock-out animals are screened and evaluated to select those animals having the phenotype of interest. Initial screening can be performed using, for example, Southern blot analysis or PCR techniques to analyze animal tissues to verify that integration of the knock-out gene has taken place. The level of mRNA expression of the knock-out gene in the tissues of the knock-out animals can also be assessed using techniques which include, but are not limited to, Northern blot analysis of tissue samples obtained from the animal, in situ hybridization analysis, and reverse transcriptase-PCR (rt-PCR). Samples of the suitable tissues can be evaluated immunocytochemically using antibodies specific for Qpct or with a tag such as EGFP. The knock-out non-human mammals can be further characterized to identify those animals having a phenotype useful in methods of the invention. In particular, knock-out non-human mammals overexpressing Qpct can be screened using the methods disclosed herein. For example, tissue sections can be viewed under a fluorescent microscope for die present of fluorescence, indicating the presence of the reporter gene.

Another method to affect tissue specific expression is through the use of tissue-specific promoters. Non-limiting examples of suitable tissue-specific promoters include the albumin promoter (liver-specific; Pinkert et al., (1987) Genes Dev. 1:268-277); lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al., (1983) Cell 33:729-740; Queen and Baltimore (1983) Cell 33:741-748), neuron-specific promoters (e.g., the neurofilament promoter, the Thy-1 promoter or the Bri-protein promoter; Sturchler-Pierrat et al., (1997) Proc. Natl. Acad. Sci. USA 94:13287-13292, Byrne and Ruddle (1989) PNAS 86:5473-5477), pancreas-specific promoters (Edlund et al., (1985) Science 230:912-916), cardiac specific expression (alpha myosin heavy chain promoter, Subramaniam, A, Jones W K, Gulick J, Wert S, Neumann J, and Robbins J. Tissue-specific regulation of the alpha-myosin heavy chain gene promoter in transgenic mice. J Biol Chem 266: 24613-24620, 1991), and mammary gland-specific promoters (e.g., milk whey promoter; U.S. Pat. No. 4,873,316 and European Application Publication No. 264,166).

The invention further provides an isolated cell containing a DNA construct of the invention. The DNA construct can be introduced into a cell by any of the well-known transfection methods (Sambrook et al., Molecular Cloning: A Laboratory Manual, 2nd ed., Cold Spring Harbor Press, Plainview, N.Y. (1989); Ausubel et al., supra, (1999)). Alternatively, the cell can be obtained by isolating a cell from a mutant non-human mammal created as described herein. Thus, the invention provides a cell isolated from a Qpct mutant non-human mammal of the invention, in particular, a Qpct mutant knock-out mouse. The cells can be obtained from a homozygous Qpct mutant non-human mammal such as a mouse or a heterozygous Qpct mutant non-human mammal such as a mouse.

Effectors

Effectors, as that term is used herein, are defined as molecules that bind to enzymes and increase (i.e. promote) or decrease (i.e. inhibit) their activity in vitro and/or in vivo. Some enzymes have binding sites for molecules that affect their catalytic activity; a stimulator molecule is called an activator. Enzymes may even have multiple sites for recognizing more than one activator or inhibitor. Enzymes can detect concentrations of a variety of molecules and use that information to vary their own activities.

Effectors can modulate enzymatic activity because enzymes can assume both active and inactive conformations: activators are positive effectors, inhibitors are negative effectors. Effectors act not only at the active sites of enzymes, but also at regulatory sites, or allosteric sites, terms used to emphasize that the regulatory site is an element of the enzyme distinct from the catalytic site and to differentiate this form of regulation from competition between substrates and inhibitors at the catalytic site (Darnell, J., Lodish, H. and Baltimore, D. 1990, Molecular Cell Biology 2"d Edition, Scientific American Books, New York, page 63).

Peptides

If peptides or amino acids are mentioned in the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

QC

The terms "QC" or "Qpct" as used herein are both intended to refer to the same and comprise glutaminyl cyclase (QC), i.e. glutaminyl-peptidecyclotransferase (EC 2.3.2.5). Preferably, the Qpct as used herein is a mammalian Qpct, more preferably a non-human Qpct, most preferably a murine Qpct.

QC-Like Enzymes

QC and QC-like enzymes have identical or similar enzymatic activity, further defined as QC activity. In this regard, QC-like enzymes can fundamentally differ in their molecular structure from QC.

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See schemes 1 and 2.

Scheme 1: Cyclization of glutamine by QC

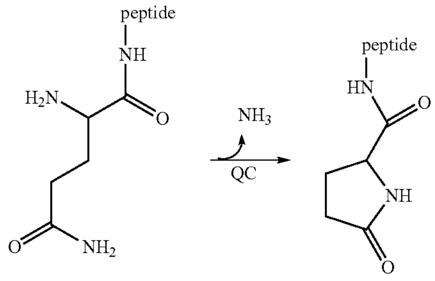

Scheme 2: Cyclization of L-homoglutamine by QC

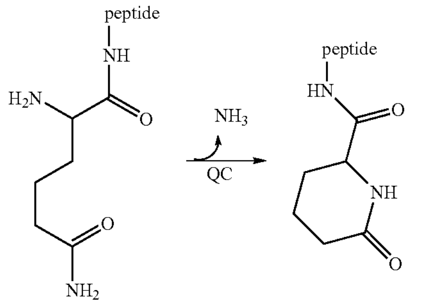

The term “EC” as used herein comprises the side activity of QC and QC-like enzymes as glutamate cyclase (EC), further defined as EC activity.

The term “EC activity” as used herein is defined as intramolecular cyclization of N-terminal glutamate residues into pyroglutamic acid (pGlu*) by QC. See scheme 3.

The term “metal-dependent enzyme” as used herein is defined as enzyme(s) that require a bound metal ion in order to fulfil their catalytic function and/or require a bound metal ion in order to form the catalytically active structure.

Moreover, the methods and compositions of the present invention are also useful in the evaluation of effectors of Qpct and for the development of drugs and therapeutic agents for the treatment and prevention of chronic and acute inflammatory diseases, e.g. rheumatoid arthritis, atherosclerosis, restenosis, pancreatitis.

The knock-out animal or the cells of the knock-out animal of the invention can be used in a variety of screening assays. For example, any of a variety of potential agents suspected of affecting Qpct and amyloid accumulation, as well as the appropriate antagonists and blocking therapeutic agents, can be screened by administration to the knock-out animal and assessing the effect of these agents upon the function and phenotype of the cells and on the phenotype, i.e. the neurological phenotype, of the knock-out animals.

Behavioral studies may also be used to test potential therapeutic agents, such as those studies designed to assess motor skills, learning and memory deficits. An example of such a test is the Morris Water maze (Morris (1981) Learn Motivat 12:239-260). Additionally, behavioral studies may include evaluations of locomotor activity such as with the rotor-rod and the open field.

A preferred embodiment of the present invention is directed to an in vivo animal model for examining the phenotypic consequences resulting from heterozygous or homozygous deficiency of the Qpct gene, wherein the animal model is a mammal having a heterozygous or homozygous disruption of the Qpct gene.

In a further preferred embodiment of the present invention, the Qpct gene is of human origin, more preferably of murine origin. The Qpct gene according to the present invention can also be a recombinant gene.

Most preferred according to the present invention is the murine Qpct gene of SEQ ID No. 22. In some embodiments, an animal of the model comprises a sequence having at least about 80% sequence identity to SEQ ID NO: 22, where the Qpct gene is disrupted. As an example, an animal of the model comprises a sequence having at least about 85%, at least about 90%, at least about 95%, or at least about 99% sequence identity to SEQ ID NO: 22, wherein the Qpct gene Scheme 3: N-terminal cyclization of glutamyl peptides by QC (EC)

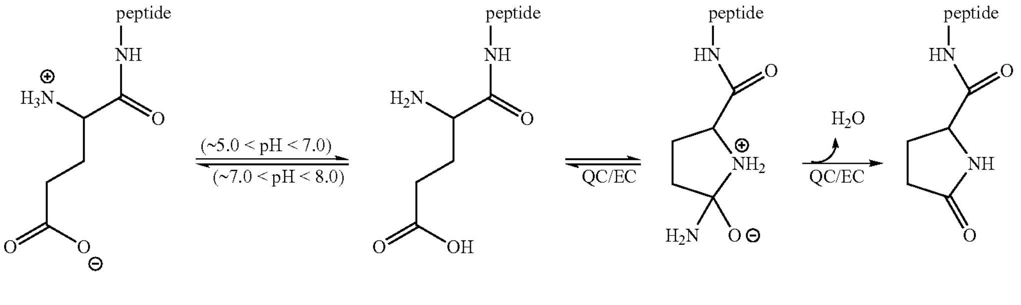

The term “Qpct-related disease” as used herein refers to all those diseases, disorders or conditions that are modulated by Qpct.

Assays and Identification of Therapeutic Agents

The methods and compositions of the present invention are particularly useful in the evaluation of effectors of Qpct and for the development of drugs and therapeutic agents for the treatment and prevention of amyloid-associated diseases such as Mild Cognitive Impairment, Alzheimer's disease, neurodegeneration in Down Syndrome, Familial Danish Dementia and Familial British Dementia.

is disrupted. As another example, a an animal of the model can comprise a nucleotide sequence that hybridizes under stringent conditions to SEQ ID NO: 22 over the entire length of SEQ ID NO: 22, wherein the Qpct gene is disrupted. As a further example, an animal of the model can comprise the complement to any of the above sequences.

The disruption of the murine Qpct gene (e.g., the murine Qpct gene of SEQ ID NO. 22) can, for example, be achieved by gene mutations, which lead to single amino acid deletions or replacements in the Qpct protein. Preferred according to the present invention are mutations in the Qpct gene, which lead to the deletion in the Qpct protein of at least one of the amino acids selected from the group consisting of residues H141 and D160 in exon 3, residues E202 and E203 in exon 4, residue D249 in exon 5 and residue H331 in exon 7. Preferably, sequence variants thereto retain at least one or more of such mutations.

In a further embodiment of the present invention, the disruption of the Qpct gene can also be achieved by deletion of one or more exons. The deletion of any single exon of the Qpct gene can lead to a Qpct gene disruption. Preferred according to the present invention is the deletion of exons 4 and/or 5 of the Qpct gene, more preferably of the murine Qpct gene. Most preferably, the murine Qpct gene has, after deletion of exons 4 and 5, the sequence of SEQ ID NO. 23. In some embodiments, the murine gene comprises a sequence at least about 80%, 85%, 90%, 95%, or 99% identical to SEQ ID NO: 23, in which the Qpct gene is disrupted.

In a further embodiment, an animal of the model comprises SEQ ID NO: 24, which is a fragment of the Qpct DNA sequence, or a sequence having at least about 80%, 85%, 90%, 95%, or 99% identity thereto in which Qpct is disrupted. In a further embodiment, an animal of the model comprises SEQ ID NO: 25, which is a fragment of the Qpct DNA sequence, or a sequence having at least about 80%, 85%, 90%, 95%, or 99% identity thereto in which Qpct is disrupted.

Also provided is an isolated nucleic acid sequence of a Qpct gene, in which Qpct is disrupted. In one embodiment, the isolated nucleic acid comprises SEQ ID NO: 23. In one embodiment, the isolated nucleic acid comprises SEQ ID NO: 24. In one embodiment, the isolated nucleic acid comprises SEQ ID NO: 25. In a further embodiment, the isolated nucleic acid comprises a sequence at least about 80%, 85%, 90%, 95%, or 99% identical to SEQ ID NO: 23, SEQ ID NO: 24, or SEQ ID NO: 25, wherein the Qpct is disrupted.

Any of the polynucleotide molecule sequences described above can be provided in a construct. Constructs of the present invention generally include a promoter functional in an animal of the model, such as a mouse or rat, operably linked to a polynucleotide molecule for a Qpct gene in which the gene is disrupted. One or more additional promoters may also be provided in the recombinant construct.

Since Qpct is involved in a variety of biological, medical or physiological processes or phenomena, including, but not limited to neurodegenerative diseases, e.g. Mild Cognitive Impairment, Alzheimer's disease, neurodegeneration in Down Syndrome, Familial Danish Dementia and Familial British Dementia; and chronic and acute inflammatory diseases, e.g. rheumatoid arthritis, atherosclerosis, restenosis, pancreatitis, the animal model having heterozygous or homozygous deficiency of the Qpct gene is useful for studying mechanisms and/or etiology of the above-mentioned processes/phenomena. In a particular embodiment, the animal model of the present invention having heterozygous or homozygous deficiency of the Qpct gene will be useful as a mammalian in vivo screening model for studying these and other processes/phenomena.

By "animal model" is meant that an animal sufficiently like humans in its anatomy, physiology, or response to a pathogen to be used in medical research that is used to investigate a physio- or pathological circumstances in question. According to the present invention, an animal model can be an exploratory model, aiming to understand a biological mechanism, e.g., amyloid beta peptide formation, or an explanatory model, aiming to understand a more or less complex biological problem.

The analysis of the physiological function of Qpct in vivo for the development of neurodegenerative diseases, e.g. Mild Cognitive Impairment, Alzheimer's disease, neurodegeneration in Down Syndrome, Familial Danish Dementia and Familial British Dementia; and chronic and acute inflammatory diseases, e.g. rheumatoid arthritis, atherosclerosis, restenosis, pancreatitis can be performed employing the heterozygous or homozygous Qpct knockout animals of the present invention. An effective screening for Qpct inhibitors, which are useful in the treatment of the aforementioned diseases, could be performed by treating existing animal models for the specific diseases with test compounds and comparing the results of such treatment with the effects of the Qpct gene disruption in the Qpct knockout animals.

Preferred methods for screening for biologically active agents that inhibit or promote Qpct production in vivo thus comprise the following steps:

i) administering a test compound to a non-human animal model, which is specific for the treatment of at least one disease selected from Mild Cognitive Impairment, Alzheimer's disease, neurodegeneration in Down Syndrome, Familial Danish Dementia, Familial British Dementia, rheumatoid arthritis, atherosclerosis, restenosis, and pancreatitis,
ii) determining the effect of the test compound;
iii) compare the effect of the test compound with the effect of the Qpct gene disruption in the Qpct knockout animal models, and
iv) select test compounds that have an efficacy similar to the effect of the Qpct gene disruption on the specific disease.

In particular preferred is the use of this method for screening of Qpct inhibitors.

In a further preferred embodiment, this method is used for the screening of Qpct inhibitors for the treatment of Alzheimer's disease or neurodegeneration in Down syndrome.

In yet another preferred embodiment, this method is used for the screening of Qpct inhibitors for the treatment of Familial British Dementia or Familial Danish Dementia.

Furthermore, this method is preferably used for the screening of Qpct inhibitors for the treatment of a disease selected from rheumatoid arthritis, atherosclerosis, restenosis, and pancreatitis.

The efficacy of Qpct-inhibitors for the treatment of Alzheimer's Disease, Familial British Dementia or Familial Danish Dementia and, e.g. neurodegeneration in Down Syndrome can be tested in existing animal models of Alzheimer's disease.

Suitable animal models of Alzheimer's Disease are reviewed in McGowan et al., TRENDS in Genetics, Vol. 22, No. May 2006, pp 281-289, and are selected from PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP, 3×TgAD, as described below.

PDAPP: First mutant APP transgenic model with robust plaque pathology. Mice express a human APP cDNA with the Indiana mutation ($APPV_{717F}$). Plaque pathology begins between 6-9 months in hemizygous PDAPP mice. There is synapse loss but no overt cell loss and not NFT pathology is observed. This model has been used widely in vaccination therapy strategies.

Tg2576: Mice express mutant $APP_{SWE}$ under control of the hamster prion promoter. Plaque pathology is observed from 9 months of age. These mice have cognitive deficits but no cell loss or NFT pathology. It is one of the most widely used transgenic models.

APP23: Mice express mutant $APP_{SWE}$ under control of the Thy1 promoter. Prominent cerebrovascular amyloid, amyloid deposits are observed from 6 months of age and some hippocampal neuronal loss is associated with amyloid plaque formation.

TgCRND8: Mice express multiple APP mutations (Swedish plus Indiana). Cognitive deficits coincide with rapid extracellular plaque development at ~3 months of age. The cognitive deficits can be reversed by Aβ vaccination therapy.

$PSEN_{1M146V}$ or $PSEN_{1M146L}$ (lines 6.2 and 8.9, respectively): These models where the first demonstration in vivo that mutant PSEN1 selectively elevates Aβ42. No overt plaque pathology is observed.

PSAPP (Tg2576×$PSEN_{1M146L}$, PSEN1-A246E+$APP_{SWE}$): Bigenic transgenic mice, addition of the mutant PSEN1 transgene markedly accelerated amyloid pathology compared with singly transgenic mutant APP mice, demonstrating that the PSEN1-driven elevation of Aβ42 enhances plaque pathology.

$APP_{Dutch}$: Mice express APP with the Dutch mutation that causes hereditary cerebral hemorrhage with amyloidosis-Dutch type in humans. $APP_{Dutch}$ mice develop severe congophilic amyloid angiopathy. The addition of a mutant PSEN1 transgene redistributes the amyloid pathology to the parenchyma indicating differing roles for Aβ40 and Aβ42 in vascular and parenchymal amyloid pathology.

BRI-Aβ40 and BRI-Aβ42: Mice express individual Aβ isoforms without APP over-expression. Only mice expressing Aβ42 develop senile plaques and CAA, whereas BRI-Aβ40 mice do not develop plaques, suggesting that Aβ42 is essential for plaque formation.

JNPL3: Mice express 4R0N MAPT with the P301L mutation. This is the first transgenic model, with marked tangle pathology and cell loss, demonstrating that MAPT alone can cause cellular damage and loss. JNPL3 mice develop motor impairments with age owing to server pathology and motor neutron loss in the spinal cord.

$Tau_{P301S}$: Transgenic mice expressing the shortest isoform of 4R MAPT with the P301S mutation. Homozygous mice develop severe paraparesis at 5-6 months of age with widespread neurofibrillary pathology in the brain and spinal cord and neuronal loss in the spinal cord.

$Tau_{V337M}$: Low level synthesis of 4R MAPT with the V337M mutation (1/10 endogenous MAPT) driven by the promoter of platelet-derived growth factor (PDGF). The development of neurofibrillary pathology in these mice suggests the nature of the MAPT rather than absolute MAPT intracellular concentration drives pathology.

$Tau_{R406W}$: Mice expressing 4R human MAPT with the R406W mutation under control of the CAMKII promoter. Mice develop MAPT inclusions in the forebrain from 18 months of age and have impaired associative memory.

rTg4510: Inducible MAPT transgenic mice using the TET-off system. Abnormal MAPT pathology occurs from one month of age. Mice have progressive NFT pathology and severe cell loss. Cognitive deficits are evident from 2.5 months of age. Turning off the transgene improves cognitive performance but NT pathology worsens.

$H_{tau}$: Transgenic mice expressing human genomic MAPT only (mouse MAPT knocked-out). Htau mice accumulate hyperphosphorylated MAPT form 6 month and develop Thio-5-positive NFT by the time they are 15 months old.

TAPP (Tg2576×JNPL3): Increased MAPT forebrain pathology in TAPP mice compared with JNPL3 suggesting mutant APP and/or Aβ can affect downstream MAPT pathology.

3×TgAD: Triple transgenic model expressing mutant $APP_{SWE}$, $MAPT_{P301L}$ on a $PSEN1_{M146V}$ 'knock-in' background (PSNE1-K1). Mice develop plaques from 6 months and MAPT pathology from the time they are 12 months old, strengthening the hypothesis that APP or Aβ can directly influence neurofibrillary pathology.

Non-human transgenic animals that overexpress Qpct, and which are useful in the screening method described above, are disclosed in WO 2008/087197.

Suitable study designs could be as outlined in the table below. QC inhibitors could be applied via the drinking solution or chow, or any other conventional route of administration, e.g. orally, intravenously or subcutaneously.

TABLE

Animal groups for the treatment of animal models of Alzheimer's disease with Qpct-inhibitors

| Group | Treatment | Mode |
|---|---|---|
| 1.) negative control | vehicle | 10 months old (41-45 weeks) |
| 2.) positive control | Ibuprofen | treatment for 6 months (25-26 weeks) starting at age of 4 months (15-20 weeks) |
| 3.) Qpct-inhibitor | low dose | treatment for 6 months (25-26 weeks) starting at age of 4 months (15-20 weeks) |
| 4.) Qpct-inhibitor | high dose | treatment for 6 months (25-26 weeks) starting at age of 4 months (15-20 weeks) |

In regard to Alzheimer's disease, the efficacy of the Qpct inhibitors can be assayed by sequential extraction of Aβ using SDS and formic acid. Initially, the SDS and formic acid fractions containing the highest Aβ concentrations can be analyzed using an ELISA quantifying total Aβ(x-42) or Aβ(x-40) as well as $[pGlu^3]$Aβ3-40/42/43 or $[pGlu^{11}]$Aβ11-40/42/43. Test compounds that are identified employing the screening method above and which are suitable for further pharmaceutical development should reduce the formation of $[pGlu^3]$Aβ3-40/42/43 or $[pGlu^{11}]$Aβ11-40/42/43. In particular, suitable test compounds are capable to reduce the formation of $[pGlu^3]$Aβ3-40 and/or $[pGlu^3]$Aβ3-42.

An ELISA kit for the quantification of $[pGlu^3]$Aβ3-42 is commercially available from IBL, Cat-no. JP27716.

An ELISA for the quantification of $[pGlu^3]$Aβ3-40 is described by Schilling et al., 2008 (Schilling S, Appl T, Hoffmann T, Cynis H, Schulz K, Jagla W, Friedrich D, Wermann M, Buchholz M, Heiser U, von Horsten S, Demuth H U. Inhibition of glutaminyl cyclase prevents pGlu-Abeta formation after intracortical/hippocampal microinjection in vivo/in situ. J. Neurochem. 2008 August; 106(3):1225-36.)

An alternative treatment regime is shown below.

TABLE

Animal groups involved, examination of the effect of inhibitors of Qpct on progression of plaque formation in animal models of AD

| Group | Treatment | Mode |
|---|---|---|
| 1) negative control | Vehicle | 16 months old (67-70 weeks) |
| 2) positive control | Ibuprofen (0.2 mg/ml) | treatment for 5 months (21-22 weeks) starting at the age 11 months (46-49 weeks) |

TABLE-continued

Animal groups involved, examination of the effect of inhibitors of Qpct on progression of plaque formation in animal models of AD

| Group | Treatment | Mode |
|---|---|---|
| 3) QC-inhibitor | low dose | treatment for 5 months (21-22 weeks) starting at age 11 months (46-49 weeks) |
| 4) QC-inhibitor | high dose | treatment for 5 months (21-22 weeks) starting at age 11 months (46-49 weeks) |

Subsequently after Qpct-inhibitor treatment, the AD animal can be tested regarding behavioral changes. Suitable behavioral test paradigms are, e.g. those, which address different aspects of hippocampus-dependent learning. Examples for such neurological tests are the Morris water maze test and the Fear Conditioning test looking at contextual memory changes (Comery, T A et al, (2005), J Neurosci 25:8898-8902; Jacobsen J S et al, (2006), Proc Natl. Acad. Sci. USA 103:5161-5166).

The animal model of inflammatory diseases, e.g. atherosclerosis contemplated by the present invention can be an existing atherosclerosis animal model, e.g., apoE deficient mouse, or can be prepared, for example, by preparing a transgenic mouse having Qpct gene overexpression or gene deficiency with apoE deficient background. The apolipoprotein E knockout mouse model has become one of the primary models for atherosclerosis (Arterioscler Thromh Vasc Biol., 24: 1006-1014, 2004; Trends Cardiovasc Med, 14: 187-190, 2004). The studies may be performed as described by Johnson et al. in Circulation, 111: 1422-1430, 2005, or using modifications thereof. Apolipoprotein E-Deficient Mouse Model Apolipoprotein E (apoE) is a component of several plasma lipoproteins, including chylomicrons, VLDL, and HDL. Receptor-mediated catabolism of these lipoprotein particles is mediated through the interaction of apoE with the LDL receptor (LDLR) or with LDLR-related protein (LRP). ApoE-deficient mice exhibit hypercholesterolemia and develop complex atheromatous lesions similar to those seen in humans. The efficacy of the compounds of the present invention was also evaluated using this animal model.

Other animal models for inflammatory diseases, which are suitable for use in the aforementioned screening method, are the thioglycollate-induced inflammation model in mice, the collagen-induced Arthritis Model in Rat and in rat models of restenosis (e.g. the effects of the test compounds on rat carotid artery responses to the balloon catheter injury).

In regard to inflammatory diseases, the efficacy of the Qpct inhibitors can be assayed by measuring the inhibition of the chemotaxis of a human monocytic cell line (THP-1 cells) induced by human MCP-1 in vitro. The assay is described in example 16. This inhibitory effect has also been observed in vivo. Effective test compounds should show a reduced monocyte infiltration in a thioglycollate-induced inflammation model in mice.

Furthermore, the inhibition of the formation of pGlu-MCP-1 can be tested in vitro and in vivo.

The methods of the invention can advantageously use cells isolated from a homozygous or heterozygous Qpct mutant non-human mammal, to study amyloid accumulation as well as to test potential therapeutic compounds. The methods of the invention can also be used with cells expressing Qpct such as a transfected cell line.

A Qpct knock-out cell can be used in an in vitro method to screen compounds as potential therapeutic agents for treating Aβ associated disease. In such a method, a compound is contacted with a Qpct knock-out cell, a transfected cell or a cell derived from a Qpct mutant non-human animal, and screened for alterations in a phenotype associated with expression of Qpct. The changes in Aβ production in the cellular assay and the knock-out animal can be assessed by methods well known to those skilled in the art.

A Qpct fusion polypeptide such as Qpct can be particularly useful for such screening methods since the expression of Qpct can be monitored by fluorescence intensity. Other exemplary fusion polypeptides include other fluorescent proteins, or modifications thereof, glutathione-S-transferase (GST), maltose binding protein, poly His, and the like, or any type of epitope tag. Such fusion polypeptides can be detected, for example, using antibodies specific to the fusion polypeptides. The fusion polypeptides can be an entire polypeptide or a functional portion thereof so long as the functional portion retains desired properties, for example, antibody binding activity or fluorescence activity.

The invention further provides a method of identifying a potential therapeutic agent for use in treating the diseases as mentioned above. The method includes the steps of contacting a cell containing the above DNA construct with a compound and screening the cell for the results to be observed, thereby identifying a potential therapeutic agent for use in treating Qpct-related diseases. The cell can be isolated from a knock-out non-human mammal having nucleated cells containing the Qpct DNA construct. Alternatively, the cell can contain a DNA construct comprising a nucleic acid encoding a green fluorescent protein fusion, or other fusion polypeptide, with a Qpct polypeptide.

Additionally, Qpct knock-out cells expressing a Qpct polypeptide can be used in a preliminary screen to identify compounds as potential therapeutic agents having activity that alters a phenotype associated with Qpct expression. As with in vivo screens using Qpct knock-out non-human mammals, an appropriate control cell can be used to compare the results of the screen. The effectiveness of compounds identified by an initial in vitro screen using Qpct knock-out cells can be further tested in vivo using the invention Qpct knock-out non-human mammals, if desired. Thus, the invention provides methods of screening a large number of compounds using a cell-based assay, for example, using high throughput screening, as well as methods of further testing compounds as therapeutic agents in an animal model of Aβ-related disorders.

The present invention also provides a new method for the treatment of Mild Cognitive Impairment (MCI), Alzheimer's disease, Familial Danish Dementia, Familial British Dementia and neurodegeneration in Down syndrome. The N-termini of the amyloid β-peptides deposited in the Alzheimer's disease and Down syndrome brain and the amyloid peptides ADan and ABri deposited in Familial Danish Dementia and Familial British Dementia as well, bear pyroglutamic acid. The pGlu formation is an important event in the development and progression of the disease, since the modified amyloid β-peptides, ADan and ABri show an enhanced tendency to amyloid aggregation and toxicity, likely worsening the onset and progression of the disease. (Russo, C. et al. 2002 J Neurochem 82, 1480-1489; Ghiso, J. et al. 2001 Amyloid 8, 277-284).

In the natural Aβ-peptides (3-40/42), glutamic acid is present as an N-terminal amino acid.

Qpct is involved in the formation of pyroglutamic acid that favors the aggregation of amyloid β-peptides. Thus, an inhibition of Qpct leads to a prevention of the precipitation of the plaque-forming $[pGlu^3]A\beta 3\text{-}40/42/43$ or $[pGlu^{11}]$ Aβ11-40/42/43, causing the onset and progression of Alzheimer's disease and Down Syndrome.

Glutamate is found in positions 3, 11 and 22 of the amyloid β-peptide. Among them the mutation from glutamic acid (E) to glutamine (Q) in position 22 (corresponds to amino acid 693 of the amyloid precursor protein APP770, Swissprot entry: P05067) has been described as the so-called Dutch type cerebroarterial amyloidosis mutation.

The β-amyloid peptides with a pyroglutamic acid residue in position 3, 11 and/or 22 have been described to be more cytotoxic and hydrophobic than Aβ1-40/4243 (Saido T. C. 2000 Medical Hypotheses 54(3): 427-429).

The multiple N-terminal variations can be generated by the β-secretase enzyme β-site amyloid precursor protein-cleaving enzyme (BACE) at different sites (Huse J. T. et al. 2002 Biol. Chem. 277 (18): 16278-16284), and/or by aminopeptidase processing.

There had been no experimental evidence supporting the enzymatic conversion of $Glu^1$-peptides into pGlu-peptides by an unknown glutamyl cyclase (EC) (Garden, R. W., Moroz, T. P., Gleeson, J. M., Floyd, P. D., Li, L. J., Rubakhin, S. S., and Sweedler, J. V. (1999) J Neurochem 72, 676-681; Hosoda R. et al. (1998) J Neuropathol Exp Neurol. 57, 1089-1095). No such enzyme activity had been identified, capable of cyclizing $Glu^1$-peptides, which are protonated N-terminally and possess a negatively charged $Glu^1$ γ-carboxylate moiety under mildly alkaline or neutral pH-conditions.

QC-activity against $Gln^1$-substrates is dramatically reduced below pH 7.0. In contrast, it appears that $Glu^1$-conversion can occur at acidic reaction conditions (e.g. Iwatsubo, T., Saido, T. C., Mann, D. M., Lee, V. M., and Trojanowski, J. Q. (1996) Am J Pathol 149, 1823-1830).

Earlier, it was investigated whether Qpct is able to recognize and to turnover amyloid-β derived peptides under mildly acidic conditions (WO 2004/098625). Therefore, the peptides $[Gln^3]$A1-11a, Aβ3-11a, $[Gln^3]$Aβ3-11a, Aβ3-21a, $[Gln^3]$Aβ3-21a and $[Gln^3]$Aβ3-40 as potential substrates of the enzyme were synthesized and investigated. These sequences were chosen for mimicking natural N-terminally and C-terminally truncated $[Glu^3]$Aβ peptides and $[Gln^3]$Aβ peptides which could occur due to posttranslational Glu-amidation.

It was shown that papaya and human Qpct catalyze both glutaminyl and glutamyl cyclization. Apparently, the primary physiological function of Qpct is to finish hormone maturation in endocrine cells by glutamine cyclization prior or during the hormone secretion process. Such secretory vesicles are known to be acidic in pH. Thus, a side activity of the enzyme in the narrow pH-range from 5.0 to 7.0 could be its newly discovered glutamyl cyclase activity cyclizing also Glu-Aβ peptides. However, due to the much slower occurring Glu-cyclization compared to Gln-conversion, it is questionable whether the glutamyl cyclization plays a significant physiological role. In the pathology of neurodegenerative disorders, however, the glutamyl cyclization is of relevance.

Investigating the pH-dependency of this enzymatic reaction, it has been shown that the unprotonated N-terminus was essential for the cyclization of $Gln^1$-peptides and accordingly that the pKa-value of the substrate was identical to the pKa-value for Qpct-catalysis. Thus, Qpct stabilizes the intramolecular nucleophilic attack of the unprotonated α-amino moiety on the 7-carbonyl carbon.

In contrast to the monovalent charge present on N-terminal glutamine containing peptides, the N-terminal Glu-residue in Glu-containing peptides is predominantly bivalently charged at neutral pH. Glutamate exhibits $pK_a$-values of about 4.2 and 7.5 for the γ-carboxylic and for the α-amino moiety, respectively, i.e. at neutral pH and above, although the α-amino nitrogen is in part or fully unprotonated and nucleophilic, the γ-carboxylic group is unprotonated, and so exercising no electrophilic carbonyl activity. Hence, intramolecular cyclization is impossible.

However, in the pH-range of about 5.2-6.5, between their respective $pK_a$-values, the two functional groups are present both in non-ionized forms, in concentrations of about 1-10% ($—NH_2$) or 10-1% (—COOH) of total N-terminal Glu-containing peptide. As a result, over a mildly acidic pH-range species of N-terminal Glu-peptides are present which carry both groups uncharged, and, therefore, it is possible that Qpct could stabilize the intermediate of intramolecular cyclization into the pGlu-peptide, i.e. if the γ-carboxylic group is protonated, the carbonyl carbon is electrophilic enough to allow nucleophilic attack by the unprotonated α-amino group. At this pH the hydroxyl ion functions as a leaving group. These assumptions are corroborated by the pH-dependence data obtained for the Qpct catalyzed conversion of Glu-βNA. In contrast to glutamine conversion of Gln-βNA by Qpct, the pH-optimum of catalysis shifts to the acidic range around pH 6.0, i.e. the pH-range, in which substrate molecule species are simultaneously abundant carrying a protonated 7-carboxyl and unprotonated α-amino group. Furthermore, the kinetically determined pKa-value of 7.55+/−0.02 is in excellent agreement with that of the α-amino group of Glu-β3NA, determined by titration (7.57±0.05).

Physiologically, at pH 6.0 the second-order rate constant (or specificity constant, $k_{cat}/K_M$) of the Qpct-catalyzed glutamate cyclization might be in the range of $1*10^5$-$1*10^6$ fold slower than the one for glutamine cyclization. However, the nonenzymatic turnover of both model substrates Glu-βNA and Gln-βNA is negligible, being conform with the observed negligible pGlu-peptide formation. Hence, for the pGlu-formation by Qpct an acceleration of at least $10^8$ can be estimated from the ratio of the enzymatic versus non-enzymatic rate constants (comparing the second-order rate constants for the enzyme catalysis with the respective non-enzymatic cyclization first-order rate constants the catalytic proficiency factor is $10^9$-$10^{10}$ $M^{-1}$ for the Gln- and the Glu-conversion, respectively). The conclusion from these data is, that in vivo only an enzymatic path resulting pGlu-formations seems conceivable.

Since Qpct is highly abundant in the brain and taking into account the high turnover rate of 0.9 $min^{-1}$ recently found for the maturation of 30 μM of (Gln-)TRH-like peptide (Prokal, L., Prokai-Tatrai, K., Ouyang, X., Kim, H. S., Wu, W. M., Zharikova, A., and Bodor, N. (1999) J Med Chem 42, 4563-4571), one can predict a cyclization half-life of about 100 hours for an appropriate glutamate-substrate, if similar reaction conditions are provided. Moreover, given compartmentalization and localization of brain Qpct in the secretory pathway, the actual in vivo enzyme and substrate concentrations and reaction conditions might be even more favorable for the enzymatic cyclization in the intact cell. And, if N-terminal Glu is transformed to Gln a much more rapid pGlu-formation mediated by Qpct could be expected. In vitro, both reactions were suppressed by applying inhibitors of Qpct-activity.

In summary, it was shown that human Qpct, which is highly abundant in the brain, is likely a catalyst of the formation of the amyloidogenic pGlu-Ap peptides from Glu-Ap and Gln-Ap precursors, which make up more than 50% of the plaque deposits found in Alzheimer's disease.

These findings identify Qpct as a player in senile plaque formation and thus as a novel drug target in the treatment of Alzheimer's disease, neurodegeneration in Down Sydrome, Familial Danish Dementia and Familial British Dementia. See, e.g. WO 2004/098625 and WO 2005/039548.

In a preferred embodiment, the present invention provides the use of activity-decreasing effectors of Qpct, as selected with use of the present inventive animal model, for the suppression of pGlu-Amyloid peptide formation in Mild Cognitive Impairment, Alzheimer's disease, Down Syndrome, Familial Danish Dementia and Familial British Dementia.

In a further embodiment, the present invention provides the use of activity-increasing effectors of Qpct, as selected with use of the present inventive animal model, for the stimulation of gastrointestinal tract cell proliferation, especially gastric mucosal cell proliferation, epithelial cell proliferation, the differentiation of acid-producing parietal cells and histamine-secreting enterochromaffin-like (ECL) cells, and the expression of genes associated with histamine synthesis and storage in ECL cells, as well as for the stimulation of acute acid secretion in mammals by maintaining or increasing the concentration of active[$pGlu^1$]-Gastrin.

In a preferred embodiment, the present invention provides the use of activity-decreasing effectors of Qpct, as selected with use of the present inventive animal model, for the suppression of pGlu-cytokine function, preferably chemokine function, most preferably monocyte chemoattractant function in Alzheimer's disease, Down Syndrome, Familial Danish Dementia and Familial British Dementia, atherosclerosis and restenosis.

A number of studies have underlined in particular the crucial role of MCP-1 for the development of atherosclerosis (Gu, L., et al., (1998) *Mol. Cell.* 2, 275-281; Gosling, J., et al., (1999) *J. Clin. Invest* 103, 773-778); rheumatoid arthritis (Gong, J. H., et al., (1997) *J Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J. Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J. Oncol.* 22, 773-778; Li, S., et al., (2005) *J Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

The mature form of human and rodent MCP-1 is post-translationally modified by Glutaminyl Cyclase (Qpct) to possess an N-terminal pyroglutamyl (pGlu) residue. The N-terminal pGlu modification makes the protein resistant against N-terminal degradation by aminopeptidases, which is of importance, since chemotactic potency of MCP-1 is mediated by its N-terminus (Van Damme, J., et al., (1999) *Chem Immunol* 72, 42-56). Artificial elongation or degradation leads to a loss of function although MCP-1 still binds to its receptor (CCR2) (Proost, P., et al., (1998), *J Immunol* 160, 4034-4041; Zhang, Y. J., et al., 1994, *J Biol Chem* 269, 15918-15924; Masure, S., et al., 1995, *J Interferon Cytokine Res.* 15, 955-963; Hemmerich, S., et al., (1999) *Biochemistry* 38, 13013-13025).

Due to the major role of MCP-1 in a number of disease conditions, an anti-MCP-1 strategy is required. Therefore, small orally available compounds inhibiting the action of MCP-1 are promising candidates for a drug development. Inhibitors of Glutaminyl Cyclase are small orally available compounds, which target the important step of pGlu-formation at the N-terminus of MCP-1 (Cynis, H., et al., (2006) *Biochim. Biophys. Acta* 1764, 1618-1625; Buchholz, M., et al., (2006) *J Med Chem* 49, 664-677). In consequence, caused by Qpct-inhibition, the N-terminus of MCP-1 is not protected by a pGlu-residue. Instead, the N-terminus possesses a glutamine-proline motif, which is prone to cleavage by dipeptidylpeptidases, e.g. dipeptidylpeptidase 4 and fibroblast activating protein (FAP, Seprase), which are abundant on the endothelium and within the blood circulation. This cleavage results in the formation of N-terminal truncated MCP-1. These molecules unfold, in turn, an antagonistic action at the CCR2 and therefore, monocyte-related disease conditions are inhibited efficiently.

In a further embodiment, the present invention provides the use of activity decreasing effectors of Qpct, as selected with use of the present inventive animal model, for the treatment of duodenal ulcer disease and gastric cancer with or without *Helicobacter pylori* in mammals by decreasing the conversion rate of inactive [$Gln^1$]Gastrin to active [$pGlu^1$]Gastrin.

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioural and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

In another embodiment, the present invention provides the use of activity increasing effectors of Qpct, as selected with use of the present inventive animal model, for the preparation of antipsychotic drugs and/or for the treatment of schizophrenia in mammals. The effectors of Qpct either maintain or increase the concentration of active [$pGlu^1$] neurotensin.

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (incapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in incapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", and others possibly being involved in the acrosome reaction itself. Calcitonin and angiotensin II, also found in seminal plasma, have similar effects in vitro on incapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

In a further embodiment, the present invention provides the use of activity-lowering effectors of Qpct, as selected with the present inventive animal model, for the preparation of fertilization prohibitive drugs and/or to reduce the fertility in mammals. The activity lowering effectors of Qpct decrease the concentration of active [$pGlu^1$]FPP, leading to a prevention of sperm capacitation and deactivation of sperm cells. In contrast it could be shown that activity-increasing effectors of Qpct are able to stimulate fertility in males and to treat infertility.

In another embodiment, the present invention provides the use of effectors of Qpct, as selected with use of the present inventive animal model, for the preparation of a medicament for the treatment of pathophysiological conditions, such as suppression of proliferation of myeloid progenitor cells, neoplasia, inflammatory host responses, cancer, malign metastasis, melanoma, psoriasis, rheumatoid arthritis, atherosclerosis, lung fibrosis, liver fibrosis, renal fibrosis, graft rejection, acquired immune deficiency syndrome, impaired humoral and cell-mediated immunity responses, leukocyte adhesion and migration processes at the endothelium.

In a further embodiment, the present invention provides the use of effectors of Qpct, as selected with use of the present inventive animal model, for the preparation of a medicament for the treatment of impaired food intake and sleep-wakefulness, impaired homeostatic regulation of energy metabolism, impaired autonomic function, impaired hormonal balance and impaired regulation of body fluids.

Polyglutamine expansions in several proteins lead to neurodegenerative disorders, such as Chorea Huntington, Parkinson disease and Kennedy's disease. The mechanism therefore remains largely unknown. The biochemical properties of polyglutamine repeats suggest one possible explanation: endolytic cleavage at a glutaminyl-glutaminyl bond followed by pyroglutamate formation may contribute to the pathogenesis through augmenting the catabolic stability, hydrophobicity, amyloidogenicity, and neurotoxicity of the polyglutaminyl proteins (Saido, T. C.; Med Hypotheses (2000) March; 54(3):427-9).

In a further embodiment, the present invention therefore provides the use of effectors of Qpct, as selected with the present inventive animal model, for the preparation of a medicament for the treatment of Parkinson disease and Huntington's disease.

In another embodiment, the present invention provides a general way to reduce or inhibit the enzymatic activity of Qpct by using the test agent selected above.

Inhibition of a mammalian Qpct was only detected initially for 1,10-phenanthroline and reduced 6-methylpterin (Busby, W. H. J. et al. 1987 J Biol Chem 262, 8532-8536). EDTA did not inhibit Qpct, thus it was concluded that Qpct is not a metal-dependent enzyme (Busby, W. H. J. et al, 1987 J Biol Chem 262, 8532-8536, Bateman, R. C. J. et al. 2001 Biochemistry 40, 11246-11250, Booth, R. E. et al. 2004 BMC Biology 2). However, it was shown, that human Qpct and other animal Qpcts are metal-dependent enzymes, as revealed by the inhibition characteristics of Qpct by 1,10-phenanthroline, dipicolinic acid, 8-hydroxy-quinoline and other chelators and by the reactivation of Qpct by transition metal ions. Finally, the metal dependence is outlined by a sequence comparison to other metal-dependent enzymes, showing a conservation of the chelating amino acid residues also in human Qpct. The interaction of compounds with the active-site bound metal ion represents a general way to reduce or inhibit Qpct activity.

The agents selected by the above-described screening methods can work by decreasing the conversion of at least one substrate of Qpct (negative effectors, inhibitors), or by increasing the conversion of at least one substrate of Qpct (positive effectors, activators).

The compounds of the present invention can be converted into acid addition salts, especially pharmaceutically acceptable acid addition salts.

The salts of the compounds of the invention may be in the form of inorganic or organic salts.

The compounds of the present invention can be converted into and used as acid addition salts, especially pharmaceutically acceptable acid addition salts. The pharmaceutically acceptable salt generally takes a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or triflu-oroacetic acid. All pharmaceutically acceptable acid addition salt forms of the compounds of the present invention are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention.

The compounds, including their salts, can also be obtained in the form of their hydrates, or include other solvents used for their crystallization.

In a further embodiment, the present invention provides a method of preventing or treating a condition mediated by modulation of the Qpct enzyme activity in a subject in need thereof which comprises administering any of the compounds of the present invention or pharmaceutical compositions thereof in a quantity and dosing regimen therapeutically effective to treat the condition. Additionally, the present invention includes the use of the compounds of this invention, and their corresponding pharmaceutically acceptable acid addition salt forms, for the preparation of a medicament for the prevention or treatment of a condition mediated by modulation of the Qpct activity in a subject. The compound may be administered to a patient by any conventional route of administration, including, but not limited to, intravenous, oral, subcutaneous, intramuscular, intradermal, parenteral and combinations thereof.

In a further preferred form of implementation, the invention relates to pharmaceutical compositions, that is to say, medicaments, that contain at least one compound of the invention or salts thereof, optionally in combination with one or more pharmaceutically acceptable carriers and/or solvents.

The pharmaceutical compositions may, for example, be in the form of parenteral or enteral formulations and contain appropriate carriers, or they may be in the form of oral formulations that may contain appropriate carriers suitable for oral administration. Preferably, they are in the form of oral formulations.

The effectors of Qpct activity administered according to the invention may be employed in pharmaceutically administrable formulations or formulation complexes as inhibitors or in combination with inhibitors, substrates, pseudosubstrates, inhibitors of Qpct expression, binding proteins or antibodies of those enzyme proteins that reduce the Qpct protein concentration in mammals. The compounds of the invention make it possible to adjust treatment individually to patients and diseases, it being possible, in particular, to avoid individual intolerances, allergies and side-effects.

The compounds also exhibit differing degrees of activity as a function of time. The physician providing treatment is thereby given the opportunity to respond differently to the individual situation of patients: he is able to adjust precisely, on the one hand, the speed of the onset of action and, on the other hand, the duration of action and especially the intensity of action.

A preferred treatment method according to the invention represents a new approach for the prevention or treatment of a condition mediated by modulation of the Qpct enzyme activity in mammals. It is advantageously simple, susceptible of commercial application and suitable for use, especially in the treatment of diseases that are based on unbalanced concentration of physiological active Qpct substrates in mammals and especially in human medicine.

The compounds may be advantageously administered, for example, in the form of pharmaceutical preparations that contain the active ingredient in combination with customary additives like diluents, excipients and/or carriers known from the prior art. For example, they can be administered parenterally (for example i.v. in physiological saline solution) or enterally (for example orally, formulated with customary carriers).

Depending on their endogenous stability and their bioavailability, one or more doses of the compounds can be given per day in order to achieve the desired normalisation of the blood glucose values. For example, such a dosage range in humans may be in the range of from about 0.01 mg to 250.0 mg per day, preferably in the range of about 0.01 to 100 mg of compound per kilogram of body weight.

By administering effectors of Qpct activity to a mammal it could be possible to prevent or alleviate or treat conditions selected from Mild Cognitive Impairment, Alzheimer's disease, Down Syndrome, Familial Danish Dementia, Familial British Dementia, Huntington's Disease, ulcer disease and gastric cancer with or w/o *Helicobacter pylori* infections, pathogenic psychotic conditions, schizophrenia, infertility, neoplasia, inflammatory host responses, cancer, psoriasis, restenosis, pancreatitis, rheumatoid arthritis, atherosclerosis, lung fibrosis, liver fibrosis, renal fibrosis, graft rejection, acquired immune deficiency syndrome, impaired humoral and cell-mediated immune responses, leukocyte adhesion and migration processes in the endothelium, impaired food intake, sleep-wakefulness, impaired homeostatic regulation of energy metabolism, impaired autonomic function, impaired hormonal balance and impaired regulation of body fluids.

Further, by administering effectors of Qpct activity to a mammal it could be possible to stimulate gastrointestinal tract cell proliferation, preferably proliferation of gastric mucosal cells, epithelial cells, acute acid secretion and the differentiation of acid producing parietal cells and histamine-secreting enterochromaffin-like cells.

In addition, administration of Qpct inhibitors to mammals may lead to a loss of sperm cell function thus suppressing male fertility. Thus, the prevent invention provides a method for the regulation and control of male fertility and the use of activity lowering effectors of Qpct for the preparation of contraceptive medicaments for males.

Furthermore, by administering effectors of Qpct activity to a mammal it may be possible to suppress the proliferation of myeloid progenitor cells.

The compounds used according to the invention can accordingly be converted in a manner known per se into conventional formulations, such as, for example, tablets, capsules, dragées, pills, suppositories, granules, aerosols, syrups, liquid, solid and cream-like emulsions and suspensions and solutions, using inert, non-toxic, pharmaceutically suitable carriers and additives or solvents. In each of those formulations, the therapeutically effective compounds are preferably present in a concentration of approximately from 0.1 to 80% by weight, more preferably from 1 to 50% by weight, of the total mixture, that is to say, in amounts sufficient for the mentioned dosage latitude to be obtained.

The substances can be used as medicaments in the form of dragées, capsules, biteable capsules, tablets, drops, syrups or also as suppositories or as nasal sprays.

The formulations may be advantageously prepared, for example, by extending the active ingredient with solvents and/or carriers, optionally with the use of emulsifiers and/or dispersants, it being possible, for example, in the case where water is used as diluent, for organic solvents to be optionally used as auxiliary solvents.

Examples of excipients useful in connection with the present invention include: water, non-toxic organic solvents, such as paraffins (for example natural oil fractions), vegetable oils (for example rapeseed oil, groundnut oil, sesame oil), alcohols (for example ethyl alcohol, glycerol), glycols (for example propylene glycol, polyethylene glycol); solid carriers, such as, for example, natural powdered minerals (for example highly dispersed silica, silicates), sugars (for example raw sugar, lactose and dextrose); emulsifiers, such as non-ionic and anionic emulsifiers (for example polyoxyethylene fatty acid esters, polyoxyethylene fatty alcohol ethers, alkylsulphonates and arylsulphonates), dispersants (for example lignin, sulphite liquors, methylcellulose, starch and polyvinylpyrrolidone) and lubricants (for example magnesium stearate, talcum, stearic acid and sodium lauryl sulphate) and optionally flavourings.

Administration may be carried out in the usual manner, preferably enterally or parenterally, especially orally. In the case of enteral administration, tablets may contain in addition to the mentioned carriers further additives such as sodium citrate, calcium carbonate and calcium phosphate, together with various additives, such as starch, preferably potato starch, gelatin and the like. Furthermore, lubricants, such as magnesium stearate, sodium lauryl sulphate and talcum, can be used concomitantly for tabletting. In the case of aqueous suspensions and/or elixirs intended for oral administration, various taste correctives or colourings can be added to the active ingredients in addition to the above-mentioned excipients.

In the case of parenteral administration, solutions of the active ingredients using suitable liquid carriers can be employed. In general, it has been found advantageous to administer, in the case of intravenous administration, amounts of approximately from 0.01 to 2.0 mg/kg, preferably approximately from 0.01 to 1.0 mg/kg, of body weight per day to obtain effective results and, in the case of enteral administration, the dosage is approximately from 0.01 to 2 mg/kg, preferably approximately from 0.01 to 1 mg/kg, of body weight per day.

It may nevertheless be necessary in some cases to deviate from the stated amounts, depending upon the body weight of the experimental animal or the patient or upon the type of administration route, but also on the basis of the species of animal and its individual response to the medicament or the interval at which administration is carried out. Accordingly, it may be sufficient in some cases to use less than the above-mentioned minimum amount, while, in other cases, the mentioned upper limit will have to be exceeded. In cases where relatively large amounts are being administered, it may be advisable to divide those amounts into several single doses over the day. For administration in human medicine, the same dosage latitude is provided. The above remarks apply analogously in that case.

For examples of pharmaceutical formulations, specific reference is made to the examples of WO 2004/098625, pages 50-52, which are incorporated herein by reference in their entirety.

EXAMPLES

The above disclosure describes the present invention in general. A more complete understanding can be obtained by reference to the following examples. These examples are described solely for purposes of illustration and are not intended to limit the scope of the invention. Although specific terms have been employed herein, such terms are intended in a descriptive sense and not for purposes of limitation. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Figure 1B:
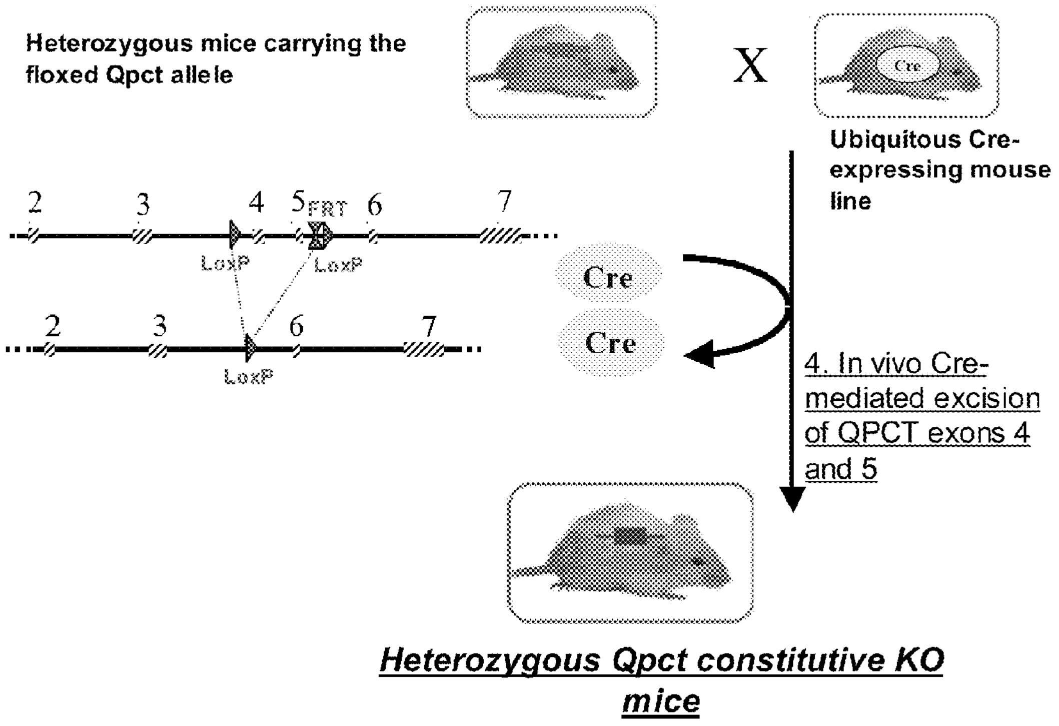

Using the general strategy illustrated in FIG. 1, the development of the Qpct constitutive and conditional knock-out mouse lines according to the present invention comprised the following steps:

- Cloning and sequencing of the targeted region of the murine Qpct locus in a 129Sv/Pas genetic background
- Targeting vector and positive control vector design and construction
- Set-up of the screening conditions for the detection of homologous recombination events, Cre-mediated and Flp-mediated excision events (PCR and Southern blot)
- Homologous recombination in ES cells
- ES cell injection into blastocysts and generation of chimeras
- Breeding of chimeras with ubiquitous Flp-expressing animals and generation of Qcpt floxed heterozygous mouse line.
- Breeding of chimeras or heterozygous with ubiquitous Cre-expressing animals and generation of heterozygous mutant mice carrying a Knock-out Qpct allele.

Using the general strategy illustrated in FIG. 1, the development of the Qpct constitutive and conditional Knock-out mouse lines according to the present invention comprised the following steps:

- Cloning and sequencing of the targeted region of the murine Qpct locus in a 129Sv/Pas genetic background
- Targeting vector and positive control vector design and construction
- Set-up of the screening conditions for the detection of homologous recombination events, Cre-mediated and Flp-mediated excision events (PCR and Southern blot)
- Homologous recombination in ES cells
- ES cell injection into blastocysts and generation of chimeras
- Breeding of chimeras with ubiquitous Flp-expressing animals and generation of Qcpt floxed heterozygous mouse line.
- Breeding of chimeras or heterozygotes with ubiquitous Cre-expressing animals and generation of heterozygous mutant mice carrying a Knock-out Qpct allele.

Example 1

1. Mouse Qpct Gene Characterisation

The murine Qpct gene encodes for glutaminyl cyclase, which is responsible for the presence of pyroglutamyl residues in many neuroendocrine peptides.

1.1 Mouse Qpct locus

The mouse Qpct gene is located on chromosome 17 and extends over 37.5 kb. The C57BL/6 mouse sequence is available on the Ensembl database (www.ensembl.org, ENSMUSG00000024084). Using the cDNA sequence NM_128770, the exon/intron organisation of the gene was established. This mouse gene consists in 7 exons interrupted by 6 introns. The translation initiation site is located in the first exon and the stop codon is located in exon 7.

The Ensembl database search also revealed the presence of the PRKCN gene, located on the same strand, 40 kb upstream of the Qpct gene. No genes are known or predicted within the 80 kb region downstream of Qpct gene, nor on the complementary strand. The targeting of the Qpct locus is thus not predicted to influence any other gene expression.

1.2 Mouse Qpct protein

Two isoforms are known for the murine QPCT protein. These two isoforms (362 and 313 aa, respectively) are translated from two mRNAs: one containing all the exons (AK045974) and a splice variant in which exon 2 is spliced out (BC020023).

Figure 2:
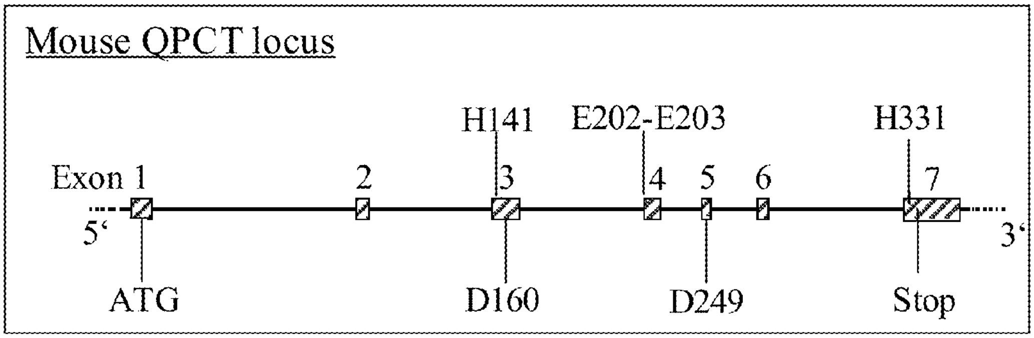
FIG. 2 is a schematic representation of the Qpct locus organization. The diagram is not depicted to scale. Hatched boxes represent exons. Solid line represents chromosome sequence. Functionally relevant residues are highlighted.

At the functional level, residues important for the catalytic function of the protein are known in exon 3 (residue H141, see FIG. 2), exon 4 (E202 and E203) and exon 7

(H331). Residues important for binding to the substrate were also characterised in exon 3 (D160) and exon 5 (D249).

2. Strategy for the Development of Qpct Knock-Out Models

The aim of the present invention—the generation of both constitutive and conditional Qpct Knock-out models—has been achieved by flanking the targeted region with two LoxP sites, allowing its ubiquitous or tissue specific deletion following Cre-recombinase action.

Due to the size of Qpct gene, it is not possible to delete the whole gene using classical genome engineering methodology. Based on the functional data described below, Qpct exons 4 and 5 were targeted.

Figure 3:
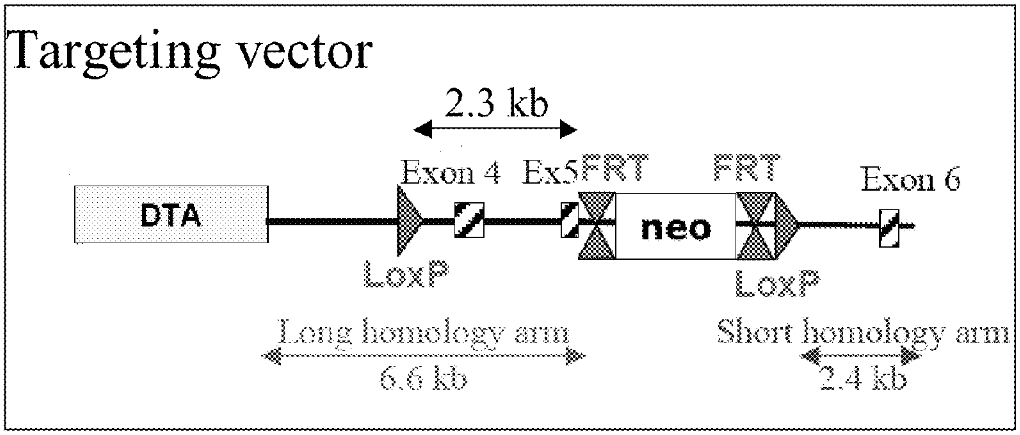
FIG. 3 is a schematic representation of the targeting vector. Hatched boxes represent Qpct exons. Solid line represents Qpct intronic sequence. LoxP and FRT elements are shown as differently oriented triangles and are indicated. Neo and DTA boxes represent the neomycin positive selection cassette and the DTA negative selection cassette, respectively.

Qpct Exon 4 and 5 Targeting:

- Two catalytic residues encoded in exon 4 are deleted.
- Substrate binding residue D248 encoded in exon 5 is deleted.
- Reduced size of the targeted region to be deleted. This increases the probability of the homologous recombination step and allows efficient Cre-mediated recombination.
- The knock-out results in a frame shift leading to the generation of an early stop codon in exon 6 and thus in the loss of the N terminal part of the protein.
- Should an alternative splicing even occur between exon 3 and 7 after the deletion of the targeted region, an early stop codon also appears at the beginning of exon 7. This guarantees that neither exon 6 nor exon 7 can be translated with the Knock-out strategy proposed.
- The design of a targeting vector, central to the development of the two models, is illustrated in FIG. 3, and displays the following features:
- Introduction of two LoxP sites flanking the Qpct exons 4 and 5. One of these LoxP sites (distal LoxP site) will be inserted in intron 3, in the long homology arm. The second LoxP site will be inserted in intron 5. This LoxP site will be associated with the neomycin selection cassette (see below).
- Insertion of negative and positive selection cassettes:
  - An FRT-flanked neomycin positive selection cassette will be inserted (in association with a LoxP site) in the targeting vector, to allow the selection of the transfected ES cell clones. The FRT sites allow the deletion of the neomycin selection cassette under the Flp-recombinase action.
  - A Diphtheria Toxin A (DTA) negative selection cassette will also be included at one extremity of the targeting vector in order to enhance the homologous recombination event at the 5' of the targeting vector Example 2

Figure 4:
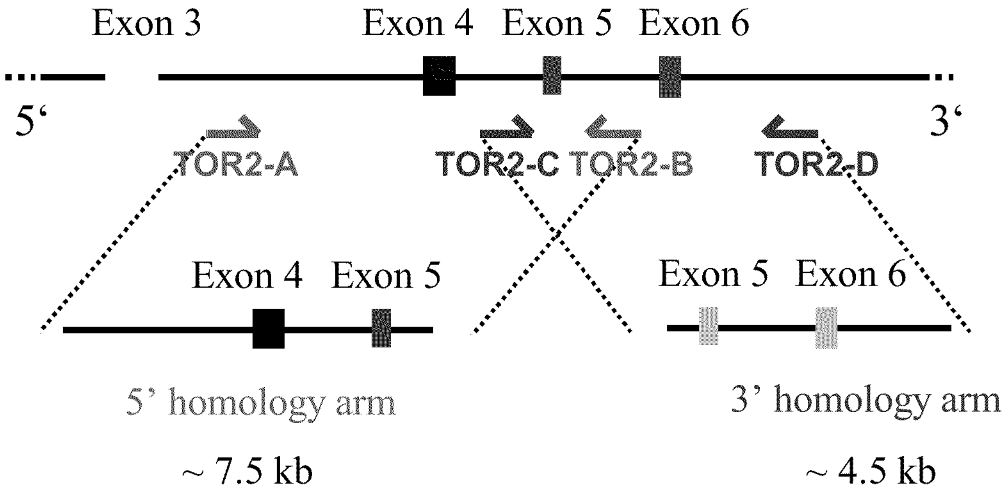
FIG. 4 is a schematic representation of the murine Qpct gene cloning. The diagram is not depicted to scale. Boxes represent exons. Solid line represents intronic sequence. The approximate locations of the primers that were designed for the amplification of the 2 fragments of homology are represented by half arrows. The two resulting fragments are depicted above.

2.1. Cloning and Sequencing of the Mouse Qpct Homology Regions 2.1.1 Cloning of the Mouse Qpct Homology Regions The first step of the project consisted of the cloning of about 12 kb mouse genomic DNA fragment encompassing Qpct exons 4 to 6. This material was used to generate the homology arms required for the construction of the targeting vector. As illustrated in FIG. 4, it was cloned as two overlapping fragments:

- A 5' fragment containing the Qpct exons 4 and 5 corresponding to the 5' homology arm.
- A 3' fragment containing the Qpct exons 5 and 6 corresponding to the 3' homology arm.

In order to ensure the successful amplification of the homology regions, two BAC clones were isolated by screening of a murine 129-mouse BAC DNA library (CT7/Invitrogen) with a 544 bp probe containing Qpct exon 5. These BAC clones are localised on membrane 201 of the library (Invitrogen/ResGen, BAC membrane order Cat#96051). The clones are referenced 201L13 and 201L14 (Invitrogen/ResGen, BAC clone order Cat#96022).

Three primer sets were designed for the amplification of each homology fragment. The three primer pairs were tested for each amplification and the optimal combination was selected for the amplification of the Qpct homology arms. The amplifications were performed on the 201L13 BAC clone with 15 PCR cycles in order to reduce the risk of mutations introduced during the amplification.

The details of the PCR amplification for the two fragments are as follows:

- Proof reading thermostable Taq polymerase: "Expand long template PCR system" kit (Roche Diagnostics).
- PCR matrix: the amplifications were performed using the 201L13 BAC vector (Invitrogen/ResGen, BAC clone order Cat#96022).
- Primer sequences:

| | SEQ ID No: |
|---|---|
| Amplification of the 5' long homology arm | |
| TOR2-A1: 5' GTAGCTGGGATTACAGGAATGTGCC 3' | 1 |
| TOR2-B1: 5' GTCCTGAAGTTTGAGAACCACTGGC 3' | 2 |
| Amplification of the 3'short homology arm | |
| TOR2-C3: 5' GCTAACTTTGCTAAGTCAGGAGGCC 3' | 3 |
| TOR2-D3: 5' TCTACCTCACACCAGTCAGAATGGC 3' | 4 |

PCR Conditions:

94° C. for 2 min
94° C. for 30 s,
65° C. for 30 s×15 cycles
68° C. for 7 min for A/B primers
4 min for C/D primers
68° C. for 10 min Expected Sizes:

A1/B1 fragment: 7299 pb
C3/D3 fragment: 4901 pb 2.2 Sequencing of the Mouse Qpct Homology Regions The A1/B1 and C3/D3 PCR fragments, containing the long and short homology arms, respectively, were then sub-cloned into the pCR4-TOPO vector (Stratagene). For each fragment, three independent subclones have been fully sequenced.

Long Arm of Homology

The sequences obtained from the 3 clones containing the 129Sv/Pas genetic background PCR amplified A1/B1 fragment were first aligned with each other to identify putative mutations introduced by the PCR amplification.

Then, the 129Sv/Pas sequences generated were aligned with the C57BL/6 sequence available in a public database. This enabled the determination of the polymorphism between the C57BL/6 and 129Sv/Pas strains in the region of interest.

One of the sequenced clones presented no mutation in the whole amplified region. This clone has been chosen for the following cloning steps and is referred to as TOR2-TOPO- LA. The fragment of the Qpct DNA sequence, which is contained in the TOR2-TOPO-LA clone, is represented by the sequence of SEQ ID NO. 24. The two other clones presented 2 and 5 mutations, respectively.

The alignment with the C57BL/6 sequence leads to the following conclusions:

- Sequence deletions: 5 small regions (between 1 and 22 bp long) are absent in the 129Sv/Pas sequence compared to the C57BL/6 one. These deletions are all located in intron 3.
- Sequence insertions: 3 small regions (between 1 and 9 bp long) are present only in the 129Sv/Pas sequence. Two of these insertions are located in intron 3, the last one is inserted in intron 4.
- 184 base substitutions are distributed all over the long arm of homology sequence.

Taken together, these data suggest that the polymorphism rate between the C57BL/6 and the 129Sv/Pas genetic background within the 7.3 kb long arm of homology is about 2.5%. This polymorphism rate is 10 times higher than the average rate usually observed in other loci.

Short Arm of Homology

The sequences obtained from the 3 clones containing the 129Sv/Pas genetic background PCR amplified C3/D3 fragment were first aligned with each other to identify putative mutations introduced by the PCR amplification.

Then, the 129Sv/Pas sequences generated were aligned with the C57BL/6 sequence available in a public database. This enabled the determination of the polymorphism between the C57BL/6 and the 129Sv/Pas strains in the region of interest.

Two of the sequenced clones presented no mutation in the whole amplified region. One of these two clones was chosen for the following cloning steps and is referred to as TOR2-TOPO-SA. The fragment of the Qpct DNA sequence, which is contained in the TOR2-TOPO-SA clone is represented by the sequence of SEQ ID NO. 25. The third clone sequenced presented 2 mutations.

The alignment with the C57BL/6 sequence leads to the following conclusions:

- Sequence insertion: a 28-bp region is present only in the 129Sv/Pas sequence, in a region presenting some repeats.
- 122 base substitutions are distributed all over the short arm of homology sequence.

Taken together, these data suggest that the polymorphism rate between the C57BL/6 and the 129Sv/Pas genetic background within the 4.9 kb short arm of homology is fairly high (about 3%).

The targeting vector construction strategy and screening strategies were designed based on the sequence generated from the cloning of Qcpt exons 3 to 6.

Example 3

Construction of the Targeting Vector and Positive Control Vector

Figure 5:
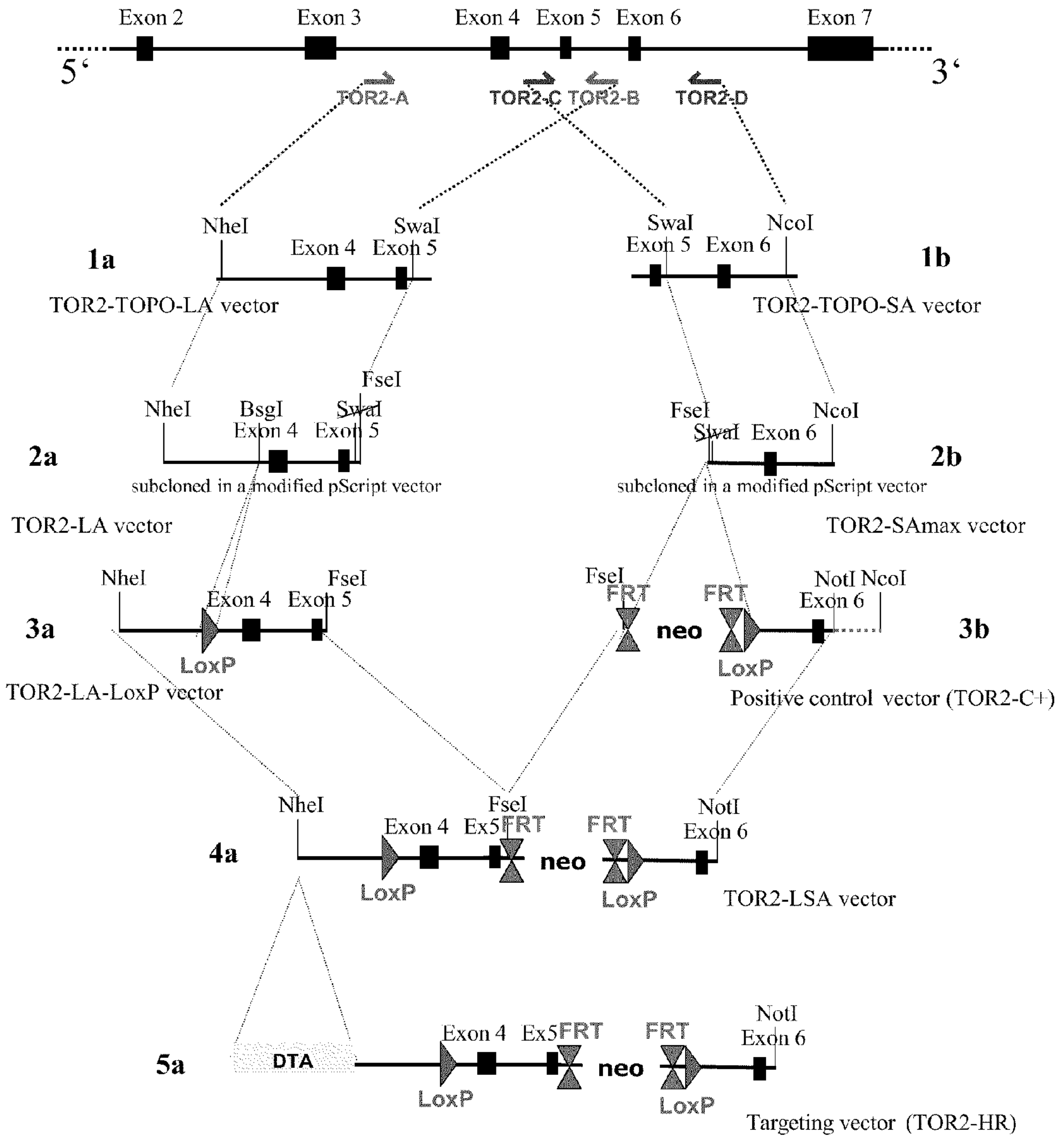
FIG. 5 is a schematic representation of the targeting vector construction strategy. The diagram is not depicted to scale. Cloning steps are represented by circled numbers and are described in the working examples.

The global strategy for the final targeting vector construction is depicted schematically in FIG. 5. This construction can be sub-divided into 8 steps (circled numbers in FIG. 5) performed in parallel.

Steps 1a and 1b: The 5' and 3' homology arms were PCR amplified from mouse 129Sv/Pas genomic DNA. The short arm of homology contains an extended region (indicated as a green dotted line in 3b FIG. 5) that is not present in the final targeting vector (see 4a and 5a, FIG. 5).

Steps 2a and 2b: The two homology arms were subcloned in pScript vectors containing a modified linker with all the restriction sites used for the construction of the targeting vector.

Step 3a: A distal LoxP site was introduced at the BsgI site in intron 3. This distal LoxP site was introduced together with a SwaI and BamHI restriction sites located downstream of the LoxP site. The restriction sites are used for the detection of the distal LoxP site in ES cell clones and for the Southern analysis of the clones.

Step 3b: An FRT-PGK-neomycin-FRT-LoxP positive selection cassette, proven to be efficient in ES cells, was subcloned into intron 5, upstream of the extended 3' homology arm. This step leads to the generation of the positive control vector subsequently used for PCR screening set up (see below).

Step 4: The 5' long homology arm, containing the distal LoxP site, was cloned together with the 3' short arm of homology. This latter short arm is shortened at its final size, ending at the NotI site in intron 6.

The resulting vector, referred to as TOR2-LSA vector, was used as a targeting vector and was electroporated in ES cells.

Step 5: Sub-cloning of a Diphteria Toxin A (DTA) negative selection cassette upstream of the 5' long homology arm.

The TOR2-LSA vector (vector without DTA) was electroporated into ES cells while trying to subclone the DTA cassette. Indeed, the DTA selection cassette helps to counterselect the ES cell clones in which the targeting vector has been integrated randomly in the genome, but is not mandatory.

The targeting vector displays the following features:

- Homology arms isogenic with the ES cell line that will be used (129Sv/Pas).
- Presence of exons 4 to 6 of the Qpct gene.
- Total homology with targeted allele about 9 kb.
- Asymmetrical homology arms (5' long arm: 6.6 kb, 3' short arm: 2.4 kb).
- Positive selection neomycin gene flanked by FRT sites. The FRT-flanked selection cassette can be removed using the Flp recombinase.
- LoxP sites flanking the exons 4 and 5 and allowing their deletion under the Cre-recombinase action. This deletion generating Qpct Knock-out animals can be performed in vivo by breeding the line with Cre-expressing mice. Depending on the ubiquitous or tissue specific expression of the Cre in the mouse line used, a constitutive or conditional Qpct Knock-out will be obtained.
- The distal LoxP site is introduced at a reduced distance (3 kb) from the neomycin selection cassette. This favours its integration during the homologous recombination step.

Example 4

Design and Setting Up of the Screening Strategy for the Detection of Homologous Recombination Events It is absolutely crucial to design screening strategies allowing a quick and unequivocal identification of the homologous recombination event in ES cells. The screening strategy is based on an initial PCR screening for a 3' targeting event, then a PCR screening for a 5' targeting event. The clones identified by PCR will then be confirmed by Southern blot analysis.

4.1 PCR Screening for Detection of a Homologous Recombination Event

Screening for 3' Targeting Event:

The initial screening for detection of the expected integration of the targeting vector is achieved by PCR amplification over the 3' short arm of homology. This PCR is performed using a forward primer (TOR2-H, FIG. 6) hybridizing in the neomycin selection cassette and a reverse primer (TOR2-I, FIG. 6) located downstream of the targeting vector homology sequence. Because of its localisation, this primer set allows unequivocal and specific detection of the 3' integration of the targeting vector in the Qpct locus.

Three sets of H/I primers (TOR2-H1/TOR2-I1 to TOR2-H3/TOR2-I3, see below) were designed to optimise the quality of the screening. This screening was first set up on a positive control vector (see below and FIG. 6), on wild type 129Sv/Pas genomic DNA and on positive control vector diluted in genomic DNA as follows:

- No DNA
- 0.1 copy equivalent genome* of control DNA
- 0.5 copy equivalent genome* of control DNA
- 1 copy equivalent genome of control DNA
- 10 copy equivalent genome of control DNA
- 150 ng of 129Sv/Pas genomic DNA
- 150 ng of genomic DNA+0.1 copy equivalent genome of control DNA
- 150 ng of genomic DNA+0.5 copy equivalent genome of control DNA
- 150 ng of genomic DNA+1 copy equivalent genome of control DNA
- 150 ng of genomic DNA+10 copy equivalent genome of control DNA (*) 1 copy equivalent genome of control DNA is the weight of control DNA containing the same number of copies as in 150 ng of genomic DNA.

1 copy equivalent genome=length of control vector (bp)× 150/6.109 bp. Thus, for TOR2-C+ vector of 7975 bp, 1 copy equivalent genome is 2.0 10-4 ng.

This procedure allows to set-up a PCR screening which is sensitive enough to detect 1 copy equivalent genome of control DNA in genomic DNA. This is required for a reliable screening of the ES cells.

3' End PCR Conditions:

Taq polymerase: from the "Expand long template PCR system" kit (Roche diagnostics).

| Primer sequences: | SEQ ID No: |
|---|---|
| TOR2-H1: 5' GTGCTACTTCCATTTGTCACGTCC 3' | 5 |
| TOR2-I1: 5' TGTGGGACATCAATGAGAGGAGAG 3' | 6 |
| TOR2-H2: 5' CTACTTCCATTTGTCACGTCCTGCACG 3' | 7 |
| TOR2-I2: 5' GTGCTACTTCCATTTGTCACGTCC 3' | 8 |
| TOR2-H3: 5' CCAGTCATAGCCGAATAGCCTCTCC 3' | 9 |
| TOR2-I3: 5' AGGAGTTGGTGGGTTAGTGAGCAGG 3' | 10 |

PCR mix and program:

| Reaction Mix | |
|---|---|
| Genomic DNA from ES cells | 400.0 ng |
| dNTP 10 mM | 2.5 μl |

-continued

| | |
|---|---|
| Buffer 3 (10 x) | 5 μl |
| Taq Polymerase (Qiagen) | 0.75 μl |
| Primer 1 (100 pMol/μl) | 0.15 μl |
| Primer 2 (100 pMol/μl) | 0.15 μl |
| Reaction Volume | 50 μl |

Reaction conditions

| Step | Temp. | Time | Cycles |
|---|---|---|---|
| Denaturing | 94° C. | 120 s | 1x |
| Denaturing | 94° C. | 30 s | 35x |
| Annealing | 65° C. | 30 s | 35x |
| Extension | 68° C. | 180 s | 35x |
| Completion | 68° C. | 600 s | 1x |

Expected sizes:

| | |
|---|---|
| TOR2-H1/TOR2-I1 primer set: | 3284 bp |
| TOR2-H2/TOR2-I2 primer set: | 2900 bp |
| TOR2-H3/TOR2-I3 primer set: | 3555 bp |

No amplification is expected on wild type DNA as TOR2-H hybridises with the neomycin cassette.

The three sets of primers were tested on serial dilutions of the positive control vector plasmid TOR2-C+ spiked in genomic DNA extracted from wild type 129Sv/Pas ES cells as described above.

Figure 7:
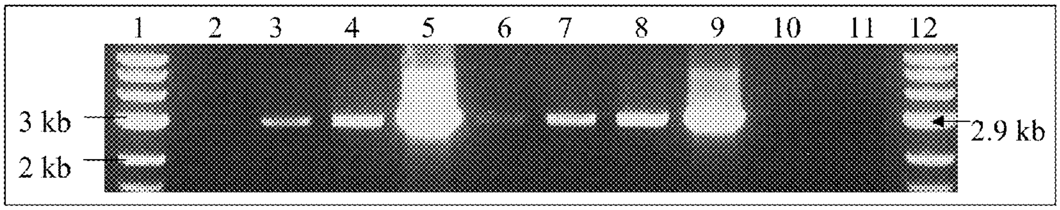
FIG. 7 is an image of a gel showing setting up of the 3' end PCR screening (GX1406-TOR2-H2/GX2141-TOR2-I2 primers). Lanes 1 and 12: 1 kb DNA ladder (NEBioLabs). Lane 2 to 5: 0.1, 0.5, 1, 10 genomic equivalent copies of TOR2-C+ plasmid. Lane 6 to 9: 0.1, 0.5, 1, 10 genomic equivalent copies of TOR2-C+ plasmid diluted in 150 ng of genomic DNA extracted from wild type 129Sv/Pas ES cells. Lane 10: 150 ng of genomic DNA extracted from wild type 129Sv/Pas ES cells. Lane 11: dd H2O.

The primer set TOR2-H2/TOR2-I2 gave the optimal results and was selected for the screening. As illustrated in FIG. 7, TOR2-H2/TOR2-I2 primers give rise to the detection of the expected 2.9 kb band. The PCR sensitivity allows the detection of 0.1 copy equivalent genome (lanes 2 and 6 in FIG. 7), fulfilling the PCR set up requirement. Furthermore, specificity of the PCR reaction is validated since no signal is observed on genomic DNA extracted from wild type 129Sv/Pas ES cells (see lane 10 in FIG. 7).

Primer set TOR2-H2/TOR2-I2 was tested under conditions similar to recombinant genomic structure. This was achieved by transfecting TOR2-C+ positive control vector into ES cell. This protocol has been established to test the specificity of the primers and the sensitivity of the PCR reaction. The results are illustrated in FIG. 8.

Figure 8:
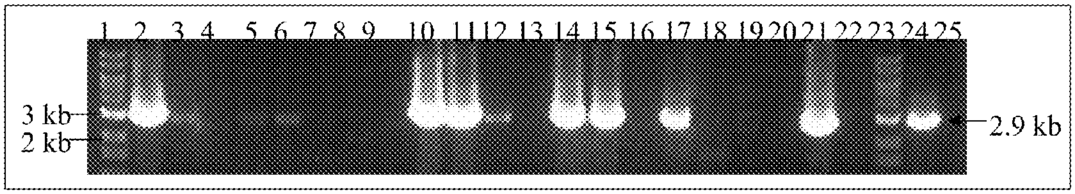
FIG. 8 is an image of a gel showing setting up of the 3' integration event PCR reaction on ES cells transfected with TOR2-C+ vector. Lanes 1 and 23: 1 Kb ladder (NEBioLabs). Lanes 2 to 22: ES cell clones transfected with TOR2-C+ vector. Lane 24: 1 copy of TOR2-C+ vector. Lane 25: dd H2O.

Among 39 resistant control ES cell clones screened, 13 showed the expected 2.9 kb band, as illustrated for 7 clones in FIG. 8. This demonstrated that the PCR screening is reliable for the screening of resistant clones obtained after electroporation of TOR2-C+ vector. ES cell stable transfectant clones 1B9 and 1A1 were selected in order to be used as positive control during the screening of the homologous recombination event.

Screening for 5' Targeting Event:

TOR2-J2/TOR2-K2 primers were designed to detect the expected integration of the 5' end of the targeting vector. The forward primer (TOR2-J2, FIG. 9) is located upstream of the long arm of homology and the reverse primer (TOR2-K2, FIG. 9) is located in intron 4. Because of its localisation, this primer set allows unequivocal and specific detection of the 5' integration of the targeting vector in the Qpct locus.

5' End PCR Conditions:

Taq polymerase: from the "Expand long template PCR system" kit (Roche diagnostics).

| Primer sequences: | SEQ ID No: |
|---|---|
| TOR2-J2: 5' GCCTTCTAAGTAGCTGGGATTACAGG 3' | 11 |
| TOR2-K2: 5' GAGACCCATACAGAGAATCTTGAGGG 3' | 12 |

PCR mix and program:

| Reaction Mix | | Reaction conditions Step | Temp. | Time | Cycles |
|---|---|---|---|---|---|
| Genomic DNA from ES cells | 400.0 ng | | | | |
| dNTP 10 mM | 2.5 µl | Denaturing | 94° C. | 120 s | 1x |
| Buffer 3 (10x) | 5 µl | Denaturing | 94° C. | 30 s | 35x |
| Taq Polymerase (Qiagen) | 0.75 µl | Annealing | 65° C. | 30 s | 35x |
| Primer 1 (100 pMol/µl) | 0.15 µl | Extension | 68° C. | 180 s | 35x |
| Primer 2 (100 pMol/µl) | 0.15 µl | Completion | 68° C. | 600 s | 1x |
| Reaction Volume | 50 µl | | | | |

Expected size for PCR products are:

| PCR product Profile after SwaI digestion | | |
|---|---|---|
| Wild type allele | 4597 bp | 4597 bp |
| Targeted allele | 4649 bp | 4018 + 631 bp |

The 5' end PCR screening using the TOR2-J2/TOR2-K2 set of primers was set up on wild type DNA extracted from ES cells and tail biopsies. The results are illustrated in FIG. 10 below.

Figure 10:
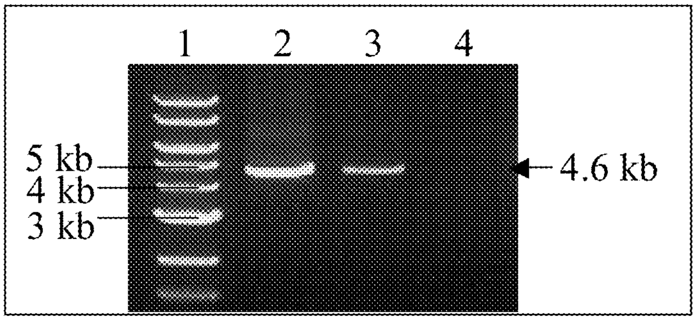
FIG. 10 is an image of a gel showing setting up of the 5' end PCR screening (GX2633-TOR2-J2/GX2634-TOR2-K2 primers). Lane 1: 1 kb DNA ladder (NEBioLabs). Lane 2: 150 ng of genomic DNA extracted from wild type 129Sv/Pas ES cells. Lane 3: 10 ng of genomic DNA extracted from wild type C57BL/6 tail biopsies. Lane 4: dd H2O.

As illustrated in FIG. 10, the expected 4.6 kb band is observed after amplification on genomic DNA (extracted from ES cells and tail biopsies), using GX2633-TOR2-J2/GX2634-TOR2-K2 primers. This validates the PCR screening for the detection of the distal LoxP site both in ES cells and on tail biopsies.

4.2 Southern Blot Analysis for the Detection of the 5' and 3' Targeting Event

The integrity of both 5' and 3' end regions after the homologous recombination at the Qpct locus is assessed on the PCR-selected ES cell clones using Southern blot. The restriction maps of the endogenous, targeted Qpct Flp- and Cre-deleted loci are depicted in FIG. 11.

Figure 11:
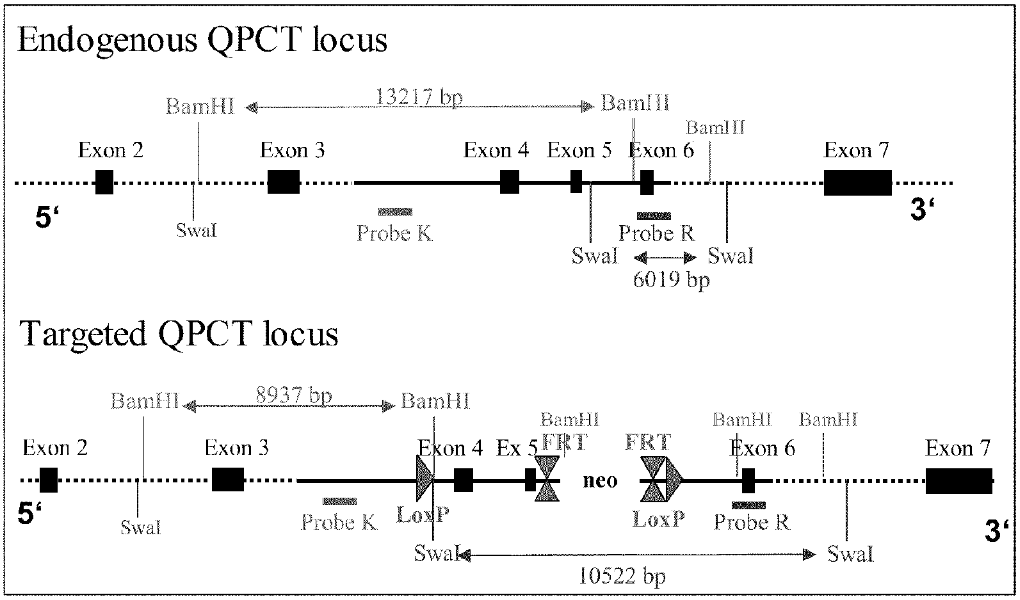
FIG. 11 is a schematic representation of the 5' and 3' Southern blot screening for the homologous recombination event. Solid and dotted lines represent the intronic gene sequences located inside and outside of the targeted region, respectively; hatched boxes represent Qpct exons. LoxP sites are shown as triangles, FRT sites are represented as double triangles. Small rectangles represent the K and R Southern probes. Relevant restriction sites for Southern blot screening and the corresponding detected fragments are indicated with double arrows. The diagram is not depicted to scale.

Both 5' and 3' Southern blots were performed using restriction enzymes cutting upstream of the 5' homology arm or downstream of the 3' homology arm (FIG. 11).

The K and R probe sequences were BLASTed against murine genomic databases in order to select the probes with the best specificity based on in silico analysis. Southern blots were set up on wild type genomic DNA in order to validate probe specificity before proceeding to the confirmation screening itself.

Southern Blot Validation of 5' Targeting Event:

Southern blot analysis to test the 5' end homologous recombination is based on a BamHIH digestion of the genomic DNA and detection using a 482 bp 5' internal K probe located in intron 3 (see FIG. 11). This K probe is AvrII/SacI subcloned from the TOR2-TOPO-LA vector.

Wild type genomic DNA digested by BamHI and hybridized with the designed K probe gives a band, the size is around 13.2 kb, while recombinated genomic DNA is expected to give a 8.9 kb band (see FIG. 11).

The hybridisation conditions used are indicated below:

Pre-hybridisation and hybridisation: 4×SSC, 1% SDS, 0.5% skimmed milk, 20 mM EDTA, 100 µg/ml herring sperm, at 65° C. for 18 h.

Washings: 2 times 3×SSC, 1% SDS at 65° C. for 15 min, then 2 times 0.5×SSC, 1% SDS at 65° C. for 15 min.

Exposure: 3 days on BioMax MS films with BioMax intensifying screens.

Preparation of the 5' K Southern blot probe:

TOR2-TOPO-LA vector is digested by AvrII/SacI enzymes to obtain 3 fragments at 8231, 2588 and 482 bp The K probe is obtained by purification of the 482 bp fragment.

Expected band sizes: Wild type Qpct allele: 13.2 kb

Recombinated Qpct allele: 8.9 kb

This Southern blot strategy was tested on genomic DNA extracted from wild type 129Sv/Pas and 129Ola ES cells and C57BL/6 wild type tail biopsies (data not shown). The 5' K probe has been successfully validated for both ES cell genotyping and characterisation of heterozygous and homozygous mice.

Southern Blot Validation of 3' Targeting Event:

Southern blot analysis to test the 3' end homologous recombination is based on a SwaI digestion of the genomic DNA and detection using a 406 bp 3' internal R probe located in exon 6 (see FIG. 11). This R probe is amplified by PCR using TOR2-R1 and TOR2-R2 primers (see below).

Wild type genomic DNA digested by SwaI and hybridized with the designed R probe gives a band whose size is about 6 kb, while recombinated genomic DNA is expected to give a 10.5 kb band (see FIG. 11).

The hybridisation conditions used are indicated below:

Pre-hybridisation and hybridisation: 4×SSC, 1% SDS, 0.5% skimmed milk, 20 mM EDTA, 100 µg/ml herring sperm, at 65° C. for 18 h.

Washings: 2 times 3×SSC, 1% SDS at 65° C. for 15 min, then 2 times 0.5×SSC, 1% SDS at 65° C. for 15 min.

Exposure: 3 days on BioMax MS films with BioMax intensifying screens.

| Amplification of the 3'Southern blot probe: | SEQ ID No |
|---|---|
| TOR2-R1 5' GGGCTTTCTCAGTGTTCTTAACATTCC 3' | 13 |
| TOR2-R2 5' TCTATCATTGATTCTCAGGATGCGG 3' | 14 |

This Southern blot strategy was tested on genomic DNA extracted from wild type 129Sv/Pas and 129Ola ES cells and C57BL/6 wild type tail biopsies (see FIG. 12) in order to validate the probe for both ES cell genotyping and characterisation of heterozygous and homozygous mice.

Figure 12:
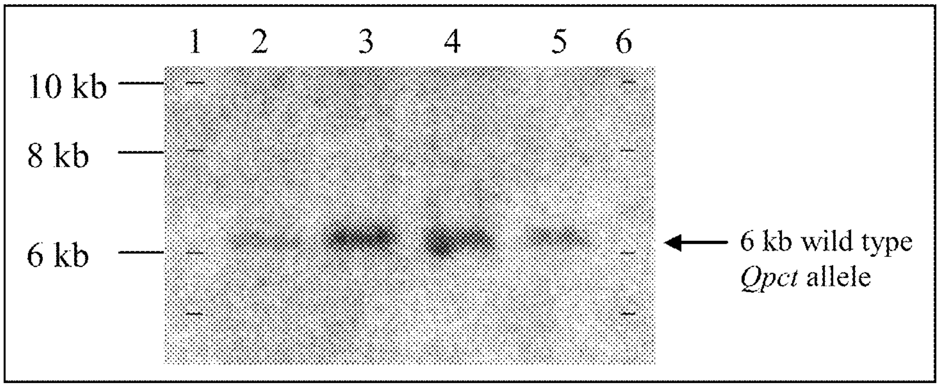
FIG. 12 is an image of a gel showing setting up of the 3' Southern blot screening strategy on wild type DNA. Lane 1 and 6: 1 Kb ladder (NEBioLabs). Lane 2: 4 μg of genomic DNA extracted from wild type 129Sv/Pas ES cells. Lane 3: 15 μg of genomic DNA extracted from wild type 129Sv/Pas ES cells. Lane 4: 15 μg of genomic DNA extracted from wild type 129Ola ES cells. Lane 5: 15 μg of genomic DNA extracted from wild type C57BL/6 tail biopsies.

As presented in FIG. 12, the expected 6 kb band was observed after SwaI digestion of 129Sv/Pas and C57BL/6 genomic DNA. This result validates the 3' end Southern blot strategy.

Example 5

Design of the Screening Strategy for the FLP- and CRE-Mediated Excision Events The Flp-mediated excision enables the deletion of the neomycin cassette. This deletion can be performed in vitro, by transfection of the targeted ES cell clones with a validated Flp-expressing plasmid, or in vivo, by breeding the Qpct targeted animals with ubiquitous Flp-expressing mice.

The Cre-mediated deletion of the Qpct exons 4 and 5, leading to the Qpct Knock-out mouse line will be performed in vivo.

PCR and Southern blot screening enable the detection of the wild type, the targeted Flp-mediated neomycin-deleted and the Cre-mediated Knock-out alleles.

Figure 13:
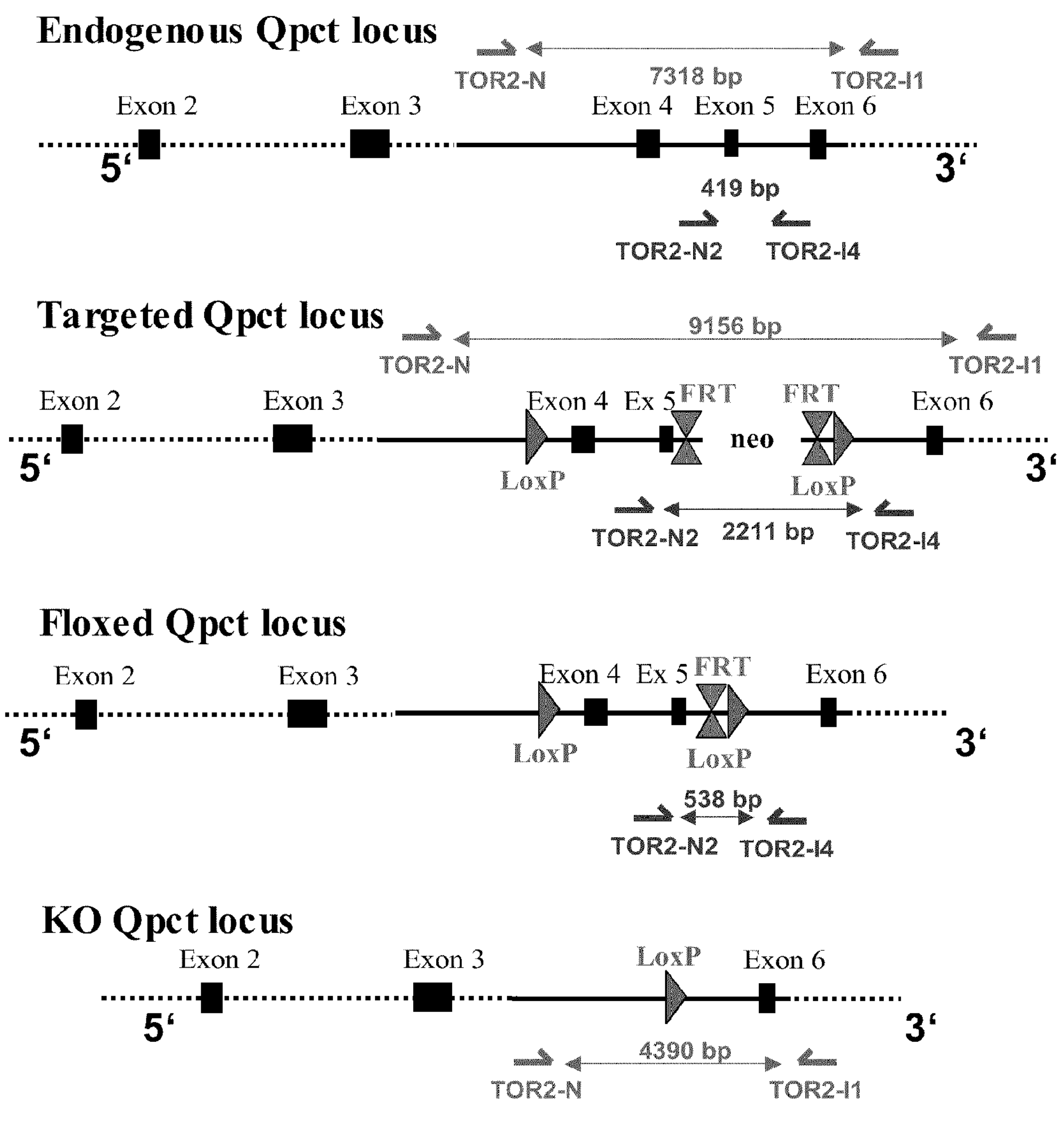
FIG. 13 is a schematic representation of PCR identification of the Cre-mediated and Flp-mediated excisions events. Solid and dotted lines represent Qpct intronic sequences located inside and outside of the targeting vector, respectively. Hatched boxes represent Qpct exons. FRT sites are shown as double triangles, LoxP sites are represented by triangles. Half arrows illustrate the primers' localizations. The primers used for the detection of the Cre-mediated events are TOR2-N and TOR2-I1, and for the Flp-mediated events TOR2-N2 and TOR2-I4. The size of the PCR product is given below the primers.

5.1 PCR Screening Strategy for the Detection of the Flp- and Cre-Mediated Excision Events TOR2-N/TOR2-I1 primers were designed for the detection of Cre-mediated excision events. The forward primer TOR2-I1 is located in the long arm of homology, upstream of the neomycin cassette (FIG. 13). The forward primer TOR2-N is located downstream of the 3' short arm of homology.

Due to the primer set localisation, this PCR allows an unequivocal detection of the Cre-mediated excision of the exons 4-5 and neomycin selection cassette.

TOR2-N2/TOR2-I4 primers were designed for the detection of Flp-mediated excision events. The forward primer TOR2-N2 is located in the long arm of homology, right upstream of the neomycin cassette (FIG. 13). The forward primer TOR2-I4 is located in the short homology arm, downstream of the neomycin cassette.

Due to the primer set localisation, this PCR allows the detection of the Flp-mediated excision of the neomycin selection cassette. Since this PCR is using primers located internally to the targeting vector, the genotyping of the animals has to be confirmed by Southern blot analysis.

Cre-Mediated Excision PCR Conditions:

Taq polymerase: from the "Expand long template PCR system" kit (Roche Diagnostics).

| Primer sequences: | SEQ ID No |
|---|---|
| GX2147-TOR2-N:<br>5' AGAGAATGACCACTGCTGAGGATG 3' | 15 |
| GX2140-TOR2-12:<br>5' TGTGGGACATCAATGAGAGGAGAG 3' | 16 |

PCR program:

| PCR cycles | | | |
|---|---|---|---|
| 94° C. | 2 min | | |
| 94° C. | 30 sec | ] | x35 cycles |
| 65° C. | 30 sec | ] | |
| 68° C. | 5 min | | |
| 68° C. | 10 min | | |

| PCR mix | | |
|---|---|---|
| DNA | 30 µl | |
| dNTP | 2.5 µl | 10 mM |
| Buffer | 5 µl | 10x |
| Taq Long expand | 0.75 µl | |
| Forward primer | 0.15 µl | 100 pMol/µl |
| Reverse primer | 0.15 µl | 100 pMol/µl |
| $H_2O$ | to 50 µl | |

Expected size for PCR products is:

| | PCR product |
|---|---|
| Wild type allele | 7318 bp |
| Targeted allele | 9156 bp |
| Cre-mediated excised allele | 4390 bp |

Flp-Mediated Excision PCR Conditions:

Taq polymerase: from the "Expand long template PCR system" kit (Roche Diagnostics).

| Primer sequences: | SEQ ID No |
|---|---|
| GX4354-TOR2-N2:<br>5' TTGGTAAGCATCCAGTTACTAAAGAGC 3' | 17 |
| GX4353-TOR2-14:<br>5' GCAATCGGTTTTAATCACAGTAAGG 3' | 18 |

PCR program:

| PCR cycles | | | |
|---|---|---|---|
| 94° C. | 2 min | | |
| 94° C. | 30 sec | ] | x35 cycles |
| 60° C. | 30 sec | ] | |
| 68° C. | 5 min | | |
| 68° C. | 10 min | | |

| PCR mix | | |
|---|---|---|
| DNA | 30 µl | |
| dNTP | 2.5 µl | 10 mM |
| Buffer | 5 µl | 10x |
| Taq Long expand | 0.75 µl | |
| Forward primer | 0.15 µl | 100 pMol/µl |
| Reverse primer | 0.15 µl | 100 pMol/µl |
| H2O | to 50 µl | |

Expected size for PCR products is:

| | PCR product |
|---|---|
| Wild type allele | 419 bp |
| Targeted allele | 2211 bp |
| Flp-mediated excised allele | 538 bp |

The PCR screening for the detection of the Cre-mediated and Flp-mediated excision events (using the GX2147-TOR2-N/GX2140-TOR2-I2 set of primers and the GX4354-TOR2-N2/GX4353-TOR2-I4 set of primers, respectively) was successfully set up on wild type DNA extracted from ES cells and tail biopsies (data not shown).

Example 6

Preparation of the Targeting Vector

TOR2-LSA plasmid was digested by NotI to obtain its linearization. The 13.6 kb resulting fragment was purified by phenol/chloroform extraction followed by ethanol precipitation. This preparation was then used for ES cell electroporation.

Example 7

Selection and Amplification of Geneticin Resistant ES CELL CLONES

The linear TOR2-LSA plasmid was transfected into ES cells according to the following electroporation procedures:

$100 \times 10^6$ ES cells in the presence of 100 µg of linearized plasmid, 800 Volt, 300 µF. Positive selection was started 48 hours after electroporation, by addition of 200 µg/ml of G418.

This electroporation gave rise to 237 resistant clones. These ES cell clones were amplified in 96-well plates and duplicates of 96-well plates were made. The set of plates containing ES cell clones amplified on gelatin was screened by PCR for the detection of a homologous recombination event.

In order to bypass the difficulties as encountered with the injection of the first series of clones obtained (see below), a second electroporation of the linear TOR2-LSA plasmid was performed under the same conditions. This second electroporation gave rise to 184 resistant clones. These clones were amplified and duplicated as for the first electroporation.

Example 8

Screening of Geneticin Resistant ES Cell Clones 8.1 PCR Screening for Homologous Recombination at the 3' End Using PCR the 237 geneticin-resistant clones (harvested after the first electroporation)+184 geneticin-resistant clones (harvested after the second electroporation) were screened for the detection of the expected homologous recombination event at the 3' end of the targeting vector.

Figure 14:
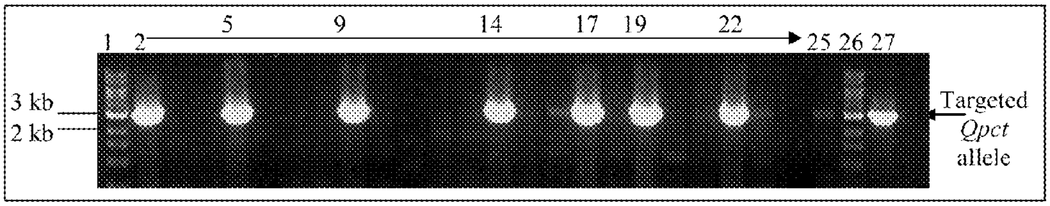
FIG. 14 is an image of a gel showing 3' PCR screening of ES cell clones for detection of correct homologous recombination event. Lanes 1, 26: 1 Kb ladder (NEBioLabs). Lanes 2 to 25: 24 resistant ES cell clones. Lane 2: positive ES cell clone #5A1. Lane 5: positive ES cell clone #5B2. Lane 9: positive ES cell clone #5B4. Lane 14: positive ES cell clone #5A7. Lane 17: positive ES cell clone #5B8. Lane 19: positive ES cell clone #5B9. Lane 22: positive ES cell clone #5A11. Lane 27: Positive control ES clone #6A10.

3' PCR screening using GX1406-TOR2-H2/GX2141-TOR2-I2 primers revealed 14 (1st electroporation)+21 (2nd electroporation) positive clones displaying an amplified fragment of the expected size (2.9 kb). Seven of these positive clones are illustrated in FIG. 14.

The 3' PCR positive clones were confirmed by a second 3' PCR. The 14 positive clones identified from the first electroporation and 10 of the positive clones identified from the second electroporation were further analysed for the homologous recombination event at the 5' end of the targeting vector.

8.2 PCR Screening for a Homologous Recombination at the 5' End

Figure 9:
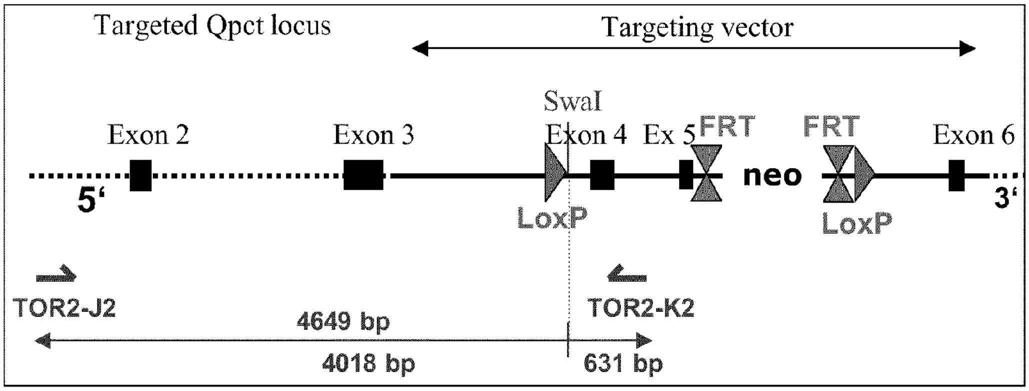
FIG. 9 is a schematic representation of PCR identification of the 5' end homologous recombination event. Solid and dotted lines represent Qpct intronic sequences located inside and outside of the targeting vector, respectively. Boxes represent Qpct exons. FRT sites are shown as double triangles, LoxP sites are represented by triangles. Half arrows illustrate the primers' localizations. The size of the PCR product is given below the primers, as well as the restriction profile obtained after digestion of the PCR product by SwaI.

The screening for the detection of the homologous recombination event at the 5' end of the targeting vector was performed using TOR2-J2 (GX2633) and TOR2-K2 (GX2634) primers (see FIG. 9). The forward primer (GX2633-TOR2-J2) is located upstream of the targeting vector and the reverse primer (GX2634) is located in the long homology arm, downstream of the distal LoxP site (see FIG. 9).

A SwaI digestion of the PCR product enables to discriminate between wild type and targeted alleles and to detect the presence of the distal LoxP site inside the long homology arm (see FIG. 9). Due to the primer set localisation, this PCR, followed by a SwaI digestion of the PCR products, allows an unequivocal and specific detection of the 5' integration of the targeting vector at the Qpct locus.

Figure 15:
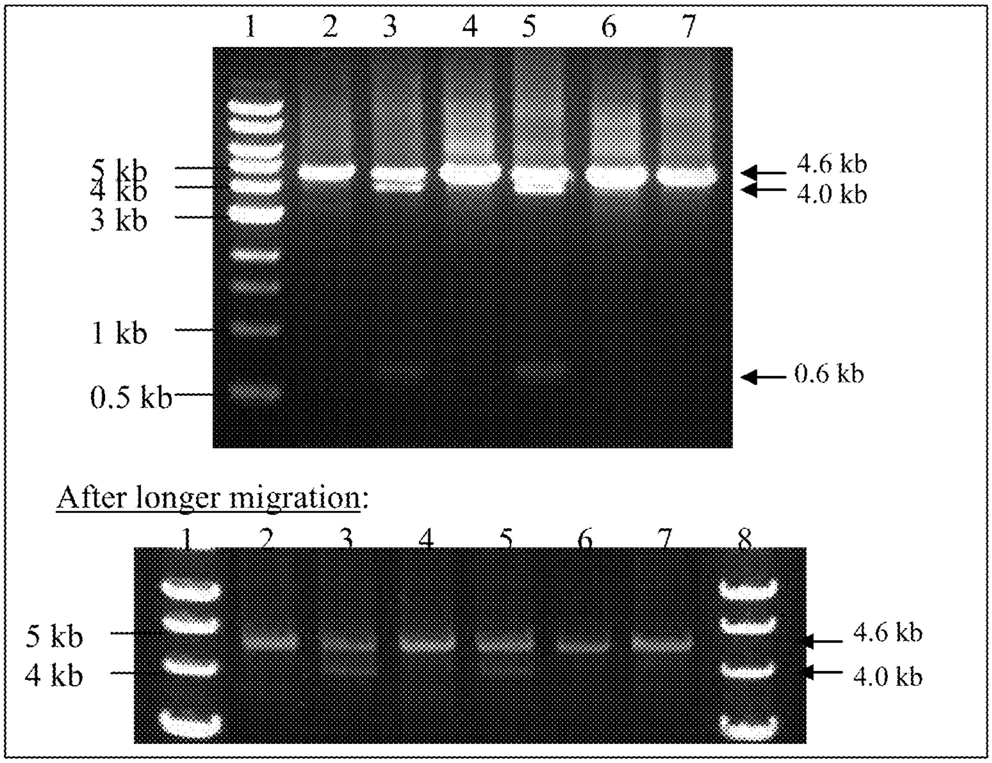
FIG. 15 is a series of images of gels showing 5' PCR screening of ES cell clones for detection of correct homologous recombination event. The panel at the bottom is the same as the top panel after a longer migration of the gel. Lanes 1, 8: 1 Kb ladder (NEBioLabs). Lane 2: ES cell clone #6A3, uncut. Lane 3: clone #6A3, after SwaI digestion. Lane 4: ES cell clone #6C10, uncut. Lane 5: clone #6C10, after SwaI digestion. Lane 6: ES cell clone #6C3, uncut. Lane 7: clone #6C3, after SwaI digestion.

The 5' PCR results are illustrated below for three clones (in FIG. 15).

Among the 14+10 ES cell clones identified positive using the 5' PCR:

- Eleven clones were unambiguously positive at the 5' side: namely clones #6A3, #6C3, 6C10, 5B8, 5C5 5C12, 10A9, 10B2, 11B4, 12A2 and 15B2. As the two clones #6A3 and #6C10 illustrated in FIG. 15, the six positive clones displayed a 4.6 PCR product that was subdivided into a 4 kb and a 0.6 kb fragments after SwaI digestion.
- The results of the 5' PCR were ambiguous for the two clones #5A11 and #5D4 (weak PCR amplification for these two clones).
- For the remaining 11 clones (#5A1, 5B2, 5B4, 5A7, 5B9, 5D4, 9A2, 9B1, 10A3, 10A10 and 11B7), the PCR product was not cut by SwaI, as illustrated for clone #6C30 in FIG. 15. This indicates that these 11 clones did not undergo the expected homologous recombination at the 5' side of the targeting vector.

The 11 positive clones #6A3, #6C3, 6C10, 5B8, 5C5 5C12, 10A9, 10B2, 11B4, 12A2 and 15B2 are thus positive for both 5' and 3' PCR screening. This demonstrated that these clones underwent the expected recombination event on both the 5' long homology arm and the 3' short homology arm. Furthermore, the presence of the LoxP site at the targeted Qpct locus was demonstrated by the SwaI digestion of the PCR product. This point is crucial to allow the future deletion of exons 4 and 5 under Cre-recombinase action, and thus the Qpct gene Knock-Out.

The 11 positive clones were re-amplified in 24-well plates and further analysed by Southern blot at the 5' and 3' sides of the targeting vector.

8.3 Southern Blot Screening

The 11 positive ES cell clones identified by PCR were further tested by 5' Southern blot. This 5' Southern blot is based on a BamHI digestion of the genomic DNA and detection using a 482 bp probe, 5'K probe, located in intron 3, in the long homology arm (see Example 4, item 1.2 and FIG. 5).

Expected band sizes: Wild type Qpct allele: 13.2 kb

Recombinated Qpct allele: 8.9 kb

Figure 16:
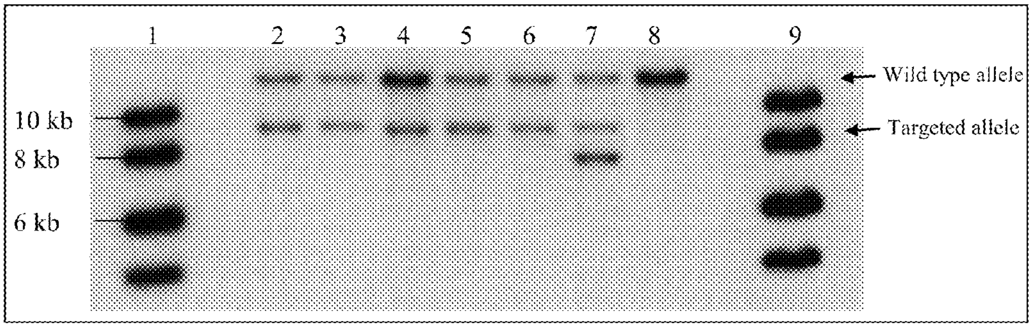
FIG. 16 is an image of a gel showing Southern blot results for the detection of the 5' homologous recombination event. Lanes 1, 9: 1 Kb ladder (NEBioLabs). Lane 2: ES cell clone #5B8. Lane 3: ES cell clone #5C5. Lane 4: ES cell clone #5C12. Lane 5: ES cell clone #6A3. Lane 6: ES cell clone #6C3. Lane 7: ES cell clone #6C10. Lane 8: Wild type ES cell DNA.

As illustrated in FIG. 16 for the 6 positive clones of the first electroporation, the presence of the two bands corresponding to the wild type and targeted Qpct alleles confirmed the PCR screening results for the 11 clones analysed. 4 of the clones, clones #6C10, 10A9, 11B4 and 12A2, displayed an additional band at an unexpected size. Since the probe used was an internal probe (hybridizing inside the targeting vector), the detection of this additional band demonstrated the existence of a random integration of the targeting vector at an unknown locus, in addition to the expected integration of the targeting vector, through a homologous recombination event, at the Qpct locus. Even if this random integrant would be easily segregated from the targeted Qpct allele, the other clones were preferentially selected for the further development of the project.

The 11 ES cell clones were then tested by 3' Southern blot. The 3' Southern blot is based on a SwaI digestion of the genomic DNA and detection using a 406 bp 3' internal R probe located in exon 6 (see Example 4, 1.2 and FIG. 5).

Expected band sizes: Wild type Qpct allele: 6.0 kb

Recombinated Qpct allele: 10.5 kb

Figure 17:
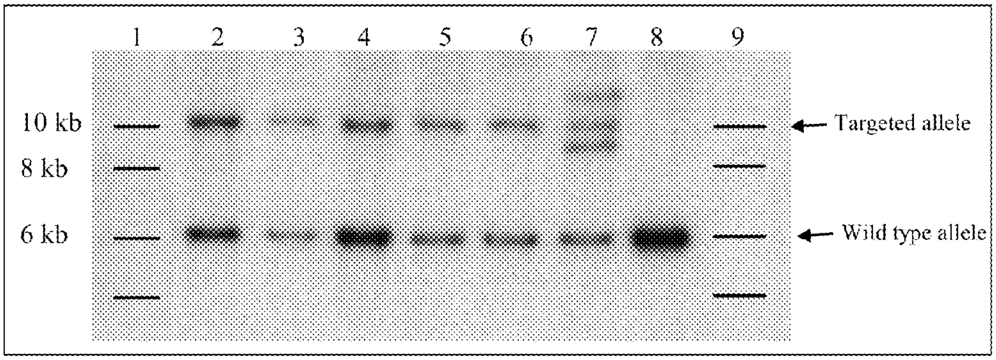
FIG. 17 is an image of a gel showing Southern blot results for the detection of the 3' homologous recombination event. Lanes 1, 9: 1 Kb ladder (NEBioLabs). Lane 2: ES cell clone #5B8. Lane 3: ES cell clone #5C5. Lane 4: ES cell clone #5C12. Lane 5: ES cell clone #6A3. Lane 6: ES cell clone #6C3. Lane 7: ES cell clone #6C10. Lane 8: Wild type ES cell DNA.

As illustrated in FIG. 17 for the 6 positive clones of the first electroporation, the presence of the two bands corresponding to the wild type and targeted Qpct alleles confirmed the PCR screening for the 11 clones analysed. Again, clones #6C10, 10A9, 11B4 and 12A2 displayed additional bands with unexpected sizes, confirming the existence of random integrations of the targeting vector at an unknown locus, in addition to the expected integration of the targeting vector, through a homologous recombination event, at the Qpct locus.

The 7 ES cell clones #5B8, #5C5, #5C12, #6A3 #6C3, #10B2 and #15B2 were thus confirmed by Southern blot as correctly targeted at both 5' and 3' ends of the targeting vector. The last 4 clones #6C10, 10A9, 11B4 and 12A2 were also confirmed as correctly targeted at both 5' and 3' ends of the targeting vector but these clones present an additional random integration of the targeting vector at an unknown locus.

The ES cell clones #5C5, #5C12, #6A3 #6C3, #15B2, #10B2 and #11B4 were selected for the next phase of the project corresponding to the injection into blastocysts.

Example 9

Recombinant ES Cell Blastocyst Injections and Generation of Chimeras 9.1 Injection Sessions Recipient blastocysts were isolated from pregnant C57BL/6 females (Health status SPF-Specific Pathogens free). Based on morphological features, the ES cell clones #5C5, #5C12, #6A3, #6C3, #15B2, #10B2 and #11B4 were selected to be injected into blastocysts.

Injected blastocysts were then re-implanted into OF1 pseudo-pregnant females (Health status SOPF—Specific and Opportunist Pathogens Free). Table 1 summarizes the results obtained from the injection sessions.

9.2 Chimeras

Clone #6A3 was injected into 86 blastocysts and gave rise to 19 pups. 11 chimeras were identified:

8 male chimeras with a percentage of chimerism of 20%, 15%, 10%, 5% (2 chimeras each).

3 female chimeras with a percentage of chimerism of 20% (2 chimeras), 10% Clone #6C3 was injected into 90 blastocysts and gave rise to 16 pups. 8 chimeras were identified:

3 male chimeras with a percentage of chimerism of 30% and 5% (2 chimeras).

5 female chimeras with a percentage of chimerism of 20% (3 chimeras), 15% and 2%. Clone #5C12 was injected into 54 blastocysts and gave rise to 4 pups. 2 chimeras were identified:

2 male chimeras with a percentage of chimerism of 35% and 15%. Clone #5C5 was injected into 54 blastocysts and gave rise to 3 pups. 3 chimeras were identified:

3 female chimeras with a percentage of chimerism of 90%, 60% and 10%. Clone #15B2 was injected into 30 blastocysts and gave rise to 6 pups. 3 chimeras were identified:

1 male chimera with a percentage of chimerism of 75%.

2 female chimeras with a percentage of chimerism of 90% and 1%. Clone #10B2 was injected into 30 blastocysts and did not give rise to any pup. Clone #11B4 was injected into 30 blastocysts and gave rise to 4 pups. 3 chimeras were identified:

3 male chimeras with a percentage of chimerism of 75%, 35% and 8%.

Table 1 below compiles the results of the ES cell blastocyst injection sessions performed and the chimera generation.

TABLE 1

Results from ES cell clones #6A3, #6C3, #5C12, #5C5, #15B2, #10B2 and #11B4 blastocyst injections

| Sessions | Clone number | Injected blastocysts | Foster mothers reimplanted | Pregnant foster mothers | Number of pups/ Date of birth | Still born | Male chimeras (% chimerism) | Female chimeras (% chimerism) |
|---|---|---|---|---|---|---|---|---|
| #1 28/10/05 | #6A3 | 26 | 2 | 1 | 4 16 Nov. 2005 | 0 | 20% | 20%, 10% |
| #2 4/11/05 | #6A3 | 30 | 2 | 1 | 6 24 Nov. 2005 | 0 | 20%, 15%, 10%, 5% | 20% |
| | #6C3 | 60 | 4 | 4 | 13 24 Nov. 2005 | 0 | 30%, 5%, 5% | 20%, 20%, 2% |
| #3 18/11/05 | #6A3 | 30 | 2 | 1 | 9 7 Nov. 2005 | 0 | 15%, 10%, 5% | — |
| #4 2/12/05 | #6C3 | 30 | 2 | 2 | 3 21 Dec. 2005 | 0 | — | 20%, 15% |
| #5 6/01/06 | #5C12 | 24 | 2 | 1 | 4 25 Jan. 2006 | 0 | 35%, 15% | — |
| | #5C5 | 24 | 2 | 0 | — | — | — | — |
| #6 | #5C12 | 30 | 2 | 0 | — | — | — | — |
| 5/03/06 | #5C5 | 30 | 2 | 1 | 3 | 0 | — | 90%, 60%, 10% |
| #7 21/04/06 | #15B2 | 30 | 2 | 1 | 6 10 May 2006 | 0 | 75% | 90%, 1% |
| | #10B2 | 30 | 2 | 0 | — | — | — | — |
| #8 24/04/06 | #11B4 | 30 | 2 | 2 | 4 19 May 2006 | 1 | 75%, 35%, 8% | — |

As the female chimeras have a low probability of germ line transmission, the female chimeras obtained were not selected for further breeding.

Among the male chimeras generated, the four males at 20% (clone #6A3, 2 chimeras), 30% (clone #6C3) and 35% (clone #5C12) were selected for the breeding phase. As germline transmission was obtained from one of these chimeras before the last chimera generated (75% of chimerism, clones #15B2 and #11B4) were sexually mature, these latter chimeras were not used in the following breeding phase.

Example 10

Breeding of Chimeras and Generation of F1 Heterozygous for the Targeted or Cre-Excised Alleles Four chimeric males (displaying 20% to 35% chimerism), generated in the previous phase by blastocyst injection of the ES clone #6A3, #6C3 and #5C12, were mated with wild type C57BL/6J females (health status SOPF—Specific and Opportunist Pathogen Free) to investigate whether the targeted ES cells have contributed to the germ layer. The chimeras were also bred with Flp or Cre “deleter” females (health status SOPF—Specific and Opportunist Pathogen Free) to obtain the deletion of the neomycin selection cassette or Qpct exons 4-5 and selection cassette, respectively.

Table 2 below summarizes the results of chimeras breeding.

TABLE 2

Reporting results of chimera breeding.

| Male Chimera | male | Number of pups | Date of birth | Still born | No. of agouti pups | Tail biopsy No. (genotype) |
|---|---|---|---|---|---|---|
| 20% male chimera (clone #6A3) cage 4134 | C57BL/6 wild type | — | — | — | — | — |
| | C57BL/6 | 9 | 26 May 2006 | 1 | 0 | / |
| | CAG-Flp #196 and #206 | 8 | 28 Apr. 2005 | 1 | 0 | / |
| 20% male chimera (clone #6A3) cage 4135 | C57BL/6 wild type | — | — | — | — | — |
| | C57BL/6 CAG-Flp #199 and #224 | — | — | — | — | — |
| 30% male chimera (clone #6C3) cage 4136 | C57BL/6 wild type | 3<br>8<br>8 | 6 Feb. 2006<br>10 Mar. 2006<br>24 Apr. 2006 | 2<br>2<br>0 | 0<br>0<br>0 | /<br>/<br>/ |
| | 129Sv/Pas CMV-Cre #53 | — | — | — | — | — |
| 35% male chimera (clone #5C12) cage 4416 | C57BL/6 wild type | 10 | 17 May 2006 | 1 | 2 | 35296 (WT)<br>35297 (WT) |
| | 129Sv/Pas CMV-Cre #91 | 9<br>7 | 10 Apr. 2006<br>29 May 2006 | 1<br>0 | NA (129Sv/Pas female) | 34709 (WT)<br>34710 (WT)<br>34711 (WT)<br>34712 (WT)<br>34713 (WT)<br>34714 (WT)<br>34715 (WT)<br>34716 (WT)<br>35437 (Het partially Cre-excised)<br>35438 (Het Cre-excised)<br>35439 (WT)<br>35440 (WT)<br>35441 (Het targeted)<br>35442 (WT)<br>35443 (WT) |

The genotype of the animals is given in bracket (see also text below).
WT: wild type;
Het targeted: heterozygote carrying the targeted Qpct allele;
Het partially Cre-excised: heterozygote carrying the Cre-mediated excised Qpct allele and the targeted Qpct allele;
Het Cre-excised: heterozygote carrying the Cre-mediated excised Qpct allele.

To assess whether the ES cells have contributed to the germ layer of the chimeras, mouse coat colour markers were used. The coat colour marker of the 129Sv/Pas ES cells is dominant over the black coat colour of the C57BL/6J mice. Therefore, mating the chimeras with C57BL/6J mice should yield either black pups, when the germ cells of the chimera are derived from the C57BL/6J cells, or agouti-coloured pups, when the ES cells have contributed to the germ cells.

The presence of agouti pups in the F1 generation when using C57BL/6J mice for breeding is thus evidence for the germline transmission of the ES cells. In ES cells, only one copy of the autosomal target gene is targeted and consequently, assuming germ line transmission occurs, 50% of the resulting agouti offspring should receive the mutated chromosome from the ES cells and 50% should receive the wild type chromosome.

As documented above, the 20% male chimera (clone #6A3) in cage 4135 seems to be sterile as no litter was observed during the 3 month of breeding, despite mating with several different females.

With the 20% male chimera (clone #6A3) in cage 4134 and the 30% male chimera (clone #6C3) in cage 4136, no germ line transmission was observed as the chimeras gave rise to 2 and 3 black litters, respectively.

Finally, the observation of 2 agouti coloured F1 animals derived from the C57BL/6 wild type female mated with the 35% male chimera (clone #5C12) in cage 4416 is evidence of successful germline transmission of the Qpct mutation. These animals were genotyped as wild type (data not shown).

The F1 animals derived from this male chimera and the 129Sv/Pas CMV-Cre #91 female were genotyped to identify heterozygous mice carrying the constitutive Knock-out allele. As the female background is 129Sv/Pas, the mouse coat colour markers cannot be used. All the F1 animals #34709 to 34716 and 35437 to 35443 were thus genotyped as described below.

10.1 PCR Genotyping of the F1 Generation

DNA was prepared from tail biopsies, taken from the 15 resulting pups and was genotyped by two different PCR strategies:

Cre-excision PCR (see FIG. 18) for the detection of the Cre-mediated excision of the LoxP flanked region within the targeted Qpct allele. This PCR yields an amplification product of different size depending on the template used: wild type, targeted or Cre-excised allele.

3' PCR screening (see FIG. 19) that was already used for detection of a homologous recombination event in ES cells. This PCR strategy detects the non-excised, targeted Qpct allele carrying the exons 4 and 5 flanked by the LoxP-FRT-neomycin-FRT cassette and the distal LoxP site.

10.2 PCR Screening for Cre-Mediated Excision Event

The Cre-excision PCR was performed using a forward primer TOR2-N hybridizing in the 5' homology arm, upstream of the distal LoxP site, and a reverse primer TOR2-I1 hybridizing downstream of exon 6 (see FIG. 13). Because of its localisation, this primer pair allows the specific detection of the Cre mediated excision event.

Figure 18:
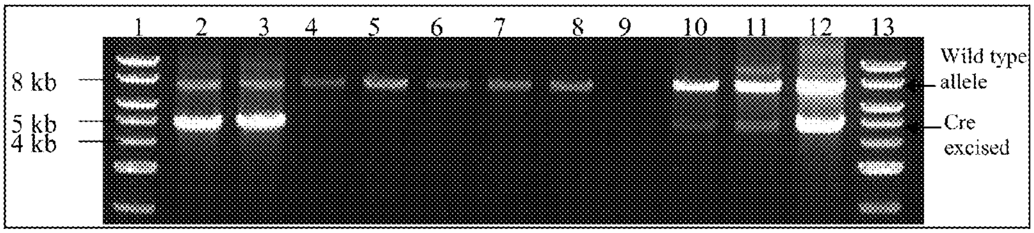
FIG. 18 is an image of a gel showing screening of the F1 animals for the detection of the Cre-mediated excision event. The genotypes of the 7 pups (35437 to 35443 in lanes 2 to 8, respectively) derived from the breeding with Cre deleter mice were tested by PCR using the primer combination TOR2-N/TOR2-I1 to analyse the excision status of the Qpct allele. PCR using DNA from the targeted ES clone 5C12 (lane 11), wild type mouse tail (lane 10) and a 1:100 mixture (lane 12) was used as positive controls. PCR without template (lane 9) served as a negative control. M: 1 kb DNA-Ladder (NEBioLabs).

The Cre-excised allele yields an amplification product of 4.4 kb using the above primer pair, whereas the targeted (non-excised) allele yields an amplification product of 9.2 kb (see FIG. 13). Since both primers hybridize on the wild type non-targeted allele, a further amplification product of 7.3 kb will be obtained from all animals corresponding to the wild type allele. A representative example of the genotyping PCR results is illustrated in FIG. 18. As shown in FIG. 18, the PCR always favours the amplification of the allele yielding the smaller PCR product. The large size of amplification product of the heterozygous wild type or the heterozygous targeted allele may result in a poor amplification efficiency.

The genotyping by Cre-excision PCR indicated that among the 15 tested animals born, 2 animals (#35437 and #35438) carry the Cre-excised allele. The other 13 tested animals were either wild type mice or carry the targeted allele. This latter targeted allele was not unequivocally detected by this PCR strategy, because of the preferential amplification of the shorter PCR products corresponding to the Cre-excised and wild type alleles.

10.3 3' PCR Screening for Homologous Recombination Event

To further confirm the excision of the neomycin cassette and Qpct targeted region in putative excised heterozygotes, the 3' PCR screening was used to detect the targeted allele. Animals tested positive for this PCR thus still have the neomycin cassette integrated within the Qpct locus.

Figure 6:
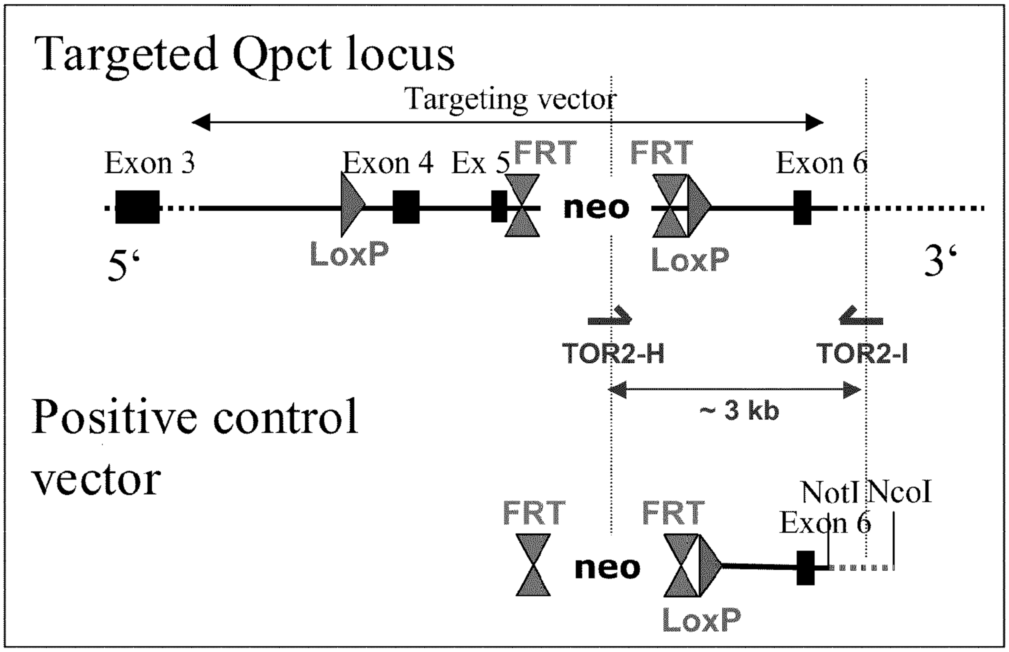
FIG. 6 is a schematic representation of PCR identification of the 3' end homologous recombination event. Solid and dotted lines represent Qpct intronic sequences located inside and outside of the targeting vector, respectively. Boxes represent Qpct exons. FRT sites are shown as double triangles, LoxP sites are represented by triangle. Half arrows illustrate the primer localization. The positive control vector will be used for the screening setting up. The dotted line within the positive control vector represents the portion of sequence that is absent in the final targeting vector.

The 3' PCR screening was performed using a forward primer TOR2-H2 located within the neomycin selection cassette and a reverse primer TOR2-I2 hybridizing downstream (see FIG. 6). The primer sequences and the optimised PCR condition are listed in tables 4 and 5.

Figure 19:
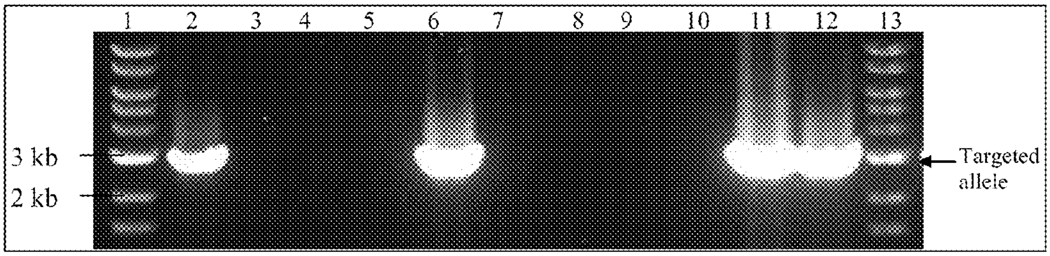
FIG. 19 is an image of a gel showing screening of the F1 animals for the detection of the non-excised targeted allele. The genotypes of the 7 pups 35437 to 35443 derived from the breeding with Cre deleter mouse were tested by PCR using the primer combination TOR2-H2/TOR2-I2 (lanes 2 to 8, respectively) to analyse the presence of the neomycin cassette. PCR using DNA from the targeted ES clone 5C12 (lane 11) and its 1:100 dilution in wild type DNA lane 12) was used as positive control. PCR using wild type DNA (lane 10) and H2O (lane 9) served as negative control. M: 1 kb DNA-Ladder (NEBioLabs).

Because of its localisation, this primer set allows the specific detection of the targeted, non-excised Qpct allele, yielding an amplification product of 2900 bp in size in heterozygous offspring carrying the targeted, but non-excised Qpct allele. A representative example of the genotyping PCR results is illustrated in FIG. 19.

The genotyping by 3' PCR screening indicated that among the 15 tested animals born, 2 animals (#35437 and #35441) carry the targeted allele.

Altogether, the results of these two PCR screenings showed that among the 15 tested animals:

2 animals (#35437 and #35438) yielded amplification products corresponding to the excised allele, suggesting that these mice are heterozygous for the Cre-excised Knock-out allele.

Male #35437 showed amplification products corresponding to both the Cre-excised and the targeted non-excised allele. This suggests that this mouse carries an incomplete excision event, meaning that it is a mosaic of excised and non-excised cell types. This animal was sacrificed.

Male #35438 showed no amplification product for a PCR specific for the targeted non-excised allele, thus confirming the complete excision event. Therefore, this male is the first heterozygous constitutive Qpct Knock-out mouse characterised. This heterozygous male was then mated with wild type females in order to generate more heterozygous constitutive Qpct Knock-out animals. The results are described below in Example 11.

Finally, the female #35441 carries the wild type allele and the targeted non-excised allele but not the Cre-excised allele. This female is thus a heterozygous Qpct targeted animal in which the Qpct targeted region is floxed and still contains the neomycin selection cassette. This female #35441 was mated with a Flp-expressing male, in order to obtain the in vivo excision of the selection cassette. The results are described below in Example 12.

Example 11

Breeding of the First Heterozygous Constitutive Qpct Knock-Out Animal with Wild Type Mice The first heterozygous constitutive Qpct Knock-out mouse generated (see Example 10) was mated with wild type females in order to generate several heterozygous constitutive Qpct Knock-out animals.

Table 3 below summarizes the results of this breeding.

TABLE 3

Reporting results of first heterozygous constitutive Qpct Knock-out animal breeding.

| Male | male | Number of pups | Date of birth | Still born | Males | Females. |
|---|---|---|---|---|---|---|
| Heterozygous constitutive Qpct Knock-out male (#35438) cage 5217 | C57BL/6 wild type | 7 | 6 Sep. 2006 | 0 | 18156 (Het Cre-excised) 18157 (WT) 18158 (WT) 18159 (Het Cre-excised) | 18160 (WT) 18161 (WT) 18162 (WT) |
| | C57BL/6 wild type | 9 | 15 Sep. 2006 | 2 | 18242 (WT) 18243 (WT) 18244 (Het Cre excised) 18245 (WT) | 18246 (WT) |

The genotype of the animals is given in bracket (see also text below).
WT: wild type;
Het Cre-excised: heterozygote carrying the Cre-mediated excised Qpct allele.

As documented above, 12 pups were obtained from this breeding: 8 males and 4 females.

These animals were genotyped to identify additional heterozygous mice carrying the constitutive Knock-out allele.

11.1 PCR Genotyping of the Animals

DNA was prepared from tail biopsies, taken from the 12 resulting pups, and was genotyped by two different PCR strategies:

- Cre-excision PCR (see FIG. 20, §13.2) for the detection of the Cre-mediated excision of the LoxP flanked region within the targeted Qpct allele. This PCR yields an amplification product of different size depending on the template used: wild type, targeted or Cre-excised allele.
- 3' PCR screening (see §13.3) that was already used for the detection of a homologous recombination event in ES cells. This PCR strategy detects the non-excised, targeted Qpct allele carrying the exons 4 and 5 flanked by the LoxP-FRT-neomycin-FRT cassette and the distal LoxP site.

11.2 PCR Screening for the Cre-Mediated Excision Event

The Cre-excision PCR was performed using a forward primer TOR2-N hybridizing in the 5' homology arm, upstream of the distal LoxP site, and a reverse primer TOR2-I1 hybridizing downstream of exon 6 (see FIG. 13). Because of its localisation, this primer pair allows the specific detection of the Cre mediated excision event.

Figure 20:
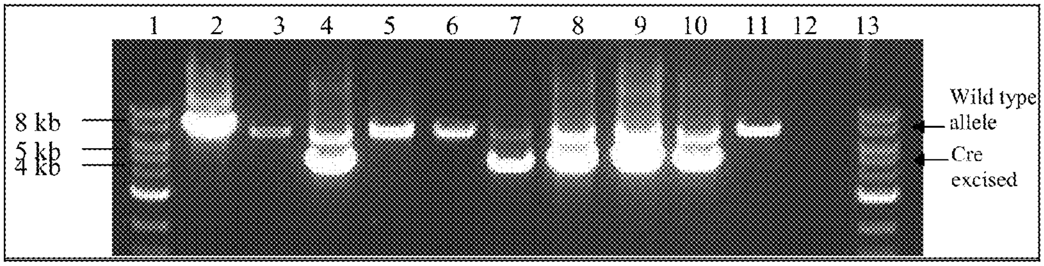
FIG. 20 is an image of a gel showing screening of the animals derived from the heterozygous constitutive Qpct Knock-out male, for the detection of the Cre-mediated excision event. The genotypes of the 12 pups (18242 to 18246, in lanes 2 to 6, and #18156, #18159 in lanes 7 and 8, respectively) derived from the breeding of the first heterozygous constitutive Qpct Knock-out male with wild type females were tested by PCR using the primer combination TOR2-N/TOR2-I1 to analyse the excision status of the Qpct allele. PCR using DNA from the targeted ES clone 5C12 (lane 9), wild type mouse tail (lane 11) and a 1:100 mixture (lane 10) was used as positive controls. PCR without template (lane 12) served as a negative control. Lanes 1 and 13: 1 kb DNA-Ladder (NEBioLabs).

The Cre-excised allele yields an amplification product of 4.4 kb using the above primer pair, whereas the targeted (non-excised) allele yields an amplification product of 9.2 kb (see FIG. 13). Since both primers hybridize to the wild type non-targeted allele, a further amplification product of 7.3 kb will be obtained from all animals corresponding to the wild type allele. A representative example of the genotyping PCR results is illustrated in FIG. 20.

The genotyping by Cre-excision PCR indicated that among the 12 tested animals born, 3 animals (#18244, #18156 and #18159) carry the Cre-excised allele. The other 9 tested animals are wild type mice.

11.3 3' PCR Screening for the Homologous Recombination Event

To obtain a last validation of the excision of the neomycin cassette in the new heterozygous constitutive Qpct Knock-out mice, the 3' PCR screening was used to detect the targeted allele, as performed for the first heterozygote identified, using the primers TOR2-H2/TOR2-I2.

The 12 animals tested were negative for the TOR2-H2/TOR2-I2 PCR (data not shown). This demonstrated that the neomycin selection cassette was totally deleted from the mutated Qpct allele.

Altogether, the PCR results of these two screening showed that among the 12 tested animals born, the 3 males #18244, #18156 and #18159 are heterozygous constitutive Qpct Knock-out animals. An ultimate Southern blot confirmation of this genotype was performed on these animals.

11.4 Southern Blot Genotyping Confirmation for the Final Heterozygous Constitutive Qpct Knock-Out Animals.

The 5' Southern blot screening strategy was used to further confirm the genotype of the four F1 heterozygous constitutive Qpct Knock-out animals and validate the PCR genotyping. This 5' Southern blot is based on a BamHI digestion of the genomic DNA and detection using a 482 bp 5' internal K probe (5'K probe) (see Example 5, item 1.2).

Figure 21:
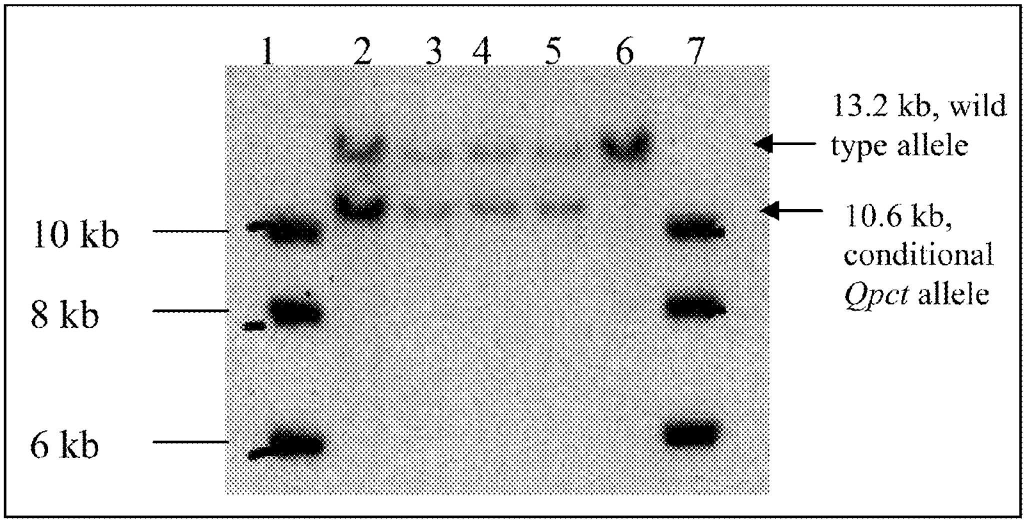
FIG. 21 is an image of a gel showing 5' Southern blot screening of four F1 heterozygous Qpct Knock-out mice genomic DNA digested with BamHI. Lanes 1 and 7: 1 kb DNA ladder (NEBioLabs). Lane 2: 15 μg of genomic DNA from tail biopsy #35438. Lane 3: 15 μg of genomic DNA from tail biopsy #18156. Lane 4: 15 μg of genomic DNA from tail biopsy #18159. Lane 5: 15 μg of genomic DNA from tail biopsy #18244. Lane 6: 15 μg of wild type genomic DNA from C57Bl/6 tail biopsies.

The results obtained are illustrated in FIG. 21.

As illustrated in FIG. 21, the Southern blot analysis confirmed the PCR results and gave an ultimate demonstration of the genotype of these animals: the 4 males #35438, #18156, #18159 and #18244 are heterozygous constitutive Qpct Knock-out animals.

Example 12

Breeding of a Heterozygous Qpct Targeted Female with an Flp Expressing Male

Previously a female #35441 heterozygous Qpct targeted animal was generated in which the Qpct targeted region is floxed and still contains the neomycin selection cassette (see Example 10). This female #35441 was mated with a Flp-expressing male, in order to obtain the in vivo excision of the selection cassette.

Table 4 below summarizes this breeding.

TABLE 4

Results of the heterozygous targeted Qpct female with Flp-expressing male breeding.

| Male | male | Number of pups | Date of birth | Still born | Males | Females. |
|---|---|---|---|---|---|---|
| C57BL/6 CAG-Flp expressing male #262 | Hetero-zygous female #35441 | 7 | 21 Aug. 2006 | 0 | 17971 (WT)<br>17972 (Het targeted)<br>17973 (Het partially Flp excised)<br>17974 (Het partially Flp excised) | 17975 (Het targeted)<br>17976 (Het partially Flp excised)<br>17977 (Het partially Flp excised) |

The genotype of the animals is given in bracket (see also text below).
WT: wild type;
Het targeted: heterozygous carrying the targeted Qpct allele;
Het partially Flp-excised: heterozygote carrying the Flp-mediated excised Qpct allele and the targeted Qpct allele.

This breeding gave rise to 7 animals that were genotyped to identify heterozygous mice carrying the conditional Knock-out allele.

12.1 PCR Genotyping of the Animals

DNA was prepared from tail biopsies, taken from the 7 resulting pups and was genotyped by two different PCR strategies:

- Flp-excision PCR (see FIG. 22, Example 12, 2) for the detection of the Flp-mediated excision of the neomycin selection cassette. This PCR yields an amplification product of different sizes depending on the template used: wild type, targeted or Cre-excised allele.
- 3' PCR screening (see FIG. 23, Example 12, 3) that was already used for detection of a homologous recombination event in ES cells. This PCR strategy detects the non-excised, targeted Qpct allele carrying the exons 4 and 5 flanked by LoxP-FRT-neomycin-FRT cassette and the distal LoxP site.

12.2 PCR Screening for the Flp-Mediated Excision Event

The Flp-excision PCR was performed using a forward primer TOR2-N2 hybridizing in the long 5' homology arm, upstream of the neomycin selection cassette, and a reverse primer TOR2-I4 hybridizing in the short 3' homology arm, downstream of the neomycin selection cassette (see FIG. 13, Example 5.2). Due to the primer set localisation, this PCR allows the detection of the Flp-mediated excision of the neomycin selection cassette.

Figure 22:
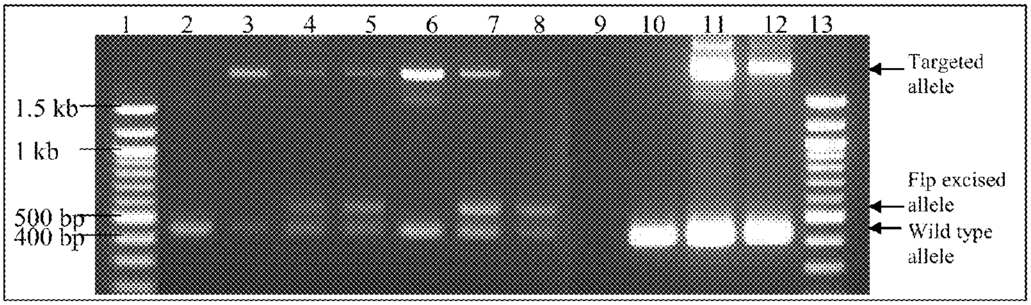
FIG. 22 is an image of a gel showing screening of the animals for the Flp-mediated excision event. The genotypes of the 7 pups (17971 to 17977 in lanes 2 to 8, respectively) derived from the breeding of the Qpct targeted female with Flp deleter male were tested by PCR using the primer combination TOR2-N2/TOR2-I4 to analyse the excision status of the Qpct allele. PCR using DNA from the targeted ES clone 5C12 (lane 11), wild type mouse tail DNA (lane 10) and a 1:100 mixture of the two previously cited DNA (lane 12) were used as positive controls. PCR without template (lane 9) served as a negative control. Lanes 1 and 13: 1 kb DNA-Ladder (NEBioLabs).
Figure 23:
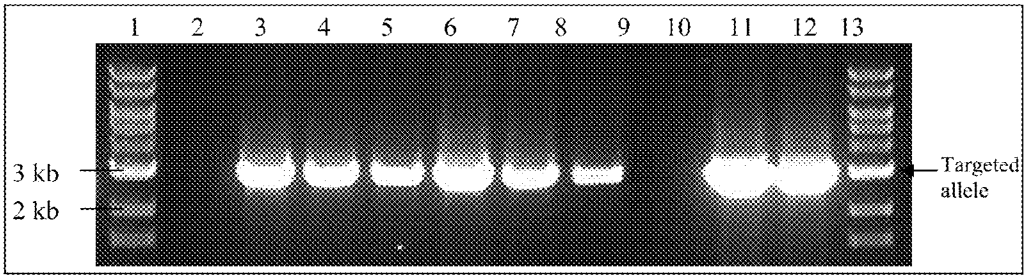
FIG. 23 is an image of a gel showing screening of the animals for the detection of the non-excised targeted allele. The genotypes of the 7 pups 17971 to 17977 derived from the breeding of the Qpct targeted female with Flp deleter male were tested by PCR using the primer combination TOR2-H2/TOR2-I2 (lanes 2 to 8, respectively) to analyse the presence of the neomycin cassette. PCR using DNA from the targeted ES clone 5C12 (lane 11) and its 1:100 dilution in wild type DNA (lane 12) were used as positive controls. PCR using wild type DNA (lane 10 served as negative control. Lanes 1 and 13: 1 kb DNA-Ladder (NEBioLabs).

The Flp-excised allele should yield an amplification product of 538 bp using the above primer pair, whereas the targeted (non-excised) allele should yield an amplification product of 2211 bp (see FIG. 13). Since both primers hybridize to the wild type non-targeted allele, a further amplification product of 419 bp will be obtained from all animals corresponding to the wild type allele. The genotyping PCR results are illustrated in FIG. 22.

The genotyping by Flp-excision PCR indicated that among the 7 tested animals born, 4 animals (#17973, #17974, #1796 and #17977) carried the Flp-excised allele. The other 3 animals tested were either wild type mice or carried the targeted allele 12.3 3' PCR Screening for the Homologous Recombination Event To assess the complete excision of the neomycin cassette in the animals carrying the Flp-mediated excised allele, the 3' PCR screening (with TOR2-H2/TOR2-I2 primers) was used to detect the targeted allele. Animals tested positive for this PCR thus still have the neomycin cassette integrated within the Qpct locus.

The genotyping by 3' PCR screening indicated that among the 7 tested animals born, 6 animals (#17972 to #17977) carry the targeted allele.

Altogether, the results of these two PCR screenings showed that among the 7 tested animals born:

- The male #17971 carried only the wild type Qpct allele. This animal was sacrificed.
- The animals #17972 and #17975 carried the wild type allele and the targeted non-excised allele but not the Flp-excised allele. These 2 animals are thus heterozygous Qpct targeted animal in which the Qpct targeted region is floxed and still contains the neomycin selection cassette. These animals were sacrificed.
- Finally, 4 animals (2 males #17973 and #17974 and 2 females #17976 and #17977) yielded amplification products corresponding to the Flp-mediated excised allele, wild type allele and Qpct targeted allele. This suggests that these mice carry an incomplete excision of the neomycin selection cassette, meaning that they consist in a mosaic of excised and non-excised cell types. These animals were then bred with wild type mice in order to generate the heterozygous conditional Qpct Knock-out mouse line.

Example 13

Breeding of the Partially Flp-Mediated Neomycin Excised Animals 13.1 Breeding Among the 4 partially Flp-mediated neomycin excised animals generated, the male #17973 was mated with wild type mice in order to segregate the targeted Qpct allele from the conditional Qpct Knock-out allele and thus generated pure heterozygous conditional Qpct Knock-out mice. The results of this breeding is summarised in table 5 below.

TABLE 5

Results of the heterozygous partially Flp excised Qpct male with wild type females breeding.

| Male | male | Number of pups | Date of birth | Still born | Males | Females. |
|---|---|---|---|---|---|---|
| F1 heterozygous partially Flp excised #17973 | C57BL/6J wild type female C57BL/6J wild type female | 14 | 2 Nov. 2006 | 0 | 18823 (Het Flp excised)<br>18824 (Het Flp excised)<br>18825 (Het Flp excised)<br>18826 (Het partially Flp excised)<br>18827 (WT)<br>18828 (Het Flp excised)<br>18829 (Het targeted)<br>18830 (Het Flp excised)<br>18831 (WT) | 18832 (WT)<br>18833 (Het partially Flp excised)<br>18834 (WT)<br>18835 (WT)<br>18836 (Het Flp excised) |

The genotype of the animals is given in brackets (see also text below).
WT: wild type;
Het targeted: heterozygote carrying the targeted Qpct allele;
Het partially Flp-excised: heterozygote carrying the Flp-mediated excised Qpct allele and the targeted Qpct allele;
Het Flp-excised: heterozygote carrying the Flp-mediated excised Qpct allele.

13.2 PCR Screening for the Flp-Mediated Excision Event

The Flp-excision screening was performed as previously described using the TOR2-N2/TOR2-I4 PCR.

The Flp-excised allele yields an amplification product of 538 bp using the above primer pair, whereas the targeted (non-excised) allele yields an amplification product of 2211 bp (see FIG. 13). Since both primers hybridize to the wild type non-targeted allele, a further amplification product of 419 bp will be obtained from all animals corresponding to the wild type allele. A representative example of the genotyping PCR results is illustrated in FIG. 24.

Figure 24:
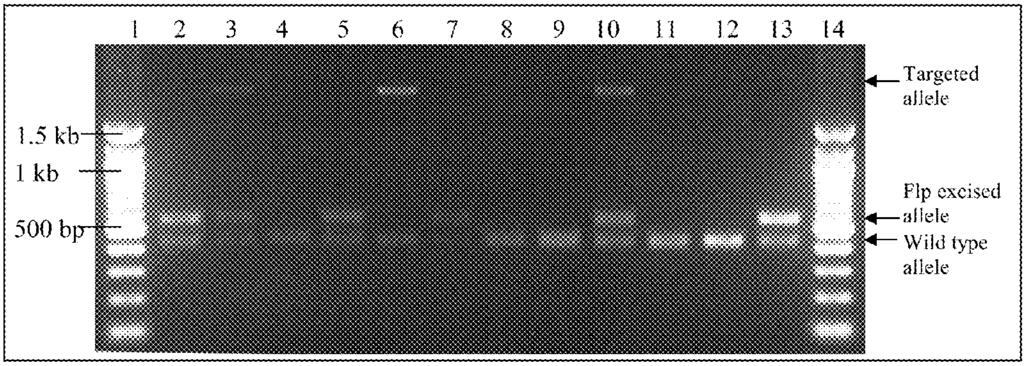
FIG. 24 is an image of a gel showing screening of the animals for the detection of the Flp-mediated excision event. The genotypes of the 12 pups (18825 to 18836 in lanes 2 to 13, respectively) derived from the breeding of the Qpct partially Flp excised male #17973 with wild type females were tested by PCR using the primer combination TOR2-N2/TOR2-I4 to analyse the excision status of the Qpct allele. Lanes 1 and 14: 1 kb DNA-Ladder (NEBioLabs).
Figure 25:
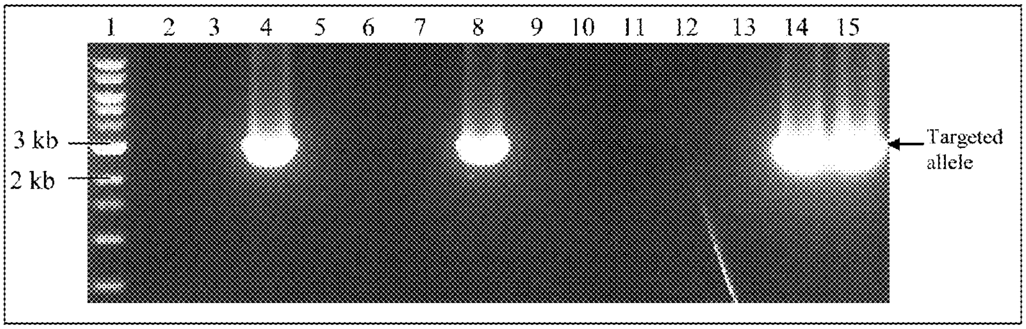
FIG. 25 is an image of a gel showing screening of the animals for the detection of the non-excised targeted allele. The genotypes of the 10 pups 18827 to 18836 derived from the breeding of the Qpct partially Flp excised male #17973 with wild type females were tested by PCR using the primer combination TOR2-H2/TOR2-I2 (lanes 2 to 11, respectively) to analyse the presence of the neomycin cassette. PCR using DNA from the targeted ES clone (lane 14) and its 1:100 dilution in wild type DNA (lane 15) were used as positive controls. PCR using H2O (lane 12) and wild type DNA (lane 13) served as negative controls. Lane 1:1 kb DNA-Ladder (NEBioLabs).

As illustrated in FIG. 24, the genotyping by Flp-excision PCR indicated that among the 14 tested animals, 8 animals (#18823, #18824, #18825, #18826, #18828, #18830,

#18833 and #18836) carried the Flp-excised allele. The other 6 tested animals were either wild type mice or carry the targeted allele.

13.3 3' PCR Screening for Homologous Recombination Event

To assess the complete excision of the neomycin cassette in the animals carrying the Flp-mediated excised allele, the 3' PCR screening (with TOR2-H2/TOR2-I2 primers) was used to detect the targeted allele. Animals tested positive for this PCR thus still have the neomycin cassette integrated within the Qpct locus.

The genotyping by 3' PCR screening indicated that among the 14 tested animals born, 3 animals (#18826, #18829 and #18833) carry the targeted allele.

Altogether, the results of these two PCR screenings showed that among the 14 tested animals born:

The animals #18827, #18831, #18832, #18834 and #18835 carry only the wild type Qpct allele. These animals were sacrificed.

The animal #18829 carried the wild type allele and the targeted non-excised allele but not the Flp-excised allele. This animal is thus a heterozygous Qpct targeted animal in which the Qpct targeted region is floxed and still contains the neomycin selection cassette. This animal was sacrificed.

The animals #18826 and #18833 yielded amplification products corresponding to the Flp-mediated excised allele, wild type allele and Qpct targeted allele. This suggests that these mice carried an incomplete excision of the neomycin selection cassette, meaning that they consist in a mosaic of excised and non-excised cell types. These animals were sacrificed.

Finally, 6 animals (5 males #18823, #18824, #18825, #18828, #18830 and the female #18836) yielded amplification products corresponding to both the Flp excised allele and the wild-type allele. These mice thus carry a complete excision of the neomycin selection cassette and are pure heterozygous conditional Qpct Knock-out animals. An ultimate Southern blot confirmation of this genotype was performed on these animals.

13.4 Southern Blot Genotyping Confirmation for the Final Heterozygous Conditional Qpct Knock-Out Animals.

The 3' Southern blot screening strategy was used to further test the genotype of the three F1 heterozygous conditional Qpct Knock-out animals and confirm the PCR genotyping. This 3' Southern blot is based on a SwaI digestion of the genomic DNA and detection using a 406 bp 3' internal R probe (3'R probe) (see Exampled 4, 1.2, 7, 1.2 and FIG. 11).

Figure 26:
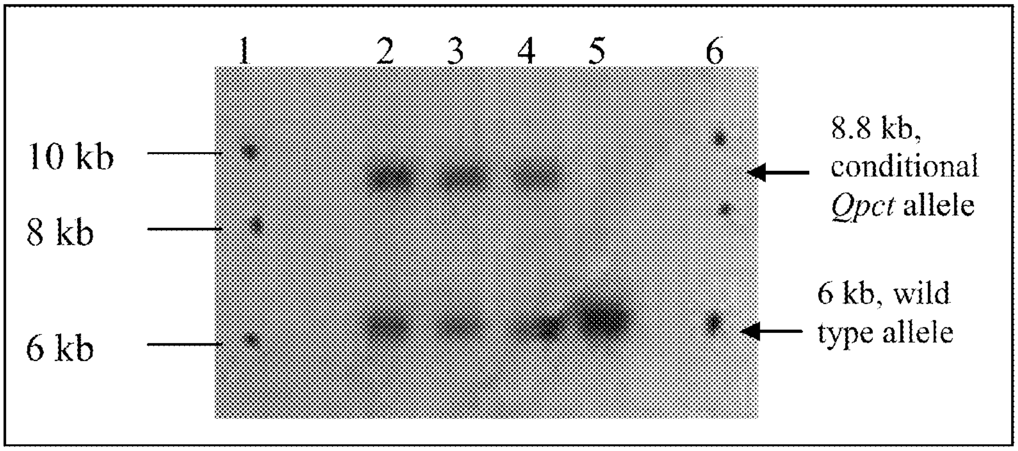
FIG. 26 is an image of a gel showing 3'Southern blot screening of three F1 heterozygous conditional Qpct Knock-out mice genomic DNA digested with SwaI. Lanes 1 and 6: 1 kb DNA ladder (NEBioLabs). Lane 2: 15 μg of genomic DNA from tail biopsy #18823. Lane 3: 15 μg of genomic DNA from tail biopsy #18824. Lane 4: 15 μg of genomic DNA from tail biopsy #18825. Lane 5: 15 μg of wild type genomic DNA from C57Bl/6 tail biopsies.

The results obtained are illustrated in FIG. 26.

As illustrated in FIG. 26, the Southern blot analysis confirmed the PCR results and gave an ultimate demonstration of these animals genotype: the 3 males #18823, #18824 and #18825 are heterozygous conditional Qpct Knock-out animals.

The strategy for the development a conditional Qpct Knock-out model was achieved by flanking the targeted exons 4 and 5 with two LoxP sites, allowing its ubiquitous or tissue specific deletion under the action of the Cre-recombinase.

The inventors succeeded in the amplification, cloning and sequencing of the two homology arms needed for the generation of the TOR2-HR targeting vector.

They isolated and sequenced for both homology arms at least one clone devoid of any mutation.

Theses clones were used for the construction of the targeting vector.

The targeting and positive control vectors were generated following state of the art methodologies and according to the strategy presented above.

PCR and Southern blot screening strategies were designed and validated to identify the following events:

Homologous recombination event at the Qpct locus, at both 5' and 3' end of the targeting vector.

Flp-mediated excision of the neomycin selection cassette, allowing the generation of the final conditional Qpct Knock-out allele.

Cre-mediated excision of the Qpct exons 4 and 5, allowing the generation of the constitutive Qpct Knock-out allele.

Following the TOR2-HR targeting vector electroporation, 421 G418 resistant clones were isolated and amplified in 96-well plates in duplicate. The PCR and Southern blot screening of these ES cell clones allowed the full characterisation of 7 clones as correctly targeted: clones #5C5, #5C12, #6A3 #6C3, #15B2, #10B2 and #11B4.

Based on the ES cell screening results and on morphological criteria, the seven ES cell clones 5C5, #5C12, #6A3 #6C3, #15B2, #10B2 and #11B4 were selected for the blastocyst injections. These ES cell clones were injected and re-implanted into a total of 374 blastocysts, giving rise to a total of 17 male chimeras with the following rate of chimerism:

Clone #6A3 gave rise to 8 male chimeras with a percentage of chimerism ranging from 5% to 20%.

Clone #6C3 gave rise to 3 male chimeras with a percentage of chimerism ranging from 5% to 30%.

Clone #5C12 gave rise to 2 male chimeras with a percentage of chimerism of 35% and 15%.

Clone #5C5 did not give rise to any male chimera.

Clone #15B2 gave rise to 1 male chimera with a percentage of chimerism of 75%.

Clone #10B2 did not give rise to any pup.

Clone #11B4 gave rise to 3 male chimeras with a percentage of chimerism of 75%, 35% and 8%.

Four chimeric males (displaying 20% to 35% chimerism, derived from ES clone #6A3, #6C3 and #5C12) were mated with wild type C57BL/6J females (health status SOPF—Specific and Opportunist Pathogen Free) to obtain the germline transmission and generate Qpct targeted heterozygous animals. The chimeras were also bred with Flp or Cre deleter females (health status SOPF—Specific and Opportunist Pathogen Free) to obtain the deletion of the neomycin selection cassette and Qpct exons 4-5 and selection cassette, respectively.

This breeding resulted in the generation of 17 F1 pups. These mice were screened using PCR and Southern blot screening, allowing the characterization of:

1 male #35438 carrying the Cre-mediated neomycin excised Qcpt allele. This male was the first F1 heterozygous constitutive Qpct Knock-out mouse. It was mated with wild type females to generate 3 additional heterozygous constitutive Qpct Knock-out mice.

1 female #35441 carrying the targeted allele. This female represented F1 heterozygous Qpct targeted mouse and was mated with Flp-expressing mice in order to obtain the in vivo deletion of the neomycin selection cassette.

The breeding of the first heterozygous constitutive Qpct Knock-out male #35438 with wild type females allowed the generation of 3 additional heterozygous constitutive Qpct Knock-out males #18156, #18159 and #18244.

The breeding of the heterozygous targeted Qpct Knock-out female #35441 with a C57BL/6J CCAG-Flp-expressing deleter male gave rise to 7 animals among which 4 animals (2 males #17973 and #17974 and 2 females #17976 and #17977) carrying both the Qpct targeted allele and the Flp-mediated neomycin excised Qpct allele (conditional Qpct Knock-out allele) in addition to the wild type allele. These animals thus underwent a partial excision of the neomycin selection cassette, meaning that the Flp-recombinase resulted in the deletion of the selection cassette in some but not all in these F1 animals.

One of these mosaic animals, partially Flp-mediated excised, namely the male #17973 was then mated with wild type females, in order to segregate the Flp-mediated excised allele (conditional Qpct Knock-out allele) from the targeted allele still containing the neomycin selection cassette. This third F1 breeding gave rise to a new series of 14 F1 animals. Their PCR and Southern blot genotyping allowed the characterisation of 6 animals (5 males #18823, #18824, #18825, #18828, #18830 and the female #18836) displaying both the Flp excised allele and the wild-type allele. These mice thus carry a complete excision of the neomycin selection cassette and are pure heterozygous conditional Qpct Knock-out animals.

Example 14

Generation of a Mouse Model Carrying a Constitutive Knock-Out Mutation in the Qpct Gene 14.1 Targeting Strategy and Generation of the $Qpct^{KO}$ Mouse Line PBD2

For the development of a mouse line with inactivated Qpct protein function, mouse embryonal stem cells (ES cells, derived from line 129SvPas) were genetically engineered and clones were selected which carried in the genome

- a neomycin selection cassette flanked by FRT sites and followed by a LoxP site inserted into Qpct intron 5 and
- a distal LoxP site located in Qpct intron 3

Figure 27:
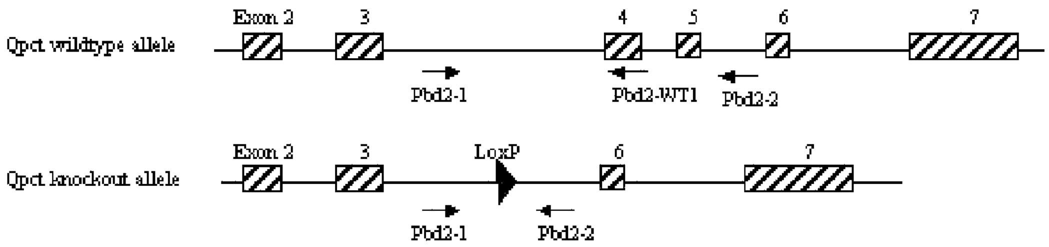
FIG. 27 depicts schematic organisation of the Qpct alleles in heterozygous animals of mouse line Pbd2.

ES cells were injected into blastocycts and chimeras were generated via embryo transfer. For removal of the neomycin selection cassette the chimeras were mated to Flp-expressing animals followed by breeding of the pups with Cre-expressing animals for deletion of Qpct1 exons 4 and 5. Pups were identified which are heterozygous for the Qpct locus and carry a Qpct allele where exons 4 and 5 are deleted in addition to the wildtype allele (FIG. 27). These animals served as the founders for mouse line Pbd2.

14.2 Genotyping Assay for Mouse Line Pbd2

For PCR assessment of the Qpct genotypes of line Pbd2 the following oligonucleotide primers were designed:

| Primer name | Sequence | binding site | SEQ ID No |
|---|---|---|---|
| Pbd2-1 | GTCCGGTAAGGTGAGGAGAA | Qpct intron 3 | 19 |
| Pbd2-2 | TGATGTGTGCGTTTCAGAGA | Qpct intron 5 | 20 |
| Pbd2-WT1 | CCAGAGACATCCTGGTAAAACA | Qptc exon 4 | 21 |

Figure 28:
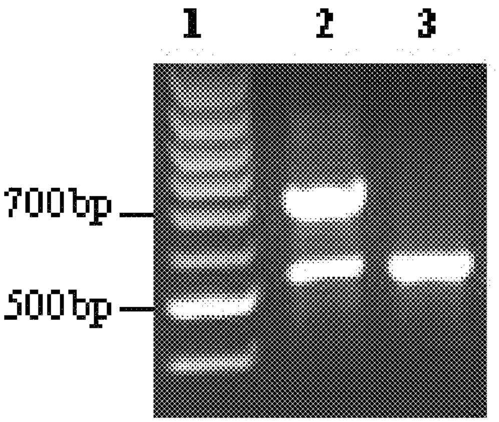
FIG. 28 is an image of a gel showing PCR genotyping assay for the Qpct locus in mouse line Pbd2. Lane 1: Molecular weight marker (100 bp ladder). Lane 2: PCR fragments generated on Pbd2 heterozygous animals. Lane 3: PCR fragments generated on Pbd2 homozygous animals (Qpct knockout).

In a standard PCR reaction on 50 ng chromosomal DNA containing primers Pbd2-1, Pbd2-2 and Pbd2-WT1, the wildtype allele can be detected as an approx. 735 bp fragment whereas the targeted knockout allele is detected as an approx. 525 bp fragment (s. FIG. 28).

Example 15

Characterization of Mice Carrying a Constitutive Knock-Out Mutation in the Qpct Gene In order to proof that the generation of the knock-out animals was successful, plasma of the wild-type, heterozygous and homozygous animals with respect to the genetic manipulation was analyzed and the enzymatic activity of Qpct was measured. If the strategy was successful, then a significant lowering or depletion of Qpct-activity was expected.

The Qpct-activity in the plasma was determined, applying a method, which is based on detection of formation of L-pGlu-beta-naphthylamine from L-glutaminyl-beta-naphthylamine catalyzed by Qpct in plasma (Cynis, H. et al. 2006 Biochim Biophys Acta 1764, 1618-1625). Briefly, the assay is based on conversion of H-Gln-βNA to pGlu-βNA. The sample consisted of 50 μM H-Gln-βNA in 25 mM MOPS, pH 7.0, 0.1 mM N-Ethylmaleinimide (NEM) and enzyme solution in a final volume of 1 ml. Substrate and NEM were pre-incubated for 15 min at 30° C. The sample was centrifuged at 4° C. for 20 min at 16.000×g. The reaction was started by addition of 10011 plasma sample. The reaction mix was further incubated at 30° C. and constantly shaken at 300 rpm in a thermomixer (Eppendorf, Germany). Test samples were removed at time points of 0, 5, 10, 15, 22, 30 and 45 min. The reaction was immediately stopped by boiling for 4 min. Test samples were cooled on ice and stored at −20° C. For analysis, samples were thawed on ice and centrifuged at 4° C. for 20 min at 16,000×g. All HPLC measurements were performed using a RP18 LiChroCART HPLC-Cartridge and the HPLC system D-7000 (Merck-Hitachi). Briefly, 20 μl of the sample were injected and separated by increasing concentration of solvent A (acetonitrile containing 0.1% TFA) from 8% to 20% in solvent B ($H_2O$ containing 0.1% TFA).

Qpct activity was quantified from a standard curve of pGlu-βNA (Bachem, Bubendorf, Switzerland) determined under assay conditions.

Figure 29:
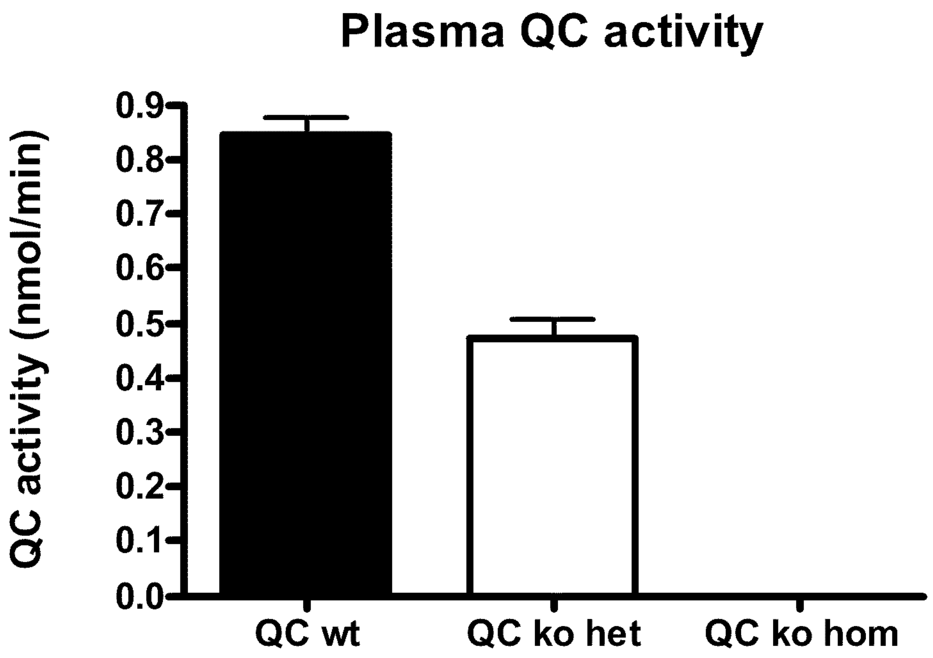
FIG. 29 is a bar graph showing QC-activity in plasma of wild-type, heterozygous and homozygous knock-out animals with respect to the Qpct locus in mouse line Pbd2.

The Qpct-activity depending on the genotype of the animals is depicted in FIG. 29. Caused by the complete loss of a functional Qpct gene in the homozygous Qpct knock-out animals, no Qpct-activity can be detected in plasma. In heterozygous animals, i.e., animals, which still carry one intact allele of Qpct together with one functionally destroyed allele, approximately 60% of the activity in plasma of wild-type animals is still left.

The results thus proof, that: 1. The strategy to target the Qpct allele as depicted in examples 1 to 14 was successful and sufficient to provoke a complete loss of Qpct in these animals. 2. There is a gene-dose dependency of Qpct-activity observed. Loss of one copy already results in partial loss of Qpct activity. This observation is important for following studies involving cross-breeding of these animals with other animal models of human diseases to proof attempts to generate drugs targeting Qpct activity. 3. Importantly, an enzymatically active QPCT is not necessary for development of viable pups and development of animals, which proofs that the pharmacological inhibition of Qpct does not has obvious deleterious side effects.

In order to further characterize the effects of the depletion of Qpct on the function of hormonal regulation cascades, the concentrations of testosterone and thyroxine were determined in serum from pbd2 mice.

Testosterone (6,17-dodecahydrocyclopenta[α] phenanthren-3-one) is the principal male sex hormone and a steroid hormone, which is primarily secreted in the testes of males and the ovaries of females. Testosterone is also secreted by the adrenal glands. Testosterone plays a key role in health and well-being as well as in sexual functioning. The release of sexual hormones from the gonads is regulated by the hypophyseal hormones LH and FSH. The release of these pituitary hormones, in turn, is stimulated by the hypothalamic hormone gonadotropin-releasing hormone (GnRH). GnRH (Gonadotropin-releasing hormone) is secreted from parvicellular neurons in the arcuate nucleus into the median eminence. GnRH then enters the hypophyseal portal system, traveling in the long vein until reaching the anterior pituitary, where it acts on gonadotropes to release LH (luteinizing hormone) and FSH (follicle stimulating hormone) back into the blood stream. LH and FSH both act on the gonads to produce varying effects, including release of sex hormones and keeping the gonadal integrity. By that cascade of events involving secretion of GnRH, pituitary and gonadal hormones the so-called hypothalamic-pituitary-gonadal axis (HPG) axis is built. Similar to other hormonal axes, there is a negative feed-back regulation on the secretion of gonadotopes. GnRH is N-terminally modified by pGlu and is therefore a substrate of Qpct. A reduction of the pGlu-formation at the N-terminus of GnRH is intended to result in deactivation of the hormone and, consequently, in disturbance of the HPG axis and deregulated testosterone concentrations.

Figure 30:
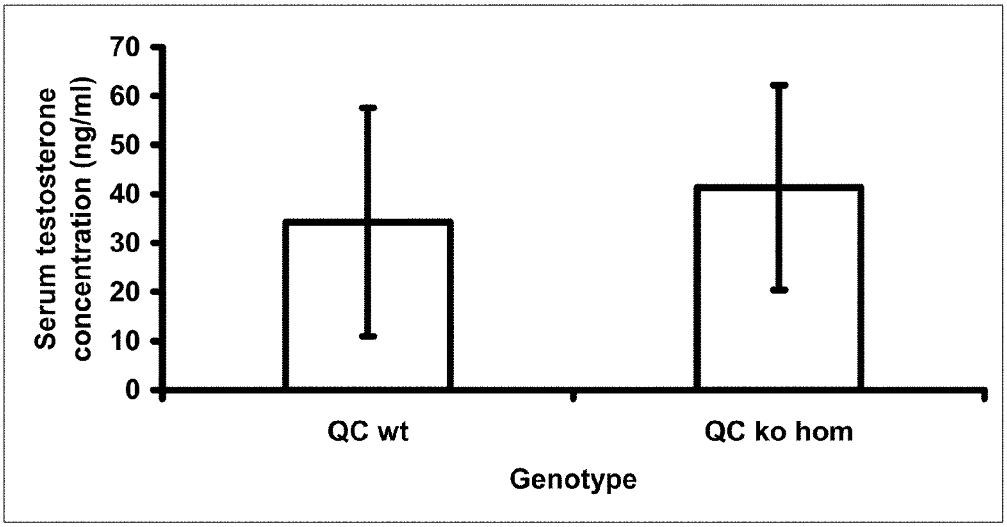
FIG. 30 is a bar graph showing the testosterone concentration in serum of male wild-type, male heterozygous and male homozygous knock-out animals with respect to the Qpct locus in mouse line Pbd2.

The effect of depletion of Qpct on the testosterone concentration is depicted in FIG. 30. The concentration of testosterone in serum of male mice was determined applying a competitive ELISA method (IBL, Hamburg, Germany, Cat.-no. RE52631). The determinations were performed according to the instructions of the manufacturer.

The results show no difference in the testosterone concentration between wild-type and QPCT knock-out mice. Even a total loss of QPCT does not result in disturbance of the gonadal hormone, proving that pharmacological inhibition of Qpct does not result in unwanted side effects on the reproductive axis.

Thyroxine (3,5,3',5'-tetraiodothyronine, $T_4$) is a hormone, which is secreted by the follicular cells of the thyroid gland. $T_4$ plays a role in the control of metabolic processes. Thyroxine increases cardiac output, heart rate and the basal metabolic rate and potentiates brain development. The secretion of the thyroid hormones thyroxin and triiodothyronine ($T_3$) is regulated via the hypothalamic-pituitary-thyroid axis. The hypothalamus senses low circulating levels of thyroid hormone and responds by releasing thyrotropin releasing hormone (TRH). The tripeptide TRH is N-terminally modified by pGlu and is therefore a substrate of Qpct. The TRH stimulates the pituitary to produce thyroid stimulating hormone (TSH). The TSH, in turn, stimulates the thyroid to produce thyroid hormones. A reduction of the pGlu-formation at the N-terminus of TRH is intended to result in deactivation of the hormone and, consequently, in disturbance of the HPT axis and deregulated thyroxine concentrations.

Figure 31:
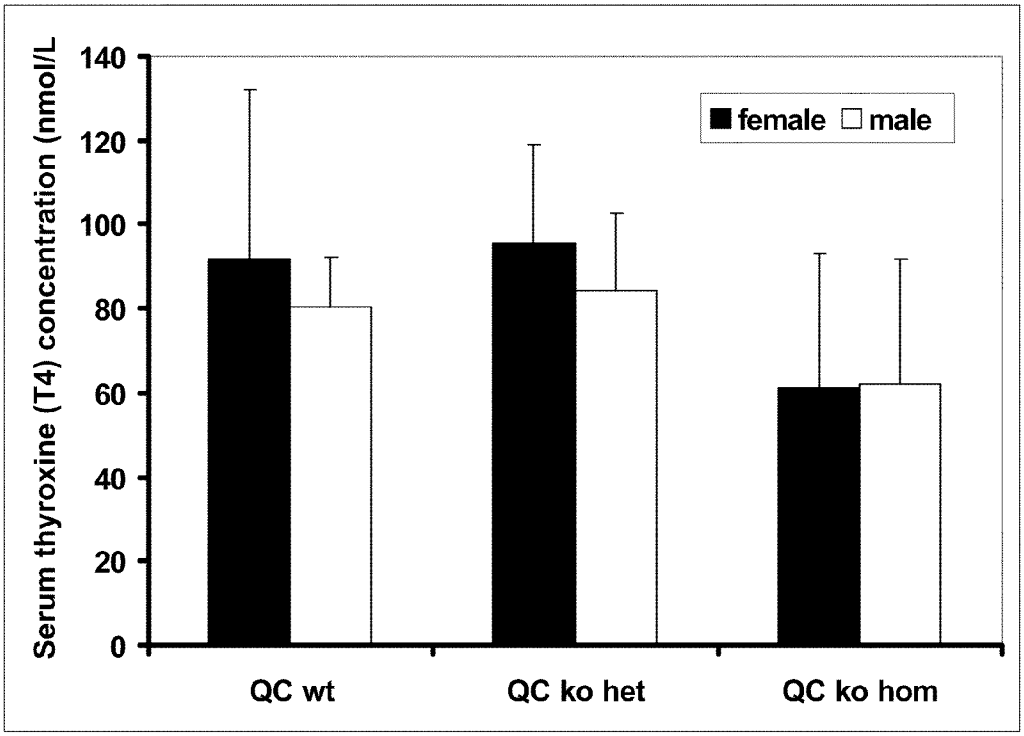
FIG. 31 is a bar graph showing the thyroxine (T4) concentration in serum of wild-type, heterozygous and homozygous knock-out animals with respect to the Qpct locus in mouse line Pbd2.

The effect of depletion of Qpct on the thyroxine concentration is depicted in FIG. 31. The concentration of thyroxine in plasma of the mice was determined applying a competitive ELISA method (IBL, Hamburg, Germany, Cat.-no. RE55261). The determinations were performed according to the instructions of the manufacturer.

The results imply a slight but statistically not significant reduction of the T4 concentration in homozygous constitutive QPCT knock-out mice. In heterozygous mice, no difference of the thyroxine level was observed. The results suggest that a partial reduction of Qpct does not influence the HPT-axis at all. Even a total loss of QPCT does not result in disturbance of the thyroid hormone, proving that pharmacological inhibition of Qpct does not result in unwanted side effects.

Example 16

Transwell Chemotaxis Assay

Human acute monocytic leukaemia cell line THP-1 was cultured in RPI1640, 10% FBS, in a humidified atmosphere of 5% $CO_2$ at 37° C. The chemotactic assay was performed using 24-well TransWell plates with a pore size of 5 μm (Corning). 600 μl of chemoattractant solution were applied to the lower chamber. Serum-free RPMI was applied as negative control. THP-1 cells were harvested and resuspended in RPMI 1640 in a concentration of $1*10^6$ cells/100 μl and applied in 100 μl aliquots to the upper chamber. Cells were allowed to migrate towards the chemoattractant for 2 h at 37° C. Subsequently, cells from the upper chamber were discarded and the lower chamber was mixed with 50 μl 70 mM EDTA in PBS and incubated for 15 min at 37° C. to release cells attached to the membrane. Afterwards, migrated cells were counted using a cell counter system (Scharfe System, Reutlingen). The chemotactic index was calculated by dividing cells migrated to the stimulus from cells migrated to the negative control.

What is claimed is:

1. A mouse comprising mouse cells comprising a glutaminyl peptide cyclotransferase (Qpct) gene carrying a knock-out mutation;

wherein the Qpct gene is a murine Qpct gene;

the murine Qpct gene comprises a nucleotide sequence of SEQ ID No. 22; and the mouse has decreased Qpct activity compared to a wild-type mouse.

2. The mouse of claim 1, wherein the animal is heterozygous for the Qpct gene carrying the knock-out mutation.

3. The mouse of claim 1, wherein the animal is homozygous for the Qpct gene carrying the knock-out mutation.

4. The mouse of claim 1, wherein the mouse is a transgenic mouse and the Qpct gene is a recombinant gene.

5. The mouse of claim 1, wherein the Qpct gene carries a constitutive knock-out mutation.

6. The mouse of claim 1, wherein the Qpct gene carries a conditional knock-out mutation.

7. The mouse of claim 1, for use in determining effects of target compounds on Qpct-related disorders and/or diseases.

8. The mouse of claim 1, wherein the animal carries at least one Qpct allele where exons 4 and 5 are deleted.

9. The mouse of claim 8, wherein said Qpct allele comprises the nucleotide sequence of SEQ ID No. 23.

10. The mouse of claim 8, wherein the mouse is a mouse of the mouse line Pbd2.

11. The mouse of claim 8, wherein the Qpct gene carrying a knock-out mutation is operably linked to a tissue-specific promoter.

12. The mouse of claim 1, wherein the mouse demonstrates a phenotype comprising reduced Qpct activity compared to a wild type mouse; and the reduced Qpct activity can be further reduced with administration of a Qpct inhibitor.

13. A cell or cell line derived from the mouse according to claim 1.

14. A method for screening for therapeutic agents that inhibit or promote Qpct activity comprising (a) administering test agents to the mouse of claim 1, (b) evaluating the effects of the test agent on the phenotype of the mouse, and (c) selecting a test agent which inhibits or promotes glutaminyl peptide cyclotransferase (Qpct) activity.

15. A method for analyzing the disease-related physiological function of Qpct catalysis with regard to pyroglutamate-peptide formation comprising (a) administering of test agents to the mouse of claim 1, (b) evaluating the pyroglutamate-peptide concentration and effects of the test agent on the phenotype of the mouse, and (c) selecting a test agent which inhibits or promotes pyroglutamate-peptide activity.

16. The mouse of claim 1, wherein the Qpct is expressed in specific tissue, particular points in time only, or specific tissue and particular points in time only.

17. A screening method for biologically active compounds that inhibit or promote Qpct activity in vivo comprising steps of:

(a) administering a test compound to a mouse model, which is specific for the treatment of at least one disease selected from Mild Cognitive Impairment, Alzheimer's disease, neurodegeneration in Down Syndrome, Familial Danish Dementia, Familial British Dementia, rheumatoid arthritis, atherosclerosis, restenosis, and pancreatitis;

(b) determining the effect of the test compound in said mouse model;

(c) comparing the effect of the test compound in said mouse model with the effect of the glutaminyl peptide cyclotransferase (Qpct) gene disruption in the Qpct knock-out mouse of claim 1; and (d) selecting a test compound that in said mouse model alleviate the specific disease similar to the effect of the Qpct gene disruption in the Qpct knock-out mouse of claim 1.

18. The screening method of claim 17, wherein said mouse model is specific for a diseases selected from the group consisting of Mild Cognitive Impairment, Alzheimer's disease, neurodegeneration in Down Syndrome, Familial Danish Dementia and Familial British Dementia.

19. The screening method of claim 18, wherein said mouse model is specific for Alzheimer's disease.

20. The screening method of any of claim 17, wherein said mouse model is selected from the group consisting of PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP and 3×TgAD.

21. The screening method of claim 17, wherein the effect of the test compounds is the lowering of the $[pGlu^3]A\beta3$-40/42/43 or $[pGlu^{11}]A\beta40/42/43$ peptides.

22. The screening method of claim 17, wherein the effect of the test compounds is the lowering of the $[pGlu^3]A\beta3$-40 peptides.

23. The screening method of claim 17, wherein the effect of the test compounds is the lowering of the $[pGlu^3]A\beta3$-42 peptides.

24. The screening method of claim 17, wherein said mouse model is specific for a disease selected from the group consisting of rheumatoid arthritis, atherosclerosis, restenosis, and pancreatitis.

25. The screening method of claim 24, wherein said mouse model is specific for rheumatoid arthritis.

26. The screening method of claim 24, wherein said mouse model is specific for atherosclerosis.

27. The screening method of claim 24, wherein said mouse model is selected from the group consisting of the apolipoprotein E knock out mouse model and the thioglycollate-induced inflammation model in mice.

28. The screening method of claim 24, wherein the effect of the test compounds is the inhibition of the chemotaxis of THP-1 cells.

29. The screening method of claim 24, wherein the effect of the test compounds is the inhibition of the formation of pGlu-MCP-1.

30. The mouse of claim 1, wherein the mouse demonstrates a phenotype comprising reduced or eliminated Qpct activity in a tissue compared to a wild type mouse.

31. The mouse of claim 1, wherein the mouse demonstrates a phenotype comprising reduced Qpct activity in a tissue compared to a wild type mouse.

32. The mouse of claim 1, wherein the mouse is heterozygous for the Qpct gene carrying the knock-out mutation; and the mouse demonstrates a phenotype comprising reduced Qpct activity in a tissue compared to a wild type mouse.

33. The mouse of claim 1, wherein the mouse demonstrates a phenotype comprising substantially no Qpct activity in a tissue compared to a wild type mouse.

34. The mouse of claim 1, wherein the mouse is homozygous for the Qpct gene carrying the knock-out mutation; and the mouse demonstrates a phenotype comprising eliminated Qpct activity in a tissue compared to a wild type mouse.

35. The mouse of claim 1, wherein the Qpct gene carrying the knock-out mutation is localized in a specific tissue of the mouse.

36. A method for producing a mouse model for Alzheimer's disease comprising:

breeding the mouse of claim 1 with a mouse model of Alzheimer's disease to obtain a cross-bred mouse comprising the Qpct knock-out mutation;

wherein the cross-bred mouse has decreased Qpct activity compared to the mouse model of Alzheimer's disease.

37. The method of claim 36, wherein the mouse model of Alzheimer's disease is selected from the group consisting of PDAPP, Tg2576, APP23, TgCRND8, $PSEN_{1M146V}$ or $PSEN_{1M146L}$, PSAPP, $APP_{Dutch}$, BRI-Aβ40 and BRI-Aβ42, JNPL3, $Tau_{P301S}$, $Tau_{V337M}$, $Tau_{R406W}$, rTg4510, $H_{tau}$, TAPP and 3×TgAD.

* * * * *

SEQUENCE LISTING

```
<160> NUMBER OF SEQ ID NOS: 25

<210> SEQ ID NO 1
<211> LENGTH: 25
<212> TYPE: DNA
<213> ORGANISM: Artificial sequence
<220> FEATURE:
<223> OTHER INFORMATION: Primer sequence

<400> SEQUENCE: 1

gtagctggga ttacaggaat gtgcc                                           25


<210> SEQ ID NO 2
<211> LENGTH: 25
<212> TYPE: DNA
<213> ORGANISM: artificial sequence
```

<220> FEATURE:
<223> OTHER INFORMATION: Primer sequence

<400> SEQUENCE: 2
gtcctgaagt ttgagaacca ctggc 25

<210> SEQ ID NO 3
<211> LENGTH: 25
<212> TYPE: DNA
<213> ORGANISM: artificial sequence
<220> FEATURE:
<223> OTHER INFORMATION: Primer sequence

<400> SEQUENCE: 3
gctaactttg ctaagtcagg aggcc 25

<210> SEQ ID NO 4
<211> LENGTH: 25
<212> TYPE: DNA
<213> ORGANISM: artificial sequence
<220> FEATURE:
<223> OTHER INFORMATION: Primer sequence

<400> SEQUENCE: 4
tctacctcac accagtcaga atggc 25

<210> SEQ ID NO 5
<211> LENGTH: 24
<212> TYPE: DNA
<213> ORGANISM: artificial sequence
<220> FEATURE:
<223> OTHER INFORMATION: Primer sequence

<400> SEQUENCE: 5
gtgctacttc catttgtcac gtcc 24

<210> SEQ ID NO 6
<211> LENGTH: 24
<212> TYPE: DNA
<213> ORGANISM: artificial sequence
<220> FEATURE:
<223> OTHER INFORMATION: Primer sequence

<400> SEQUENCE: 6
tgtgggacat caatgagagg agag 24

<210> SEQ ID NO 7
<211> LENGTH: 27
<212> TYPE: DNA
<213> ORGANISM: Artificial sequence
<220> FEATURE:
<223> OTHER INFORMATION: Primer sequence

<400> SEQUENCE: 7
ctacttccat ttgtcacgtc ctgcacg 27

<210> SEQ ID NO 8
<211> LENGTH: 24
<212> TYPE: DNA
<213> ORGANISM: Artificial sequence
<220> FEATURE:
<223> OTHER INFORMATION: Primer sequence

<400> SEQUENCE: 8
gtgctacttc catttgtcac gtcc 24

-continued

<210> SEQ ID NO 9
<211> LENGTH: 25
<212> TYPE: DNA
<213> ORGANISM: Artificial sequence
<220> FEATURE:
<223> OTHER INFORMATION: Primer sequence

<400> SEQUENCE: 9
ccagtcatag ccgaatagcc tctcc 25

<210> SEQ ID NO 10
<211> LENGTH: 25
<212> TYPE: DNA
<213> ORGANISM: Artificial sequence
<220> FEATURE:
<223> OTHER INFORMATION: Primer sequence

<400> SEQUENCE: 10
aggagttggt gggttagtga gcagg 25

<210> SEQ ID NO 11
<211> LENGTH: 26
<212> TYPE: DNA
<213> ORGANISM: Artificial sequence
<220> FEATURE:
<223> OTHER INFORMATION: Primer sequence

<400> SEQUENCE: 11
gccttctaag tagctgggat tacagg 26

<210> SEQ ID NO 12
<211> LENGTH: 26
<212> TYPE: DNA
<213> ORGANISM: Artificial sequence
<220> FEATURE:
<223> OTHER INFORMATION: Primer sequence

<400> SEQUENCE: 12
gagacccata cagagaatct tgaggg 26

<210> SEQ ID NO 13
<211> LENGTH: 27
<212> TYPE: DNA
<213> ORGANISM: Artificial sequence
<220> FEATURE:
<223> OTHER INFORMATION: Primer sequence

<400> SEQUENCE: 13
gggctttctc agtgttctta acattcc 27

<210> SEQ ID NO 14
<211> LENGTH: 25
<212> TYPE: DNA
<213> ORGANISM: Artificial sequence
<220> FEATURE:
<223> OTHER INFORMATION: Primer sequence

<400> SEQUENCE: 14
tctatcattg attctcagga tgcgg 25

<210> SEQ ID NO 15
<211> LENGTH: 24
<212> TYPE: DNA
<213> ORGANISM: artificial sequence
<220> FEATURE:
<223> OTHER INFORMATION: Primer sequence

<400> SEQUENCE: 15
agagaatgac cactgctgag gatg 24

<210> SEQ ID NO 16
<211> LENGTH: 24
<212> TYPE: DNA
<213> ORGANISM: Artificial sequence
<220> FEATURE:
<223> OTHER INFORMATION: Primer sequence

<400> SEQUENCE: 16
tgtgggacat caatgagagg agag 24

<210> SEQ ID NO 17
<211> LENGTH: 27
<212> TYPE: DNA
<213> ORGANISM: Artificial sequence
<220> FEATURE:
<223> OTHER INFORMATION: Primer sequence

<400> SEQUENCE: 17
ttggtaagca tccagttact aaagagc 27

<210> SEQ ID NO 18
<211> LENGTH: 25
<212> TYPE: DNA
<213> ORGANISM: Artificial sequence
<220> FEATURE:
<223> OTHER INFORMATION: Primer sequence

<400> SEQUENCE: 18
gcaatcggtt ttaatcacag taagg 25

<210> SEQ ID NO 19
<211> LENGTH: 20
<212> TYPE: DNA
<213> ORGANISM: Artificial sequence
<220> FEATURE:
<223> OTHER INFORMATION: Primer sequence

<400> SEQUENCE: 19
gtccggtaag gtgaggagaa 20

<210> SEQ ID NO 20
<211> LENGTH: 20
<212> TYPE: DNA
<213> ORGANISM: Artificial sequence
<220> FEATURE:
<223> OTHER INFORMATION: Primer sequence

<400> SEQUENCE: 20
tgatgtgtgc gtttcagaga 20

<210> SEQ ID NO 21
<211> LENGTH: 22
<212> TYPE: DNA
<213> ORGANISM: Artificial sequence
<220> FEATURE:
<223> OTHER INFORMATION: Primer sequence

<400> SEQUENCE: 21
ccagagacat cctggtaaaa ca 22

<210> SEQ ID NO 22
<211> LENGTH: 38338

-continued

<212> TYPE: DNA
<213> ORGANISM: Mus musculus

<400> SEQUENCE: 22
ccttccttcc ttccttcctt ccttccttcc ttccttcctt ctttcctccc tctctctccc 60
tccctccctc ccttcctttt ttccctccat cctttctaaa ataaggaagt gttttctttg 120
tcccttggat tccaaagctc ctgtcaccca gggaagctca gtcccctggc ttccaggctt 180
ctgggagagg actgctggtt tgtgcttgcg ctgcacagcg ggaggccaca ggaggcgact 240
gggaggcaga cacaatcaat ccaggggtgg agaagggaga aggcagggcg accggcgcgc 300
gttcccgggc tcgtgaccgc tggcggcccc gggaatccac gcccacacac tcttgcagag 360
atggcaggca gcgaagacaa gctcgtcgtg ggcactctcc acctgctgct actgcaggcg 420
accgtcctgt ctctgacagc tgggaatctg agtctggtct ccgctgcctg gacgcaggag 480
aaggtgaggg gccactgctg cgttctgaac ttgagtggcg ttggagggtg ccaggacctg 540
ggactcggcc accttctctt ggactagcgg gaggcgggtc agggatgctg tccccctgct 600
caggcaccaa gtcctcaccc aactcctggg aaccagtgct ctctctccca agtctgggcg 660
ccagggctgg tctcggggct gcgctagtgt cgcctggggg ctgagtgatg tcacccgcct 720
ccctttggct gcgctctgat ggggggtggt ggtgctgctg ataggcacag gaagtatgtc 780
tcgctggctg tgcaagaaca gggacatggg ggcgccactg cccaatcgcg acccgcgagc 840
tccgcgctcc ccgcgcttgc tcctggatgc ctagaccgcg cgtctagggg tgtccccatg 900
gatgcccaac tacagcattc aaggatgcta catggggatt gagtttcctg gtggactcag 960
cgccagcata ttgttaaata tttaaaagag acgcacgctg ttttcagata aatgaattca 1020
gttgtggaaa tctcatttaa ggaattcaga ataaaaatga tttgccaagt cgctttgtgt 1080
gaagaaaata gattcacaat tacttccttt tcttgtgcaa cagttttgaa atcatgaaat 1140
tgctacgagc tgtgcaaacg atgacggttt gggaataaaa tggcatgtct ttaaagaaac 1200
taggaaaagc atcagtctag ggatagaacc ttgcgcgcga cattactaaa caagtacttt 1260
aagtgctttt agcgtttctg cacgtccaac atgctcattc ccagctagtt tcatgcacta 1320
gtgtatgaat ggcccacttc aggtgagctc aagcatagcc aacttctttt caggactcac 1380
aacagatccc catttacacg gggagtctgg agtgggtgtg ggaagtcaac accgtacaac 1440
ttcagtctct ccagaatgag tcaaacggct tcccccagag gctgggaagt acttctcaag 1500
ccgttgagta gaatcctctc ctgcactgct ttggggtacc tgggaggtca agcaccgaga 1560
agggacttta aaaccagagt gtcgcacaag gccaaatgtg tctttaaaac gtattttaat 1620
ggatgagaaa tattgtcagg ggctgagctc cactcggggt ctgtctgtgg gcaggtgtag 1680
cagccagggt tgtttctagg tgggagaaca tcctgtgatt ctttttcttt aagagaaaat 1740
ttccttttta ttgattcgtc tctcatatat taatccctac tgcaatttcc cctccctctg 1800
ctcccctctt tccttctgga ttcactctct cctccacctc tcctcagaaa agagcaggcc 1860
tcctagggat gttaaccaaa caggacgtta caacctacat taggaccagg cacacattct 1920
cacatcaagg ctggatgagg caacccagta atgggaagag ggtcccaaag tcaggcaaaa 1980
gaatcggaga cagctcctgc tcccactgtt aggaatcccc caagaacacc aggctacata 2040
actgtaacat gtatgtggag gacccaggtc agactcctac aggctctctg atctctgaac 2100
ccacttgagt tctggtcagt tgattccgag agccgtgttc ttgtggtatt ctcaaaatgt 2160
tttaaactaa attcagattt aacttttgag aaatgtctta agaagcttct aacagttgtt 2220

-continued

```
ttactgggaa aacaaacact ctcaaatggc aggagtggat gacagtcagc catgacgtct   2280
ctcagttaat agctcctcct gctttcctag ttttaaaggt ctccataaag tcttctgggc   2340
agccagctac actttacagc ctgggagatg aatcagccta tactcaaatg tgccttcctg   2400
ccttttatga catttgactg ttttaatcag acaaggcaca gtcttggtat actggtctgc   2460
caacaggaga agtacgataa cgagagcatc agttctgaaa tccattgcct tgtttagaaa   2520
tagaggcgtg tctcttggag tagcatccgc tgtgtgaaag cacatcgacc ctagtttatg   2580
gctgtcgtta gaaccacgct tcagtgattc gaagcctaga aaccattcat agaaacaaat   2640
gactacacct ccgacggggc ccacgtatgt gtgtatgcgg aagggtgttg acacgaaggt   2700
accagttgtc agatagatag aaccacgtca tgtgaatctc acggtaccgg gaaagagtgt   2760
gcttatcgcc atttataaag tggaaatcag gaaccctggt cttcccagtt ctgctttatt   2820
ttctcctttt ttaaaggtag ataaatgctg gctggctgag gaagagtgtc tagctagccc   2880
aggagtgtgt gcgtgtgtgc gtgtgtgcgt gtgtgtgtgt gcgcgtgtgt gtgaatgtat   2940
gtgtgggatc tatatgttag gggcatcat ttcttcccac acccccagat tcctagttcc   3000
ttggcctctc tcttccagtt ttcgagttat cattatgctg aaagttgatc tgtatctggt   3060
tactgtccct gatctatcta tctatctatc tatctatcta tctatctatc tatctatcta   3120
tctatctatt tatttctggt ttagtggtat ttatttattt atttctggtt tagtggtttt   3180
gtttttttctt tccctttttaa atctcattaa atcagctctc ctttagatga gaactgctgg   3240
ctgtcgagac gctgcctaca tttgaaaagg aatgttagct ccgctgagct aaacagtgca   3300
gcttcacttg tcatgttcta gttgtgaagg tagcatgtac tcactctaga aaggttcaaa   3360
aacacagaac aatgtattct aaaaaaaaaa aagaaaaaaa aaaggacacc acctacaatc   3420
tcattttcca gataattcct tttaatcttt ttgggtcttc ttattgccag ctcccatgta   3480
cacacacaca cacacacaca cacacacaca cacacacacg cacacacaca gatttataga   3540
gatgagtaat gatgattgaa tttcagcttg ttatagggac tgaatgagtt tgtaaaacag   3600
cacagtgtct agcttacatt gaaggctcaa tgcatgttaa ttattgaaaa ataagcatac   3660
attagtattt tgcagtcagc actgcacatg cagtttaata tgattaatag tgtcatgaat   3720
cgtaccataa gccggtaaaa tcccctgaaa acataacttg atgattgcaa aactatcatc   3780
agttgatgat ttatttcttc atcttgaaca ttgaggttgc tagcaaatct ctatcaataa   3840
agctgagaca taatgtattt tgacgggaag aattttccct tactgtgaca atgttgaagg   3900
aggaaaattc aagtcgcatt agaggtggag aggcaaagac tcggaagggc ccaggagagc   3960
tgtaaacagt tatctgcgac acttcacgtt tctctggttt tgaaccactt gctattccaa   4020
atgtccataa gatttccccc tctctacctc actcggccac ccagccacct gtgagtggaa   4080
agaggcgact ccaaggcagg gacagagagg ctcgtgaaga cctctagggc aggaaaaaag   4140
ccaactgtca tcttgaaatc tctactatcc tgtggtttag aaacagtgac acccatttta   4200
cacattaggg cacttttctt cgacgtaact gttcaatgag gagctggggt ctctctgttg   4260
tacttccctc tcggccctga tttttaagaa gcgagcctgt gtgcactgga cagaaaggca   4320
gaatcttggt cagtttccag ttcctttccg tgctgtgtct gtgctgacca tggcttgcac   4380
acatttcagt cactgctggc agagtggaac ttgcaggtag caaaagttta atctgaggac   4440
tgtctggaat gttcataaag gaagcttgga tcagctgcat ttctgcaatg gtctccctta   4500
caggcagtgt tttggcctct ccatttcgcc tgcaggcaag gccgcctctc caaattatgt   4560
aatgaaatgc ctgggccgtg tgattagaca ggagatgctt caggatatct ggttcacagg   4620
```

-continued

```
tttgtttcag ctgattcttg tcacctggag cagacttcat tgtcctttct gcctggatga   4680
aaagacaagg ccctgggtgt aacagagcct tgttcctctg agaacgttgg caccagcaga   4740
aatggctgaa gtacctttca attgaaatgc acctagagca agcctgggat ttacacttgc   4800
ccttggcctt tattctgttt tgttttgttt gtttggggcc agagtatcac tataccgccg   4860
tgttgtaggg ctggagctca ctgtgtagat caggctggct tcagacttgg ggtgattctc   4920
ctgtctctgg ctctcatgtg ctgggaatca cgggtgtgca cccccacatt cagcttcggc   4980
actgttttgg ggccaggtac tgtcctctga gcctatcctt cccacttctg tcttactcat   5040
tcctgttttg aaacaggttt tgtacttagt gagttctgag agtaagagcc ctttacttca   5100
gtggttttca accttcctaa ggctgtgacc ccttgatacc gttcctcatg tcgtggtgac   5160
tcccaagcat aaaattattt tcgtcactac ttcataactg taattttcct tttattttga   5220
gttgtaattc agatatctga tacacagatg atcttaggtg accccctttga aaaggtcaat   5280
tgaacctcca gactggggtc gagacccagg ttgagaaaca ctgcctgtaa attgactgta   5340
tgctgtttag catatgcaag ctgtatgctt ttctgtaaga gctttttgtg aatcaagggg   5400
cttgtacaac tgaatttagt tgctctgctt tcaatactct tcactaacta ggaagtttga   5460
tatttctgtg atttttcaga tctggtccag aaagaagggg gaaggaactc tttattgaag   5520
tgcacttatg aaatcaacca tttttgttgt ttagctcagg aggttgaaga gcagatagtg   5580
cttattcaaa agcacccgtg ggtctgtccg cttcactcac tatcagctac taagaattta   5640
aaaaatgtcc tttgacatgt tgctttcaga cacagtatct tttgctgctg gagactgtga   5700
tacttagata ccgttcacca atttgacaag actctagaac cacccaggag acagccctct   5760
gtgcacgtct gtgggagact ttctagattg ggttaaagag gtgggaagac acatcctcca   5820
cgtgcatagg ctagagtctc agttaagatg gctaaatggc aaaaagaagc aaggtagcag   5880
cagccatcgc tctctgcctc cgaactgaac tgcgctgtac catgagcagc tgtctcattt   5940
atcgctgtgc tctatgcaca tttactttgt atcaaagagc cttcaaactg agcaaactga   6000
acctttcctt tcttaaactg tgattgaatg gcactgtgcc ccagcaactt gggaaggagc   6060
aaatagagag atcatgaagg ctgatttatt tcattcttgc ttttctgaag tcttgtgaga   6120
ttttccaagt tcctgtaaag catgtattta aacatgactt tgatttcctt tcactgtgga   6180
catgaagaac acagcccaca gtgactaggt tggctctggg gttggcacag tgggcagcga   6240
ataggaaaga agccatcgat aaaatagttg tgtaagagag aatagtaatt catttattta   6300
tgcagtgtgg gtagaaggag gaatatgaaa gggtatcttg ctggagtcag ttccttccta   6360
caatagagaa tctggggatt ggactcgggc ttcaacagtg aataccttta accacagaga   6420
cacatcgtgc ccctgaaaca gattctgaca tgaaagttta catctgtcat cattactgcc   6480
ctgggccaag ccaaggagct gtcagttgtc tgaagcattg tgcagaagtt taaaagaagc   6540
aaagctgaca agcacggaac taggatgtcc ccttgcaaca ggcagccacc tggaaccagg   6600
ccatgtcttg tccccttgtg ccaggcagcc acatgtctct tctggctttt atgcctgtct   6660
atgaattcag ctagtttagt atttacgaag acagaggtgt gactcttacg cctttattat   6720
ataaacacgt ttatagctgc agaagtttta gaaaaatact tagtttgtct ctccattact   6780
tgaaattacc cagtagttac caggtgctca atgtgagcca cacccctgcg actctggaga   6840
gaggcaggaa actgggagag ggttctagct ttcctggagc tcctgactta tgtgaaatac   6900
agatatgaaa cacgacaccc gagaacagtc ttcaggcagg agcatgaaga agacaggcat   6960
```

-continued

```
tttgaaggtg aagagacacg gaaacagttt gaagggcaga ctgcattgct gaggtgccga   7020
gaccctaagg agtagatctc aaagtggctg ggtgctaggg tgaccaaagt gggatgaatg   7080
ggagcctgca gctcatgctg gggcttgcaa ggcagtggga gagacacaca ggcatttgtt   7140
gggaaggaac aaccatgcag atcccccttt ctgcccccat ttactttggc tcacacttca   7200
cactttttc ccctttagat tcagctttct tgttcaaatg ctgtttaatt ctaacacgag   7260
gacttagaca ttggaggcac taaggaattt aaaggcttca gtagaagttt gtttagaaaa   7320
tatatctatc tgttgcatag ggctacataa ggccatttcc atgcaagtgt gtaatatact   7380
ttaagcatag tctacctccg gtgctctgca agtgttcctc ccagacacac tcagagaccc   7440
ctttgctcct ccttcctccc ccctccccct gtttggtttc cactctcatg gcatgtcatc   7500
ttatgagttt atgtctatgg tttctagtca aatctgtttt tccccaggga acgacatttg   7560
aaagaaatat acttcttaat gtgtgtctgt gtgtgtgtgt gtgtgtgtgt gtgtgtgtgt   7620
ctgtgtgtgt gtatgtatgt atgtatgtat gtgtgtgtgt gtgtgtgtgt gtgtgtacca   7680
ttgcacctat gtggagctca gaggacaaca tgcaggagat ggttttctcc ttccaccatg   7740
tgggttcaag ggattgaact taggttccca agacttgaca gtagctgtct gtacccattg   7800
tgtcatctcc ctgtccccta gaaatatgct ttaaagtgta ttattcccaa gaacaaaacc   7860
aaaaccttaa tacattcagt tacggtatca atattcaaga gtaaagcaga agtgaggaaa   7920
tgaagcagaa cactgaatgc tggggttagaa atcctcctgc cgggatttac tttacgtatt   7980
tacctttaac tctctaccgt tggtttttac agacctcagt tcccattggt ggaggtcagg   8040
gggttggact agttatctct aagtgacata tccaggtctc acattctata ctagtttact   8100
gtacgatggg ggaaattagc accctgggta tttactaggc aatctgtatg ctttggctcg   8160
tttagtccta agtaccttcg ggtgcaggta ctatcacctc catttttcag acaaggaaat   8220
ggagccttga taaggttaag taacatagcc agagttactg ctagtggtgg gtgctaagtt   8280
gaaaggctgt atctgatcca atagcctgtg ctctttgcat gataaacact ggagagaaac   8340
actgcgttat ttcaaagtct agagggatct aagcaacgag gcagcagcag tcagtatttc   8400
tacagtgttt cattagccgt gtgggtggtt catgtggagt gaattacctg catgattatt   8460
taatgtatcc agtaaacact aatcctggaa ggaactgcag gatgggcgga gtctcccaat   8520
ttctgttttg cattccaaag aatgtcccta ccaccgttct cctcattctc cttagggaag   8580
aactggtttg agcaaccatt catttccctt tgagcagaag tgccacaatc cctaggagtg   8640
tctgatgaac ttgtaatgaa tggctgattc atcattttgg gtgtcctaag acaagttcag   8700
catgtgtaag gtcatattca ggatacacat ttgaacatta ggtctactga gcttttaaag   8760
ttttatttta atatgtaaat gtactaaaga gtattaaaac cttaatagac tataagataa   8820
ttaggttgat gatggaaaag agttcctatt tagccagctt tacaattgtc agactcacat   8880
tgagaggggc atcattcatc ccgggtacac actgatagaa attgagggcc aggaagaagg   8940
ctcagtgcgt aaaagtgctt gctgtgcaaa catgaggaca tgagtttgaa ccctcagaat   9000
ccatgcaaga gccaggcaga gtgtgagaga tgagagattg agacaggaaa agccccaaag   9060
tgtgtaggca tcgagcctgg tatcattttg tttttaaggc ctgtttttat tttatattat   9120
gtatatcctc cttaggctta ctatggctgg gatgaaacat catgaccaaa gcagcttggg   9180
gagggaggaa agggtttatt taagcttata ctttcaggtg acagtccatc actgagggat   9240
agtcagggca ggaacttaaa catggcagga gctgatgcag aggccttgga gggatgctgc   9300
ttactggctc gctccttgtg gcttgctcag cctgctttct tatagaacct agaaccacca   9360
```

gcaaaaggat ggcaccacct ataataggct gggcccttcc ccagcaatcc ctaattacaa 9420
aaatgtcctg caggcttgcc tacagcctga tcttgtggag gcattttccc agttgggggg 9480
gttcctcctc tcagataact ctagcttgtg tcaagttgac ataaaatcag ccagcacccc 9540
agcacttggg aggcagaggc aggtagattt ctgagttcga ggccagcctg gtctacagag 9600
tgagttccag gacagccagg gctacacaga gaaaccctgt ctcgaaaaac aaacaacaac 9660
aacaacaaca acaaaatcag ccagcacaat gtatgtgtgt gcattctgtc tgcatgtatg 9720
cctgtaccat tagtgtgcct gatacataca gaaaccagaa gaaggcattg ggtcctgcca 9780
gaactgaagg tttagacgct tataagccac catataggtg ctgggaatta aaaccttgtc 9840
ttctataaga gcagccagtg ctcttctctt cagccccaag aatgaaattt aaaatattct 9900
agtatctaca ttaagaggtt aaggttggaa ttaattttaa caaatatttc acttatagca 9960
tagtaaaaac tgtttcatca catacccaga gaaatataaa tgacataatt ctatttttat 10020
aaaaaggtct ttaaaagtga tgtattttcc agatgtggtg gtacacgctt ttaatcccag 10080
agcttggtag atggaggcca gcctggtcta cataatgcac tccagatcag ccaaggacac 10140
acagtgagac attgtctcaa aaaacaaaaa caaaaacaaa aacaaaaaca aatccaaacg 10200
ccccaaacct ggtgtataca ttgcacttga agcacacctc gattttctac ttttcaagtc 10260
ttaatagtca caaatggctc gtagtctcct gtactggaca gtgcagatct agaacaacta 10320
gagaactggc tgacgtcatg gcgtctgcac atggcagctg gaggtcttgc ttaggcctcc 10380
ctgccttgcc gttctgaagt gcctctctgc ctgttataaa acagctctac tgacagtgtg 10440
tttctttgct gtcttcagct ttttaaatat tacattttct tcagataata atctcaaaat 10500
tgttatgttg ttgttgttat gttgttgttt tgacataggg ttctattgcg gtaaatctcc 10560
aacccaatta tgcctggcaa tgaaaacaaa actcaattaa tatgattaca tgctgtgagc 10620
ctagattggg cagatctact gctacactac catcttccac atgagacccc gtagaacttg 10680
cggtttctcc aggccatgtg cttctgctct gcttttcttc ttcttcttct tcttcttctt 10740
cttcttcttc ttcttcttct tcttcttctt cttcttcttc ttcttcttct tcttcttctt 10800
cttcttcctc ttcctcttcc tcttcctctt cctcttcctc ttcctcttcc tcttcctctt 10860
cctcttcctc ttcctcttcc tcttcctctt cctcttcctc ttcctcttcc tcttcctctt 10920
cctcttcctc ttcctcttcc tcttcctctt cctcttcctc ttcctcttcc tcttcctctt 10980
cctcttcctc ttcctcctcc tcctcctcct cctcctcctc ctcctcctcc tcctcctcct 11040
cctcctcctc ctcctcctct gcatcctctc cctcttccat tttctccttc tctccctccc 11100
ctcacctttt gctccacctt cccatcatca gctcttcttt attttacaaa ttaaggtggg 11160
aagcaggttt acaggaaatc acctgagtgc tgactcattc ctggttggaa gacactccca 11220
ggagaatgga cttaacatca aatataatta gctccagggc tctccacaac agggttcctc 11280
tgtgtagtcc aggctggcgc tgaacttgta attttcatgc ctctgcctcc tcagtgttgg 11340
tactctgtat agttgttatt aattttttaa attacgtgtg tgtgtgtgtg tgtgtgtgtg 11400
tgtgtgtgtg tgtgtgtata ccttggtgta tgtgtggagg acaatttgct agagtcagtt 11460
ctcttcttac accatgtagg tcccagagat agaactcagc tcttcaaact tgttggcaag 11520
tgctcatcca ctgagccatt tcaccagccc agaactgtta tttttaaacc tcagttttac 11580
aaaacaatta ttcagaaaat ttatctgaag ttacaccagt tgtgtgactt accatgaaag 11640
catactttca attttgtttt tcaaacaagc tgccaaaatc tagacatttc aaggggacaa 11700

-continued

```
ttttatagtt gagcccttta cctcatatga cataaacctt ctcctttatt ttgaagtttt  11760
tttttttgtt ttttttttg ttgttgtttt ttttgagaca ggatttctct gtatagccct  11820
ggctgtcctg gaactcactt tgtagaccag ggtggcctcg aactcagaaa tatacctgcc  11880
tctgcctccc aagtgctggg attaaaggcg tgcgccacca tgcccggcta ttttgaagtt  11940
tttaaagcca ctaatcacaa atgtaccatg ctaagtctta aacacataca attggagcta  12000
agtacttttt atttgatcac agaaccacca ccaaccagca catttgaatt cttcatctct  12060
tcagcaagtt gcagaaggca ctagcatttc tgaaatgtgg caaaacgact tgagaccatt  12120
gctgatagaa cgatatcctg gatcgcccgg aagctattct gctcggcagg tgaggaagaa  12180
cagagttcac acctaaaggt tttaaatact ttgctttccc ttgagggatg agatggtggc  12240
taaagttctg agtcatgtat aacattatct cactacacac taccagaggt aaccaagaaa  12300
gacatacacc tgagagtaag tgtctatttt gagttgattg ctacacattt actgaaaatc  12360
agtttatgtt tatgtgtgac atcattgtcc tgactatagc agcaataatt caggatacta  12420
aggccccaat cttggtcact tcaaggacac attcctagct tactaaccat tttttgtgac  12480
ccctagaatc caaacttcaa cagcttttca cagtgcttgc ttagcagttc cagggcaagt  12540
gtgagtcacc gaactgtcag ccttttttcct cttgagggaa attgttttct tggctgaggc  12600
caatgattag cttctgtcta cagttgagct tctcagacat ctactttgac ccacagtaaa  12660
aacatggtgg attttacaga caaggatgtt taacaatgta tttagctgca atgaaagttt  12720
ttggaaaaac tactcattgt tattatctgt aatttattta gatattgtaa gttctatttt  12780
tatttccagg tttattgatt ttaccactgc tgtttggagg acagtgatgt agagggaagc  12840
tataagatgg gctagacttt gaatttcttt gtcaatctgc ctgagcaaca cgaaatctta  12900
cctctcaatg tctgcttttt tccaaactaa tctcattcaa gggggagctt gggaaggaat  12960
aggaccggcc tctcaaagcc tcttcctaaa tattctactt gctcaacttc ctagacaaaa  13020
acattggcaa ctactgctgt gtctagagag acctgcatgc ttcatctatg cagctcacag  13080
ctcttatttt tctactgtgt agctctgccc tgcaagtgta cccttgacag atgtgtgtgt  13140
tggctttttt tagcctcctt cttcccatct gaatagctcc tcagatgagg cctgttgtgg  13200
tgagtttagc taactgttct gtgctcccga caggtcgcac atgtgcaccc acccaagagc  13260
tatctggatt tgtgaatgga agacagacag acagacagac agacagacag acacacacac  13320
acacacacac tcaccccagt taattttaaa tgccttgact agcttaatgg ctgagcattt  13380
ctaatccttc ccactgctag caaacactcc tctcctgtac tcctgagtta acaactttta  13440
aagtctatat ttcatctctg ctaccccaac acatttgggg aagtgggtca tgtggccact  13500
ttccatgatt ctcatatgtc agtgggcctt tgggtctggt ctttcctctt ccccatcaag  13560
gtgatttctg ccctttcctc tctcccaatc tctagtctgg gcaaatctaa aggtctggtt  13620
tcagtccact tgcccaggca ttggctgttg gctctttatt gattgatcaa aagaccagtt  13680
ggggacaagg accttcagta tttggacaca cagatttccg atttgagggg cgaggttaat  13740
tcaaagcatt agaaccaatc cccaacaaag ctctaacaaa cttggttatt ttagccttca  13800
gaaacattga ggaatggtga tgaggaggag gggaaggaag aagaggaagg ggaggaggag  13860
ggagggggag gaggaaaagg gggaggatga tggtggtggc caacttccat cctttcctag  13920
ctcccttcct tcttttcttt ctttttattc atatatgttt ttttgataaa cagtatcact  13980
ctacaaccca ggctggccta gaacttacca tgtagcccag ggtagcctta aacttgaggt  14040
gttccttgtg tttgattctc tcaggatgta gggttgcagt tgtgaattac catgcctgga  14100
```

tatccatcct ggatggtcaa ctttcggaca gcacataata gcacatttag tttccacaac 14160
aatgctacat tcctatccca atatacttat ttaaagagat ccaaggctta gttatctgaa 14220
ttaatttatt tgcagttatg tgtgttatag cagtttgaac tcagttctac ttgattttct 14280
aatcactaga gatttgagag aaattagatc aaggataaat gaagctaata gcttcagctc 14340
tgcatcttcc catggcacac tggagagtga ggtacacaat atttattgca cagttttccc 14400
aaggccccat gttctaagaa ttttcttgaa agtttcagaa tgtttgcttc tcaaagtcct 14460
cagctcacct ggaaacaatc cggctatga tacttgatcc aacctttccc attttcttac 14520
tctgttggct cagaaggcta tttacatgca gatacacata tgcatacatg aggcccaagt 14580
tccttattcc taaaaggcca taaacatagt gaacattgtt gaaactttgt cttctatgga 14640
tatatagcat aatcagtata taggtattgt tatgatttaa aagatataca ttcagtggct 14700
ggagaaatgg ctcaacagtt aagagagcat attgctcttg cagaggacca cagtctggtt 14760
cctagcaccc atactgagtg gttcacaact gcttgtaact ctagctctag agaaactcaa 14820
cacctctggc ctcacatgca cacactcata cacagacgca tgcatacaca aaataaaaaa 14880
aaaacttttt aaatgttcga agataaatat ccacataatg accaagtcta caatagcatt 14940
gaccactgtc ttgaaggggt agaagcaaag gggaaatgta ttgacagtat tttagaatgt 15000
gttaggccct aggcaggact gcctgtatgt ggcctgactg atgtggtggt agatgataac 15060
aggataatca tgttagaaat tttatttaac cctggccctt atgggagagc tggccctgcc 15120
ccccccaaca acctttggtt ctcttaagtt atggcttctg gggagggata caggcagaga 15180
aagactcatc ctcccctggg ttgctggcca ctgggaatct gaccctatcc cggtgagaat 15240
atggctaaca caacatggac gtgctttttc ctctttttga taagaataaa taaattataa 15300
aataaataat acgaaagaaa ttttacctaa gagattcagt cttattattt ttaataagaa 15360
aattgctatc actaatctag aatgatgtcc cttaagttgt ggaagagaaa aggctccttc 15420
atttgaaaat gaaaaagaga caattattat gaggggacca tactcagggt tttacatcga 15480
tgtaaaactc aagtaggatc acagcctttc attcagagcc aaatttaagc agccccaata 15540
acaaaaattg ttccccttag gcctcttggg aactaggtca ggtactctgt agttcacaga 15600
gacacgcagt catgacttaa gaagactttt ggctctggaa tcctgaggac ttgatccaaa 15660
gtcaagttgt aggttgactt tgcagtcaca gggtagatgc atatctctat gagtgctttt 15720
ggagagaaag tatttttgga cagatgtgtc ttaaaattta cacttatgac ccttgagcaa 15780
caaagcccaa agtgactatt gaatttaaat tttgatctaa agaaataact tatttattaa 15840
aaaaatatat tgaaggcatt cacttgtggg catttcagtg atttccagtg tagacataga 15900
aagtaaactg agtcacaagg atggcaaatt ttcatgaggg acagtcaaga tccttttcta 15960
ggagagacaa gctagagaaa tcagggatgc acagagtgtg gaaagtcaaa actgaatttc 16020
tgtgaaaggt atgtaggtat tgttattgtt ggtgtacagt taccaatgga gaaccctgtg 16080
tggagtatgg tcagcttgga tccccagagc cttgtgtaga gatagtctag aaaagagtta 16140
actggaaaaa gtggcagggc caggaccctc acaacagtgc atttgcagat ttagttgcac 16200
acactggaga gtctacttcc ccagagcaat cctgatctgc ggctgacagc accatttctc 16260
agatacccaa aattagaatt tacgcataac cccatcacac ctaggaccaa gtactaacgt 16320
taccccagaa tagcttcctc tactgcctca cccagaatca gaatgccaaa tggtagtctc 16380
tctagcctga cccctcatca cgcctggagg cccaaccttt gatccctcgg agtcaagcgt 16440

```
gaactgctgc ttagacttta ggaatattgt gataaaaagc agtggtttgg gaaatctcct  16500
tcagagcctt ctggtggaga catggagcct aaataaatct gaaagctcaa gacaccactg  16560
agtactggtg tcctaatttc atcctggtta ctaagataaa tgaaaatatt tattttgtat  16620
acaaaaaggt tacttcagag acagctgttt ggggctcttg gtgatatctt tcgtggaagt  16680
cagtatacat aggaatgtta ggagtcattg cccagggtgg gggaattgag ttgaggaatg  16740
aggttctggg tgaaacttct gcacaatgct agcagataac cttcaacaga tcctttaaaa  16800
tctcagtgca tctccctggc taccatcggt ggtaagaagc cattttatgg agcagtttat  16860
catctggact ccagatgtgc tggagttaaa caaagtctag ggataactca tttttttatc  16920
ttctttagaa aacctcgtcg tagatgcaca gcgatctccc tcgatagtga aacaatgaac  16980
gatctgtgtc atgtgatttt atgtatcctc atcacattaa ctcccatttt ctgctacagt  17040
caattcaagt tccctgcggt agaacactgt gaacaaaagc acagtatagg acttgtgggg  17100
aataacaaaa taagggagct ggttgtggaa aggctctaag cgtttctttt gatgaataga  17160
aaaagagcat gtctgtagag tagcagctgt aaagcaaggt aagggatgca gagcgctgtc  17220
tgggttaaag tctaccagcc acacacaaca aagggatctg tctatttggc tttctcaggg  17280
tcgatggtgt gccgcagagc ctccacccac tctgtgtaag tttcccctct ccttggaagc  17340
ctcctgctgg aatttgtgca aagctctctg ggcctgtgtg tcatgttaca tcagcaggct  17400
gtaggccaca caagacttgg ccagaataga aaatcctgta tttctttggg aggaacaaaa  17460
ccctcccatt tgtttccagc tattgtgagt tatttgctca tttatctcaa ggtccctcct  17520
gtctagatgt taatggtggg acaaactgtc agtgattcta atggctcatt tgtgatctga  17580
ggtttaggaa tgtgttttaa taaggcacct tacaaagatg gaaacaacac tggagggaaa  17640
caaagaaatg gagtgaggaa caagtccaag gaaaaataag gacaggaaaa aaagagcaga  17700
gtgagacagt gtcaagctca ttccaaactt ctcaggtcac acattttaca tccctaagga  17760
agacactgtc agtctctgtc atggtgggcc tttcttcccg attcctgcta ctgtccccat  17820
gctgcctaga aggtccaatg tgtccatgag gcagtgctga gagatttctc tgagcttcag  17880
atctggacct accttggata caaaatgaaa gctgggatga gagttgctta ttgattctta  17940
ctgtgggtag ggtctgaccg tatacccatc tatccgttgc tatggggact ttccctacag  18000
ccctcagtag gtgggtgctc atatgtttcc cctactactc tggaagcatt tcagggcttg  18060
gagagcattc tgtgcacttg gcacacgtgc acatacgccc acagctgcca tttgtgattc  18120
ttcgaaagct tggagtggag gtttacagat ctgctatgct tactttctca aagagagcac  18180
cccggcttgt tacaaatgtt agaagtagtc tttaggggcg ctgagctgaa cttgctccct  18240
gagctgtaga tgtgcccatg acagattgtt aagtaaagta ggctgctttc cctgcaaaag  18300
aacacactcc tctttcaaat atacgcgctt gtatgctggt gaggtttgca caatcaaaga  18360
gaagtctgta gaaagatccc catcaggttg ctagtgttgg taaatattga caactgaacg  18420
ggatgaataa gtaggcgaaa ggttaggact gggggagact agtctctcct ttcaacgaga  18480
agctgctact aactaaaaat aacaactagt agtaacgtta ttactatcag taaacatgca  18540
aggcatgtct gccgttaatc ctagtgcttg gaatgaggag gaaggaggat taccataaat  18600
tctgtgctag cctggggcct gatcatgccg ccatttttca gtccagcctg gcctgaatgt  18660
tgttccaaca gcagcaaaag aaggcatcac attcgagatg tagagacaca gctaaccaat  18720
gaaaaccatt ttttgtttgt ttgtttgttt atttgttttt tgctcagcac atcatgcaac  18780
gaattcagag acttcaggct gagtgggtcg tggaagttga caccttcctg agtaggactc  18840
```

```
cctatggcta tcggtccttc tcaaatatca tcagcactct taacccggaa gcgaaacgac  18900
acctggtcct cgcctgccac tacgactcca aatattttcc tcgatgggac agcagagtgt  18960
ttgtgggagc cacggattca gctgtgccat gtgcaatgat gttggaactt gcccgtgcct  19020
tagacaagaa actccattcc ttgaaggtat ctgctctctt cttgttgact cctagggtaa  19080
aacaataaac aaacaaacaa acaaacaaac aaagacagca tcaactccat gaatttggga  19140
atccttggag tggggaggtc atttggaaag caaaactttg gggtgcactt caaaataatt  19200
tgttaaaaaa tatgaaatgg aggaagtatt atttggaaga gcacatgatt taaagtatct  19260
accatgggca ataattcaca gatagataag ggtgggttca ttaactgata tatattcata  19320
cctggttata tattaaattg ggaataactt tttttttttt tgcaaataat gaaataagag  19380
ggaagctggt gatggcatat gtgtgtggat tatgttttct atcaagtcat gcttacttct  19440
tgtttacaca gctgagaaac atcatcacct cctgctggga gagaggtggg ctctggagtt  19500
ggggggtgc attatgggag atcttcagtg tgtggggaat tcagatatac caagatgaaa  19560
agcagaagtg tgctatggtt gtagctgtga atcagggctc agttttacac agtgtagcag  19620
agcttctgtt atgcctgcag ctcagaatgc gtttgggact cccaggtttg atttctgtct  19680
ctgtgttctt aagggtgcac ggggtagggt gggggtaagt gggagggaaa tgctagccta  19740
gatgaggaca ttttattctg atactgctca taaccaagta aacatgacaa agtgaataca  19800
aaaacttggt tcacaggcaa caaatgcctc cccactagcc gggcctttag tttttgatac  19860
aataagtgta aagaaatgaa gggtttatct tgtaatggaa gtaatagaga tatgtgcttc  19920
tgtttttgct ggatatgctg aatttgaaga aagcaaggat tgtttgtacc cccttaatat  19980
ccttttcaca gctgtgttgt ttttctgagc cttctgggat ggctttgttt caggccctgc  20040
cctgctttga actggtaacc attcctgagg gaattcacaa gccggcatgc ccttttggtg  20100
ttttatactt aacgttccta acagaaagac atgggcgggc gaggcgagac ttaaagacac  20160
atttctgctt gtcacaaata aatgtactgc tccaaatgag acagcacagc cacggagcaa  20220
gaggtggaac cagagtgctt ggtaccaaag cattctgcgc atgcccaaag cagagagatg  20280
ccttccgacc aagcccggcc agagaccttt tgttcatgtc caaggtagag acaataagag  20340
gtagttttca tttccttcag gcataaggcc acacggatct cactgaaaag tcagcagtca  20400
gatgacacct aaaggtagcg aaatgactta cattcattca ttccattctc agcattaatt  20460
tatttagact cctgtgaata ctgattcgaa gtcccttgtg gcaagctgct cttttgtttc  20520
tttttacagc tggcaggaaa ataatcatgg tctgcaactt ttactaattt agctttatac  20580
ctggacacca ggaggatctt tgcggcctgg cagttttagt atttttcttt tcagtgattg  20640
ggttgaagcc aaggcctcct gcatgtaggt aaatgttgta ttgctgtcct acaaccccag  20700
ccatatatat atatgtgtgt gtgtgtgtgt gtgtgtgtgt gtgtgtgtgt gtgtgtgtgt  20760
gtgtgtgtat gtatatatat acatatatat atatgtgtgt gtgtgtgtgt atgtatgtat  20820
atgtatatac ataaaaattt ataatttatg tattataaaa tatatttata tttttgtatt  20880
atttatattt tatgtatata aatatattta tattttataa ttatatgtat atacatatat  20940
ataaaatttt aaggcagtat ctaaataagt tggttaggct ggcctcttgg tagtctaaaa  21000
aagctttgaa cttgcaatct tcctttagcc ttctaagtag ctgggattac aggaatgtgc  21060
caccaagatg gctttgaagg tttggttgat gatattataa aggctcagct attatggaat  21120
ccaaagtatc aaatttcgta atctatttgg gaggcattca aggctagcct aatttagatt  21180
```

-continued agagtttcaa gccagccagg gatacaaaac aaaacaatcc acaaagagac aaactgttca 21240
aacccctaat ttctctttta tctggtacca ctctaaagca acagggaaac tctgtctttg 21300
aagaaactag cggatgtgtg ttagtgggaa acacaatatg gagacaagtg gatgtcacag 21360
caaagtggag agaagttagt taaatgggaa tccttcagaa agtacaggat agtctcttga 21420
caatatccta aggggaggta gttagaggat tgacacatta ggaaggcaga agagaggcgg 21480
tgtgtgtgtg tgtgtgtgtg tgtgtgtgtg tgtgtgtgtg tgtgtgtgtg tgtatacaca 21540
gatgtgtata agaaacgtat ggatgtatag attttgaatc catgccaggc agggaggtga 21600
gcattctgct ggctctcagg aaattctaaa agaaattaaa cagagggtat tttggacttg 21660
ggaggacaag ctttaaagaa gggtgatgag gaaccctagg gagatcaagg ggattaggta 21720
aatatcatgt tggacagtgg ggtcttcagg ctttcttcca ttcctagcac cagaaagcca 21780
gtagcagaca taggactgga gaatctgtgt ccagagaatg cagatgccac agacaaggat 21840
gccaagggag acatttggca accttaaatg agaacactga atagacacca gattgctcta 21900
aagtgactac attagagcca accaatttgt gtcttcagtg aacattttag taccttgttc 21960
ttcagtacaa acaaatacca ggcgtggtca gctattggag tatagtttcc attgtggaag 22020
aaaaactaat tatgcaaatt gaaacatgaa gttggagggg tagggtagat actgccaggg 22080
cagcagaaga tagcgtgatg ctattttaaa atccttagag atgagagaac ttgtattcat 22140
aaaataaagc agtcttcaat cacagagtaa tctcatcata gcaaagagct cttggaaatt 22200
tgaaattaaa agtacaattt tcaagaaagg cactaagaac actggactct gaagtaggta 22260
atatatcctt tttagaaagg aaaaaaaaaa caaaataaaa tgattttttt ttcatgggat 22320
cattccaggt catataaaaa gctgtaagaa tgaaagtggt gctggactta gtagaaatcc 22380
tggaagctag aaaacaatga ggttgggcct gcaacattgt ggcatgtgtt atatacatgc 22440
atgctcagat gttagtttgc caactgatgt gttggtctgg agatcagatg tgagaacaca 22500
cacacacaca cacacacaca cacacacaca cacacacaca cacacacaca cacacacact 22560
attcagaata ggtatccaag gatagatgcc agcagagatg agaaaaaaat taggcatcaa 22620
gccctagtgc tctttgatat taagagggag gaggcatgaa ggaatctgta ttttcttctt 22680
ccattcactc tcacagtgag tgtttcacac tcttcctctc cctaacctgc agttccttac 22740
cttgcccatc ctcactccca aggaatagcc ttgacttctt cttgccagtc tcattagctg 22800
ctaagctccc cacgcatgca ttgaattcca tctcctgaat gagggaggca gagcgtgttc 22860
ttctaggagg caaatggaag gattttaccc aggacagagc atcagttatg ctggatgctg 22920
tcagtaagtc agggatgata aagactgaga gctgatcttt ggatttattg atgtgtaggt 22980
cgtaggtgtg cttgacactt atgtttcagt agatggagga gatgaagcct gaaggatagg 23040
cataagaaca gacctcctag aaagcctggg ggaagttaag atagacgttc cagtgatgta 23100
cctaaaagtg acaaaattgg tagactaggt gttgttatta tatctattat tatagtttac 23160
ataactgtta taactatgtt caatgtatat ctaagagaga aggccttttt attggacaaa 23220
aagggtgaga tgttgtggat ttgatttaat gcttacatta tggcttccca aattacacag 23280
ggattcaaat gtctactgcc aatggctggg ctgggagaca gaggcgggac tttgagattc 23340
cccaggcaag gaactcgagg gaggaagaga atgaccactg ctgaggatgg agaaggtccc 23400
cacttgagaa gtgtaggaca gaaagacaga gacactgcca acatgtaaga gtcagagatc 23460
atggcccagg aggactacag gcctgggtct gtggcagcca ggacagaata taacataggt 23520
tttagcaagt gataattcag gaatattgga ggggagagtg tgttagctgt ggggaggttt 23580
ggaagtgccc agcattgagc tgtttaagac atattaaaat aaaaggctgt tgtggtgtgt 23640
gtgtgtgtgt gtgtgtgtgt gtgtgtgtgt gtgtgtgtgt gtgtgtgtgt ctttcatttg 23700
caattccaca acattagggt ggtaggaaga agtgtgtgcg cacccgctgg gatgtttgga 23760
gagaattaat ttattaccac ttcaggggga catgatttat ttggtagagc aatggccttg 23820
catggttcag gcttctggtt caacaccgag aattttaaaa aatggagctg aagaataaga 23880
ctgaggaaca ctgcatatat aaaatccttc cagtgagtta acaaagatag caaacccgca 23940
gaactatcga gcagtggcag aacacctgat gtggaagaaa tggcgtatgc taaagcaatg 24000
cccttgagca gacaagagga gatggaattt agtgcatatg tggggagact ggcatctaag 24060
gagactggca agaagaaatc aagggcatca cttgggagtg cggatgggtg ggctggggag 24120
ctgcaggcta gggaaaggga aagtgtggaa tactcagggt cagtcaacaa acccagaaaa 24180
tatagcacaa ctgtgttctg tgtgtataca gcacagtaca gaaaggctgt attaaaatct 24240
gtgctcgtgg attttaagtt agcaaatagc atggtggttc attttttttt tctagccggg 24300
tttagcatct tgagaatagt cacagaatag gtagagaatg gccctccatg ttattattat 24360
tttgttccat gaaagtgtga ttatgaagag aggccaagga gctgacagtg tacttagggg 24420
aaggaccaga aggattacca gaaattggtc aaaactggag taaacggggt cattatagga 24480
gtgtagctgt gaagaggtga gattaagtgg gcttggaaga tttgaacacc aaaaggacta 24540
tctgtaccgg agagtcatag cccgattaaa aactgtaaag cttttcggtt ttctcaaata 24600
gtgtctctca caaagccttg cttgatgtcc caagggctcc atcagtcagt cattcctccc 24660
agccttcaat ggatgcaagc ttcacacttg agccccttgg catattacaa accatactta 24720
tgtatttgtt ctctttctcc taacctgcca aatgtatagg atctcttaag agaaacacta 24780
taattattct gtttgtgtcc ctacattgtt cctagggcag actcttgaac ttaggtccaa 24840
taacgaattt ccaagtccgg taaggtgagg agaaggtacc cagttgtttt aggttgggtt 24900
ccagggaagc acattgggag gtggaacatc acctgtccca ttcaggtcag tgattaggga 24960
gtggccttgg atcaactctg gaggcaggga gagggatgag acaggattag gaggagtgag 25020
ccatgaagct gcagtgcagg ttttacagca gcctcagcta actctggaga gctgtggagg 25080
tggtggccta tggagaggct caggtgtctg actaggtagt catgggaggt tcatcccagg 25140
agaggctaca actggggcaa cccatccacc tgagggagaa ttcagtggca ggtcacagtg 25200
ctcgtcacag cagtcctaca gtgtaacagc ttgttaggga gtacgtgcaa gaccttttgt 25260
tttggaagca gtatgatggg gtttgggttg gaactggtgt caagtaactt ctggcacatc 25320
ttcctttgcc tggacctctt cgcttcttgg aacatctgcc ttttggccca gttactagga 25380
aagaatgtga atttttaatt gactggagcc tatttgctct ttgtttccac tgatgatcat 25440
catgaaccca tcttgaagat atactgttca taggtctctc tggagacaat cccaggtcaa 25500
tatgtcctgt ggttgcttga agttagtttc cattggtttt gttttacttt tcaaattgtt 25560
ctttgtgttt taccaggatg tctctggttc caagccagat ctctcactcc ggctaatttt 25620
ctttgatggt gaagaggctt ttcatcactg gtcccctcaa gattctctgt atgggtctcg 25680
gcacttagct cagaagatgg catcaagccc tcaccctcct ggatcaagag gcaccaacca 25740
actggatggc atggttagtc tgagtaatta ccttggctct gtagctcagt ccctgtctcc 25800
agaggcaagg ctgctaagac caagtaaaga cctaaacgtg cctcgaaatc ctcggagcac 25860
tgtttatggt agaacattcc ttggcaagca ctggagtttt gaggaatccc agacctaaaa 25920

-continued

```
agaatggttc tgtgttagaa gctgtgtttg gctgagctta attaaaatga tgtgacaatc  25980
agattaagaa ggcattagat tcattatggt ttagtgagag taccgccccc tcccaacccc  26040
tcaacactgg gtagtgtgga gagaaagaga cctttttca ggcagaggag gctgggaacc  26100
ccaggacagg gaggaaagag gaattcccca tgtgtttaaa gcagtatatt gactgcagta  26160
tactgatgtt taattttatg tggtaggttg atgtagcatt tatgatgtga gggtagagac  26220
attttgaaga tgtcttaaaa ttctgctgtt actaaatagt ggtttcagca tccgacctcc  26280
atacgttctc ctgtggccta ccagtaaatt cccttcagtg actctctgcc catactggat  26340
cttcactctg tcaccaagtc cacaccactc ccagtttaga accttatgct accctcggga  26400
agtcatttgt ctctgacact cttcctaaac cctccaccct gccttcacac attcccgctc  26460
tttgtcgccc tatgactcaa atgagcaact ggtgtcttct agattcccta acgctcctca  26520
tgtgagcatg actttctttt gtttgcggac agctcactat gagtcaaaag catgtggtca  26580
tcatttcact cattcactcg tgcctgagca actcagaggg gcttggacaa atgagaagag  26640
atgcagataa ttagcagtta cttatcagtc cagatatacg atccgcagtg atggaaaggc  26700
tcatctattt ctcagagact tatccaatct catgaatatg ttcctatttc aaacaagcat  26760
tttttcccaa atgaatgagt atgtatatca gttatacata catgtacgta tatatcattc  26820
atgtatacca tatctctgga atcttgaaac ctgataacat ttttcccgta tacatcaggc  26880
ttcagagtcg gcagttaccc acacagtatg tattctgcta actttgctaa gtcaggaggc  26940
ctttatctag gcgggggtct tcaggaatgg agttctcaag cgagctgatg ctttgtggct  27000
aaaccaagct aagagaaatt ggtctagttg ggaaggctat aaccaggaga ctttagagag  27060
cagctggact gaactccttg tttgttactg aaggaaatgg cgccccagta gcacgatgca  27120
tatagtttcc tttaaaggga tgtttcctta cacgctgtgt gagttatagc ttatgctccc  27180
aagctcacca atcattacag attaaagtta aaaatgccta attacaacgg catagattag  27240
acaggtttga actcccacgt ggacatacag caaatgtgat cttttctcaa actgtaaaat  27300
atgcatcaaa tctccctttc tagtttatcc ttagttatgc tcctttgatg cataaaaaaa  27360
tccccatttg tccatgttat gtaagcaagg tctacaatgt tctctaagat ggttagcaaa  27420
caatgccact aagccccttt ccatttaaaa agctctccgt gtgattctcg cttgttaaaa  27480
tgtgttagct ttgactggtt ttcttgatgg gtctgaaaca tgcctgggtg actatgacaa  27540
agcaatattt ttctctcgta ggatctgttg gtcttactag atttaattgg agcagcaaat  27600
ccaacattcc ctaatttttt ccccaagact accagatggt ttaatagact tcaagcaatt  27660
ggtaagcatc ccagttacta aagagcaaaa ggctgtttct tcctgctggc aagcactaca  27720
cctgcaaact cacaatttat ggtttaaatg tacaatttaa atagttaaca taccttgctg  27780
gcatttgtct tcccctacca atttgtttat tattcctaat tcttcagcag gcccagttta  27840
gtttcttagg tggaattcta ttttgaaagg cagatgtcaa aatactacat gtatatattt  27900
ttagaaatga tgccaaaagg tactctggaa tttcatttca ttttccatct caaatttgtc  27960
tgcttctgtt ttctcccttt gtctttctcc cccaaggact ctgtgtgctt cccttacttc  28020
ctttctctga aacgcacaca tcaacagatt gtaccttact gtgattaaaa ccgattgcac  28080
tgccctcgtt tgtggaattt acatttttaa ctatttaatt gtataagaaa aatgtacatg  28140
atggttaagg aaatataagt attgatagat aagaatatta tattttgtgg tacttggggc  28200
tttctcagtg ttcttaaaat cccattatac ttgtttccta cttgatacag ttttacccta  28260
gaaatttaac aatcacaaaa atgaccagct atcctgggca ttatttcctt gttttgtcat  28320
```

-continued ctgatgctat cttgccattt tgtatcaagc agcacatggg ttatatacac gacttatgtg 28380
ctacaagaca ccaggagtga gggactgtgt aggccagtgg ttctcaaact tcaggacaga 28440
tcagaatccc ctgggttcat gctaacgcgt ggattaccag ccggtacccc gaatttctga 28500
ttcattaagc cagaggtagt accagctgat ttgcatctct gcgttattct caggtgatac 28560
tgaagctctt gatgaggaac cgcatcctga gaatcactga tagaggtcac agtagtcttt 28620
tcccacagag tggccagttg atatacttca tcctactctg ttggcatatt ccgctttaag 28680
ccccccacat ctctacatgg gcattcgcca cacaccacct ggatctatga acatctgcat 28740
ctgagtttcc aacacctttg actccttttt ctctttctct ttctcaatct cagttgttct 28800
agtgagcatc tactcttttt ttggcattag ctacttggtc tcttttaatc tttttaaaaa 28860
attggttatt ttatttattt acatttcaaa tgtactcccc ttcccagtgt cccatccaca 28920
acccccccat tccctcctct gcctctataa gagtgcttcc cccacctgca tacccactcc 28980
agcctctgcc atagcattcc cctaccctgg gagcctccac agtaccaagg gtctcccctc 29040
ccactgatgc ctgataaggc aatcctctgc tacggatgca gtgggagcca tgtgttctcc 29100
ccatgtgtac tttttggttg gtggtttagt ccctgggagc tttgggggtt ctggttggtt 29160
gacattgttg ttcttcctat ggggttgtta accccttcaa ctccttcagt ccttccccca 29220
actcctccat tggggtctcc atgctcagtc ctatggttga ctgcaagcat ccgcatctgt 29280
atcagtaagg gtctggcaga gcctctcagg ggacagcttt accaggctcc tgtcagcaag 29340
cccttcttgg catcagcaat aatggttggg tttggtgtct gccgataggg tggatcccta 29400
ggtgaggcag tctctggatg gcctttcccc cagtctctga ttccattctt tgtccctgca 29460
tttcctgtga tccttggtgt gtcaaggcac ctgggagttg agcttcctct gggtgttgta 29520
ggagtgggta gtgagccagc gccccaggtt tgctctgggc actggttcaa actggaagct 29580
ggaatcttag aggttttcac cagcactgtc aatgtcatgt gtgcctctct gtctctattc 29640
tcctctactc caaagtatag ataggtgcag cttagactct tactgtcata gatgtggcta 29700
tgtttactga tacagatcta gggaagaatt ccatgtgtga taagatttca agctccctaa 29760
ataaggatgt attctgagtc ttgatcagag aaaattagat gttcatctac tgtctactga 29820
tgttcatctt gctgtccaca gaaaaggaac tctatgaatt gggattactc aaggatcatt 29880
ctttggagag gaagtatttt cagaattttg gctatggaaa tattatccag gatgaccaca 29940
ttccattttt aagaaaaggt aactgtgtgt gtattgttgt gcattgtgtt ttctctactg 30000
tgtctactgt aattattata ttttatgtgc attttgaaat tttaaaaata ttattttcac 30060
atttcttttt ctggttcttt tttattatat gttaattgta tgtagtattt cattatgaca 30120
tttttataga tgtatattgt tgcggccgcc agcagctcgc aacatgaacc gttcgactga 30180
gaaggctact cgagctgtaa gagaggaatc tagacggggc gaaagaagaa atggagctaa 30240
aacaaattca ttctgatcaa agctcaaatt ttattgttgc aacactagtt ataaaggaag 30300
ggggagggga cccgattccc gccgaataat ctctggtcca gtagaaaggt gcacgtgtgt 30360
ggctccgcag gttctagcag tgggcgtggc agaccgaatg agcaggaagc tccacccctg 30420
agcaagcagg tttcaggctg ggggagggga gactacagta tataatatag tttgatcata 30480
ttcctctccc tttgccctct ctttttttaa tttttcattt tttattacat agtttcttta 30540
tctacatttc aaattttatc ccctttcccc atttcccctc tgaccccccc catcccattc 30600
cccctccccc tgctcactaa cccaccaact cctgctccct tgtcctggga ttcccctaca 30660

```
ctggggcatc cagccttcac aagaccaagg gcctctcctc tcattgatgt cccacaaggc  30720
catcctctcc taatatgcgg ctggagccat gagtcccctt gtgtactctg gttggtggtt  30780
tagtccctgg gagatctggg ggtactggtt ggttcatatt gttgttcctc ctatggagct  30840
gcaaacccct acagctcctt gggtcctttc tctagctcct tcactgggga ccctgtgatc  30900
agtccaaatg gttggctgtg aacatccact taatatttgt caggcactgg cagagcctct  30960
caggaaacag ctatatcagg ctcctgtctg caaggtctgg gtttggtgac tgtatatggg  31020
atggatcccc aggtgggaca gtcactggat ggcctttcct tcagtctctg ctccatactt  31080
tgtctctgta actcctccca tgggtagttt gatccccctt cttcttctcc ttctccttct  31140
ccttctcctt ctccttctcc ttcttcttct tttggttttt tgagacagga tttctctata  31200
tagccctggc tgtcctggaa ttcactttgt agaccatgaa agaccaaagt atccacactg  31260
tggtcttcct tcttcttgaa tttcatgtgg tctgtgaatt gtatcttggg tatcctgaat  31320
ttctgggtta atatccactt atcagtgagc gcataccatg tgtgttcttt tgtgattggg  31380
ttatctcact gaggatgata ttctctagtt ccatccattt gcctaagaac ttcatgaatt  31440
catcattttt aatagctgag tagtactcca ttgtgtaaat gtaccacatt ttctgtatcc  31500
attcctttgt tgaaggatat ctgggttctt tccaacttct ggctattata aataaggatg  31560
caatgaacat agtggagcat gtgtccttat tacatgtgga gcattttctg ggtatacgct  31620
caggattggt atagctgggt cctcagatag tactatgtcc aattttctga ggaactgtca  31680
gactgatttc cagagtggtt gaaccatcct gaaatcccac cagcaatgga ggagtgttcc  31740
tctttctaca tattctcgcc agcatctgct gtcacctgag tttttgatct tagccattct  31800
gactggtgtg aggtagaatc tcagggttgt tttgatttgc atttccctga tgactaagga  31860
tattgaacat ttctttaggt gcttctcagt catttggtat tcctcagctg agaactcttt  31920
gtttagcttt gaacaccatt tttaatagga ttatttgggt ctctggagtc taacttcttg  31980
agttctttgt atatattgga tattagccct ctctcagatg tagggttggt aaaaatcttt  32040
tcccaatctg ttggttgcca ttttgtccta ttgacagtgt ttttatcctt atagaagctt  32100
tgcaatttta tgaggtccca tttgtcaatt cttgatctta gagtgtaagc tattgttcta  32160
ttcaggaaaa tttcccctgt gcccatgtgc ttgagactca tccccacttt cttttctatt  32220
attttcagtg tatctggttt tatgtggagg tccttgatcc acttggactt gagctttgaa  32280
caaggagata agaatggatt gatttgcatt cttctacatg ctaaccacca gttggaccag  32340
caccatttgt taaaaatgct gtctttttcc actggatggt tttagatccg ttgtcaaaga  32400
tcaagtgacc ataggtgtat gggttcattt ctgggttttc aattctatcc cacagaacaa  32460
cctgcctgtc actgtaccag tacaatgcag tttttttttg tttttttgtt tttgtttttg  32520
ttttaatcac gattgctctg tagtacagct tgaggtcagg gatggtgatt tccccagacg  32580
ttcttttatt gagaatagtt ttcactatcc tggtttttgt tgttgttgtt gttgttgtta  32640
ttattccaga tgaatttgca aattgtcctt tcttactcta tgaagaattg attgggaatt  32700
ttgatgtgca ttgcattgaa tctgtagatt gctttctgca ggatggccat tttaactata  32760
ttattcctgc caatccatgg gcatggaaga tctttctatc ctttgagatc tttgattctt  32820
tcttcagaga cttgaagttc ttgtcattaa gatctttcac ttgcttagtt agagtcacac  32880
caaggtattt tatattattt gtgactattg tgaaagatgt tgcttcccta atttctttct  32940
cagcctgttt atcctttgag tagaggaagg ccactgattt gtttaatttt atatccggcc  33000
actttgctga ggttgcttat ctgatgtagg agttctttgg tggaattttt gggacactta  33060
```

tatatactat catttcatct gcaaatagtg atattttgac ttcttccttt ccaatttgta 33120
tccccttgac ctccttttgt tgtctaagtg ctctggctag gactttgagt actatattgg 33180
gtttgttagg tctgcttaca ggagaacaga tgagaattta tttacagaag tatgggtacc 33240
ttaccagtag gttcaccaca gaagtatatg tctcttcccc cctccccaca ccaaccatta 33300
ataattatgt gcaaatcctc agagaggggt gaggcctcat gagatcttct gctctccatg 33360
atatggtgtt gtgggcccaa tcttacaaag atctcataaa ggtcatggct gttgtgagtt 33420
caagagtgta cttgcatttc ataccattct cccatccatc cccctgcttc tcccatcttt 33480
agtgtccctt ttccttgatg cttactgagt gttagatgat ataaatgtct aatttacatc 33540
atagcttaac attcaacagt catttattct cctcatttta accagttatg agacagttac 33600
cattgtctaa tgtaaaaaga atctccctgt tccccaaact ttacctagca acttagtgcc 33660
attagatagc gttctttaaa actgaaaatt tccaggtctc caactgctgc atatatttaa 33720
gaaacaaatt aagcatgaat aatattagtg tactttggat cactaagccc atacttcctt 33780
aagtttgaat gatttaaatt tatataatta atgttttgac ctatataaaa gtattttaaa 33840
agatctaaaa taggcactgg attaatttga atgagagcct atctttaaaa ggaaacatac 33900
ttattttgct ataaataagt tttggccaac atgtgcttta tggatttata tctataagat 33960
aaatgttaga taattaaacc aaattaaata ataaggaaga catctagcta caccctcacc 34020
tggtttatac tgatgaaagg tactattcag atgcagcttg taacacttta gcatctcttt 34080
accagaacat gcccctaact aaaaagtcca atccctaacc aagaatctat ttgcaattta 34140
tacccactga gagaggggat tttttttcc cagtagagtg acactgggta tattaaccac 34200
actccagagc aggctccatt ggtcaatttt gtgtgtgtat gtgtgtgcat acacgagcta 34260
atgcatatgc atgtgtgtgc gaatgtgtat tcacttgcta tctctttgtt ttgttttggt 34320
attttttgtc tttttgtttt gattgagaga gagagggaga gagagagaaa gagagagaga 34380
ggagagagag agagaaagag agagagagag gagagagaga gggatggaga gagagaggga 34440
gggagagaga gagggaggga gagagagagg gtatgaaatt gggaggatag ggaggtgggg 34500
agatctggaa gatgctgagg aaggggaaag aaaatgatca aaatatattg tataaaaaat 34560
taaagctaat aaatacaaac aaaacaaaat gaaacataaa gaccatttct ttatcagccc 34620
ctttctttgg attatcagat gaaatgatag agcccattat tgttcattga cttggaagaa 34680
tatgcgtcat ggaatattcc tttccttgtc ttgcgtattt aagttttaaa gatgaccatc 34740
taagttgaat cttatataca acactggact tacacaataa ttcccacttc ccctgatttg 34800
taacaatcta ggagtgatag gaatcattaa atataataaa ccaatcagtt tgataggaat 34860
cattaaatca ataaatcaat ccgtttggcc atgatgtcat ttgttcatgg cttctctttc 34920
ctcatgagag acattttgaa atcttgatgg catctttata tatctttata tatctgttat 34980
atagttagaa aatcccagaa tcttctgata tcctgccttg ccttgcataa agttaagcta 35040
ttttcttgct cttcattcaa ctttgatgtg gcatggttgg taagaaagat gtcctggggc 35100
atggagagat ggctcagtag ttaagggcac tggctgttct tccaaaggac ctgggttcaa 35160
ttcccagcac ccatgtgaca gcttacagat ttcggtaatt ctggtccccg gggatttgac 35220
accttacaca gacacacatg gagacagaac accaatgcac ataaaataaa aacaaataaa 35280
ttattaaaat agagaaagct gtcctgtatt gcgatgtgaa agtctaaaat taactcagtg 35340
acttttagga agcttccaca ctggtctcta aattttacta ttgcttctct ctctctctct 35400

-continued

```
ctctctctct ctctctctct ctctctctgt ctctctctct ctctctctct ctctctctct  35460
ctctctctct ctctctctct ctctgtctct ctctctctct ctctctctct ctctctctct  35520
ctctctctct ctctctctct ctctctctct cctctctctc tctctctctc tgtctctctc  35580
tctctctgtc tctctctctc tctctctctg tctctctctc tgtctctctc tctctctgtc  35640
tctctgtctc tctctctctc tgtctctctc tctctctctc tctctgtctc tctctctgtc  35700
tctctctgtc tctctctctg tctctctctc tctctctctc tgtctctctc tctctgtctg  35760
tctctctctc tctctctgtc tgtctctctc tctctctctg tctctctctc tctctctctc  35820
tgtctctgtc tctctctctc tctgtctgtc tctctctctc tctgtctctc tctctctctc  35880
tgtctctctc tctctctctg tctctctgtc tctctctgtc tctctctctc tctctctctc  35940
tctctctctc tctctctctc tctgtctctc tctctgtctc tctctctctc tctctgtctc  36000
tctctctctc tctctctctc tgtctctctc tctctctctg tctctctctc tctctctctg  36060
tctctgtctc tctctctctc tgtctgtctc tctctctctc tgtctctctc tctctctgtc  36120
tctctctctc tctctgtctc tctctgtctc tctctctgtc tctctctgtc tctctctctc  36180
tctctctctc tctctctctc tctctctctc tctctctctc tctctctctc tgtctctctc  36240
tctctctctc tctctctctc tctctctctc tctctctctc tctctctctc tctctctctc  36300
tctctctctc tctctgtctc tctctctctc tctctctctc tctctctctg tctctctctc  36360
tctctctctc tgtctctctc tctgtctctc tctctctctg tctctctgtc tctctctctc  36420
tctgtctctc tctctgtctc tctctctgtc tctctctctg tctctctctg tctctctctc  36480
tgtctctctc tctctctctc tctgtctctc tctctctgtc tgtctctctc tctctctctg  36540
tctgtctctc tctctctctc tgtctctctc tctctctctc tctgtctctg tctctctctc  36600
tctctgtctg tctctctctc tctctgtctc tctctctctc tctgtctctc tctctctctc  36660
tgtctctctg tctctctctg tctctctctg tctctctctc tctctgtctc tctgtctctc  36720
tctctgtctc tctctctgtc tctctctctc tctctctgtc tctctctctc tctgtctctg  36780
tctgtctctc tctctctctc tgtctctctc tctctctctc tgtctctgtc tctctctctc  36840
tctgtctgtc tctctctctc tctgtctctc tctctctctg tctctctctc tctctctgtc  36900
tctctctgtc tctctctctg tctctctctg tctctctctg tctgtctctg tctctctctc  36960
acacacacat aaaatagaat tatcttttag aatcaaatta tgctaatact tactgtttta  37020
aatgtcctgg tttgctgtct tatagagtaa gacagaaagt ctttaccatg gcctaagaag  37080
acttccattt tctgattctg tttcaaaatc atctcttcct tggcttctca cttctttcag  37140
tgatttggcc acactggctg tcttgtgctc cctgctcagc acaagcctca tgctctttac  37200
atgcaggaat attggtgccc accatgctca ttcctaggtc tttgcctggc ctgctttctg  37260
ttgggtttgt accactcttt aaatattagc ttctggagag gctcttccct ggttttaaat  37320
ggctccccat tcattcaatt cccttgcctg ccctccatct tgatccctgt atcttgtttt  37380
gttgttttcg aacaacttta gcacagtcta tgattatgtt tcgtatgtgc ccgtttcttt  37440
cttcactaga atataaaatc cacataggca tggtcttgcc attccactcc ttgaatacga  37500
gctttgcagg cacttggctg acttatcatc ccttactgga ttcattgatg tttgattgac  37560
aagccttgag gtacctatac gcttggagat gtgcttgtga aaccaggagt tatcgactgg  37620
cttaaaggat atggatcttt ctttgcctgc aaatgtaact ttctagttca cccccctggg  37680
aattcttact cattcacgag ttgcttctct cccacaggtg tcccagttct tcacctgata  37740
gcttctcctt tccctgaagt ctggcacacc atggatgaca atgaagaaaa tctacatgcg  37800
```

tcaaccattg acaatctcaa caaaatcatt caagtctttg tgttggaata tcttcacttg 37860
taatgtttgg atttagtttc tggtaattgc ttctacagca acttcaagac accatttata 37920
caatctgctt ccagataaat gtgtgtagac ttctgtccta tagattcatt ctgtaggtgt 37980
ttttgaatat gtgatcagcg aactgtagaa ttctatgatg ccttcactaa ttttcctcta 38040
gagatgagaa agaaacatgt aaagaaataa aataataata atttttaaaa ttcttttgga 38100
ttaaaacttt aacataaagt tagatttatt taccaatacc atagatttgt aaacaatact 38160
tagatacaat gatgctgtat ggtatagtgg tagttttata tgtgatatta tatagtgtgt 38220
tatataatat gtaataaaac acaggcatat actttgacag cctttaagtt tctttaaaaa 38280
aagctttgga aattaaagtc tgaattaaat tgcatattgt gaatttattt tcatgtcc 38338

<210> SEQ ID NO 23
<211> LENGTH: 35669
<212> TYPE: DNA
<213> ORGANISM: Mus musculus

<400> SEQUENCE: 23
cttccttcct tccttccttc cttccttcct tccttccttc tttcctccct ctctctccct 60
ccctccctcc cttccttttt tccctccatc ctttctaaaa taaggaagtg ttttctttgt 120
cccttggatt ccaaagctcc tgtcacccag ggaagctcag tcccctggct tccaggcttc 180
tgggagagga ctgctggttt gtgcttgcgc tgcacagcgg gaggccacag gaggcgactg 240
ggaggcagac acaatcaatc caggggtgga gaagggagaa ggcagggcga ccggcgcgcg 300
ttcccgggct cgtgaccgct ggcggccccg ggaatccacg cccacacact cttgcagaga 360
tggcaggcag cgaagacaag ctcgtcgtgg gcactctcca cctgctgcta ctgcaggcga 420
ccgtcctgtc tctgacagct gggaatctga gtctggtctc cgctgcctgg acgcaggaga 480
aggtgagggg ccactgctgc gttctgaact tgagtggcgt tggagggtgc caggacctgg 540
gactcggcca ccttctcttg gactagcggg aggcgggtca gggatgctgt ccccctgctc 600
aggcaccaag tcctcaccca actcctggga accagtgctc tctctcccaa gtctgggcgc 660
cagggctggt ctcggggctg cgctagtgtc gcctgggggc tgagtgatgt cacccgcctc 720
cctttggctg cgctctgatg gggggtggtg gtgctgctga taggcacagg aagtatgtct 780
cgctggctgt gcaagaacag ggacatgggg gcgccactgc ccaatcgcga cccgcgagct 840
ccgcgctccc cgcgcttgct cctggatgcc tagaccgcgc gtctaggggt gtccccatgg 900
atgcccaact acagcattca aggatgctac atggggattg agtttcctgg tggactcagc 960
gccagcatat tgttaaatat ttaaaagaga cgcacgctgt tttcagataa atgaattcag 1020
ttgtggaaat ctcatttaag gaattcagaa taaaaatgat ttgccaagtc gctttgtgtg 1080
aagaaaatag attcacaatt acttcctttt cttgtgcaac agttttgaaa tcatgaaatt 1140
gctacgagct gtgcaaacga tgacggtttg ggaataaaat ggcatgtctt taaagaaact 1200
aggaaaagca tcagtctagg gatagaacct tgcgcgcgac attactaaac aagtacttta 1260
agtgctttta gcgtttctgc acgtccaaca tgctcattcc cagctagttt catgcactag 1320
tgtatgaatg gcccacttca ggtgagctca agcatagcca acttcttttc aggactcaca 1380
acagatcccc atttacacgg ggagtctgga gtgggtgtgg gaagtcaaca ccgtacaact 1440
tcagtctctc cagaatgagt caaacggctt cccccagagg ctgggaagta cttctcaagc 1500
cgttgagtag aatcctctcc tgcactgctt tggggtacct gggaggtcaa gcaccgagaa 1560

-continued

```
gggactttaa aaccagagtg tcgcacaagg ccaaatgtgt ctttaaaacg tattttaatg   1620
gatgagaaat attgtcaggg gctgagctcc actcggggtc tgtctgtggg caggtgtagc   1680
agccagggtt gtttctaggt gggagaacat cctgtgattc tttttcttta agagaaaatt   1740
tcctttttat tgattcgtct ctcatatatt aatccctact gcaatttccc ctccctctgc   1800
tcccctcttt ccttctggat tcactctctc ctccacctct cctcagaaaa gagcaggcct   1860
cctagggatg ttaaccaaac aggacgttac aacctacatt aggaccaggc acacattctc   1920
acatcaaggc tggatgaggc aacccagtaa tgggaagagg gtcccaaagt caggcaaaag   1980
aatcggagac agctcctgct cccactgtta ggaatccccc aagaacacca ggctacataa   2040
ctgtaacatg tatgtggagg acccaggtca gactcctaca ggctctctga tctctgaacc   2100
cacttgagtt ctggtcagtt gattccgaga gccgtgttct tgtggtattc tcaaaatgtt   2160
ttaaactaaa ttcagattta acttttgaga aatgtcttaa gaagcttcta acagttgttt   2220
tactgggaaa acaaacactc tcaaatggca ggagtggatg acagtcagcc atgacgtctc   2280
tcagttaata gctcctcctg ctttcctagt tttaaaggtc tccataaagt cttctgggca   2340
gccagctaca ctttacagcc tgggagatga atcagcctat actcaaatgt gccttcctgc   2400
cttttatgac atttgactgt tttaatcaga caaggcacag tcttggtata ctggtctgcc   2460
aacaggagaa gtacgataac gagagcatca gttctgaaat ccattgcctt gtttagaaat   2520
agaggcgtgt ctcttggagt agcatccgct gtgtgaaagc acatcgaccc tagtttatgg   2580
ctgtcgttag aaccacgctt cagtgattcg aagcctagaa accattcata gaaacaaatg   2640
actacacctc cgacggggcc cacgtatgtg tgtatgcgga agggtgttga cacgaaggta   2700
ccagttgtca gatagataga accacgtcat gtgaatctca cggtaccggg aaagagtgtg   2760
cttatcgcca tttataaagt ggaaatcagg aaccctggtc ttcccagttc tgctttattt   2820
tctccttttt taaaggtaga taaatgctgg ctggctgagg aagagtgtct agctagccca   2880
ggagtgtgtg cgtgtgtgcg tgtgtgcgtg tgtgtgtgtg cgcgtgtgtg tgaatgtatg   2940
tgtgggatct atatgttagg gggcatcatt tcttcccaca cccccagatt cctagttcct   3000
tggcctctct cttccagttt tcgagttatc attatgctga aagttgatct gtatctggtt   3060
actgtccctg atctatctat ctatctatct atctatctat ctatctatct atctatctat   3120
ctatctattt atttctggtt tagtggtatt tatttattta tttctggttt agtggttttg   3180
ttttttcttt ccccttttaaa tctcattaaa tcagctctcc tttagatgag aactgctggc   3240
tgtcgagacg ctgcctacat ttgaaaagga atgttagctc cgctgagcta aacagtgcag   3300
cttcacttgt catgttctag ttgtgaaggt agcatgtact cactctagaa aggttcaaaa   3360
acacagaaca atgtattcta aaaaaaaaaa agaaaaaaaa aaggacacca cctacaatct   3420
cattttccag ataattcctt ttaatctttt tgggtcttct tattgccagc tcccatgtac   3480
acacacacac acacacacac acacacacac acacacacgc acacacacag atttatagag   3540
atgagtaatg atgattgaat ttcagcttgt tatagggact gaatgagttt gtaaaacagc   3600
acagtgtcta gcttacattg aaggctcaat gcatgttaat tattgaaaaa taagcataca   3660
ttagtatttt gcagtcagca ctgcacatgc agtttaatat gattaatagt gtcatgaatc   3720
gtaccataag ccggtaaaat cccctgaaaa cataacttga tgattgcaaa actatcatca   3780
gttgatgatt tatttcttca tcttgaacat tgaggttgct agcaaatctc tatcaataaa   3840
gctgagacat aatgtatttt gacgggaaga attttccctt actgtgacaa tgttgaagga   3900
ggaaaattca agtcgcatta gaggtggaga ggcaaagact cggaagggcc caggagagct   3960
```

```
gtaaacagtt atctgcgaca cttcacgttt ctctggtttt gaaccacttg ctattccaaa   4020
tgtccataag atttccccct ctctacctca ctcggccacc cagccacctg tgagtggaaa   4080
gaggcgactc caaggcaggg acagagaggc tcgtgaagac ctctagggca ggaaaaaagc   4140
caactgtcat cttgaaatct ctactatcct gtggtttaga aacagtgaca cccattttac   4200
acattagggc acttttcttc gacgtaactg ttcaatgagg agctggggtc tctctgttgt   4260
acttccctct cggccctgat ttttaagaag cgagcctgtg tgcactggac agaaaggcag   4320
aatcttggtc agtttccagt tcctttccgt gctgtgtctg tgctgaccat ggcttgcaca   4380
catttcagtc actgctggca gagtggaact tgcaggtagc aaaagtttaa tctgaggact   4440
gtctggaatg ttcataaagg aagcttggat cagctgcatt tctgcaatgg tctcccttac   4500
aggcagtgtt ttggcctctc catttcgcct gcaggcaagg ccgcctctcc aaattatgta   4560
atgaaatgcc tgggccgtgt gattagacag gagatgcttc aggatatctg gttcacaggt   4620
ttgtttcagc tgattcttgt cacctggagc agacttcatt gtcctttctg cctggatgaa   4680
aagacaaggc cctgggtgta acagagcctt gttcctctga gaacgttggc accagcagaa   4740
atggctgaag tacctttcaa ttgaaatgca cctagagcaa gcctgggatt tacacttgcc   4800
cttggccttt attctgtttt gttttgtttg tttggggcca gagtatcact ataccgccgt   4860
gttgtagggc tggagctcac tgtgtagatc aggctggctt cagacttggg gtgattctcc   4920
tgtctctggc tctcatgtgc tgggaatcac gggtgtgcac ccccacattc agcttcggca   4980
ctgttttggg gccaggtact gtcctctgag cctatccttc ccacttctgt cttactcatt   5040
cctgttttga aacaggtttt gtacttagtg agttctgaga gtaagagccc tttacttcag   5100
tggttttcaa ccttcctaag gctgtgaccc cttgataccg ttcctcatgt cgtggtgact   5160
cccaagcata aaattatttt cgtcactact tcataactgt aattttcctt ttattttgag   5220
ttgtaattca gatatctgat acacagatga tcttaggtga ccccttttgaa aaggtcaatt  5280
gaacctccag actggggtcg agacccaggt tgagaaacac tgcctgtaaa ttgactgtat   5340
gctgtttagc atatgcaagc tgtatgcttt tctgtaagag ctttttgtga atcaaggggc   5400
ttgtacaact gaatttagtt gctctgcttt caatactctt cactaactag gaagtttgat   5460
atttctgtga tttttcagat ctggtccaga aagaaggggg aaggaactct ttattgaagt   5520
gcacttatga aatcaaccat ttttgttgtt tagctcagga ggttgaagag cagatagtgc   5580
ttattcaaaa gcacccgtgg gtctgtccgc ttcactcact atcagctact aagaatttaa   5640
aaaatgtcct ttgacatgtt gctttcagac acagtatctt ttgctgctgg agactgtgat   5700
acttagatac cgttcaccaa tttgacaaga ctctagaacc acccaggaga cagccctctg   5760
tgcacgtctg tgggagactt tctagattgg gttaaagagg tgggaagaca catcctccac   5820
gtgcataggc tagagtctca gttaagatgg ctaaatggca aaaagaagca aggtagcagc   5880
agccatcgct ctctgcctcc gaactgaact gcgctgtacc atgagcagct gtctcattta   5940
tcgctgtgct ctatgcacat ttactttgta tcaaagagcc ttcaaactga gcaaactgaa   6000
cctttccttt cttaaactgt gattgaatgg cactgtgccc cagcaacttg ggaaggagca   6060
aatagagaga tcatgaaggc tgatttattt cattcttgct tttctgaagt cttgtgagat   6120
tttccaagtt cctgtaaagc atgtatttaa acatgacttt gatttccttt cactgtggac   6180
atgaagaaca cagcccacag tgactaggtt ggctctgggg ttggcacagt gggcagcgaa   6240
taggaaagaa gccatcgata aaatagttgt gtaagagaga atagtaattc atttatttat   6300
```

-continued

```
gcagtgtggg tagaaggagg aatatgaaag ggtatcttgc tggagtcagt tccttcctac   6360
aatagagaat ctggggattg gactcgggct tcaacagtga ataccttttaa ccacagagac   6420
acatcgtgcc cctgaaacag attctgacat gaaagtttac atctgtcatc attactgccc   6480
tgggccaagc caaggagctg tcagttgtct gaagcattgt gcagaagttt aaaagaagca   6540
aagctgacaa gcacggaact aggatgtccc cttgcaacag gcagccacct ggaaccaggc   6600
catgtcttgt ccccttgtgc caggcagcca catgtctctt ctggctttta tgcctgtcta   6660
tgaattcagc tagtttagta tttacgaaga cagaggtgtg actcttacgc ctttattata   6720
taaacacgtt tatagctgca gaagttttag aaaaatactt agtttgtctc tccattactt   6780
gaaattaccc agtagttacc aggtgctcaa tgtgagccac acccctgcga ctctggagag   6840
aggcaggaaa ctgggagagg gttctagctt tcctggagct cctgacttat gtgaaataca   6900
gatatgaaac acgacacccg agaacagtct tcaggcagga gcatgaagaa gacaggcatt   6960
ttgaaggtga agagacacgg aaacagtttg aagggcagac tgcattgctg aggtgccgag   7020
accctaagga gtagatctca aagtggctgg gtgctagggt gaccaaagtg ggatgaatgg   7080
gagcctgcag ctcatgctgg ggcttgcaag gcagtgggag agacacacag gcatttgttg   7140
ggaaggaaca accatgcaga tccccctttc tgcccccatt tactttggct cacacttcac   7200
actttttcc cctttagatt cagctttctt gttcaaatgc tgtttaattc taacacgagg   7260
acttagacat tggaggcact aaggaattta aaggcttcag tagaagtttg tttagaaaat   7320
atatctatct gttgcatagg gctacataag gccatttcca tgcaagtgtg taatatactt   7380
taagcatagt ctacctccgg tgctctgcaa gtgttcctcc cagacacact cagagacccc   7440
tttgctcctc cttcctcccc cctcccccctg tttggtttcc actctcatgg catgtcatct   7500
tatgagttta tgtctatggt ttctagtcaa atctgttttt ccccagggaa cgacatttga   7560
aagaaatata cttcttaatg tgtgtctgtg tgtgtgtgtg tgtgtgtgtg tgtgtgtgtc   7620
tgtgtgtgtg tatgtatgta tgtatgtatg tgtgtgtgtg tgtgtgtgtg tgtgtaccat   7680
tgcacctatg tggagctcag aggacaacat gcaggagatg gttttctcct tccaccatgt   7740
gggttcaagg gattgaactt aggttcccaa gacttgacag tagctgtctg tacccattgt   7800
gtcatctccc tgtcccctag aaatatgctt taaagtgtat tattcccaag aacaaaacca   7860
aaaccttaat acattcagtt acggtatcaa tattcaagag taaagcagaa gtgaggaaat   7920
gaagcagaac actgaatgct gggttagaaa tcctcctgcc gggatttact ttacgtattt   7980
acctttaact ctctaccgtt ggtttttaca gacctcagtt cccattggtg gaggtcaggg   8040
ggttggacta gttatctcta agtgacatat ccaggtctca cattctatac tagtttactg   8100
tacgatgggg gaaattagca ccctgggtat ttactaggca atctgtatgc tttggctcgt   8160
ttagtcctaa gtaccttcgg gtgcaggtac tatcacctcc atttttcaga caaggaaatg   8220
gagccttgat aaggttaagt aacatagcca gagttactgc tagtggtggg tgctaagttg   8280
aaaggctgta tctgatccaa tagcctgtgc tctttgcatg ataaacactg gagagaaaca   8340
ctgcgttatt tcaaagtcta gagggatcta agcaacgagg cagcagcagt cagtatttct   8400
acagtgtttc attagccgtg tgggtggttc atgtggagtg aattacctgc atgattattt   8460
aatgtatcca gtaaacacta atcctggaag gaactgcagg atgggcggag tctcccaatt   8520
tctgttttgc attccaaaga atgtccctac caccgttctc ctcattctcc ttagggaaga   8580
actggtttga gcaaccattc atttcccttt gagcagaagt gccacaatcc ctaggagtgt   8640
ctgatgaact tgtaatgaat ggctgattca tcattttggg tgtcctaaga caagttcagc   8700
```

-continued

```
atgtgtaagg tcatattcag gatacacatt tgaacattag gtctactgag cttttaaagt   8760
tttattttaa tatgtaaatg tactaaagag tattaaaacc ttaatagact ataagataat   8820
taggttgatg atggaaaaga gttcctattt agccagcttt acaattgtca gactcacatt   8880
gagaggggca tcattcatcc cgggtacaca ctgatagaaa ttgagggcca ggaagaaggc   8940
tcagtgcgta aaagtgcttg ctgtgcaaac atgaggacat gagtttgaac cctcagaatc   9000
catgcaagag ccaggcagag tgtgagagat gagagattga gacaggaaaa gccccaaagt   9060
gtgtaggcat cgagcctggt atcattttgt ttttaaggcc tgtttttatt ttatattatg   9120
tatatcctcc ttaggcttac tatggctggg atgaaacatc atgaccaaag cagcttgggg   9180
agggaggaaa gggtttattt aagcttatac tttcaggtga cagtccatca ctgagggata   9240
gtcagggcag gaacttaaac atggcaggag ctgatgcaga ggccttggag ggatgctgct   9300
tactggctcg ctccttgtgg cttgctcagc ctgctttctt atagaaccta gaaccaccag   9360
caaaaggatg gcaccaccta taataggctg ggcccttccc cagcaatccc taattacaaa   9420
aatgtcctgc aggcttgcct acagcctgat cttgtggagg cattttccca gttggggggg   9480
ttcctcctct cagataactc tagcttgtgt caagttgaca taaaatcagc cagcacccca   9540
gcacttggga ggcagaggca ggtagatttc tgagttcgag gccagcctgg tctacagagt   9600
gagttccagg acagccaggg ctacacagag aaaccctgtc tcgaaaaaca aacaacaaca   9660
acaacaacaa caaaatcagc cagcacaatg tatgtgtgtg cattctgtct gcatgtatgc   9720
ctgtaccatt agtgtgcctg atacatacag aaaccagaag aaggcattgg gtcctgccag   9780
aactgaaggt ttagacgctt ataagccacc atataggtgc tgggaattaa aaccttgtct   9840
tctataagag cagccagtgc tcttctcttc agccccaaga atgaaattta aaatattcta   9900
gtatctacat taagaggtta aggttggaat taattttaac aaatatttca cttatagcat   9960
agtaaaaact gtttcatcac atacccagag aaatataaat gacataattc tatttttata  10020
aaaaggtctt taaaagtgat gtattttcca gatgtggtgg tacacgcttt taatcccaga  10080
gcttggtaga tggaggccag cctggtctac ataatgcact ccagatcagc caaggacaca  10140
cagtgagaca ttgtctcaaa aaacaaaaac aaaaacaaaa acaaaaacaa atccaaacgc  10200
cccaaacctg gtgtatacat tgcacttgaa gcacacctcg attttctact tttcaagtct  10260
taatagtcac aaatggctcg tagtctcctg tactggacag tgcagatcta gaacaactag  10320
agaactggct gacgtcatgg cgtctgcaca tggcagctgg aggtcttgct taggcctccc  10380
tgccttgccg ttctgaagtg cctctctgcc tgttataaaa cagctctact gacagtgtgt  10440
ttctttgctg tcttcagctt tttaaatatt acattttctt cagataataa tctcaaaatt  10500
gttatgttgt tgttgttatg ttgttgtttt gacatagggt tctattgcgg taaatctcca  10560
acccaattat gcctggcaat gaaaacaaaa ctcaattaat atgattacat gctgtgagcc  10620
tagattgggc agatctactg ctacactacc atcttccaca tgagaccccg tagaacttgc  10680
ggtttctcca ggccatgtgc ttctgctctg cttttcttct tcttcttctt cttcttcttc  10740
ttcttcttct tcttcttctt cttcttcttc ttcttcttct tcttcttctt cttcttcttc  10800
ttcttcctct tcctcttcct cttcctcttc ctcttcctct tcctcttcct cttcctcttc  10860
ctcttcctct tcctcttcct cttcctcttc ctcttcctct tcctcttcct cttcctcttc  10920
ctcttcctct tcctcttcct cttcctcttc ctcttcctct tcctcttcct cttcctcttc  10980
ctcttcctct tcctcctcct cctcctcctc ctcctcctcc tcctcctcct cctcctcctc  11040
```

-continued

```
ctcctcctcc tcctcctctg catcctctcc ctcttccatt ttctccttct ctccctcccc  11100
tcaccttttg ctccaccttc ccatcatcag ctcttcttta ttttacaaat taaggtggga  11160
agcaggttta caggaaatca cctgagtgct gactcattcc tggttggaag acactcccag  11220
gagaatggac ttaacatcaa atataattag ctccagggct ctccacaaca gggttcctct  11280
gtgtagtcca ggctggcgct gaacttgtaa ttttcatgcc tctgcctcct cagtgttggt  11340
actctgtata gttgttatta attttttaaa ttacgtgtgt gtgtgtgtgt gtgtgtgtgt  11400
gtgtgtgtgt gtgtgtatac cttggtgtat gtgtggagga caatttgcta gagtcagttc  11460
tcttcttaca ccatgtaggt cccagagata gaactcagct cttcaaactt gttggcaagt  11520
gctcatccac tgagccattt caccagccca gaactgttat ttttaaacct cagttttaca  11580
aaacaattat tcagaaaatt tatctgaagt tacaccagtt gtgtgactta ccatgaaagc  11640
atactttcaa ttttgttttt caaacaagct gccaaaatct agacatttca aggggacaat  11700
tttatagttg agccctttac ctcatatgac ataaaccttc tcctttattt tgaagttttt  11760
tttttgttt ttttttttgt tgttgttttt tttgagacag gatttctctg tatagccctg  11820
gctgtcctgg aactcacttt gtagaccagg gtggcctcga actcagaaat atacctgcct  11880
ctgcctccca agtgctggga ttaaaggcgt gcgccaccat gcccggctat tttgaagttt  11940
ttaaagccac taatcacaaa tgtaccatgc taagtcttaa acacatacaa ttggagctaa  12000
gtacttttta tttgatcaca gaaccaccac caaccagcac atttgaattc ttcatctctt  12060
cagcaagttg cagaaggcac tagcatttct gaaatgtggc aaaacgactt gagaccattg  12120
ctgatagaac gatatcctgg atcgcccgga agctattctg ctcggcaggt gaggaagaac  12180
agagttcaca cctaaaggtt ttaaatactt tgctttccct tgagggatga gatggtggct  12240
aaagttctga gtcatgtata acattatctc actacacact accagaggta accaagaaag  12300
acatacacct gagagtaagt gtctattttg agttgattgc tacacattta ctgaaaatca  12360
gtttatgttt atgtgtgaca tcattgtcct gactatagca gcaataattc aggatactaa  12420
ggccccaatc ttggtcactt caaggacaca ttcctagctt actaaccatt ttttgtgacc  12480
cctagaatcc aaacttcaac agcttttcac agtgcttgct tagcagttcc agggcaagtg  12540
tgagtcaccg aactgtcagc ctttttcctc ttgagggaaa ttgttttctt ggctgaggcc  12600
aatgattagc ttctgtctac agttgagctt ctcagacatc tactttgacc cacagtaaaa  12660
acatggtgga ttttacagac aaggatgttt aacaatgtat ttagctgcaa tgaaagtttt  12720
tggaaaaact actcattgtt attatctgta atttatttag atattgtaag ttctattttt  12780
atttccaggt ttattgattt taccactgct gtttggagga cagtgatgta gagggaagct  12840
ataagatggg ctagactttg aatttctttg tcaatctgcc tgagcaacac gaaatcttac  12900
ctctcaatgt ctgctttttt ccaaactaat ctcattcaag ggggagcttg ggaaggaata  12960
ggaccggcct ctcaaagcct cttcctaaat attctacttg ctcaacttcc tagacaaaaa  13020
cattggcaac tactgctgtg tctagagaga cctgcatgct tcatctatgc agctcacagc  13080
tcttattttt ctactgtgta gctctgccct gcaagtgtac ccttgacaga tgtgtgtgtt  13140
ggcttttttt agcctccttc ttcccatctg aatagctcct cagatgaggc ctgttgtggt  13200
gagtttagct aactgttctg tgctcccgac aggtcgcaca tgtgcaccca cccaagagct  13260
atctggattt gtgaatggaa gacagacaga cagacagaca gacagacaga cacacacaca  13320
cacacacact caccccagtt aattttaaat gccttgacta gcttaatggc tgagcatttc  13380
taatccttcc cactgctagc aaacactcct ctcctgtact cctgagttaa caacttttaa  13440
```

```
agtctatatt tcatctctgc taccccaaca catttgggga agtgggtcat gtggccactt  13500
tccatgattc tcatatgtca gtgggccttt gggtctggtc tttcctcttc cccatcaagg  13560
tgatttctgc cctttcctct ctcccaatct ctagtctggg caaatctaaa ggtctggttt  13620
cagtccactt gcccaggcat tggctgttgg ctctttattg attgatcaaa agaccagttg  13680
gggacaagga ccttcagtat ttggacacac agatttccga tttgaggggc gaggttaatt  13740
caaagcatta gaaccaatcc ccaacaaagc tctaacaaac ttggttattt tagccttcag  13800
aaacattgag gaatggtgat gaggaggagg ggaaggaaga agaggaaggg gaggaggagg  13860
gagggggagg aggaaaaggg ggaggatgat ggtggtggcc aacttccatc ctttcctagc  13920
tcccttcctt cttttctttc tttttattca tatatgtttt tttgataaac agtatcactc  13980
tacaacccag gctggcctag aacttaccat gtagcccagg gtagccttaa acttgaggtg  14040
ttccttgtgt ttgattctct caggatgtag ggttgcagtt gtgaattacc atgcctggat  14100
atccatcctg gatggtcaac tttcggacag cacataatag cacatttagt ttccacaaca  14160
atgctacatt cctatcccaa tatacttatt taaagagatc caaggcttag ttatctgaat  14220
taatttattt gcagttatgt gtgttatagc agtttgaact cagttctact tgattttcta  14280
atcactagag atttgagaga aattagatca aggataaatg aagctaatag cttcagctct  14340
gcatcttccc atggcacact ggagagtgag gtacacaata tttattgcac agttttccca  14400
aggccccatg ttctaagaat tttcttgaaa gtttcagaat gtttgcttct caaagtcctc  14460
agctcacctg gaaacaatcc gggctatgat acttgatcca acctttccca ttttcttact  14520
ctgttggctc agaaggctat ttacatgcag atacacatat gcatacatga ggcccaagtt  14580
ccttattcct aaaaggccat aaacatagtg aacattgttg aaactttgtc ttctatggat  14640
atatagcata atcagtatat aggtattgtt atgatttaaa agatatacat tcagtggctg  14700
gagaaatggc tcaacagtta agagagcata ttgctcttgc agaggaccac agtctggttc  14760
ctagcaccca tactgagtgg ttcacaactg cttgtaactc tagctctaga gaaactcaac  14820
acctctggcc tcacatgcac acactcatac acagacgcat gcatacacaa aataaaaaaa  14880
aaacttttta aatgttcgaa gataaatatc cacataatga ccaagtctac aatagcattg  14940
accactgtct tgaaggggta gaagcaaagg ggaaatgtat tgacagtatt ttagaatgtg  15000
ttaggcccta ggcaggactg cctgtatgtg gcctgactga tgtggtggta gatgataaca  15060
ggataatcat gttagaaatt ttatttaacc ctggccctta tgggagagct ggccctgccc  15120
cccccaacaa cctttggttc tcttaagtta tggcttctgg ggagggatac aggcagagaa  15180
agactcatcc tcccctgggt tgctggccac tgggaatctg accctatccc ggtgagaata  15240
tggctaacac aacatggacg tgctttttcc tctttttgat aagaataaat aaattataaa  15300
ataaataata cgaaagaaat tttacctaag agattcagtc ttattatttt taataagaaa  15360
attgctatca ctaatctaga atgatgtccc ttaagttgtg gaagagaaaa ggctccttca  15420
tttgaaaatg aaaaagagac aattattatg aggggaccat actcagggtt ttacatcgat  15480
gtaaaactca agtaggatca cagcctttca ttcagagcca aatttaagca gccccaataa  15540
caaaaattgt tccccttagg cctcttggga actaggtcag gtactctgta gttcacagag  15600
acacgcagtc atgacttaag aagacttttg gctctggaat cctgaggact tgatccaaag  15660
tcaagttgta ggttgacttt gcagtcacag ggtagatgca tatctctatg agtgcttttg  15720
gagagaaagt atttttggac agatgtgtct taaaatttac acttatgacc cttgagcaac  15780
```

-continued aaagcccaaa gtgactattg aatttaaatt ttgatctaaa gaaataactt atttattaaa 15840
aaaatatatt gaaggcattc acttgtgggc atttcagtga tttccagtgt agacatagaa 15900
agtaaactga gtcacaagga tggcaaattt tcatgaggga cagtcaagat ccttttctag 15960
gagagacaag ctagagaaat cagggatgca cagagtgtgg aaagtcaaaa ctgaatttct 16020
gtgaaaggta tgtaggtatt gttattgttg gtgtacagtt accaatggag aaccctgtgt 16080
ggagtatggt cagcttggat ccccagagcc ttgtgtagag atagtctaga aaagagttaa 16140
ctggaaaaag tggcagggcc aggaccctca caacagtgca tttgcagatt tagttgcaca 16200
cactggagag tctacttccc cagagcaatc ctgatctgcg gctgacagca ccatttctca 16260
gatacccaaa attagaattt acgcataacc ccatcacacc taggaccaag tactaacgtt 16320
accccagaat agcttcctct actgcctcac ccagaatcag aatgccaaat ggtagtctct 16380
ctagcctgac ccctcatcac gcctggaggc ccaacctttg atccctcgga gtcaagcgtg 16440
aactgctgct tagactttag gaatattgtg ataaaaagca gtggtttggg aaatctcctt 16500
cagagccttc tggtggagac atggagccta aataaatctg aaagctcaag acaccactga 16560
gtactggtgt cctaatttca tcctggttac taagataaat gaaaatattt attttgtata 16620
caaaaaggtt acttcagaga cagctgtttg gggctcttgg tgatatcttt cgtggaagtc 16680
agtatacata ggaatgttag gagtcattgc ccagggtggg ggaattgagt tgaggaatga 16740
ggttctgggt gaaacttctg cacaatgcta gcagataacc ttcaacagat cctttaaaat 16800
ctcagtgcat ctccctggct accatcggtg gtaagaagcc attttatgga gcagtttatc 16860
atctggactc cagatgtgct ggagttaaac aaagtctagg gataactcat ttttttatct 16920
tctttagaaa acctcgtcgt agatgcacag cgatctccct cgatagtgaa acaatgaacg 16980
atctgtgtca tgtgatttta tgtatcctca tcacattaac tcccattttc tgctacagtc 17040
aattcaagtt ccctgcggta gaacactgtg aacaaaagca cagtatagga cttgtgggga 17100
ataacaaaat aagggagctg gttgtggaaa ggctctaagc gtttcttttg atgaatagaa 17160
aaagagcatg tctgtagagt agcagctgta aagcaaggta agggatgcag agcgctgtct 17220
gggttaaagt ctaccagcca cacacaacaa agggatctgt ctatttggct ttctcagggt 17280
cgatggtgtg ccgcagagcc tccacccact ctgtgtaagt ttcccctctc cttggaagcc 17340
tcctgctgga atttgtgcaa agctctctgg gcctgtgtgt catgttacat cagcaggctg 17400
taggccacac aagacttggc cagaatagaa aatcctgtat ttctttggga ggaacaaaac 17460
cctcccattt gtttccagct attgtgagtt atttgctcat ttatctcaag gtccctcctg 17520
tctagatgtt aatggtggga caaactgtca gtgattctaa tggctcattt gtgatctgag 17580
gtttaggaat gtgttttaat aaggcacctt acaaagatgg aaacaacact ggagggaaac 17640
aaagaaatgg agtgaggaac aagtccaagg aaaaataagg acaggaaaaa aagagcagag 17700
tgagacagtg tcaagctcat tccaaacttc tcaggtcaca cattttacat ccctaaggaa 17760
gacactgtca gtctctgtca tggtgggcct ttcttcccga ttcctgctac tgtccccatg 17820
ctgcctagaa ggtccaatgt gtccatgagg cagtgctgag agatttctct gagcttcaga 17880
tctggaccta ccttggatac aaaatgaaag ctgggatgag agttgcttat tgattcttac 17940
tgtgggtagg gtctgaccgt atacccatct atccgttgct atggggactt tccctacagc 18000
cctcagtagg tgggtgctca tatgtttccc ctactactct ggaagcattt cagggcttgg 18060
agagcattct gtgcacttgg cacacgtgca catacgccca cagctgccat ttgtgattct 18120
tcgaaagctt ggagtggagg tttacagatc tgctatgctt actttctcaa agagagcacc 18180
ccggcttgtt acaaatgtta gaagtagtct ttaggggcgc tgagctgaac ttgctccctg 18240
agctgtagat gtgcccatga cagattgtta agtaaagtag gctgctttcc ctgcaaaaga 18300
acacactcct ctttcaaata tacgcgcttg tatgctggtg aggtttgcac aatcaaagag 18360
aagtctgtag aaagatcccc atcaggttgc tagtgttggt aaatattgac aactgaacgg 18420
gatgaataag taggcgaaag gttaggactg gggagacta gtctctcctt tcaacgagaa 18480
gctgctacta actaaaaata acaactagta gtaacgttat tactatcagt aaacatgcaa 18540
ggcatgtctg ccgttaatcc tagtgcttgg aatgaggagg aaggaggatt accataaatt 18600
ctgtgctagc ctggggcctg atcatgccgc catttttcag tccagcctgg cctgaatgtt 18660
gttccaacag cagcaaaaga aggcatcaca ttcgagatgt agagacacag ctaaccaatg 18720
aaaaccattt tttgtttgtt tgtttgttta tttgtttttt gctcagcaca tcatgcaacg 18780
aattcagaga cttcaggctg agtgggtcgt ggaagttgac accttcctga gtaggactcc 18840
ctatggctat cggtccttct caaatatcat cagcactctt aacccggaag cgaaacgaca 18900
cctggtcctc gcctgccact acgactccaa atattttcct cgatgggaca gcagagtgtt 18960
tgtgggagcc acggattcag ctgtgccatg tgcaatgatg ttggaacttg cccgtgcctt 19020
agacaagaaa ctccattcct tgaaggtatc tgctctcttc ttgttgactc ctagggtaaa 19080
acaataaaca aacaaacaaa caaacaaaca aagacagcat caactccatg aatttgggaa 19140
tccttggagt ggggaggtca tttggaaagc aaaactttgg ggtgcacttc aaaataattt 19200
gttaaaaaat atgaaatgga ggaagtatta tttggaagag cacatgattt aaagtatcta 19260
ccatgggcaa taattcacag atagataagg gtgggttcat taactgatat atattcatac 19320
ctggttatat attaaattgg gaataacttt tttttttttt gcaaataatg aaataagagg 19380
gaagctggtg atggcatatg tgtgtggatt atgttttcta tcaagtcatg cttacttctt 19440
gtttacacag ctgagaaaca tcatcacctc ctgctgggag agaggtgggc tctggagttg 19500
ggggggtgca ttatgggaga tcttcagtgt gtggggaatt cagatatacc aagatgaaaa 19560
gcagaagtgt gctatggttg tagctgtgaa tcagggctca gttttacaca gtgtagcaga 19620
gcttctgtta tgcctgcagc tcagaatgcg tttgggactc ccaggtttga tttctgtctc 19680
tgtgttctta agggtgcacg gggtagggtg ggggtaagtg ggagggaaat gctagcctag 19740
atgaggacat tttattctga tactgctcat aaccaagtaa acatgacaaa gtgaatacaa 19800
aaacttggtt cacaggcaac aaatgcctcc ccactagccg ggcctttagt ttttgataca 19860
ataagtgtaa agaaatgaag ggtttatctt gtaatggaag taatagagat atgtgcttct 19920
gtttttgctg gatatgctga atttgaagaa agcaaggatt gtttgtaccc ccttaatatc 19980
cttttcacag ctgtgttgtt tttctgagcc ttctgggatg gctttgtttc aggccctgcc 20040
ctgctttgaa ctggtaacca ttcctgaggg aattcacaag ccggcatgcc cttttggtgt 20100
tttatactta acgttcctaa cagaaagaca tgggcgggcg aggcgagact taaagacaca 20160
tttctgcttg tcacaaataa atgtactgct ccaaatgaga cagcacagcc acggagcaag 20220
aggtggaacc agagtgcttg gtaccaaagc attctgcgca tgcccaaagc agagagatgc 20280
cttccgacca agcccggcca gagacctttt gttcatgtcc aaggtagaga caataagagg 20340
tagttttcat ttccttcagg cataaggcca cacggatctc actgaaaagt cagcagtcag 20400
atgacaccta aaggtagcga aatgacttac attcattcat tccattctca gcattaattt 20460
atttagactc ctgtgaatac tgattcgaag tcccttgtgg caagctgctc ttttgtttct 20520

-continued ttttacagct ggcaggaaaa taatcatggt ctgcaacttt tactaattta gctttatacc 20580
tggacaccag gaggatcttt gcggcctggc agttttagta tttttctttt cagtgattgg 20640
gttgaagcca aggcctcctg catgtaggta aatgttgtat tgctgtccta caaccccagc 20700
catatatata tatgtgtgtg tgtgtgtgtg tgtgtgtgtg tgtgtgtgtg tgtgtgtgtg 20760
tgtgtgtatg tatatatata catatatata tatgtgtgtg tgtgtgtgta tgtatgtata 20820
tgtatataca taaaaattta taatttatgt attataaaat atatttatat ttttgtatta 20880
tttatatttt atgtatataa atatatttat attttataat tatatgtata tacatatata 20940
taaaatttta aggcagtatc taaataagtt ggttaggctg gcctcttggt agtctaaaaa 21000
agctttgaac ttgcaatctt cctttagcct tctaagtagc tgggattaca ggaatgtgcc 21060
accaagatgg ctttgaaggt ttggttgatg atattataaa ggctcagcta ttatggaatc 21120
caaagtatca aatttcgtaa tctatttggg aggcattcaa ggctagccta atttagatta 21180
gagtttcaag ccagccaggg atacaaaaca aaacaatcca caaagagaca aactgttcaa 21240
acccctaatt tctcttttat ctggtaccac tctaaagcaa cagggaaact ctgtctttga 21300
agaaactagc ggatgtgtgt tagtgggaaa cacaatatgg agacaagtgg atgtcacagc 21360
aaagtggaga gaagttagtt aaatgggaat ccttcagaaa gtacaggata gtctcttgac 21420
aatatcctaa ggggaggtag ttagaggatt gacacattag gaaggcagaa gagaggcggt 21480
gtgtgtgtgt gtgtgtgtgt gtgtgtgtgt gtgtgtgtgt gtgtgtgtgt gtatacacag 21540
atgtgtataa gaaacgtatg gatgtataga ttttgaatcc atgccaggca gggaggtgag 21600
cattctgctg gctctcagga aattctaaaa gaaattaaac agagggtatt ttggacttgg 21660
gaggacaagc tttaaagaag ggtgatgagg aaccctaggg agatcaaggg gattaggtaa 21720
atatcatgtt ggacagtggg gtcttcaggc tttcttccat tcctagcacc agaaagccag 21780
tagcagacat aggactggag aatctgtgtc cagagaatgc agatgccaca gacaaggatg 21840
ccaagggaga catttggcaa ccttaaatga gaacactgaa tagacaccag attgctctaa 21900
agtgactaca ttagagccaa ccaatttgtg tcttcagtga acattttagt accttgttct 21960
tcagtacaaa caaataccag gcgtggtcag ctattggagt atagtttcca ttgtggaaga 22020
aaaactaatt atgcaaattg aaacatgaag ttggaggggt agggtagata ctgccagggc 22080
agcagaagat agcgtgatgc tattttaaaa tccttagaga tgagagaact tgtattcata 22140
aaataaagca gtcttcaatc acagagtaat ctcatcatag caaagagctc ttggaaattt 22200
gaaattaaaa gtacaatttt caagaaaggc actaagaaca ctggactctg aagtaggtaa 22260
tatatccttt ttagaaagga aaaaaaaaac aaaataaaat gattttttt tcatgggatc 22320
attccaggtc atataaaaag ctgtaagaat gaaagtggtg ctggacttag tagaaatcct 22380
ggaagctaga aaacaatgag gttgggcctg caacattgtg gcatgtgtta tatacatgca 22440
tgctcagatg ttagtttgcc aactgatgtg ttggtctgga gatcagatgt gagaacacac 22500
acacacacac acacacacac acacacacac acacacacac acacacacac acacacacta 22560
ttcagaatag gtatccaagg atagatgcca gcagagatga gaaaaaaatt aggcatcaag 22620
ccctagtgct ctttgatatt aagagggagg aggcatgaag gaatctgtat tttcttcttc 22680
cattcactct cacagtgagt gtttcacact cttcctctcc ctaacctgca gttccttacc 22740
ttgcccatcc tcactcccaa ggaatagcct tgacttcttc ttgccagtct cattagctgc 22800
taagctcccc acgcatgcat tgaattccat ctcctgaatg agggaggcag agcgtgttct 22860
tctaggaggc aaatggaagg attttaccca ggacagagca tcagttatgc tggatgctgt 22920

```
cagtaagtca gggatgataa agactgagag ctgatctttg gatttattga tgtgtaggtc  22980
gtaggtgtgc ttgacactta tgtttcagta gatggaggag atgaagcctg aaggataggc  23040
ataagaacag acctcctaga aagcctgggg gaagttaaga tagacgttcc agtgatgtac  23100
ctaaaagtga caaaattggt agactaggtg ttgttattat atctattatt atagtttaca  23160
taactgttat aactatgttc aatgtatatc taagagagaa ggccttttta ttggacaaaa  23220
agggtgagat gttgtggatt tgatttaatg cttacattat ggcttcccaa attacacagg  23280
gattcaaatg tctactgcca atggctgggc tgggagacag aggcgggact ttgagattcc  23340
ccaggcaagg aactcgaggg aggaagagaa tgaccactgc tgaggatgga gaaggtcccc  23400
acttgagaag tgtaggacag aaagacagag acactgccaa catgtaagag tcagagatca  23460
tggcccagga ggactacagg cctgggtctg tggcagccag gacagaatat aacataggtt  23520
ttagcaagtg ataattcagg aatattggag gggagagtgt gttagctgtg gggaggtttg  23580
gaagtgccca gcattgagct gtttaagaca tattaaaata aaaggctgtt gtggtgtgtg  23640
tgtgtgtgtg tgtgtgtgtg tgtgtgtgtg tgtgtgtgtg tgtgtgtgtc tttcatttgc  23700
aattccacaa cattagggtg gtaggaagaa gtgtgtgcgc acccgctggg atgtttggag  23760
agaattaatt tattaccact tcagggggac atgatttatt tggtagagca atggccttgc  23820
atggttcagg cttctggttc aacaccgaga attttaaaaa atggagctga agaataagac  23880
tgaggaacac tgcatatata aaatccttcc agtgagttaa caaagatagc aaacccgcag  23940
aactatcgag cagtggcaga acacctgatg tggaagaaat ggcgtatgct aaagcaatgc  24000
ccttgagcag acaagaggag atggaattta gtgcatatgt ggggagactg gcatctaagg  24060
agactggcaa gaagaaatca agggcatcac ttgggagtgc ggatgggtgg gctggggagc  24120
tgcaggctag ggaaagggaa agtgtggaat actcagggtc agtcaacaaa cccagaaaat  24180
atagcacaac tgtgttctgt gtgtatacag cacagtacag aaaggctgta ttaaaatctg  24240
tgctcgtgga ttttaagtta gcaaatagca tggtggttca tttttttttt ctagccgggt  24300
ttagcatctt gagaatagtc acagaatagg tagagaatgg ccctccatgt tattattatt  24360
ttgttccatg aaagtgtgat tatgaagaga ggccaaggag ctgacagtgt acttagggga  24420
aggaccagaa ggattaccag aaattggtca aaactggagt aaacggggtc attataggag  24480
tgtagctgtg aagaggtgag attaagtggg cttggaagat ttgaacacca aaaggactat  24540
ctgtaccgga gagtcatagc ccgattaaaa actgtaaagc ttttcggttt tctcaaatag  24600
tgtctctcac aaagccttgc ttgatgtccc aagggctcca tcagtcagtc attcctccca  24660
gccttcaatg gatgcaagct tcacacttga gccccttggc atattacaaa ccatacttat  24720
gtatttgttc tctttctcct aacctgccaa atgtatagga tctcttaaga gaaacactat  24780
aattattctg tttgtgtccc tacattgttc ctagggcaga ctcttgaact taggtccaat  24840
aacgaatttc caagtccggt aaggtgagga gaaggtaccc agttgtttta ggttgggttc  24900
cagggaagca cattgggagg tggaacatca cctgtcccat tcaggtcagt gattagggag  24960
tggccttgga tcaactctgg aggcagggag agggatgaga caggattagg aggagtgagc  25020
catgaagctg cagtgcaggt tttacagcag cctcataact tcgtatagca tacattatac  25080
gaagttataa atagttaaca taccttgctg gcatttgtct tcccctacca atttgtttat  25140
tattcctaat tcttcagcag gcccagttta gtttcttagg tggaattcta ttttgaaagg  25200
cagatgtcaa aatactacat gtatatattt ttagaaatga tgccaaaagg tactctggaa  25260
```

```
tttcatttca ttttccatct caaatttgtc tgcttctgtt ttctcccttt gtctttctcc  25320
cccaaggact ctgtgtgctt cccttacttc ctttctctga aacgcacaca tcaacagatt  25380
gtaccttact gtgattaaaa ccgattgcac tgccctcgtt tgtggaattt acatttttaa  25440
ctatttaatt gtataagaaa aatgtacatg atggttaagg aaatataagt attgatagat  25500
aagaatatta tattttgtgg tacttggggc tttctcagtg ttcttaaaat cccattatac  25560
ttgtttccta cttgatacag ttttacccta gaaatttaac aatcacaaaa atgaccagct  25620
atcctgggca ttatttcctt gttttgtcat ctgatgctat cttgccattt tgtatcaagc  25680
agcacatggg ttatatacac gacttatgtg ctacaagaca ccaggagtga gggactgtgt  25740
aggccagtgg ttctcaaact tcaggacaga tcagaatccc ctgggttcat gctaacgcgt  25800
ggattaccag ccggtacccc gaatttctga ttcattaagc cagaggtagt accagctgat  25860
ttgcatctct gcgttattct caggtgatac tgaagctctt gatgaggaac cgcatcctga  25920
gaatcactga tagaggtcac agtagtcttt tcccacagag tggccagttg atatacttca  25980
tcctactctg ttggcatatt ccgctttaag ccccccacat ctctacatgg gcattcgcca  26040
cacaccacct ggatctatga acatctgcat ctgagtttcc aacacctttg actccttttt  26100
ctctttctct ttctcaatct cagttgttct agtgagcatc tactcttttt ttggcattag  26160
ctacttggtc tcttttaatc tttttaaaaa attggttatt ttatttattt acatttcaaa  26220
tgtactcccc ttcccagtgt cccatccaca acccccccat tccctcctct gcctctataa  26280
gagtgcttcc cccacctgca tacccactcc agcctctgcc atagcattcc cctaccctgg  26340
gagcctccac agtaccaagg gtctcccctc ccactgatgc ctgataaggc aatcctctgc  26400
tacggatgca gtgggagcca tgtgttctcc ccatgtgtac tttttggttg gtggtttagt  26460
ccctgggagc tttgggggtt ctggttggtt gacattgttg ttcttcctat ggggttgtta  26520
accccttcaa ctccttcagt ccttccccca actcctccat tggggtctcc atgctcagtc  26580
ctatggttga ctgcaagcat ccgcatctgt atcagtaagg gtctggcaga gcctctcagg  26640
ggacagcttt accaggctcc tgtcagcaag cccttcttgg catcagcaat aatggttggg  26700
tttggtgtct gccgataggg tggatcccta ggtgaggcag tctctggatg gcctttcccc  26760
cagtctctga ttccattctt tgtccctgca tttcctgtga tccttggtgt gtcaaggcac  26820
ctgggagttg agcttcctct gggtgttgta ggagtgggta gtgagccagc gccccaggtt  26880
tgctctgggc actggttcaa actggaagct ggaatcttag aggttttcac cagcactgtc  26940
aatgtcatgt gtgcctctct gtctctattc tcctctactc caaagtatag ataggtgcag  27000
cttagactct tactgtcata gatgtggcta tgtttactga tacagatcta gggaagaatt  27060
ccatgtgtga taagatttca agctccctaa ataaggatgt attctgagtc ttgatcagag  27120
aaaattagat gttcatctac tgtctactga tgttcatctt gctgtccaca gaaaaggaac  27180
tctatgaatt gggattactc aaggatcatt ctttggagag gaagtatttt cagaattttg  27240
gctatggaaa tattatccag gatgaccaca ttccattttt aagaaaaggt aactgtgtgt  27300
gtattgttgt gcattgtgtt ttctctactg tgtctactgt aattattata ttttatgtgc  27360
attttgaaat tttaaaaata ttattttcac atttcttttt ctggttcttt tttattatat  27420
gttaattgta tgtagtattt cattatgaca tttttataga tgtatattgt tgcggccgcc  27480
agcagctcgc aacatgaacc gttcgactga gaaggctact cgagctgtaa gagaggaatc  27540
tagacggggc gaaagaagaa atggagctaa aacaaattca ttctgatcaa agctcaaatt  27600
ttattgttgc aacactagtt ataaaggaag ggggaggga cccgattccc gccgaataat  27660
```

```
ctctggtcca gtagaaaggt gcacgtgtgt ggctccgcag gttctagcag tgggcgtggc  27720
agaccgaatg agcaggaagc tccacccctg agcaagcagg tttcaggctg ggggagggga  27780
gactacagta tataatatag tttgatcata ttcctctccc tttgccctct cttttttttaa  27840
tttttcattt tttattacat agtttcttta tctacatttc aaattttatc ccctttcccc  27900
atttcccctc tgaccccccc catcccattc cccctccccc tgctcactaa cccaccaact  27960
cctgctccct tgtcctggga ttcccctaca ctggggcatc cagccttcac aagaccaagg  28020
gcctctcctc tcattgatgt cccacaaggc catcctctcc taatatgcgg ctggagccat  28080
gagtcccctt gtgtactctg gttggtggtt tagtccctgg gagatctggg ggtactggtt  28140
ggttcatatt gttgttcctc ctatggagct gcaaacccct acagctcctt gggtcctttc  28200
tctagctcct tcactgggga ccctgtgatc agtccaaatg gttggctgtg aacatccact  28260
taatatttgt caggcactgg cagagcctct caggaaacag ctatatcagg ctcctgtctg  28320
caaggtctgg gtttggtgac tgtatatggg atggatcccc aggtgggaca gtcactggat  28380
ggcctttcct tcagtctctg ctccatactt tgtctctgta actcctccca tgggtagttt  28440
gatccccctt cttcttctcc ttctccttct ccttctcctt ctccttctcc ttcttcttct  28500
tttggttttt tgagacagga tttctctata tagccctggc tgtcctggaa ttcactttgt  28560
agaccatgaa agaccaaagt atccacactg tggtcttcct tcttcttgaa tttcatgtgg  28620
tctgtgaatt gtatcttggg tatcctgaat ttctgggtta atatccactt atcagtgagc  28680
gcataccatg tgtgttcttt tgtgattggg ttatctcact gaggatgata ttctctagtt  28740
ccatccattt gcctaagaac ttcatgaatt catcattttt aatagctgag tagtactcca  28800
ttgtgtaaat gtaccacatt ttctgtatcc attcctttgt tgaaggatat ctgggttctt  28860
tccaacttct ggctattata aataaggatg caatgaacat agtggagcat gtgtccttat  28920
tacatgtgga gcattttctg ggtatacgct caggattggt atagctgggt cctcagatag  28980
tactatgtcc aattttctga ggaactgtca gactgatttc cagagtggtt gaaccatcct  29040
gaaatcccac cagcaatgga ggagtgttcc tctttctaca tattctcgcc agcatctgct  29100
gtcacctgag tttttgatct tagccattct gactggtgtg aggtagaatc tcagggttgt  29160
tttgatttgc atttccctga tgactaagga tattgaacat ttctttaggt gcttctcagt  29220
catttggtat tcctcagctg agaactcttt gtttagcttt gaacaccatt tttaatagga  29280
ttatttgggt ctctggagtc taacttcttg agttctttgt atatattgga tattagccct  29340
ctctcagatg tagggttggt aaaaatcttt tcccaatctg ttggttgcca ttttgtccta  29400
ttgacagtgt ttttatcctt atagaagctt tgcaatttta tgaggtccca tttgtcaatt  29460
cttgatctta gagtgtaagc tattgttcta ttcaggaaaa tttcccctgt gcccatgtgc  29520
ttgagactca tccccacttt cttttctatt attttcagtg tatctggttt tatgtggagg  29580
tccttgatcc acttggactt gagctttgaa caaggagata agaatggatt gatttgcatt  29640
cttctacatg ctaaccacca gttggaccag caccatttgt taaaaatgct gtctttttcc  29700
actggatggt tttagatccg ttgtcaaaga tcaagtgacc ataggtgtat gggttcattt  29760
ctgggttttc aattctatcc cacagaacaa cctgcctgtc actgtaccag tacaatgcag  29820
tttttttttg tttttttgtt tttgtttttg ttttaatcac gattgctctg tagtacagct  29880
tgaggtcagg gatggtgatt tccccagacg ttcttttatt gagaatagtt ttcactatcc  29940
tggtttttgt tgttgttgtt gttgttgtta ttattccaga tgaatttgca aattgtcctt  30000
```

```
tcttactcta tgaagaattg attgggaatt ttgatgtgca ttgcattgaa tctgtagatt  30060
gctttctgca ggatggccat tttaactata ttattcctgc caatccatgg gcatggaaga  30120
tctttctatc ctttgagatc tttgattctt tcttcagaga cttgaagttc ttgtcattaa  30180
gatctttcac ttgcttagtt agagtcacac caaggtattt tatattattt gtgactattg  30240
tgaaagatgt tgcttcccta atttctttct cagcctgttt atcctttgag tagaggaagg  30300
ccactgattt gtttaatttt atatccggcc actttgctga ggttgcttat ctgatgtagg  30360
agttctttgg tggaattttt gggacactta tatatactat catttcatct gcaaatagtg  30420
atattttgac ttcttccttt ccaatttgta tccccttgac ctccttttgt tgtctaagtg  30480
ctctggctag gactttgagt actatattgg gtttgttagg tctgcttaca ggagaacaga  30540
tgagaattta tttacagaag tatgggtacc ttaccagtag gttcaccaca gaagtatatg  30600
tctcttcccc cctccccaca ccaaccatta ataattatgt gcaaatcctc agagaggggt  30660
gaggcctcat gagatcttct gctctccatg atatggtgtt gtgggcccaa tcttacaaag  30720
atctcataaa ggtcatggct gttgtgagtt caagagtgta cttgcatttc ataccattct  30780
cccatccatc cccctgcttc tcccatcttt agtgtccctt ttccttgatg cttactgagt  30840
gttagatgat ataaatgtct aatttacatc atagcttaac attcaacagt catttattct  30900
cctcatttta accagttatg agacagttac cattgtctaa tgtaaaaaga atctccctgt  30960
tccccaaact ttacctagca acttagtgcc attagatagc gttctttaaa actgaaaatt  31020
tccaggtctc caactgctgc atatatttaa gaaacaaatt aagcatgaat aatattagtg  31080
tactttggat cactaagccc atacttcctt aagtttgaat gatttaaatt tatataatta  31140
atgttttgac ctatataaaa gtattttaaa agatctaaaa taggcactgg attaatttga  31200
atgagagcct atctttaaaa ggaaacatac ttattttgct ataaataagt tttggccaac  31260
atgtgcttta tggatttata tctataagat aaatgttaga taattaaacc aaattaaata  31320
ataaggaaga catctagcta caccctcacc tggtttatac tgatgaaagg tactattcag  31380
atgcagcttg taacacttta gcatctcttt accagaacat gcccctaact aaaaagtcca  31440
atccctaacc aagaatctat ttgcaattta tacccactga gagaggggat tttttttcc  31500
cagtagagtg acactgggta tattaaccac actccagagc aggctccatt ggtcaatttt  31560
gtgtgtgtat gtgtgtgcat acacgagcta atgcatatgc atgtgtgtgc gaatgtgtat  31620
tcacttgcta tctctttgtt ttgttttggt attttttgtc tttttgtttt gattgagaga  31680
gagagggaga gagagagaaa gagagagaga ggagagagag agagaaagag agagagagag  31740
gagagagaga gggatggaga gagagaggga gggagagaga gagggaggga gagagagagg  31800
gtatgaaatt gggaggatag ggaggtgggg agatctggaa gatgctgagg aaggggaaag  31860
aaaatgatca aaatatattg tataaaaaat taaagctaat aaatacaaac aaaacaaaat  31920
gaaacataaa gaccatttct ttatcagccc ctttctttgg attatcagat gaaatgatag  31980
agcccattat tgttcattga cttggaagaa tatgcgtcat ggaatattcc tttccttgtc  32040
ttgcgtattt aagttttaaa gatgaccatc taagttgaat cttatataca acactggact  32100
tacacaataa ttcccacttc ccctgatttg taacaatcta ggagtgatag gaatcattaa  32160
atataataaa ccaatcagtt tgataggaat cattaaatca ataaatcaat ccgtttggcc  32220
atgatgtcat ttgttcatgg cttctctttc ctcatgagag acattttgaa atcttgatgg  32280
catctttata tatctttata tatctgttat atagttagaa aatcccagaa tcttctgata  32340
tcctgccttg ccttgcataa agttaagcta ttttcttgct cttcattcaa ctttgatgtg  32400
```

-continued gcatggttgg taagaaagat gtcctggggc atggagagat ggctcagtag ttaagggcac 32460
tggctgttct tccaaaggac ctgggttcaa ttcccagcac ccatgtgaca gcttacagat 32520
ttcggtaatt ctggtccccg gggatttgac accttacaca gacacacatg gagacagaac 32580
accaatgcac ataaaataaa aacaaataaa ttattaaaat agagaaagct gtcctgtatt 32640
gcgatgtgaa agtctaaaat taactcagtg acttttagga agcttccaca ctggtctcta 32700
aattttacta ttgcttctct ctctctctct ctctctctct ctctctctct ctctctctgt 32760
ctctctctct ctctctctct ctctctctct ctctctctct ctctctctct ctctgtctct 32820
ctctctctct ctctctctct ctctctctct ctctctctct ctctctctct ctctctctct 32880
cctctctctc tctctctctc tgtctctctc tctctctgtc tctctctctc tctctctctg 32940
tctctctctc tgtctctctc tctctctgtc tctctgtctc tctctctctc tgtctctctc 33000
tctctctctc tctctgtctc tctctctgtc tctctctgtc tctctctctg tctctctctc 33060
tctctctctc tgtctctctc tctctgtctg tctctctctc tctctctgtc tgtctctctc 33120
tctctctctg tctctctctc tctctctctc tgtctctgtc tctctctctc tctgtctgtc 33180
tctctctctc tctgtctctc tctctctctc tgtctctctc tctctctctg tctctctgtc 33240
tctctctgtc tctctctctc tctctctctc tctctctctc tctctctctc tctgtctctc 33300
tctctgtctc tctctctctc tctctgtctc tctctctctc tctctctctc tgtctctctc 33360
tctctctctg tctctctctc tctctctctg tctctgtctc tctctctctc tgtctgtctc 33420
tctctctctc tgtctctctc tctctctgtc tctctctctc tctctgtctc tctctgtctc 33480
tctctctgtc tctctctgtc tctctctctc tctctctctc tctctctctc tctctctctc 33540
tctctctctc tctctctctc tgtctctctc tctctctctc tctctctctc tctctctctc 33600
tctctctctc tctctctctc tctctctctc tctctctctc tctctgtctc tctctctctc 33660
tctctctctc tctctctctg tctctctctc tctctctctc tgtctctctc tctgtctctc 33720
tctctctctg tctctctgtc tctctctctc tctgtctctc tctctgtctc tctctctgtc 33780
tctctctctg tctctctctg tctctctctc tgtctctctc tctctctctc tctgtctctc 33840
tctctctgtc tgtctctctc tctctctctg tctgtctctc tctctctctc tgtctctctc 33900
tctctctctc tctgtctctg tctctctctc tctctgtctg tctctctctc tctctgtctc 33960
tctctctctc tctgtctctc tctctctctc tgtctctctg tctctctctg tctctctctg 34020
tctctctctc tctctgtctc tctgtctctc tctctgtctc tctctctgtc tctctctctc 34080
tctctctgtc tctctctctc tctgtctctg tctgtctctc tctctctctc tgtctctctc 34140
tctctctctc tgtctctgtc tctctctctc tctgtctgtc tctctctctc tctgtctctc 34200
tctctctctg tctctctctc tctctctgtc tctctctgtc tctctctctg tctctctctg 34260
tctctctctg tctgtctctg tctctctctc acacacacat aaaatagaat tatcttttag 34320
aatcaaatta tgctaatact tactgtttta aatgtcctgg tttgctgtct tatagagtaa 34380
gacagaaagt ctttaccatg gcctaagaag acttccattt tctgattctg tttcaaaatc 34440
atctcttcct tggcttctca cttctttcag tgatttggcc acactggctg tcttgtgctc 34500
cctgctcagc acaagcctca tgctctttac atgcaggaat attggtgccc accatgctca 34560
ttcctaggtc tttgcctggc ctgctttctg ttgggtttgt accactcttt aaatattagc 34620
ttctggagag gctcttccct ggttttaaat ggctccccat tcattcaatt cccttgcctg 34680
ccctccatct tgatccctgt atcttgtttt gttgttttcg aacaacttta gcacagtcta 34740

-continued tgattatgtt tcgtatgtgc ccgtttcttt cttcactaga atataaaatc cacataggca 34800
tggtcttgcc attccactcc ttgaatacga gctttgcagg cacttggctg acttatcatc 34860
ccttactgga ttcattgatg tttgattgac aagccttgag gtacctatac gcttggagat 34920
gtgcttgtga aaccaggagt tatcgactgg cttaaaggat atggatcttt ctttgcctgc 34980
aaatgtaact ttctagttca ccccccctggg aattcttact cattcacgag ttgcttctct 35040
cccacaggtg tcccagttct tcacctgata gcttctcctt tccctgaagt ctggcacacc 35100
atggatgaca atgaagaaaa tctacatgcg tcaaccattg acaatctcaa caaaatcatt 35160
caagtctttg tgttggaata tcttcacttg taatgtttgg atttagtttc tggtaattgc 35220
ttctacagca acttcaagac accatttata caatctgctt ccagataaat gtgtgtagac 35280
ttctgtccta tagattcatt ctgtaggtgt ttttgaatat gtgatcagcg aactgtagaa 35340
ttctatgatg ccttcactaa ttttcctcta gagatgagaa agaaacatgt aaagaaataa 35400
aataataata atttttaaaa ttcttttgga ttaaaacttt aacataaagt tagatttatt 35460
taccaatacc atagatttgt aaacaatact tagatacaat gatgctgtat ggtatagtgg 35520
tagttttata tgtgatatta tatagtgtgt tatataatat gtaataaaac acaggcatat 35580
actttgacag cctttaagtt tctttaaaaa aagctttgga aattaaagtc tgaattaaat 35640
tgcatattgt gaatttattt tcatgtccc 35669

<210> SEQ ID NO 24
<211> LENGTH: 7401
<212> TYPE: DNA
<213> ORGANISM: Mus musculus

<400> SEQUENCE: 24
gtagctggga ttacaggaat gtgccaccaa gatggctttg aaggtttggt tgatgatatt 60
ataaaggctc agctattatg gaatccaaag tatcaaattt cgtaatctat ttgggaggca 120
ttcaaggcta gcctaattta gattagagtt tcaagccagc cagggataca aaacaaaaca 180
atccacaaag agacaaactg ttcaaacccc taatttctct tttatctggt accactctaa 240
agcaacaggg aaactctgtc tttgaagaaa ctagcggatg tgtgttagtg ggaaacacaa 300
tatggagaca agtggatgtc acagcaaagt ggagagaagt tagttaaatg ggaatccttc 360
agaaagtaca ggatagtctc ttgacaatat cctaagggga ggtagttaga ggattgacac 420
attaggaagg cagaagagag gcggtgtgtg tgtgtgtgtg tgtgtgtgtg tgtgtgtgtg 480
tgtgtgtgtg tgtgtgtata cacagatgtg tataagaaac gtatggatgt atagattttg 540
aatccatgcc aggcagggag gtgagcattc tgctggctct caggaaattc taaaagaaat 600
taaacagagg gtattttgga cttgggagga caagctttaa agaagggtga tgaggaaccc 660
tagggagatc aaggggatta ggtaaatatc atgttggaca gtggggtctt caggctttct 720
tccattccta gcaccagaaa gccagtagca gacataggac tggagaatct gtgtccagag 780
aatgcagatg ccacagacaa ggatgccaag ggagacattt ggcaacctta aatgagaaca 840
ctgaatagac accagattgc tctaaagtga ctacattaga gccaaccaat ttgtgtcttc 900
agtgaacatt ttagtacctt gttcttcagt acaaacaaat accaggcgtg gtcagctatt 960
ggagtatagt ttccattgtg gaagaaaaac taattatgca aattgaaaca tgaagttgga 1020
ggggtagggt agatactgcc agggcagcag aagatagcgt gatgctattt taaaatcctt 1080
agagatgaga gaacttgtat tcataaaata aagcagtctt caatcacaga gtaatctcat 1140
catagcaaag agctcttgga aatttgaaat taaaagtaca attttcaaga aaggcactaa 1200

```
gaacactgga ctctgaagta ggtaatatat cctttttaga aaggaaaaaa aaaacaaaat   1260
aaaatgattt ttttttcatg ggatcattcc aggtcatata aaaagctgta agaatgaaag   1320
tggtgctgga cttagtagaa atcctggaag ctagaaaaca atgaggttgg gcctgcaaca   1380
ttgtggcatg tgttatatac atgcatgctc agatgttagt ttgccaactg atgtgttggt   1440
ctggagatca gatgtgagaa cacacacaca cacacacaca cacacacaca cacacacaca   1500
cacacacaca cacacacaca cactattcag aataggtatc caaggataga tgccagcaga   1560
gatgagaaaa aaattaggca tcaagcccta gtgctctttg atattaagag ggaggaggca   1620
tgaaggaatc tgtattttct tcttccattc actctcacag tgagtgtttc acactcttcc   1680
tctccctaac ctgcagttcc ttaccttgcc catcctcact cccaaggaat agccttgact   1740
tcttcttgcc agtctcatta gctgctaagc tccccacgca tgcattgaat tccatctcct   1800
gaatgaggga ggcagagcgt gttcttctag gaggcaaatg gaaggatttt acccaggaca   1860
gagcatcagt tatgctggat gctgtcagta agtcagggat gataaagact gagagctgat   1920
ctttggattt attgatgtgt aggtcgtagg tgtgcttgac acttatgttt cagtagatgg   1980
aggagatgaa gcctgaagga taggcataag aacagacctc ctagaaagcc tgggggaagt   2040
taagatagac gttccagtga tgtacctaaa agtgacaaaa ttggtagact aggtgttgtt   2100
attatatcta ttattatagt ttacataact gttataacta tgttcaatgt atatctaaga   2160
gagaaggcct tttattgga caaaaagggt gagatgttgt ggatttgatt taatgcttac   2220
attatggctt cccaaattac acagggattc aaatgtctac tgccaatggc tgggctggga   2280
gacagaggcg ggactttgag attccccagg caaggaactc gagggaggaa gagaatgacc   2340
actgctgagg atggagaagg tccccacttg agaagtgtag gacagaaaga cagagacact   2400
gccaacatgt aagagtcaga gatcatggcc caggaggact acaggcctgg gtctgtggca   2460
gccaggacag aatataacat aggttttagc aagtgataat tcaggaatat tggaggggag   2520
agtgtgttag ctgtggggag gtttggaagt gcccagcatt gagctgttta agacatatta   2580
aaataaaagg ctgttgtggt gtgtgtgtgt gtgtgtgtgt gtgtgtgtgt gtgtgtgtgt   2640
gtgtgtgtgt gtgtctttca tttgcaattc cacaacatta gggtggtagg aagaagtgtg   2700
tgcgcacccg ctgggatgtt tggagagaat taatttatta ccacttcagg gggacatgat   2760
ttatttggta gagcaatggc cttgcatggt tcaggcttct ggttcaacac cgagaatttt   2820
aaaaaatgga gctgaagaat aagactgagg aacactgcat atataaaatc cttccagtga   2880
gttaacaaag atagcaaacc cgcagaacta tcgagcagtg gcagaacacc tgatgtggaa   2940
gaaatggcgt atgctaaagc aatgcccttg agcagacaag aggagatgga atttagtgca   3000
tatgtgggga gactggcatc taaggagact ggcaagaaga aatcaagggc atcacttggg   3060
agtgcggatg ggtgggctgg ggagctgcag gctagggaaa gggaaagtgt ggaatactca   3120
gggtcagtca acaaacccag aaaatatagc acaactgtgt tctgtgtgta tacagcacag   3180
tacagaaagg ctgtattaaa atctgtgctc gtggatttta agttagcaaa tagcatggtg   3240
gttcattttt tttttctagc cgggtttagc atcttgagaa tagtcacaga ataggtagag   3300
aatggccctc catgttatta ttattttgtt ccatgaaagt gtgattatga agagaggcca   3360
aggagctgac agtgtactta ggggaaggac cagaaggatt accagaaatt ggtcaaaact   3420
ggagtaaacg ggtcattat aggagtgtag ctgtgaagag gtgagattaa gtgggcttgg   3480
aagatttgaa caccaaaagg actatctgta ccggagagtc atagcccgat taaaaactgt   3540
```

-continued

```
aaagcttttc ggttttctca aatagtgtct ctcacaaagc cttgcttgat gtcccaaggg   3600
ctccatcagt cagtcattcc tcccagcctt caatggatgc aagcttcaca cttgagcccc   3660
ttggcatatt acaaaccata cttatgtatt tgttctcttt ctcctaacct gccaaatgta   3720
taggatctct taagagaaac actataatta ttctgtttgt gtccctacat tgttcctagg   3780
gcagactctt gaacttaggt ccaataacga atttccaagt ccggtaaggt gaggagaagg   3840
tacccagttg ttttaggttg ggttccaggg aagcacattg ggaggtggaa catcacctgt   3900
cccattcagg tcagtgatta gggagtggcc ttggatcaac tctggaggca gggagaggga   3960
tgagacagga ttaggaggag tgagccatga agctgcagtg caggttttac agcagcctca   4020
gctaactctg gagagctgtg gaggtggtgg cctatggaga ggctcaggtg tctgactagg   4080
tagtcatggg aggttcatcc caggagaggc tacaactggg gcaacccatc cacctgaggg   4140
agaattcagt ggcaggtcac agtgctcgtc acagcagtcc tacagtgtaa cagcttgtta   4200
gggagtacgt gcaagacctt ttgttttgga agcagtatga tggggtttgg gttggaactg   4260
gtgtcaagta acttctggca catcttcctt tgcctggacc tcttcgcttc ttggaacatc   4320
tgccttttgg cccagttact aggaaagaat gtgaattttt aattgactgg agcctatttg   4380
ctctttgttt ccactgatga tcatcatgaa cccatcttga agatatactg ttcataggtc   4440
tctctggaga caatcccagg tcaatatgtc ctgtggttgc ttgaagttag tttccattgg   4500
ttttgtttta cttttcaaat tgttctttgt gttttaccag gatgtctctg gttccaagcc   4560
agatctctca ctccggctaa ttttctttga tggtgaagag gcttttcatc actggtcccc   4620
tcaagattct ctgtatgggt ctcggcactt agctcagaag atggcatcaa gccctcaccc   4680
tcctggatca agaggcacca accaactgga tggcatggtt agtctgagta attaccttgg   4740
ctctgtagct cagtccctgt ctccagaggc aaggctgcta agaccaagta aagacctaaa   4800
cgtgcctcga aatcctcgga gcactgttta tggtagaaca ttccttggca agcactggag   4860
ttttgaggaa tcccagacct aaaaagaatg gttctgtgtt agaagctgtg tttggctgag   4920
cttaattaaa atgatgtgac aatcagatta agaaggcatt agattcatta tggtttagtg   4980
agagtaccgc cccctcccaa cccctcaaca ctgggtagtg tggagagaaa gagacctttt   5040
ttcaggcaga ggaggctggg aaccccagga cagggaggaa agaggaattc cccatgtgtt   5100
taaagcagta tattgactgc agtatactga tgtttaattt tatgtggtag gttgatgtag   5160
catttatgat gtgagggtag agacattttg aagatgtctt aaaattctgc tgttactaaa   5220
tagtggtttc agcatccgac ctccatacgt tctcctgtgg cctaccagta aattcccttc   5280
agtgactctc tgcccatact ggatcttcac tctgtcacca agtccacacc actcccagtt   5340
tagaacctta tgctaccctc gggaagtcat ttgtctctga cactcttcct aaaccctcca   5400
ccctgccttc acacattccc gctctttgtc gccctatgac tcaaatgagc aactggtgtc   5460
ttctagattc cctaacgctc ctcatgtgag catgactttc ttttgtttgc ggacagctca   5520
ctatgagtca aaagcatgtg gtcatcattt cactcattca ctcgtgcctg agcaactcag   5580
aggggcttgg acaaatgaga agagatgcag ataattagca gttacttatc agtccagata   5640
tacgatccgc agtgatggaa aggctcatct atttctcaga gacttatcca atctcatgaa   5700
tatgttccta tttcaaacaa gcatttttttc ccaaatgaat gagtatgtat atcagttata   5760
catacatgta cgtatatatc attcatgtat accatatctc tggaatcttg aaacctgata   5820
acatttttcc cgtatacatc aggcttcaga gtcggcagtt acccacacag tatgtattct   5880
gctaactttg ctaagtcagg aggcctttat ctaggcgggg gtcttcagga atggagttct   5940
```

caagcgagct gatgctttgt ggctaaacca agctaagaga aattggtcta gttgggaagg 6000
ctataaccag gagactttag agagcagctg gactgaactc cttgtttgtt actgaaggaa 6060
atggcgcccc agtagcacga tgcatatagt ttcctttaaa gggatgtttc cttacacgct 6120
gtgtgagtta tagcttatgc tcccaagctc accaatcatt acagattaaa gttaaaaatg 6180
cctaattaca acggcataga ttagacaggt ttgaactccc acgtggacat acagcaaatg 6240
tgatcttttc tcaaactgta aaatatgcat caaatctccc tttctagttt atccttagtt 6300
atgctccttt gatgcataaa aaaatcccca tttgtccatg ttatgtaagc aaggtctaca 6360
atgttctcta agatggttag caaacaatgc cactaagccc ctttccattt aaaaagctct 6420
ccgtgtgatt ctcgcttgtt aaaatgtgtt agctttgact ggttttcttg atgggtctga 6480
aacatgcctg ggtgactatg acaaagcaat atttttctct cgtaggatct gttggtctta 6540
ctagatttaa ttggagcagc aaatccaaca ttccctaatt ttttccccaa gactaccaga 6600
tggtttaata gacttcaagc aattggtaag catcccagtt actaaagagc aaaaggctgt 6660
ttcttcctgc tggcaagcac tacacctgca aactcacaat ttatggttta aatgtacaat 6720
ttaaatagtt aacatacctt gctggcattt gtcttcccct accaatttgt ttattattcc 6780
taattcttca gcaggcccag tttagtttct taggtggaat tctattttga aaggcagatg 6840
tcaaaatact acatgtatat atttttagaa atgatgccaa aaggtactct ggaatttcat 6900
ttcattttcc atctcaaatt tgtctgcttc tgtttctcc ctttgtcttt ctcccccaag 6960
gactctgtgt gcttccctta cttcctttct ctgaaacgca cacatcaaca gattgtacct 7020
tactgtgatt aaaaccgatt gcactgccct cgtttgtgga atttacattt ttaactattt 7080
aattgtataa gaaaaatgta catgatggtt aaggaaatat aagtattgat agataagaat 7140
attatatttt gtggtacttg gggctttctc agtgttctta aaatcccatt atacttgttt 7200
cctacttgat acagttttac cctagaaatt taacaatcac aaaaatgacc agctatcctg 7260
ggcattattt ccttgttttg tcatctgatg ctatcttgcc attttgtatc aagcagcaca 7320
tgggttatat acacgactta tgtgctacaa gacaccagga gtgagggact gtgtaggcca 7380
gtggttctca aacttcagga c 7401

<210> SEQ ID NO 25
<211> LENGTH: 4901
<212> TYPE: DNA
<213> ORGANISM: Mus musculus

<400> SEQUENCE: 25
gctaactttg ctaagtcagg aggcctttat ctaggcgggg gtcttcagga atggagttct 60
caagcgagct gatgctttgt ggctaaacca agctaagaga aattggtcta gttgggaagg 120
ctataaccag gagactttag agagcagctg gactgaactc cttgtttgtt actgaaggaa 180
atggcgcccc agtagcacga tgcatatagt ttcctttaaa gggatgtttc cttacacgct 240
gtgtgagtta tagcttatgc tcccaagctc accaatcatt acagattaaa gttaaaaatg 300
cctaattaca acggcataga ttagacaggt ttgaactccc acgtggacat acagcaaatg 360
tgatcttttc tcaaactgta aaatatgcat caaatctccc tttctagttt atccttagtt 420
atgctccttt gatgcataaa aaaatcccca tttgtccatg ttatgtaagc aaggtctaca 480
atgttctcta agatggttag caaacaatgc cactaagccc ctttccattt aaaaagctct 540
ccgtgtgatt ctcgcttgtt aaaatgtgtt agctttgact ggttttcttg atgggtctga 600

-continued

```
aacatgcctg ggtgactatg acaaagcaat atttttctct cgtaggatct gttggtctta    660

ctagatttaa ttggagcagc aaatccaaca ttccctaatt ttttccccaa gactaccaga    720

tggtttaata gacttcaagc aattggtaag catcccagtt actaaagagc aaaaggctgt    780

ttcttcctgc tggcaagcac tacacctgca aactcacaat ttatggttta aatgtacaat    840

ttaaatagtt aacatacctt gctggcattt gtcttcccct accaatttgt ttattattcc    900

taattcttca gcaggcccag tttagtttct taggtggaat tctattttga aaggcagatg    960

tcaaaatact acatgtatat atttttagaa atgatgccaa aaggtactct ggaatttcat   1020

ttcattttcc atctcaaatt tgtctgcttc tgttttctcc ctttgtcttt ctcccccaag   1080

gactctgtgt gcttccctta cttcctttct ctgaaacgca cacatcaaca gattgtacct   1140

tactgtgatt aaaaccgatt gcactgccct cgtttgtgga atttacattt ttaactattt   1200

aattgtataa gaaaaatgta catgatggtt aaggaaatat aagtattgat agataagaat   1260

attatatttt gtggtacttg gggctttctc agtgttctta aaatcccatt atacttgttt   1320

cctacttgat acagttttac cctagaaatt taacaatcac aaaaatgacc agctatcctg   1380

ggcattattt ccttgttttg tcatctgatg ctatcttgcc attttgtatc aagcagcaca   1440

tgggttatat acacgactta tgtgctacaa gacaccagga gtgagggact gtgtaggcca   1500

gtggttctca aacttcagga cagatcagaa tcccctgggt tcatgctaac gcgtggatta   1560

ccagccggta ccccgaattt ctgattcatt aagccagagg tagtaccagc tgatttgcat   1620

ctctgcgtta ttctcaggtg atactgaagc tcttgatgag gaaccgcatc ctgagaatca   1680

ctgatagagg tcacagtagt cttttcccac agagtggcca gttgatatac ttcatcctac   1740

tctgttggca tattccgctt taagcccccc acatctctac atgggcattc gccacacacc   1800

acctggatct atgaacatct gcatctgagt ttccaacacc tttgactcct ttttctcttt   1860

ctctttctca atctcagttg ttctagtgag catctactct ttttttggca ttagctactt   1920

ggtctctttt aatcttttta aaaaattggt tattttattt atttacattt caaatgtact   1980

ccccttccca gtgtcccatc cacaaccccc ccattccctc ctctgcctct ataagagtgc   2040

ttcccccacc tgcataccca ctccagcctc tgccatagca ttcccctacc ctgggagcct   2100

ccacagtacc aagggtctcc cctcccactg atgcctgata aggcaatcct ctgctacgga   2160

tgcagtggga gccatgtgtt ctccccatgt gtactttttg gttggtggtt tagtccctgg   2220

gagctttggg ggttctggtt ggttgacatt gttgttcttc ctatggggtt gttaacccct   2280

tcaactcctt cagtccttcc cccaactcct ccattggggt ctccatgctc agtcctatgg   2340

ttgactgcaa gcatccgcat ctgtatcagt aagggtctgg cagagcctct caggggacag   2400

ctttaccagg ctcctgtcag caagcccttc ttggcatcag caataatggt tgggtttggt   2460

gtctgccgat agggtggatc cctaggtgag gcagtctctg gatggccttt cccccagtct   2520

ctgattccat tctttgtccc tgcatttcct gtgatccttg gtgtgtcaag gcacctggga   2580

gttgagcttc ctctgggtgt tgtaggagtg ggtagtgagc cagcgcccca ggtttgctct   2640

gggcactggt tcaaactgga agctggaatc ttagaggttt tcaccagcac tgtcaatgtc   2700

atgtgtgcct ctctgtctct attctcctct actccaaagt atagataggt gcagcttaga   2760

ctcttactgt catagatgtg gctatgttta ctgatacaga tctagggaag aattccatgt   2820

gtgataagat ttcaagctcc ctaaataagg atgtattctg agtcttgatc agagaaaatt   2880

agatgttcat ctactgtcta ctgatgttca tcttgctgtc cacagaaaag gaactctatg   2940

aattgggatt actcaaggat cattctttgg agaggaagta ttttcagaat tttggctatg   3000
```

-continued

```
gaaatattat ccaggatgac cacattccat ttttaagaaa aggtaactgt gtgtgtattg   3060
ttgtgcattg tgttttctct actgtgtcta ctgtaattat tatattttat gtgcattttg   3120
aaattttaaa aatattattt tcacatttct ttttctggtt ctttttttatt atatgttaat   3180
tgtatgtagt atttcattat gacattttta tagatgtata ttgttgcggc cgccagcagc   3240
tcgcaacatg aaccgttcga ctgagaaggc tactcgagct gtaagagagg aatctagacg   3300
gggcgaaaga agaaatggag ctaaaacaaa ttcattctga tcaaagctca aattttattg   3360
ttgcaacact agttataaag gaagggggag gggacccgat tcccgccgaa taatctctgg   3420
tccagtagaa aggtgcacgt gtgtggctcc gcaggttcta gcagtgggcg tggcagaccg   3480
aatgagcagg aagctccacc cctgagcaag caggtttcag gctgggggag gggagactac   3540
agtatataat atagtttgat catattcctc tccctttgcc ctctcttttt ttaatttttc   3600
attttttatt acatagtttc tttatctaca tttcaaattt tatccccttt ccccatttcc   3660
cctctgaccc cccccatccc attccccctc cccctgctca ctaacccacc aactcctgct   3720
cccttgtcct gggattcccc tacactgggg catccagcct tcacaagacc aagggcctct   3780
cctctcattg atgtcccaca aggccatcct ctcctaatat gcggctggag ccatgagtcc   3840
ccttgtgtac tctggttggt ggtttagtcc ctgggagatc tgggggtact ggttggttca   3900
tattgttgtt cctcctatgg agctgcaaac ccctacagct ccttgggtcc tttctctagc   3960
tccttcactg gggaccctgt gatcagtcca aatggttggc tgtgaacatc cacttaatat   4020
ttgtcaggca ctggcagagc ctctcaggaa acagctatat caggctcctg tctgcaaggt   4080
ctgggtttgg tgactgtata tgggatggat ccccaggtgg gacagtcact ggatggcctt   4140
tccttcagtc tctgctccat actttgtctc tgtaactcct cccatgggta gtttgatccc   4200
ccttcttctt ctccttctcc ttctccttct ccttctcctt ctccttcttc ttcttttggt   4260
tttttgagac aggatttctc tatatagccc tggctgtcct ggaattcact ttgtagacca   4320
tgaaagacca aagtatccac actgtggtct tccttcttct tgaatttcat gtggtctgtg   4380
aattgtatct tgggtatcct gaatttctgg gttaatatcc acttatcagt gagcgcatac   4440
catgtgtgtt cttttgtgat tgggttatct cactgaggat gatattctct agttccatcc   4500
atttgcctaa gaacttcatg aattcatcat ttttaatagc tgagtagtac tccattgtgt   4560
aaatgtacca cattttctgt atccattcct ttgttgaagg atatctgggt tctttccaac   4620
ttctggctat tataaataag gatgcaatga acatagtgga gcatgtgtcc ttattacatg   4680
tggagcattt tctgggtata cgctcaggat tggtatagct gggtcctcag atagtactat   4740
gtccaatttt ctgaggaact gtcagactga tttccagagt ggttgaacca tcctgaaatc   4800
ccaccagcaa tggaggagtg ttcctctttc tacatattct cgccagcatc tgctgtcacc   4860
tgagtttttg atcttagcca ttctgactgg tgtgaggtag a                         4901
```